United States Patent
Ruebling-Jass et al.

(10) Patent No.: US 9,017,961 B2
(45) Date of Patent: Apr. 28, 2015

(54) RECOMBINANT BACTERIA COMPRISING NOVEL SUCROSE TRANSPORTERS

(75) Inventors: Kristin Ruebling-Jass, Wilmington, DE (US); Jean-Francois Tomb, Wilmington, DE (US); Tina K Van Dyk, Wilmington, DE (US); Zheng You, Claymont, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 287 days.

(21) Appl. No.: 13/412,193

(22) Filed: Mar. 5, 2012

(65) Prior Publication Data

US 2013/0230893 A1 Sep. 5, 2013

(51) Int. Cl.

| | |
|---|---|
| *C12Q 1/34* | (2006.01) |
| *C12P 7/20* | (2006.01) |
| *C07K 14/195* | (2006.01) |
| *C07K 14/24* | (2006.01) |
| *C07K 14/245* | (2006.01) |
| *C07K 14/33* | (2006.01) |
| *C07K 14/335* | (2006.01) |
| *C12N 9/10* | (2006.01) |
| *C12N 9/12* | (2006.01) |
| *C12N 9/26* | (2006.01) |
| *C12P 7/18* | (2006.01) |
| *C12P 7/42* | (2006.01) |

(52) U.S. Cl.
CPC .............. *C07K 14/195* (2013.01); *C07K 14/24* (2013.01); *C07K 14/245* (2013.01); *C07K 14/33* (2013.01); *C07K 14/335* (2013.01); *C12N 9/1051* (2013.01); *C12N 9/1205* (2013.01); *C12N 9/2431* (2013.01); *C12P 7/18* (2013.01); *C12P 7/20* (2013.01); *C12P 7/42* (2013.01); *C12Y 204/01007* (2013.01); *C12Y 207/01001* (2013.01); *C12Y 207/01003* (2013.01); *C12Y 207/01004* (2013.01); *C12Y 302/01026* (2013.01)

(58) Field of Classification Search
CPC ...... C12P 7/20; C12N 9/1205; C07K 14/245; C07K 14/195; C07K 14/24; C07K 14/33; C07K 14/335; C12Y 207/01004; C12Y 204/01007; C12Y 302/01026
See application file for complete search history.

(56) References Cited

U.S. PATENT DOCUMENTS

| | | | |
|---|---|---|---|
| 5,686,276 A | 11/1997 | Laffend et al. | |
| 6,013,494 A | 1/2000 | Nakamura et al. | |
| 6,136,576 A | 10/2000 | Diaz-Torres et al. | |
| 6,514,733 B1 | 2/2003 | Emptage et al. | |
| 6,960,455 B2 | 11/2005 | Livshits et al. | |
| 7,005,291 B1 | 2/2006 | Nair et al. | |
| 7,132,527 B2 | 11/2006 | Payne et al. | |
| 7,371,558 B2 | 5/2008 | Cervin et al. | |
| 7,524,660 B2 | 4/2009 | Caimi et al. | |
| 8,129,170 B1 | 3/2012 | Van Dyk | |
| 8,222,000 B2 | 7/2012 | Van Dyk | |
| 8,629,243 B2 | 1/2014 | Chen et al. | |
| 8,673,602 B2 * | 3/2014 | Chen et al. | 435/146 |
| 8,686,114 B2 | 4/2014 | Pollak et al. | |
| 2011/0136190 A1 | 6/2011 | Eliot et al. | |
| 2011/0144377 A1 | 6/2011 | Eliot et al. | |

FOREIGN PATENT DOCUMENTS

| | | |
|---|---|---|
| WO | WO 2009078687 | 6/2009 |
| WO | WO 2010051849 | 5/2010 |

OTHER PUBLICATIONS

Schell et al., The genome sequence of Bifidobacterium longum reflects its adaptation to the human gastrointestinal tract., Proc Natl Acad Sci U S A. (2002), vol. 99(22), pp. 14422-14427.*
Q8G7X9_BIFLO (created on Mar. 1, 2003).*
C5EE18 (created on 2009).*
Q84BY1 (i.e., EC 2.4.1.7; last viewed on Apr. 29, 2014).*
T2HYK7 (i.e., EC 2.7.1.4; last viewed on Apr. 29, 2014).*
Olson et al., "Production of tyrosine from sucrose or glucose achieved by rapid genetic changes to phenylalanine . . . ", Appl. Microbiol. Biotechnol. (2007) 74:1031-1040.
Jahreis et al., "Adaptation of sucrose metabolism in the *Escherichia coli* wild-type strain EC3132", J. Bacteriol. (2002) 184:5307-5316.
Lee et al., "Develoment of sucrose-utilizing *Escherichia coli* K-12 strain by cloning b-fructofuranosidases and its . . . ", Appl. Microbiol. Biotechnol. (2010) 88:905-913.
Daniel et al., "Biochemistry of coenzyme B12-dependent glycerol and diol dehydratases and organization of the encoding genes", FEMS Microbiol. Rev. (1999) 22:553-566.
Tobimatsu et al., "Identification and expression of the genes encoding a reactivating factor for the adenosylcobalamin-dependent glycerol", J. Bacteriol. (1999) 181:4110-4113.
Toraya and Mori, "A reactivating factor for coenzyme B12-dependent diol dehydratase", J. Biol. Chem. (1999) 274:3372-3377.

* cited by examiner

*Primary Examiner* — Alexander Kim

(57) ABSTRACT

Recombinant bacteria capable of metabolizing sucrose are described. The recombinant bacteria comprise in their genome or on at least one recombinant construct, a novel nucleotide sequence encoding a polypeptide having sucrose transporter activity and a nucleotide sequence encoding a polypeptide having sucrose hydrolase activity. These nucleotide sequences are each operably linked to the same or a different promoter. Recombinant bacteria capable of metabolizing sucrose to produce glycerol and/or glycerol-derived products such as 1,3-propanediol and 3-hydroxypropionic acid are also described.

6 Claims, No Drawings

RECOMBINANT BACTERIA COMPRISING NOVEL SUCROSE TRANSPORTERS

FIELD OF THE INVENTION

The invention relates to the fields of microbiology and molecular biology. More specifically, recombinant bacteria comprising novel sucrose transporters and methods of utilizing such recombinant bacteria to produce products such as glycerol and glycerol-derived products from sucrose are provided.

BACKGROUND OF THE INVENTION

Many commercially useful microorganisms use glucose as their main carbohydrate source. However, a disadvantage of the use of glucose by microorganisms developed for production of commercially desirable products is the high cost of glucose. The use of sucrose and mixed feedstocks containing sucrose and other sugars as carbohydrate sources for microbial production systems would be more commercially desirable because these materials are usually readily available at a lower cost.

A production microorganism can function more efficiently when it can utilize any sucrose present in a mixed feedstock. Therefore, when a production microorganism does not have the ability to utilize sucrose efficiently as a major carbon source, it cannot operate as efficiently. For example, bacterial cells typically show preferential sugar use, with glucose being the most preferred. In artificial media containing mixtures of sugars, glucose is typically metabolized to its entirety ahead of other sugars. Moreover, many bacteria lack the ability to utilize sucrose. For example, less than 50% of *Escherichia coli* (*E. coli*) strains have the ability to utilize sucrose. Thus, when a production microorganism cannot utilize sucrose as a carbohydrate source, it is desirable to engineer the microorganism so that it can utilize sucrose.

Recombinant bacteria that have been engineered to utilize sucrose by incorporation of sucrose utilization genes have been reported. For example, Livshits et al. (U.S. Pat. No. 6,960,455) describe the production of amino acids using *Escherichia coli* strains containing genes encoding a metabolic pathway for sucrose utilization. Additionally, Olson et al. (*Appl. Microbiol. Biotechnol.* 74:1031-1040, 2007) describe *Escherichia coli* strains carrying genes responsible for sucrose degradation, which produce L-tyrosine or L-phenylalanine using sucrose as a carbon source. Eliot et al. (U.S. Patent Application No. 2011/0136190 A1) describe recombinant bacteria that produce glycerol and glycerol-derived products from sucrose.

However, there is a need for bacterial strains that are engineered to utilize sucrose using new sucrose utilization genes and that have an improved ability to utilize sucrose. Additionally, there is a need for bacterial strains that are capable of producing glycerol and glycerol-derived products using sucrose as carbon source.

SUMMARY OF THE INVENTION

One embodiment provides a recombinant bacterium comprising in its genome or on at least one recombinant construct:
(a) a nucleotide sequence encoding a polypeptide having sucrose transporter activity, the polypeptide having at least 95% sequence identity, based on a Clustal W method of alignment, when compared to an amino acid sequence selected from the group consisting of SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, and SEQ ID NO:94; and
(b) a nucleotide sequence encoding a polypeptide having sucrose hydrolase activity;
wherein (a) and (b) are each operably linked to the same or a different promoter, further wherein the recombinant bacterium is capable of metabolizing sucrose.

In one embodiment, the recombinant bacterium produces 1,3-propanediol, glycerol, and/or 3-hydroxypropionic acid.

Another embodiment provides a process for making glycerol, 1,3-propanediol and/or 3-hydroxypropionic acid from sucrose comprising:
a) culturing the recombinant bacterium that produces 1,3-propanediol, glycerol, and/or 3-hydroxypropionic acid, disclosed herein, in the presence of sucrose; and
b) optionally, recovering the glycerol, 1,3-propanediol and/or 3-hydroxypropionic acid produced.

BRIEF SEQUENCE DESCRIPTIONS

The following sequences conform with 37 C.F.R. 1.821 1.825 ("Requirements for Patent Applications Containing Nucleotide Sequences and/or Amino Acid Sequence Disclosures—the Sequence Rules") and consistent with World Intellectual Property Organization (WIPO) Standard ST.25 (2009) and the sequence listing requirements of the EPO and PCT (Rules 5.2 and 49.5 (a bis), and Section 208 and Annex C of the Administrative Instructions). The symbols and format used for nucleotide and amino acid sequence data comply with the rules set forth in 37 C.F.R. §1.822.

TABLE 1

Summary of Gene and Protein SEQ ID Numbers

| Gene | Coding Sequence SEQ ID NO: | Encoded Protein SEQ ID NO: |
| --- | --- | --- |
| GPD1 from *Saccharomyces cerevisiae* | 1 | 2 |
| GPD2 from *Saccharomyces cerevisiae* | 3 | 4 |
| GPP1 from *Saccharomyces cerevisiae* | 5 | 6 |
| GPP2 from *Saccharomyces cerevisiae* | 7 | 8 |
| dhaB1 from *Klebsiella pneumoniae* | 9 | 10 |
| dhaB2 from *Klebsiella pneumoniae* | 11 | 12 |
| dhaB3 from *Klebsiella pneumoniae* | 13 | 14 |
| aldB from *Escherichia coli* | 15 | 16 |
| aldA from *Escherichia coli* | 17 | 18 |
| aldH from *Escherichia coli* | 19 | 20 |
| galP from *Escherichia coli* | 21 | 22 |
| cscB from *Escherichia coli* EC3132 | 23 | 24 |
| cscB from *Escherichia coli* ATCC ® 13281 | 25 | 26 |
| cscA from *Escherichia coli* EC3132 | 27 | 28 |
| cscA from *Escherichia coli* ATCC13281 | 29 | 30 |
| bfrA from *Bifidobacterium lactis* strain DSM 10140$^T$ | 31 | 32 |
| SUC2 from *Saccharomyces cerevisiae* | 33 | 34 |
| scrB from *Corynebacterium glutamicum* | 35 | 36 |
| sucrose phosphorylase gene from *Leuconostoc mesenteroides* DSM 20193 | 37 | 38 |
| sucP *Bifidobacterium adolescentis* DSM 20083 | 39 | 40 |
| scrK from *Agrobacterium tumefaciens* | 41 | 42 |
| scrK from *Streptococcus mutans* | 43 | 44 |
| scrK From *Escherichia coli* | 45 | 46 |
| scrK from *Klebsiella pneumoniae* | 47 | 48 |
| cscK from *Escherichia coli* | 49 | 50 |
| cscK from *Enterococcus faecalis* | 51 | 52 |
| HXK1 from *Saccharomyces cerevisiae* | 53 | 54 |
| HXK2 from *Saccharomyces cerevisiae* | 55 | 56 |
| dhaT from *Klebsiella pneumoniae* | 57 | 58 |
| dhaX from *Klebsiella pneumoniae* | 59 | 60 |

TABLE 1-continued

Summary of Gene and Protein SEQ ID Numbers

| Gene | Coding Sequence SEQ ID NO: | Encoded Protein SEQ ID NO: |
|---|---|---|
| scrT1 from *Citrobacter* sp | 67 | 68 |
| scrT3 from *Enterococcus faecium* | 69 | 70 |
| scrT4 from *Corynebacterium glucuronolyticum* | 71 | 72 |
| scrT5 from *Bifidobacterium animalis* subsp. *lactis* | 73 | 74 |
| scrT6 from *Bifidobacterium gallicum* | 75 | 76 |
| scrT7 from *Bifidobacterium longum* | 77 | 78 |
| scrT8 from *Bifidobacterium adolescentis* | 79 | 80 |
| scrT9 from *Bifidobacterium longum* | 81 | 82 |
| scrT12 from *Mitsuokella multacida* | 83 | 84 |
| scrT13 from *Lactobacillus antri* | 85 | 86 |
| scrT14 from *Lactobacillus ruminis* | 87 | 88 |
| scrT21 from *Yersinia frederiksenii* | 89 | 90 |
| scrT25 from *Serratia proteamaculans* | 91 | 92 |
| scrT26 from *Escherichia coli* | 93 | 94 |
| scrT2 from *Weissella paramesenteroides* | 95 | 96 |
| scrT10 from *Bifidobacterium pseudocatenulatum* | 97 | 98 |
| scrT11 from *Bifidobacterium catenulatum* | 99 | 100 |
| scrT15 from *Clostridium thermocellum* | 101 | 102 |
| scrT16 from *Granulibacter* bethesdensis | 103 | 104 |
| scrT17 from *Cronobacter turicensis* | 105 | 106 |
| scrT18 from *Enterobacter* sp. | 107 | 108 |
| scrT19 from *Citrobacter koseri* | 109 | 110 |
| scrT20 from *Bacillus megaterium* | 111 | 112 |
| scrT22 from *Providencia rustigianii* | 113 | 114 |
| scrT23 from *Providencia alcalifaciens* | 115 | 116 |
| scrT24 from *Serratia odorifera* | 117 | 118 |
| scrT27 from *Streptomyces albus* | 119 | 120 |
| scrT28 from *Azotobacter vinelandii* | 121 | 122 |
| scrT29 from *Oenococcus oeni* | 123 | 124 |
| scrT30 from *Lactobacillus brevis* | 125 | 126 |
| scrT31 from *Weissella paramesenteroides* | 127 | 128 |
| scrT32 from *Mannheimia succiniciproducens* | 129 | 130 |
| scrT33 from *Aggregatibacter aphrophilus* | 131 | 132 |

SEQ ID NO:61 is the nucleotide sequence of the cscAKB gene cluster from *Escherichia coli* ATCC® 13281.

SEQ ID NO:62 is the nucleotide sequence of plasmid pSYCO101.

SEQ ID NO:63 is the nucleotide sequence of plasmid pSYCO103.

SEQ ID NO:64 is the nucleotide sequence of plasmid pSYCO106.

SEQ ID NO:65 is the nucleotide sequence of plasmid pSYCO109.

SEQ ID NO:66 is the nucleotide sequence of plasmid pSYCO400/AGRO.

SEQ ID NO:133 is the nucleotide sequence of plasmid pBHR-cscBKA.

SEQ ID NOs: 134-139 and 174-177 are the nucleotide sequences of primers used in the Examples herein.

SEQ ID NO:140 is the nucleotide sequence of the is promoter/MCS/double terminator insert described in Examples 1-34.

SEQ ID NOs:141-173 are codon optimized nucleic acid sequences of the sucrose transporters disclosed herein for expression in *E. coli*.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a cell" includes one or more cells and equivalents thereof known to those skilled in the art, and so forth.

In the context of this disclosure, a number of terms and abbreviations are used. The following definitions are provided.

"Open reading frame" is abbreviated as "ORF".

"Polymerase chain reaction" is abbreviated as "PCR".

"American Type Culture Collection" is abbreviated as "ATCC".

The term "recombinant glycerol-producing bacterium" refers to a bacterium that has been genetically engineered to be capable of producing glycerol and/or glycerol-derived products.

The term "polypeptide having sucrose transporter activity" refers to a polypeptide that is capable of mediating the transport of sucrose into microbial cells.

The term "polypeptide having fructokinase activity" refers to a polypeptide that has the ability to catalyze the conversion of D-fructose+ATP to fructose-phosphate+ADP. Typical of fructokinase is EC 2.7.1.4. Enzymes that have some ability to phosphorylate fructose, whether or not this activity is their predominant activity, may be referred to as a fructokinase. Abbreviations used for genes encoding fructokinases and proteins having fructokinase activity include, for example, "FrK", "scrK", "cscK", "FK", and "KHK". Fructokinase is encoded by the scrK gene in *Agrobacterium tumefaciens* and *Streptococcus mutans*; and by the cscK gene in certain *Escherichia coli* strains.

The term "polypeptide having sucrose hydrolase activity" refers to a polypeptide that has the ability to catalyze the hydrolysis of sucrose to produce glucose and fructose. Such polypeptides are often referred to as "invertases" or "β-fructofuranosidases".

The terms "glycerol derivative" and "glycerol-derived products" are used interchangeably herein and refer to a compound that is synthesized from glycerol or in a pathway that includes glycerol. Examples of such products include 3-hydroxypropionic acid, methylglyoxal, 1,2-propanediol, and 1,3-propanediol.

The term "microbial product" refers to a product that is microbially produced, i.e., the result of a microorganism metabolizing a substance. The product may be naturally produced by the microorganism, or the microorganism may be genetically engineered to produce the product.

The terms "phosphoenolpyruvate-sugar phosphotransferase system", "PTS system", and "PTS" are used interchangeably herein and refer to the phosphoenolpyruvate-dependent sugar uptake system.

The terms "phosphocarrier protein HPr" and "PtsH" refer to the phosphocarrier protein encoded by ptsH in *E. coli*. The terms "phosphoenolpyruvate-protein phosphotransferase" and "PtsI" refer to the phosphotransferase, EC 2.7.3.9, encoded by ptsI in *E. coli*. The terms "glucose-specific IIA component", and "Crr" refer to enzymes designated as EC 2.7.1.69, encoded by crr in *E. coli*. PtsH, PtsI, and Crr comprise the PTS system.

The term "PTS minus" refers to a microorganism that does not contain a PTS system in its native state or a microorganism in which the PTS system has been inactivated through the inactivation of a PTS gene.

The terms "glycerol-3-phosphate dehydrogenase" and "G3PDH" refer to a polypeptide responsible for an enzyme activity that catalyzes the conversion of dihydroxyacetone phosphate (DHAP) to glycerol 3-phosphate (G3P). In vivo G3PDH may be NAD- or NADP-dependent. When specifically referring to a cofactor specific glycerol-3-phosphate dehydrogenase, the terms "NAD-dependent glycerol-3-phosphate dehydrogenase" and "NADP-dependent glycerol-3-phosphate dehydrogenase" will be used. As it is generally the case that NAD-dependent and NADP-dependent glycerol-3-phosphate dehydrogenases are able to use NAD and NADP interchangeably (for example by the enzyme encoded by gpsA), the terms NAD-dependent and NADP-dependent glycerol-3-phosphate dehydrogenase will be used interchangeably. The NAD-dependent enzyme (EC 1.1.1.8) is encoded, for example, by several genes including GPD1, also referred to herein as DAR1 (coding sequence set forth in SEQ ID NO:1; encoded protein sequence set forth in SEQ ID NO:2), or GPD2 (coding sequence set forth in SEQ ID NO:3; encoded protein sequence set forth in SEQ ID NO:4), or GPD3. The NADP-dependent enzyme (EC 1.1.1.94) is encoded, for example, by gpsA.

The terms "glycerol 3-phosphatase", "sn-glycerol 3-phosphatase", "D,L-glycerol phosphatase", and "G3P phosphatase" refer to a polypeptide having an enzymatic activity that is capable of catalyzing the conversion of glycerol 3-phosphate and water to glycerol and inorganic phosphate. G3P phosphatase is encoded, for example, by GPP1 (coding sequence set forth in SEQ ID NO:5; encoded protein sequence set forth in SEQ ID NO:6), or GPP2 (coding sequence set forth in SEQ ID NO:7; encoded protein sequence set forth in SEQ ID NO:8).

The term "glycerol dehydratase" or "dehydratase enzyme" refers to a polypeptide having enzyme activity that is capable of catalyzing the conversion of a glycerol molecule to the product, 3-hydroxypropionaldehyde (3-HPA).

For the purposes of the present invention the dehydratase enzymes include a glycerol dehydratase (E.C. 4.2.1.30) and a diol dehydratase (E.C. 4.2.1.28) having preferred substrates of glycerol and 1,2-propanediol, respectively. Genes for dehydratase enzymes have been identified in *Klebsiella pneumoniae*, *Citrobacter freundii*, *Clostridium pasteurianum*, *Salmonella typhimurium*, *Klebsiella oxytoca*, and *Lactobacillus reuteri*, among others. In each case, the dehydratase is composed of three subunits: the large or "α" subunit, the medium or "β" subunit, and the small or "γ" subunit. The genes are also described in, for example, Daniel et al. (*FEMS Microbiol. Rev.* 22, 553 (1999)) and Toraya and Mori (*J. Biol. Chem.* 274, 3372 (1999)). Genes encoding the large or "α" (alpha) subunit of glycerol dehydratase include dhaB1 (coding sequence set forth in SEQ ID NO:9, encoded protein sequence set forth in SEQ ID NO:10), gldA and dhaB; genes encoding the medium or "β" (beta) subunit include dhaB2 (coding sequence set forth in SEQ ID NO:11, encoded protein sequence set forth in SEQ ID NO:12), gldB, and dhaC; genes encoding the small or "γ" (gamma) subunit include dhaB3 (coding sequence set forth in SEQ ID NO:13, encoded protein sequence set forth in SEQ ID NO:14), gldC, and dhaE. Other genes encoding the large or "α" subunit of diol dehydratase include pduC and pddA; other genes encoding the medium or "β" subunit include pduD and pddB; and other genes encoding the small or "γ" subunit include pduE and pddC.

Glycerol and diol dehydratases are subject to mechanism-based suicide inactivation by glycerol and some other substrates (Daniel et al., *FEMS Microbiol. Rev.* 22, 553 (1999)). The term "dehydratase reactivation factor" refers to those proteins responsible for reactivating the dehydratase activity. The terms "dehydratase reactivating activity", "reactivating the dehydratase activity" and "regenerating the dehydratase activity" are used interchangeably and refer to the phenomenon of converting a dehydratase not capable of catalysis of a reaction to one capable of catalysis of a reaction or to the phenomenon of inhibiting the inactivation of a dehydratase or the phenomenon of extending the useful half-life of the dehydratase enzyme in vivo. Two proteins have been identified as being involved as the dehydratase reactivation factor (see, e.g., U.S. Pat. No. 6,013,494 and references therein; Daniel et al., supra; Toraya and Mori, *J. Biol. Chem.* 274, 3372 (1999); and Tobimatsu et al., *J. Bacteriol.* 181, 4110 (1999)). Genes encoding one of the proteins include, for example, orfZ, dhaB4, gdrA, pduG and ddrA. Genes encoding the second of the two proteins include, for example, orfX, orf2b, gdrB, pduH and ddrB.

The terms "1,3-propanediol oxidoreductase", "1,3-propanediol dehydrogenase" and "DhaT" are used interchangeably herein and refer to the polypeptide(s) having an enzymatic activity that is capable of catalyzing the interconversion of 3-HPA and 1,3-propanediol provided the gene(s) encoding such activity is found to be physically or transcriptionally linked to a dehydratase enzyme in its natural (i.e., wild type) setting; for example, the gene is found within a dha regulon as is the case with dhaT from *Klebsiella pneumoniae*. Genes encoding a 1,3-propanediol oxidoreductase include, but are not limited to, dhaT from *Klebsiella pneumoniae*, *Citrobacter freundii*, and *Clostridium pasteurianum*. Each of these genes encode a polypeptide belonging to is the family of type III alcohol dehydrogenases, which exhibits a conserved iron-binding motif, and has a preference for the $NAD^+/NADH$ linked interconversion of 3-HPA and 1,3-propanediol (Johnson and Lin, *J. Bacteriol.* 169, 2050 (1987); Daniel et al., *J. Bacteriol.* 177, 2151 (1995); and Leurs et al., *FEMS Microbiol. Lett.* 154, 337 (1997)). Enzymes with similar physical properties have been isolated from *Lactobacillus brevis* and *Lactobacillus buchneri* (Veiga da Dunha and Foster, *Appl. Environ. Microbiol.* 58, 2005 (1992)).

The term "dha regulon" refers to a set of associated polynucleotides or open reading frames encoding polypeptides having various biological activities, including but not limited to a dehydratase activity, a reactivation activity, and a 1,3-propanediol oxidoreductase. Typically a dha regulon comprises the open reading frames dhaR, orfY, dhaT, orfX, orfW, dhaB1, dhaB2, dhaB3, and ortZ as described in U.S. Pat. No. 7,371,558.

The terms "aldehyde dehydrogenase" and "Ald" refer to a polypeptide that catalyzes the conversion of an aldehyde to a carboxylic acid. Aldehyde dehydrogenases may use a redox cofactor such as NAD, NADP, FAD, or PQQ. Typical of aldehyde dehydrogenases is EC 1.2.1.3 (NAD-dependent); EC 1.2.1.4 (NADP-dependent); EC 1.2.99.3 (PQQ-dependent); or EC 1.2.99.7 (FAD-dependent). An example of an NADP-dependent aldehyde dehydrogenase is AldB (SEQ ID NO:16), encoded by the *E. coli* gene aldB (coding sequence set forth in SEQ ID NO:15). Examples of NAD-dependent aldehyde dehydrogenases include AldA (SEQ ID NO:18), encoded by the *E. coli* gene aldA (coding sequence set forth in SEQ ID NO:17); and AldH (SEQ ID NO:20), encoded by the *E. coli* gene aldH (coding sequence set forth in SEQ ID NO:19).

The terms "glucokinase" and "Glk" are used interchangeably herein and refer to a protein that catalyzes the conversion of D-glucose+ATP to glucose 6-phosphate+ADP. Typical of glucokinase is EC 2.7.1.2. Glucokinase is encoded by glk in *E. coli*.

The terms "phosphoenolpyruvate carboxylase" and "Ppc" are used interchangeably herein and refer to a protein that catalyzes the conversion of phosphoenolpyruvate+$H_2O$+$CO_2$ to phosphate+oxaloacetic acid. Typical of phosphoenolpyruvate carboxylase is EC 4.1.1.31. Phosphoenolpyruvate carboxylase is encoded by ppc in *E. coli*.

The terms "glyceraldehyde-3-phosphate dehydrogenase" and "GapA" are used interchangeably herein and refer to a protein having an enzymatic activity capable of catalyzing the conversion of glyceraldehyde 3-phosphate+phosphate+NAD$^+$ to 3-phospho-D-glyceroyl-phosphate+NADH+H. Typical of glyceraldehyde-3-phosphate dehydrogenase is EC 1.2.1.12. Glyceraldehyde-3-phosphate dehydrogenase is encoded by gapA in *E. coli*.

The terms "aerobic respiration control protein" and "ArcA" are used interchangeably herein and refer to a global regulatory protein. The aerobic respiration control protein is encoded by arcA in *E. coli*.

The terms "methylglyoxal synthase" and "MgsA" are used interchangeably herein and refer to a protein having an enzymatic activity capable of catalyzing the conversion of dihydroxyacetone phosphate to methylglyoxal+phosphate. Typical of methylglyoxal synthase is EC 4.2.3.3. Methylglyoxal synthase is encoded by mgsA in *E. coli*.

The terms "phosphogluconate dehydratase" and "Edd" are used interchangeably herein and refer to a protein having an enzymatic activity capable of catalyzing the conversion of 6-phospho-gluconate to 2-keto-3-deoxy-6-phospho-gluconate+H$_2$O. Typical of phosphogluconate dehydratase is EC 4.2.1.12. Phosphogluconate dehydratase is encoded by edd in *E. coli*.

The term "YciK" refers to a putative enzyme encoded by yciK which is translationally coupled to btuR, the gene encoding Cob(I)alamin adenosyltransferase in *E. coli*.

The term "cob(I)alamin adenosyltransferase" refers to an enzyme capable of transferring a deoxyadenosyl moiety from ATP to the reduced corrinoid. Typical of cob(I)alamin adenosyltransferase is EC 2.5.1.17. Cob(I)alamin adenosyltransferase is encoded by the gene "btuR" in *E. coli*, "cobA" in *Salmonella typhimurium*, and "cobO" in *Pseudomonas denitrificans*.

The terms "galactose-proton symporter" and "GalP" are used interchangeably herein and refer to a protein having an enzymatic activity capable of transporting a sugar and a proton from the periplasm to the cytoplasm. D-glucose is a preferred substrate for GalP. Galactose-proton symporter is encoded by galP in *Escherichia coli* (coding sequence set forth in SEQ ID NO:21, encoded protein sequence set forth in SEQ ID NO:22).

The term "non-specific catalytic activity" refers to the polypeptide(s) having an enzymatic activity capable of catalyzing the interconversion of 3-HPA and 1,3-propanediol and specifically excludes 1,3-propanediol oxidoreductase(s). Typically these enzymes are alcohol dehydrogenases. Such enzymes may utilize cofactors other than NAD+/NADH, including but not limited to flavins such as FAD or FMN. A gene for a non-specific alcohol dehydrogenase (yqhD) is found, for example, to be endogenously encoded and functionally expressed within *E. coli* K-12 strains.

The terms "1.6 long GI promoter", "1.20 short/long GI Promoter", and "1.5 long GI promoter" refer to polynucleotides or fragments containing a promoter from the *Streptomyces lividans* glucose isomerase gene as described in U.S. Pat. No. 7,132,527. These promoter fragments include a mutation which decreases their activities as compared to the wild type *Streptomyces lividans* glucose isomerase gene promoter.

The terms "function" and "enzyme function" are used interchangeably herein and refer to the catalytic activity of an enzyme in altering the rate at which a specific chemical reaction occurs without itself being consumed by the reaction. It is understood that such an activity may apply to a reaction in equilibrium where the production of either product or substrate may be accomplished under suitable conditions.

The terms "polypeptide" and "protein" are used interchangeably herein.

The terms "carbon substrate" and "carbon source" are used interchangeably herein and refer to a carbon source capable of being metabolized by the recombinant bacteria disclosed herein and, particularly, carbon sources comprising sucrose. The carbon source may further comprise other monosaccharides, disaccharides, oligosaccharides; or polysaccharides.

The terms "host cell" and "host bacterium" are used interchangeably herein and refer to a bacterium capable of receiving foreign or heterologous genes and capable of expressing those genes to produce an active gene product.

The term "production microorganism" as used herein refers to a microorganism, including, but not limited to, those that are recombinant, used to make a specific product such as 1,3-propanediol, glycerol, 3-hydroxypropionic acid, polyunsaturated fatty acids, and the like.

As used herein, "nucleic acid" means a polynucleotide and includes a single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably herein and refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof.

"Gene" refers to a nucleic acid fragment that expresses a specific protein, and which may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise genes inserted into a non-native organism, genes introduced into a new location within the native host, or chimeric genes.

The term "native nucleotide sequence" refers to a nucleotide sequence that is normally found in the host microorganism.

The term "non-native nucleotide sequence" refers to a nucleotide sequence that is not normally found in the host microorganism.

The term "native polypeptide" refers to a polypeptide that is normally found in the host microorganism.

The term "non-native polypeptide" refers to a polypeptide that is not normally found in the host microorganism.

The terms "encoding" and "coding" are used interchangeably herein and refer to the process by which a gene, through the mechanisms of transcription and translation, produces an amino acid sequence.

The term "coding sequence" refers to a nucleotide sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, silencers, 5' untranslated leader sequence (e.g., between the transcription start site and the translation initiation codon), introns, polyadenylation recognition sequences, RNA processing sites, effector binding sites and stem-loop structures.

The term "expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence (i.e., ORF) and, 3) a 3' untranslated region (e.g., a terminator) that, in eukaryotes, usually contains a polyadenylation site. The expression cassette(s) is usually included within a vector, to facilitate cloning and transformation. Different organisms, including bacteria, yeast, and fungi, can be transformed with different expression cassettes as long as the correct regulatory sequences are used for each host.

"Transformation" refers to the transfer of a nucleic acid molecule into a host organism, resulting in genetically stable inheritance. The nucleic acid molecule may be a plasmid that replicates autonomously, for example, or it may integrate into the genome of the host organism. Host organisms transformed with the nucleic acid fragments are referred to as "recombinant" or "transformed" organisms or "transformants". "Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. Chimeric genes can be designed for use in suppression by linking a nucleic acid fragment or subfragment thereof, whether or not it encodes an active enzyme, in the sense or antisense orientation relative to a promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein.

The terms "substantially similar" and "corresponds substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences. Moreover, the skilled artisan recognizes that substantially similar nucleic acid sequences encompassed by this invention are also defined by their ability to hybridize (under moderately stringent conditions, e.g., 0.5×SSC (standard sodium citrate), 0.1% SDS (sodium dodecyl sulfate), 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences are two nucleotide sequences wherein the complement of one of the nucleotide sequences typically has about at least 80% sequence identity, or 90% sequence identity, up to and including 100% sequence identity (i.e., fully complementary) to the other nucleotide sequence.

The term "stringent conditions" or "stringent hybridization conditions" includes reference to conditions under which a probe will selectively hybridize to its target sequence. Probes are typically single stranded nucleic acid sequences which are complementary to the nucleic acid sequences to be detected. Probes are "hybridizable" to the nucleic acid sequence to be detected. Generally, a probe is less than about 1000 nucleotides in length, optionally less than 500 nucleotides in length.

Hybridization methods are well defined. Typically the probe and sample are mixed under conditions which will permit nucleic acid hybridization. This involves contacting the probe and sample in the presence of an inorganic or organic salt under the proper concentration and temperature conditions. Optionally a chaotropic agent may be added. Nucleic acid hybridization is adaptable to a variety of assay formats. One of the most suitable is the sandwich assay format. A primary component of a sandwich-type assay is a solid support. The solid support has adsorbed to it or covalently coupled to it an immobilized nucleic acid probe that is unlabeled and complementary to one portion of the sequence.

Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the thermal melting point ($T_m$) can be approximated from the equation of Meinkoth et al., *Anal. Biochem.* 138:267-284 (1984): $T_m$=81.5° C.+16.6 (log M) 4-0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, *CABIOS.* 5:151-153 (1989); Higgins, D. G. et al., *Comput. Appl. Biosci.* 8:189-191 (1992)) and found in the MegAlign™ program of the LASERGENE bioinformatics computing suite (DNASTAR Inc., Madison, Wis.). For multiple alignments, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, supra; Higgins, D. G. et al., supra) and found in the MegAlign™ v6.1 program of the LASERGENE bioinformatics computing suite (DNASTAR Inc., Madison, Wis.). Default parameters for multiple alignment correspond to GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB. After alignment of the sequences using the Clustal W program, it is possible to obtain a "percent identity" by viewing the "sequence distances" table in the same program.

"BLASTN method of alignment" is an algorithm provided by the National Center for Biotechnology Information (NCBI) to compare to nucleotide sequences using default parameters.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present invention, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

Thus, the invention encompasses more than the specific exemplary nucleotide sequences disclosed herein. For example, alterations in the gene sequence which reflect the degeneracy of the genetic code are contemplated. Also, it is well known in the art that alterations in a gene which result in the production of a chemically equivalent amino acid at a given site, but do not affect the functional properties of the encoded protein are common. Substitutions are defined for the discussion herein as exchanges within one of the following five groups:
 1. Small aliphatic, nonpolar or slightly polar residues: Ala, Ser, Thr (Pro, Gly);
 2. Polar, negatively charged residues and their amides: Asp, Asn, Glu, Gln;
 3. Polar, positively charged residues: His, Arg, Lys;
 4. Large aliphatic, nonpolar residues: Met, Leu, Ile, Val (Cys); and
 5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize under stringent conditions, as defined above.

Preferred substantially similar nucleic acid fragments of the instant invention are those nucleic acid fragments whose nucleotide sequences are at least 70% identical to the nucleotide sequence of the nucleic acid fragments reported herein. More preferred nucleic acid fragments are at least 90% identical to the nucleotide sequence of the nucleic acid fragments reported herein. Most preferred are nucleic acid fragments that are at least 95% identical to the nucleotide sequence of the nucleic acid fragments reported herein.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.*, 215: 403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, may now use all or a substantial portion of the disclosed sequences for purposes known to those skilled in this art.

The term "complementary" describes the relationship between two sequences of nucleotide bases that are capable of Watson-Crick base-pairing when aligned in an anti-parallel orientation. For example, with respect to DNA, adenosine is capable of base-pairing with thymine and cytosine is capable of base-pairing with guanine. Accordingly, the instant invention may make use of isolated nucleic acid molecules that are complementary to the complete sequences as reported in the accompanying Sequence Listing and the specification as well as those substantially similar nucleic acid sequences.

The term "isolated" refers to a polypeptide or nucleotide sequence that is removed from at least one component with which it is naturally associated.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different is tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

"3' non-coding sequences", "transcription terminator" and "termination sequences" are used interchangeably herein and refer to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989). Transformation methods are well known to those skilled in the art and are described infra.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

A "plasmid" or "vector" is an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

The term "genetically altered" refers to the process of changing hereditary material by genetic engineering, transformation and/or mutation.

The term "recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation, natural transduction, natural transposition) such as those occurring without deliberate human intervention.

The terms "recombinant construct", "expression construct", "chimeric construct", "construct", and "recombinant DNA construct", are used interchangeably herein. A recombinant construct comprises an is artificial combination of nucleic acid fragments, e.g., regulatory and coding sequences that are not found together in nature. For example, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events may result in different levels and patterns of expression (Jones et al., *EMBO J.* 4:2411-2418 (1985); De Almeida et al., *Mol. Gen. Genetics* 218:78-86 (1989)), and thus that multiple events may need be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., an mRNA or a protein [either precursor or mature]).

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

The term "homologous" refers to proteins or polypeptides of common evolutionary origin with similar catalytic function. The invention may include bacteria producing homologous proteins via recombinant technology.

Disclosed herein are recombinant bacteria that have been engineered to utilize sucrose using new sucrose transporter genes from various sources. Specifically, the recombinant bacteria disclosed herein comprise in their genome or on at least one recombinant construct: a nucleotide sequence encoding a polypeptide having sucrose transporter activity, the polypeptide having at least 95% sequence identity, based on a Clustal W method of alignment, when compared to an amino acid sequence selected from group consisting of SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, and SEQ ID NO:94; and a nucleotide sequence encoding a polypeptide having sucrose hydrolase activity. Recombinant bacteria comprising a nucleotide sequence encoding a sucrose transporter polypeptide, as described above, and a nucleotide sequence encoding a polypeptide having sucrose hydrolase activity may be constructed by introducing the nucleotide sequences into a suitable host bacterium, either into the genome or on at least one recombinant construct, using methods known in the art, as described below. In some embodiments, the recombinant bacteria are capable of metabolizing sucrose to produce glycerol and/or glycerol-derived products.

Suitable host bacteria for use in the construction of the recombinant bacteria disclosed herein include, but are not limited to, organisms of the genera: *Escherichia, Streptococcus, Agrobacterium, Bacillus, Corynebacterium, Lactobacillus, Clostridium, Gluconobacter, Citrobacter, Enterobacter, Klebsiella, Aerobacter, Methylobacter, Salmonella, Streptomyces,* and *Pseudomonas.*

In some embodiments, the host bacterium is selected from the genera: *Escherichia, Klebsiella, Citrobacter,* and *Aerobacter.*

In some embodiments, the host bacterium is *Escherichia coli.*

In some embodiments, the host bacterium is PTS minus. In these embodiments, the host bacterium is PTS minus in its native state, or may be rendered PTS minus through inactivation of a PTS gene as described below.

In production microorganisms, it is sometimes desirable to unlink the transport of sugars and the use of phosphoenolpyruvate (PEP) for phosphorylation of the sugars being transported. The term "down-regulated" refers to reduction in, or abolishment of, the activity of active protein(s), as compared to the activity of the wildtype protein(s). The PTS may be inactivated (resulting in a "PTS minus" organism) by down-regulating expression of one or more of the endogenous genes encoding the proteins required in this type of transport. Down-regulation typically occurs when one or more of these genes has a "disruption", referring to an insertion, deletion, or targeted mutation within a portion of that gene, that results in either a complete gene knockout such that the gene is deleted from the genome and no protein is translated or a protein has been translated such that it has an insertion, deletion, amino acid substitution or other targeted mutation. The location of the to disruption in the protein may be, for example, within the N-terminal portion of the protein or within the C-terminal portion of the protein. The disrupted protein will have impaired activity with respect to the protein that was not disrupted, and can be non-functional. Down-regulation that results in low or lack of expression of the protein, could also result via manipulating the regulatory sequences, transcription and translation factors and/or signal transduction pathways or by use of sense, antisense or RNAi technology, or similar mechanisms known to skilled artisans.

Sucrose transporter polypeptides are polypeptides that are capable of mediating the transport of sucrose into microbial cells. Sucrose transporter polypeptides are known in the art, for example the CscB polypeptide from *E. coli* ATCC® 13281 (set forth in SEQ ID NO:26), encoded by the cscB gene (coding sequence set forth in SEQ ID NO:25); and the CscB polypeptide from *E. coli* wild-type strain EC3132 (set forth in SEQ ID NO:24), encoded by the cscB gene (coding sequence set forth in SEQ ID NO:23), as described by Jahreis et al. (*J. Bacteriol.* 184:5307-5316, 2002). The sucrose transporter polypeptides disclosed herein are isolated from various sources, as shown in Table 1, and have amino acid sequences as set forth in SEQ ID NO:68 (coding sequence set forth in SEQ ID NO:67), SEQ ID NO:70 (coding sequence set forth in SEQ ID NO:69), SEQ ID NO:72 (coding sequence set forth in SEQ ID NO:71), SEQ ID NO:74 (coding sequence set forth in SEQ ID NO:73), SEQ ID NO:76 (coding sequence set forth in SEQ ID NO:75), SEQ ID NO:78 (coding sequence set forth in SEQ ID NO:77), SEQ ID NO:80 (coding sequence set forth in SEQ ID NO:79), SEQ ID NO:82 (coding sequence set forth in SEQ ID NO:81), SEQ ID NO:84 (coding sequence set forth in SEQ ID NO:83), SEQ ID NO:86 (coding sequence set forth in SEQ ID NO:85), SEQ ID NO:88 (coding sequence set forth in SEQ ID NO:87), SEQ ID NO:90 (coding sequence set forth in SEQ ID NO:89), SEQ ID NO:92 (coding sequence set forth in SEQ ID NO:91), and SEQ ID NO:94 (coding sequence set forth in SEQ ID NO:93). However, there is no to previously known activity demonstrated for these polypeptides.

In some embodiments, the polypeptide having sucrose transporter activity has at least 95% sequence identity, based on a Clustal W method of alignment, when compared to an amino acid sequence as set forth in SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, or SEQ ID NO:94.

In some embodiments, the polypeptide having sucrose transporter activity has the amino acid sequence set forth in SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, or SEQ ID NO:94.

In some embodiments, the nucleotide sequence encoding a polypeptide having sucrose transporter activity has at least 95% sequence identity, based on BLASTN method of alignment, when compared to a nucleotide sequence as set forth in SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, or SEQ ID NO:93.

The recombinant bacteria disclosed herein also comprise in their genome or on at least one recombinant construct, a nucleotide sequence encoding a polypeptide having sucrose hydrolase activity. Polypeptides having sucrose hydrolase activity have the ability to catalyze the hydrolysis of sucrose to produce fructose and glucose. Polypeptides having sucrose hydrolase activity are known, and include, but are not limited to CscA from *E. coli* wild-type strain EC3132 (set forth in SEQ ID NO:28), encoded by gene cscA (coding sequence set forth in SEQ ID NO:27), CscA from *E. coil* ATCC® 13281 (set forth in SEQ ID NO:30), encoded by gene cscA (coding sequence set forth in SEQ ID NO:29); BfrA from *Bifidobacterium lactis* strain DSM 10140$^T$ (set forth in SEQ ID NO:32), encoded by gene bfrA (coding sequence set forth in SEQ ID NO:31); Suc2p from *Saccharomyces cerevisiae* (set forth in SEQ ID NO:34), encoded by gene SUC2 (coding sequence set forth in SEQ ID NO:33); ScrB from *Corynebacterium glutamicum* (set forth in SEQ ID NO:36), encoded by gene scrB (coding sequence set forth in SEQ ID NO:35); sucrose phosphorylase from *Leuconostoc mesenteroides* DSM 20193 (set forth in SEQ ID NO:38), coding sequence of encoding gene set forth in SEQ ID NO:37; and sucrose phosphorylase from *Bifidobacterium adolescentis* DSM 20083 (set forth in SEQ ID NO:40), encoded by gene sucP (coding sequence set forth in SEQ ID NO:39).

In some embodiments, the polypeptide having sucrose hydrolase activity is classified as EC 3.2.1.26 or EC 2.4.1.7.

In some embodiments, the polypeptide having sucrose hydrolase activity has at least 95% sequence identity, based on the Clustal W method of alignment, to an amino acid sequence as set forth in SEQ ID NO:28, SEQ ID NO:30, SEQ ID NO:32, SEQ ID NO:34, SEQ ID NO:36, SEQ ID NO:38, or SEQ ID NO:40.

In some embodiments, the polypeptide having sucrose hydrolase activity corresponds substantially to the amino acid sequence set forth in SEQ ID NO:30.

The recombinant bacteria disclosed herein may further comprise in their genome or on at least one recombinant construct, a nucleotide sequence encoding a polypeptide having fructokinase activity to enable the bacteria to utilize the fructose produced by the hydrolysis of sucrose. Polypeptides having fructokinase activity include fructokinases (designated EC 21.1.4) and various hexose kinases having fructose phosphorylating activity (EC 2.7.1.3 and EC 2.7.1.1). Fructose phosphorylating activity may be exhibited by hexokinases and ketohexokinases. Representative genes encoding polypeptides from a variety of microorganisms, which may be used to construct the recombinant bacteria disclosed herein, are listed in Table 2. One skilled in the art will know that proteins that are substantially similar to a protein which is able to phosphorylate fructose (such as encoded by the genes listed in Table 2) may also be used.

TABLE 2

Sequences Encoding Enzymes with Fructokinase Activity

| Source | Gene Name | EC Number | Nucleotide SEQ ID NO: | Protein SEQ ID NO: |
|---|---|---|---|---|
| Agrobacterium tumefaciens | scrK (fructokinase) | 2.7.1.4 | 41 | 42 |
| Streptococcus mutans | scrK (fructokinase) | 2.7.1.4 | 43 | 44 |
| Escherichia coli | scrK (fructokinase | 2.7.1.4 | 45 | 46 |
| Klebsiella pneumoniae | scrK (fructokinase) | 2.7.1.4 | 47 | 48 |
| Escherichia coli | cscK (fructokinase) | 2.7.1.4 | 49 | 50 |
| Enterococcus faecalis | cscK (fructokinase) | 2.7.1.4 | 51 | 52 |
| Saccharomyces cerevisiae | HXK1 (hexokinase) | 2.7.1.1 | 53 | 54 |
| Saccharomyces cerevisiae | HXK2 (hexokinase) | 2.7.1.1 | 55 | 56 |

In some embodiments, the polypeptide having fructokinase activity is classified as EC 2.7.1.4, EC 2.7.1.3, or EC 2.7.1.1.

In some embodiments, the polypeptide having fructokinase activity has at least 95% sequence identity, based on the Clustal W method of alignment, to an amino acid sequence as set forth in SEQ ID NO:42, SEQ ID NO:44, SEQ ID NO:46, SEQ ID NO:48, SEQ ID NO:50, SEQ ID NO:52, SEQ ID NO:54, or SEQ ID NO:56.

In some embodiments, the polypeptide having fructokinase activity has the amino acid sequence set forth in SEQ ID NO:50.

The coding sequence of the genes encoding polypeptides having sucrose transporter activity and polypeptides having sucrose hydrolase activity may be used to isolate nucleotide sequences encoding homologous polypeptides from the same or other microbial species. For example, homologs of the genes may be identified using sequence analysis software, such as BLASTN, to search publically available nucleic acid sequence databases. Additionally, the isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202; ligase chain reaction (LCR), Tabor, S. et al., *Proc. Acad. Sci. USA* 82, 1074, 1985); or strand displacement amplification (SDA), Walker, et al., *Proc. Natl. Acad. Sci. U.S.A.*, 89: 392, (1992)). For example, the nucleotide sequence encoding the polypeptides described above may be employed as a hybridization probe for the identification of homologs.

One of ordinary skill in the art will appreciate that genes encoding these polypeptides isolated from other sources may also be used in the recombinant bacteria disclosed herein. Additionally, variations in the nucleotide sequences encoding the polypeptides may be made without affecting the amino acid sequence of the encoded polypeptide due to codon degeneracy, and that amino acid substitutions, deletions or additions that produce a substantially similar protein may be included in the encoded protein.

The nucleotide sequences encoding the polypeptides having sucrose transporter activity and polypeptides having sucrose hydrolase activity may be isolated using PCR (see, e.g., U.S. Pat. No. 4,683,202) with primers designed to bound the desired sequence.

Other methods of gene isolation are well known to one skilled in the art such as by using degenerate primers or heterologous probe hybridization. The nucleotide sequences can also be chemically synthesized or purchased from vendors such as DNA2.0 Inc. (Menlo Park, Calif.). The nucleotide sequences may be codon optimized for expression in the desired host cell.

Expression of the polypeptides may be effected using one of many methods known to one skilled in the art. For example, the nucleotide sequences encoding the polypeptides described above may be introduced into the bacterium on at least one multicopy plasmid, or by integrating one or more copies of the coding sequences into the host genome. The nucleotide sequences encoding the polypeptides may be introduced into the host bacterium separately (e.g., on separate plasmids) or in any combination (e.g., on a single plasmid).

The introduced coding regions that are either on a plasmid(s) or in the genome may be expressed from at least one highly active promoter. An integrated coding region may either be introduced as a part of a chimeric gene having its own promoter, or it may be integrated adjacent to a highly active promoter that is endogenous to the genome or in a highly expressed operon. Suitable promoters include, but are not limited to, CYC1, HIS3, GAL1, GAL10, ADH1, PGK, PHO5, GAPDH, ADC1, TRP1, URA3, LEU2, ENO, and lac, ara, tet, trp, $IP_L$, $IP_R$, T7, tac, and trc (useful for expression in *Escherichia coli*) as well as the amy, apr, npr promoters and various phage promoters useful for expression in *Bacillus*. The promoter may also be the *Streptomyces lividans* glucose isomerase promoter or a variant thereof, described by Payne et al. (U.S. Pat. No. 7,132,527).

In some embodiments, the recombinant bacteria disclosed herein are capable of producing glycerol. Biological processes for the preparation of glycerol using carbohydrates or sugars are known in yeasts and in some bacteria, other fungi, and algae. Both bacteria and yeasts produce glycerol by converting glucose or other carbohydrates through the fructose-1,6-bisphosphate pathway in glycolysis. In the method of producing glycerol disclosed herein, host bacteria may be used that naturally produce glycerol. In addition, bacteria may be engineered for production of glycerol and glycerol derivatives. The capacity for glycerol production from a variety of substrates may be provided through the expression of the enzyme activities glycerol-3-phosphate dehydrogenase (G3PDH) and/or glycerol-3-phosphatase as described in U.S. Pat. No. 7,005,291. Genes encoding these proteins that may be used for expressing the enzyme activities in a host bacterium are described in U.S. Pat. No. 7,005,291. Suitable examples of genes encoding polypeptides having glycerol-3-phosphate dehydrogenase activity include, but are not limited to, GPD1 from *Saccharomyces cerevisiae* (coding sequence set forth in SEQ ID NO:1, encoded protein sequence set forth in SEQ ID NO:2) and GPD2 from *Saccharomyces cerevisiae* (coding sequence set forth in SEQ ID NO:3, encoded protein sequence set forth in SEQ ID NO:4). Suitable examples of genes encoding polypeptides having glycerol-3-phosphatase activity include, but are not limited to, GPP1 from *Saccharomyces cerevisiae* (coding sequence set forth in SEQ ID NO:5, encoded protein sequence set forth in SEQ ID NO:6) and GPP2 from *Saccharomyces cerevisiae* (coding sequence set forth in SEQ ID NO:7, encoded protein sequence set forth in SEQ ID NO:8).

Increased production of glycerol may be attained through reducing expression of target endogenous genes. Down-regulation of endogenous genes encoding glycerol kinase and glycerol dehydrogenase activities further enhance glycerol production as described in U.S. Pat. No. 7,005,291. Increased channeling of carbon to glycerol may be accomplished by reducing the expression of the endogenous gene encoding glyceraldehyde 3-phosphate dehydrogenase, as described in U.S. Pat. No. 7,371,558. Down-regulation may be accomplished by using any method known in the art, for example, the methods described above for down-regulation of genes of the PTS system.

Glycerol provides a substrate for microbial production of useful products. Examples of such products, i.e., glycerol derivatives include, but are not limited to, 3-hydroxypropionic acid, methylglyoxal, 1,2-propanediol, and 1,3-propanediol.

In some embodiments, the recombinant bacteria disclosed herein are capable of producing 1,3-propanediol. The glycerol derivative 1,3-propanediol is a monomer having potential utility in the production of polyester fibers and the manufacture of polyurethanes and cyclic compounds. 1,3-Propanediol can be produced by a single microorganism by bioconversion of a carbon substrate other than glycerol or dihydroxyacetone, as described in U.S. Pat. No. 5,686,276. In this bioconversion, glycerol is produced from the carbon substrate, as described above. Glycerol is converted to the intermediate 3-hydroxypropionaldehyde by a dehydratase enzyme, which can be encoded by the host bacterium or can be introduced into the host by recombination. The dehydratase can be glycerol dehydratase (E.C. 4.2.1.30), diol dehydratase (E.C. 4.2.1.28) or any other enzyme able to catalyze this conversion. A suitable example of genes encoding the "α" (alpha), "β" (beta), and "γ" (gamma) subunits of a glycerol dehydratase include, but are not limited to dhaB1 (coding sequence set forth in SEQ ID NO:9), dhaB2 (coding sequence set forth in SEQ ID NO:11), and dhaB3 (coding sequence set forth in SEQ ID NO:13), respectively, from *Klebsiella pneumoniae*. The further conversion of 3-hydroxypropionaldehyde to 1,3-propandeiol can be catalyzed by 1,3-propanediol dehydrogenase (E.C. 1.1.1.202) or other alcohol dehydrogenases. A suitable example of a gene encoding a 1,3-propanediol dehydrogenase is dhaT from *Klebsiella pneumoniae* (coding sequence set forth in SEQ ID NO:57, encoded protein sequence set forth in SEQ ID NO:58).

Bacteria can be recombinantly engineered to provide more efficient production of glycerol and the glycerol derivative 1,3-propanediol. For example, U.S. Pat. No. 7,005,291 discloses transformed microorganisms and a method for production of glycerol and 1,3-propanediol with advantages derived from expressing exogenous activities of one or both of glycerol-3-phosphate dehydrogenase and glycerol-3-phosphate phosphatase while disrupting one or both of endogenous activities glycerol kinase and glycerol dehydrogenase.

U.S. Pat. No. 6,013,494 describes a process for the production of 1,3-propanediol using a single microorganism comprising exogenous glycerol-3-phosphate dehydrogenase, glycerol-3-phosphate phosphatase, dehydratase, and 1,3-propanediol oxidoreductase (e.g., dhaT). U.S. Pat. No. 6,136,576 discloses a method for the production of 1,3-propanediol comprising a recombinant microorganism further comprising a dehydratase and protein X (later identified as being a dehydratase reactivation factor peptide).

U.S. Pat. No. 6,514,733 describes an improvement to the process where a significant increase in titer (grams product per liter) is obtained by virtue of a non-specific catalytic activity (distinguished from 1,3-propanediol oxidoreductase encoded by dhaT) to convert 3-hydroxypropionaldehyde to 1,3-propanediol. Additionally, U.S. Pat. No. 7,132,527 discloses vectors and plasmids useful for the production of 1,3-propanediol.

Increased production of 1,3-propanediol may be achieved by further modifications to a host bacterium, including down-regulating expression of some target genes and up-regulating, expression of other target genes, as described in U.S. Pat. No. 7,371,558. For utilization of glucose as a carbon source in a PTS minus host, expression of glucokinase activity may be increased.

Additional genes whose increased or up-regulated expression increases 1,3-propanediol production include genes encoding:
  phosphoenolpyruvate carboxylase typically characterized as EC 4.1.1.31
  cob(I)alamin adenosyltransferase, typically characterized as EC 2.5.1.17
  non-specific catalytic activity that is sufficient to catalyze the interconversion of 3-HPA and 1,3-propanediol, and specifically excludes 1,3-propanediol oxidoreductase(s), typically these enzymes are alcohol dehydrogenases Genes whose reduced or down-regulated expression increases 1,3-propanediol production include genes encoding:
  aerobic respiration control protein
  methylglyoxal synthase
  acetate kinase
  phosphotransacetylase
  aldehyde dehydrogenase A
  aldehyde dehydrogenase B
  triosephosphate isomerase
  phosphogluconate dehydratase In some embodiments, the recombinant bacteria disclosed herein are capable of producing 3-hydroxypropionic acid. 3-Hydroxypropionic acid has utility for specialty synthesis and can be converted to commercially important intermediates by known art in the chemical industry, e.g., acrylic acid by dehydration, malonic acid by oxidation, esters by esterification reactions with alcohols, and 1,3-propanediol by reduction. 3-Hydroxypropionic acid may be produced biologically from a fermentable carbon source by a single microorganism, as described in copending and commonly owned U.S. Patent No. 2011/0144377 A1. In one representative biosynthetic pathway, a carbon substrate is converted to 3-hydroxypropionaldehyde, as described above for the production of 1,3-propanediol. The 3-hydroxypropionaldehyde is converted to 3-hydroxypropionic acid by an aldehyde dehydrogenase. Suitable examples of aldehyde dehydrogenases include, but are not limited to, AldB (SEQ ID NO:16), encoded by the *E. coli* gene aldB (coding sequence set forth in SEQ ID NO:15); AldA (SEQ ID NO:18), encoded by the *E. coli* gene aldA (coding sequence set forth in SEQ ID NO:17); and AldH (SEQ ID NO:20), encoded by the *E. coli* gene aldH (coding sequence asset forth in SEQ ID NO:19).

Many of the modifications described above to improve 1,3-propanediol production by a recombinant bacterium can also be made to improve 3-hydroxypropionic acid production. For example, the elimination of glycerol kinase prevents glycerol, formed from G3P by the action of G3P phosphatase, from being re-converted to G3P at the expense of ATP. Also, the elimination of glycerol dehydrogenase (for example, gldA) prevents glycerol, formed from DHAP by the action of NAD-dependent glycerol-3-phosphate dehydrogenase, from being converted to dihydroxyacetone. Mutations can be directed toward a structural gene so as to impair or improve the activity of an enzymatic activity or can be directed toward a regulatory gene, including promoter regions and ribosome binding sites, so as to modulate the expression level of an enzymatic activity.

Up-regulation or down-regulation may be achieved by a variety of methods which are known to those skilled in the art. It is well understood that up-regulation or down-regulation of a gene refers to an alteration in the level of activity present in a cell that is derived from the protein encoded by that gene relative to a control level of activity, for example, by the activity of the protein encoded by the corresponding (or non-altered) wild-type gene.

Specific genes involved in an enzyme pathway may be up-regulated to increase the activity of their encoded function(s). For example, additional copies of selected genes may be introduced into the host cell on multicopy plasmids such as pBR322. Such genes may also be integrated into the chromosome with appropriate regulatory sequences that result in increased activity of their encoded functions. The target genes may be modified so as to be under the control of non-native promoters or altered native promoters. Endogenous promoters can be altered in vivo by mutation, deletion, and/or substitution.

Alternatively, it may be useful to reduce or eliminate the expression of certain genes relative to a given activity level. Methods of down-regulating (disrupting) genes are known to those of skill in the art.

Down-regulation can occur by deletion, insertion, or alteration of coding regions and/or regulatory (promoter) regions. Specific down regulations may be obtained by random mutation followed by screening or selection, or, where the gene sequence is known, by direct intervention by molecular biology methods known to those skilled in the art. A particularly useful, but not exclusive, method to effect down-regulation is to alter promoter strength.

Furthermore, down-regulation of gene expression may be used to either prevent expression of the protein of interest or result in the expression of a protein that is non-functional. This may be accomplished for example, by 1) deleting coding regions and/or regulatory (promoter) regions, 2) inserting exogenous nucleic acid sequences into coding regions and/ regulatory (promoter) regions, and 3) altering coding regions and/or is regulatory (promoter) regions (for example, by making DNA base pair changes). Specific disruptions may be obtained by random mutation followed by screening or selection, or, in cases where the gene sequences in known, specific disruptions may be obtained by direct intervention using molecular biology methods know to those skilled in the art. A particularly useful method is the deletion of significant amounts of coding regions and/or regulatory (promoter) regions.

Methods of altering recombinant protein expression are known to those skilled in the art, and are discussed in part in Baneyx, *Curr. Opin. Biotechnol.* (1999) 10:411; Ross, et al., *J. Bacteriol.* (1998) 180:5375; deHaseth, et al., *J. Bacteriol.* (1998) 180:3019; Smolke and Keasling, *Biotechnol. Bioeng.* (2002) 80:762; Swartz, *Curr. Opin. Biotech.* (2001) 12:195; and Ma, et al., *J. Bacteriol.* (2002) 184:5733.

Recombinant bacteria containing the necessary changes in gene expression for metabolizing sucrose in the production of microbial products including glycerol and glycerol derivatives, as described above, may be constructed using techniques well known in the art.

The construction of the recombinant bacteria disclosed herein may be accomplished using a variety of vectors and transformation and expression cassettes suitable for the cloning, transformation and expression of coding regions that confer the ability to utilize sucrose in the production of glycerol and its derivatives in a suitable host microorganism. Suitable vectors are those which are compatible with the bacterium employed. Suitable vectors can be derived, for example, from a bacterium, a virus (such as bacteriophage T7 or a M-13 derived phage), a cosmid, a yeast or a plant. Protocols for obtaining and using such vectors are known to those skilled in the art (Sambrook et al., supra).

Initiation control regions, or promoters, which are useful to drive expression of coding regions for the instant invention in the desired host bacterium are numerous and familiar to those skilled in the art. Virtually any promoter capable of driving expression is suitable for use herein. For example, any of the promoters listed above may be used.

Termination control regions may also be derived from various genes native to the preferred hosts. Optionally, a termination site may be unnecessary; however, it is most preferred if included.

For effective expression of the instant polypeptides, nucleotide sequences encoding the polypeptides are linked operably through initiation codons to selected expression control regions such that expression results in the formation of the appropriate messenger RNA.

Particularly useful are the vectors pSYCO101, pSYCO103, pSYCO106, and pSYCO109, described in U.S. Pat. No. 7,371,558, and pSYCO400/AGRO, described in U.S. Pat. No. 7,524,660. The essential elements of these vectors are derived from the dha regulon isolated from *Klebsiella pneumoniae* and from *Saccharomyces cerevisiae*. Each vector contains the open reading frames dhaB1, dhaB2, dhaB3, dhaX (coding sequence set forth in SEQ ID NO:59; encoded polypeptide sequence set forth in SEQ ID NO:60), orfX, DAR1, and GPP2 arranged in three separate operons. The nucleotide sequences of pSYCO101, pSYCO103, pSYCO106, pSYCO109, and pSYCO400/AGRO are set forth in SEQ ID NO:62, SEQ ID NO:63, SEQ ID NO:64, SEQ ID NO:65, and SEQ ID NO:66, respectively. The differences between the vectors are illustrated in the chart below [the prefix "p-" indicates a promoter; the open reading frames contained within each "( )" represent the composition of an operon]:

pSYCO101 (SEQ ID NO:62):
   p-trc (Dar1_GPP2) in opposite orientation compared to the other 2 pathway operons,
   p-1.6 long GI (dhaB1_dhaB2_dhaB3_dhaX), and
   p-1.6 long GI (ortY_orfX_orfW).

pSYCO103 (SEQ ID NO:63):
   p-trc (Dar1_GPP2) same orientation compared to the other 2 pathway operons,
   p-1.5 long GI (dhaB1_dhaB2_dhaB3_dhaX), and
   p-1.5 long GI (orfY_orfX_orfW).

pSYCO106 (SEQ ID NO:64):
   p-trc (Dar1_GPP2) same orientation compared to the other 2 pathway operons,
   p-1.6 long GI (dhaB1_dhaB2_dhaB3_dhaX), and
   p-1.6 long GI (orfY_orfX_orfW).

pSYCO109 (SEQ ID NO:65):
- p-trc (Dar1_GPP2) same orientation compared to the other 2 pathway operons,
- p-1.6 long GI (dhaB1_dhaB2_dhaB3_dhaX), and
- p-1.6 long GI (orfY_orfX).

pSYCO400/AGRO (SEQ ID NO:66):
- p-trc (Dar1_GPP2) same orientation compared to the other 2 pathway operons,
- p-1.6 long GI (dhaB1_dhaB2_dhaB3_dhaX), and
- p-1.6 long GI (orfY_orfX).
- p-1.20 short/long GI (scrK) opposite orientation compared to the pathway operons.

Once suitable expression cassettes are constructed, they are used to transform appropriate host bacteria. Introduction of the cassette containing the coding regions into the host bacterium may be accomplished by known procedures such as by transformation (e.g., using calcium-permeabilized cells, or electroporation) or by transfection using a recombinant phage virus (Sambrook et al., supra). Expression cassettes may be maintained on a stable plasmid in a host cell. In addition, expression cassettes may be integrated into the genome of the host bacterium through homologous or random recombination using vectors and methods well known to those skilled in the art. Site-specific recombination systems may also be used for genomic integration of expression cassettes.

In addition to the cells exemplified, cells having single or multiple mutations specifically designed to enhance the production of microbial products including glycerol and/or its derivatives may also be used. Cells is that normally divert a carbon feed stock into non-productive pathways, or that exhibit significant catabolite repression may be mutated to avoid these phenotypic deficiencies.

Methods of creating mutants are common and well known in the art. A summary of some methods is presented in U.S. Pat. No. 7,371,558. Specific methods for creating mutants using radiation or chemical agents are well documented in the art. See, for example, Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.* 36, 227 (1992).

After mutagenesis has occurred, mutants having the desired phenotype may be selected by a variety of methods. Random screening is most common where the mutagenized cells are selected for the ability to produce the desired product or intermediate. Alternatively, selective isolation of mutants can be performed by growing a mutagenized population on selective media where only resistant colonies can develop. Methods of mutant selection are highly developed and well known in the art of industrial microbiology. See, for example, Brock, Supra; DeMancilha et al., *Food Chem.* 14, 313 (1984).

Fermentation media in the present invention comprise sucrose as a carbon substrate. Other carbon substrates such as glucose and fructose may also be present.

In addition to the carbon substrate, a suitable fermentation medium contains, for example, suitable minerals, salts, cofactors, buffers and other components, known to those skilled in the art, suitable for the growth of the cultures and promotion of the enzymatic pathway necessary for production of glycerol and its derivatives, for example 1,3-propanediol. Particular attention is given to Co(II) salts and/or vitamin $B_{12}$ or precursors thereof in production of 1,3-propanediol.

Adenosyl-cobalamin (coenzyme $B_{12}$) is an important cofactor for dehydratase activity. Synthesis of coenzyme $B_{12}$ is found in prokaryotes, some of which are able to synthesize the compound de novo, for example, *Escherichia blattae*, *Klebsiella species*, *Citrobacter* species, and *Clostridium* species, while others can perform partial reactions. *E. coli*, for example, cannot fabricate the corrin ring structure, but is able to catalyze the conversion of cobinamide to corrinoid and can introduce the 5'-deoxyadenosyl group. Thus, it is known in the art that a coenzyme $B_{12}$ precursor, such as vitamin $B_{12}$, needs be provided in *E. coli* fermentations. Vitamin $B_{12}$ may be added continuously to *E. coli* fermentations at a constant rate or staged as to coincide with the generation of cell mass, or may be added in single or multiple bolus additions.

Although vitamin $B_{12}$ is added to the transformed *E. coli* described herein, it is contemplated that other bacteria, capable of de novo vitamin $B_{12}$ biosynthesis will also be suitable production cells and the addition of vitamin $B_{12}$ to these bacteria will be unnecessary.

Typically bacterial cells are grown at 25 to 40° C. in an appropriate medium containing sucrose. Examples of suitable growth media for use herein are common commercially prepared media such as Luria Bertani (LB) broth, Sabouraud Dextrose (SD) broth or Yeast medium (YM) broth. Other defined or synthetic growth media may also be used, and the appropriate medium for growth of the particular bacterium will be known by someone skilled in the art of microbiology or fermentation science. The use of agents known to modulate catabolite repression directly or indirectly, e.g., cyclic adenosine 2':3'-monophosphate, may also be incorporated into the reaction media. Similarly, the use of agents known to modulate enzymatic activities (e.g., methyl viologen) that lead to enhancement of 1,3-propanediol production may be used in conjunction with or as an alternative to genetic manipulations with 1,3-propanediol production strains.

Suitable pH ranges for the fermentation are between pH 5.0 to pH 9.0, where pH 6.0 to pH 8.0 is typical as the initial condition.

Reactions may be performed under aerobic, anoxic, or anaerobic conditions depending on the requirements of the recombinant bacterium. Fed-batch fermentations may be performed with carbon feed, for example, carbon substrate, limited or excess.

Batch fermentation is a commonly used method. Classical batch fermentation is a closed system where the composition of the medium is set at the beginning of the fermentation and is not subject to artificial alterations during the fermentation. Thus, at the beginning of the fermentation, the medium is inoculated with the desired bacterium and fermentation is permitted to occur adding nothing to the system. Typically, however, "batch" fermentation is batch with respect to the addition of carbon source, and attempts are often made at controlling factors such as pH and oxygen concentration. In batch systems, the metabolite and biomass compositions of the system change constantly up to the time the fermentation is stopped. Within batch cultures, cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable for use herein and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of to the changes of measurable factors such as pH, dissolved oxygen and the partial pressure of waste gases such as $CO_2$. Batch and Fed-Batch fermentations are common and well known in the art and examples may be found in Brock, supra.

Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems, a number of factors affecting growth can be altered continuously while the cell concentration, measured by the turbidity of the medium, is kept constant. Continuous systems strive to maintain steady state growth conditions, and thus the cell loss due to medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using batch, fed-batch or continuous processes and that any known mode of fermentation would be suitable. Additionally, it is contemplated that cells may be immobilized on a substrate as whole cell catalysts and subjected to fermentation conditions for production of glycerol and glycerol derivatives, such as 1,3-propanediol.

In some embodiments, a process for making glycerol, 1,3-propanediol, and/or 3-hydroxypropionic acid from sucrose is provided. The process comprises the steps of culturing a recombinant bacterium, as described above, in the presence of sucrose, and optionally recovering the glycerol, 1,3-propanediol, and/or 3-hydroxypropionic acid produced. The product may be recovered using methods known in the art. For example, solids may be removed from the fermentation medium by centrifugation, filtration, decantation, or the like. Then, the product may be isolated from the fermentation medium, which has been treated to remove solids as described above, using methods such as distillation, liquid-liquid extraction, or membrane-based separation.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques described in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

The meaning of abbreviations is as follows: "sec" means second(s), "min" means minute(s), "h" means hour(s), "nm" means nanometers, "μL" means microliter(s), "mL" means milliliter(s), "L" means to liter(s), "mM" means millimolar, "M" means molar, "g" means gram(s), "μg" means microgram(s), "bp" means base pair(s), "kbp" means kilobase pair(s), "rpm" means revolutions per minute, "g" means the gravitation constant, "ATCC" means American Type Culture Collection, Manassas, Va., "OD" means optical density, "HPLC" means high performance liquid chromatography.

Media and Culture Conditions:

Materials and methods suitable for the maintenance and growth of bacterial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials described for the growth and maintenance of bacterial cells may be obtained from Aldrich Chemicals (Milwaukee, Wis.), BD Diagnostic Systems (Sparks, Md.), Life Technologies (Rockville, Md.), New England Biolabs (Beverly, Mass.), or Sigma Chemical Company (St. Louis, Mo.), unless otherwise specified.

LB (Luria Bertani) medium contains the following per liter of medium: Bacto-tryptone (10 g), Bacto-yeast extract (5 g), and NaCl (10 g). LB low salt medium contains the following per liter of medium: Bacto-tryptone (10 g), Bacto-yeast extract (5 g), and NaCl (5 g). Supplements were added as described in the Examples below. All additions were pre-sterilized before they were added to the medium.

Molecular Biology Techniques:

Restriction enzyme digestions, ligations, transformations, and methods for agarose gel electrophoresis were performed as described in Sambrook, J., et al., *Molecular Cloning: A Laboratory Manual*, Second Edition, Cold Spring Harbor Laboratory Press (1989). Polymerase Chain Reactions (PCR) techniques were found in White, B., *PCR Protocols: Current Methods and Applications*, Volume 15 (1993), Humana Press Inc., New York. N.Y.

Examples 1-34

Recombinant *E. coli* Strains Containing Putative Sucrose Transporter Genes

The purpose of these Examples was to construct recombinant *E. coli* strains containing various putative sucrose transporter genes. First an *E. coli* strain, referred to herein as PDO3513, lacking a sucrose transporter but containing the sucrose invertase and fructokinase genes (i.e. a cscA+K+B− (kanR) strain) was constructed. Then, various putative sucrose transporter genes were introduced into *E. coli* strain PDO3513.

Construction of *E. coli* Strain PDO3513

*E. coli* strain PDO3513 was constructed from an *E. coli* strain (referred to herein as PDO3085) containing the wild type cscAKB gene cluster from *E. coli* ATCC® 13281, integrated at the yihP gene in *E. coli* strain FM5 (ATCC® No. 53911). The cscAKB gene cluster (SEQ ID NO:61) was integrated at the yihP location in *E. coli* strain FM5 (ATCC® No. 53911) by the Lambda Red method. The cscAKB gene cluster was amplified from plasmid pBHR-cscBKA (SEQ ID NO:133), which was constructed as described in Example 1 of U.S. Patent Application Publication No. 2011/0136190 A1, using yihP cscA primer (SEQ ID NO:134) and yihP cscB primer (SEQ ID NO:135) containing flanking sequences for the yihP gene. Plasmid pBHR-cscBKA, linearized by PstI digest, was used as the PCR template. High fidelity PfuUltra® II Fusion HS DNA polymerase (Stratagene; La Jolla, Calif.) was used in the PCR reaction. PCR was performed using the following cycling conditions: 95° C. for 2 min; 35 cycles of 95° C. for 30 sec, 60° C. for 30 sec, and 72° C. for 4 min; and then 72° C. for 7 min. The resulting PCR product was stored at 4° C. The PCR product was purified using a QIAquick PCR Purification kit (Qiagen, Valencia, Calif.). The purified PCR product was electroporated into E. coli strain FM5 containing the pKD46 plasmid (Red recombinase plasmid, GenBank Acc. No. AY048746), encoding lambda recombinases, following the lambda red recombination procedure (Datsenko, K. A. and Wanner, B. L., 2000, Proc. Natl. Acad. Sol. USA 97, 6640-6645). The transformation mixture was plated on MOPS minimal plates containing 10 g/L sucrose and 100 µg/mL spectinomycin. The MOPS minimal plates contained 1×MOPS buffer (Technova, Hollister, Calif.), 1.32 mM $KH_2PO_4$ (Technova), 50 µg/L uracil and 1.5 g/L Bacto agar. Plates were incubated at 37° C. for 2-3 days. Colonies grown on minimal sucrose plates were picked to give E. coli strain PDO3085.

The cscB gene in the cluster in PDO3085 was then partially deleted by replacing it with a kanamycin resistance cassette. The kanamycin resistance cassette was amplified from the pKD4 template plasmid (Datsenko and Wanner, Proc. Natl. Acad. Sci. USA 97:6640-6645, 2000) using cscB61 up kan primer (SEQ ID NO:136) and cscB353 down kan primer (SEQ ID NO:137). High fidelity PfuUltra II Fusion HS DNA polymerase (Stratagene; La Jolla, Calif.) was used in the PCR reaction. PCR was performed using the following cycling conditions: 95° C. for 2 min; 30 cycles of 95° C. for 20 sec, 60° C. for 20 sec, and 72° C. for 1.5 min; and then 72° C. for 3 min. The resulting PCR product was stored at 4° C. The PCR product was purified using the QIAquick PCR Purification kit (Qiagen). The purified PCR product was electroporated into the PDO3085 strain containing the pKD46 plasmid encoding lambda recombinases following the lambda red recombination procedure. The transformation mixture was plated on LB plates containing 25 µg/mL kanamycin. The kanamycin resistance colonies were checked on MOPS+10 g/L sucrose plates to make sure that they were unable to grow on sucrose. Insertion of the kanamycin resistance cassette between residue 61 and 353 of CscB was confirmed by PCR using cscB 5' primer (SEQ ID NO:138) and cscB 3' primer (SEQ ID NO: 139). The resulting FM5 yihP:cscA+K$^+$B-(A61-353, kanR) strain was designated as PDO3513.

Construction of E. coli Strains Containing Putative Sucrose Transporter Genes

E. coli strains containing putative sucrose transporter genes were constructed using Vector pDMWP12, which was constructed from vectors pDMWP3 and pDMWP4 as described below.

Vector pDMWP3 was obtained from Integrated DNA Technologies, Inc. (Coralville, 10). The pDMWP3 vector was constructed by cloning a promoter/MCS/double terminator region (sequence set forth in SEQ ID NO:140), synthesized by Integrated DNA Technologies, Inc., into the pIDT-SMART vector (Integrated DNA Technologies, Inc.).

Vector pDMWP4 was constructed from plasmid pBR322. A sca1 site and a kpn1 site on the 5' end of the TetR gene and an additional kpn1 site at the 3' end of the TetR gene were introduced into plasmid pBR322. Additionally, a kpn1 site was removed from the middle of the AmpR gene. All restriction sites were either added or removed using Stratagene's QuikChange® Site-Directed Mutagenesis kit (Stratagene, La Jolla, Calif.) following the manufacturer's protocols.

Vector pDMWP3 was digested with EcoR1 and Kpn1 and the resulting 438 bp fragment was cloned into vector pDMWP4, which was also digested with EcoR1 and Kpn1, to give vector pDMWP12, which is also referred to herein as pBR*P1.20.

Various putative sucrose transporter genes were codon optimized for expression in E. coli and the codon optimized sequences (set forth in SEQ ID NOs:141-173) were synthesized by GenScript USA Inc. (Piscataway, N.J.). The synthetic genes were subcloned into vector pDMWP12 at restriction sites of HindIII and XmaI. The presence of the transporter gene in the vectors was confirmed by sequence analysis. The resulting vectors were used to transform electro-competent cells of PDO3513. Colonies were selected from LB-ampicillin agar plates. The resulting strains were named the PDO50XXseries. The control plasmid pDMWP12 without the sucrose transporter gene insert was also transformed into PDO3513 and the resulting strain was named PDO3247.

The growth rate of the E. coli strains containing the various sucrose transporters in a sucrose containing medium was determined using the Bioscreen C growth chamber (Bioscreen, Helsinki, Finland). Each strain was grown in 2 mL of LB medium containing 100 mg/L of carbenicillin at 33° C. with shaking at 250 rpm for 16 h. The overnight cultures were diluted 1:100 into 150 µL of MOPS minimal medium, containing 1×MOPS buffer (Technova, Hollister, Calif.), 1.32 mM $KH_2PO_4$ (Technova), and supplemented with 2, 5, or 10 g/L of sucrose and 100 mg/L of carbenicillin, in a Bioscreen honeycomb plate. Three replicates were run for each sample. Growth medium blank wells were also included. The honeycomb plate was placed into the Bioscreen C instrument according to the manufacturer's instructions. The plate was incubated at 33° C. with constant shaking and the OD was recorded every 15 min at 600 nm. The E. coli strain PDO3247 containing the plasmid, pDMWP12 was grown in the same manner to serve as a control. The maximum growth rate, referred to herein as $\mu_{max}$, was estimated using the following procedure. First, the background was removed by subtracting the averaged OD values in the blank wells from the OD values of non-blank wells. Then, the growth rate parameter was estimated using a sliding window consisting of 8 data points (covering 2 hours of growth) by fitting the data points to an exponential curve using non-linear regression. In each sliding window, the estimated growth rate was recorded only if the fit was good (i.e., $R^2>0.95$). The largest value from all the recorded growth rates was taken as $\mu_{max}$. The mean $\mu_{max}$ and the standard deviation of three replicates are given in Table 3.

As can be seen from the data in Table 3, the E. coli strains containing the putative sucrose transporter genes of Examples 2-15 exhibited significantly enhanced growth on sucrose compared to the strain that did not contain a sucrose transporter gene (Example 1, Comparative), thereby demonstrating the function of these putative transporters. The sucrose transporters of Comparative Examples 16-33 exhibited little or no growth on sucrose, indicating that these putative is transporters did not function as effective sucrose transporters.

TABLE 3

Growth Rates of *E. coli* Strains Grown of Sucrose

| Example | Strain | Transporter Gene (codon optimized CDS) | Growth Rate on Sucrose ($\mu_{max}$) | | |
|---|---|---|---|---|---|
| | | | 2 g/L | 5 g/L | 10 g/L |
| 1, Comparative | PDO3247 | None | 0.023 ± 0.0038 | 0.029 ± 0.0028 | 0.038 ± 0.001 |
| 2 | PDO5001 | scrT1 (SEQ ID NO: 141) | 0.411 ± 0.01 | 0.411 ± 0.002 | 0.399 ± 0.001 |
| 3 | PDO5003 | scrT3 (SEQ ID NO: 142) | 0.321 ± 0.015 | 0.390 ± 0.005 | 0.385 ± 0.005 |
| 4 | PDO5004 | scrT4 (SEQ ID NO: 143) | 0.239 ± 0.022 | 0.390 ± 0.001 | 0.390 ± 0.001 |
| 5 | PDO5005 | scrT5 (SEQ ID NO: 144) | 0.065 ± 0.015 | 0.127 ± 0.0002 | 0.176 ± 0.001 |
| 6 | PDO5006 | scrT6 (SEQ ID NO: 145) | 0.353 ± 0.0001 | 0.385 ± 0.006 | 0.382 ± 0.005 |
| 7 | PDO5007 | scrT7 (SEQ ID NO: 146) | 0.426 ± 0.002 | 0.403 ± 0.003 | 0.399 ± 0.005 |
| 8 | PDO5008 | scrT8 (SEQ ID NO: 147) | 0.072 ± 0.002 | 0.154 ± 0.0006 | 0.222 ± 0.001 |
| 9 | PDO5009 | scrT9 (SEQ ID NO: 148) | 0.251 ± 0.003 | 0.411 ± 0.0007 | 0.415 ± 0.003 |
| 10 | PDO5012 | scrT12 (SEQ ID NO: 149) | 0.028 ± 0.001 | 0.050 ± 0.003 | 0.103 ± 0.006 |
| 11 | PDO5013 | scrT13 (SEQ ID NO: 150) | 0.356 ± 0.002 | 0.359 ± 0.002 | 0.409 ± 0.005 |
| 12 | PDO5014 | scrT14 (SEQ ID NO: 151) | 0.238 ± 0.003 | 0.391 ± 0.013 | 0.387 ± 0.004 |
| 13 | PDO5021 | scrT21 (SEQ ID NO: 152) | 0.06 ± 0.0006 | 0.155 ± 0.002 | 0.271 ± 0.008 |
| 14 | PDO5025 | scrT25 (SEQ ID NO: 153) | 0.355 ± 0.0246 | 0.392 ± 0.0004 | 0.383 ± 0.004 |
| 15 | PDO5026 | scrT26 (SEQ ID NO: 154) | 0.034 ± 0.004 | 0.262 ± 0.001 | 0.287 ± 0.005 |
| 16 Comparative | PDO5017 | scrT17 (SEQ ID NO: 155) | 0.024 ± 0.003 | 0.032 ± 0.003 | 0.048 ± 0.002 |
| 17, Comparative | PDO5018 | scrT18 (SEQ ID NO: 156) | 0.047 ± 0.02 | 0.08 ± 0.01 | 0.086 ± 0.002 |
| 18, Comparative | PDO5019 | scrT19 (SEQ ID NO: 157) | 0.034 ± 0.01 | 0.06 ± 0.006 | 0.068 ± 0.008 |
| 19, Comparative | PDO5020 | scrT20 (SEQ ID NO: 158) | 0.028 ± 0.003 | 0.047 ± 0.01 | 0.052 ± 0.006 |
| 20, Comparative | PDO5022 | scrT22 (SEQ ID NO: 159) | 0.042 ± 0.003 | 0.044 ± 0.001 | 0.062 ± 0.003 |
| 21, Comparative | PDO5023 | scrT23 (SEQ ID NO: 160) | 0.029 ± 0.003 | 0.05 ± 0.001 | 0.075 ± 0.002 |
| 22, Comparative | PDO5002 | scrT2 (SEQ ID NO: 161) | no growth | no growth | no growth |
| 23, Comparative | PDO5010 | scrT10 (SEQ ID NO: 162) | no growth | no growth | no growth |
| 24, Comparative | PDO5011 | scrT11 (SEQ ID NO: 163) | no growth | no growth | no growth |
| 25, Comparative | PDO5015 | scrT15 (SEQ ID NO: 164) | no growth | no growth | no growth |
| 26, Comparative | PDO5016 | scrT16 (SEQ ID NO: 165) | no growth | no growth | no growth |
| 27, Comparative | PDO5024 | scrT24 (SEQ ID NO: 166) | no growth | no growth | no growth |
| 28, Comparative | PDO5027 | scrT27 (SEQ ID NO: 167) | no growth | no growth | no growth |
| 29, Comparative | PDO5028 | scrT28 (SEQ ID NO: 168) | no growth | no growth | no growth |
| 30, Comparative | PDO5029 | scrT29 (SEQ ID NO: 169) | no growth | no growth | no growth |
| 31, Comparative | PDO5030 | scrT30 (SEQ ID NO: 170) | no growth | no growth | no growth |
| 32, Comparative | PDO5031 | scrT31 (SEQ ID NO: 171) | no growth | no growth | no growth |
| 33, Comparative | PDO5032 | scrT32 (SEQ ID NO: 172) | no growth | no growth | no growth |
| 34, Comparative | PDO5033 | scrT33 (SEQ ID NO: 173) | no growth | no growth | no growth |

Examples 35-52

Recombinant *E. Coli* Strains Containing Sucrose Transporter Genes

The purpose of these Examples was to construct recombinant *E. coli* strains containing the sucrose transporters disclosed herein, and having the ability to produce glycerol and 1,3-propanediol (PDO) from sucrose.

The *E. coli* strains containing the sucrose transporter genes were constructed from PDO producing strain TTab pSYCO400/AGRO. *E. coli* strain TTab pSYCO400/AGRO, a PTS minus strain, was constructed as follows. Strain TTab was generated by deletion of the aldB gene from strain TT aldA, described in U.S. Pat. No. 7,371,558 (Example 17).

Briefly, an aldB deletion was made by first replacing 1.5 kbp of the coding region of aldB in *E. coli* strain MG1655 with the FRT-CmR-FRT cassette of the pKD3 plasmid (Datsenko and Wanner, *Proc. Natl. Acad. Sci. USA* 97:6640-6645, 2000). A replacement cassette was amplified with the primer pair SEQ ID NO:174 and SEQ ID NO:175 using pKD3 as the template. The primer SEQ ID NO:174 contains 80 bp of homology to the 5'-end of aldB and 20 bp of homology to pKD3. Primer SEQ ID NO:175 contains 80 bp of homology to the 3' end of aldB and 20 bp homology to pKD3. The PCR products were gel-purified and electroporated into MG1655/pKD46 competent cells (U.S. Pat. No. 7,371,558). Recombinant strains were selected on LB (Luria Bertani) plates with 12.5 mg/L of chloramphenicol. The deletion of the aldB gene was confirmed by PCR, using the primer pair SEQ ID NO:176 and SEQ ID NO:177. The wild-type strain gave a 1.5 kbp PCR product while the recombinant strain gave a characteristic 1.1 kbp PCR product. A P1 lysate was prepared and used to move the mutation to the TT aldA strain to form the TT aldAΔaldB::Cm strain. A chloramphenicol-resistant clone was checked by genomic PCR with the primer pair SEQ ID NO:176 and SEQ ID NO:177 to ensure that the mutation was present. The chloramphenicol resistance marker was removed using the FLP recombinase (Datsenko and Wanner, supra) to create TTab. Strain TTab was then transformed with pSYCO400/AGRO (set forth in SEQ ID NO:66), described in U.S. Pat. No. 7,524,660 (Example 4), to generate strain TTab pSYCO400/AGRO.

As described in the cited references, strain TTab is a derivative of *E. coli* strain FM5 (ATCC® No. 53911) containing the following modifications:
deletion of glpK, gldA, ptsHI, crr, add, arcA, mgsA, qor, ackA, pta, aldA and aldB genes;
upregulation of galP, glk, btuR, ppc, and yqhD genes; and
downregulation of gapA gene.

Plasmid pSYCO400/AGRO contains genes encoding a glycerol production pathway (DAR1 and GPP2) and genes encoding a glycerol dehydratase and associated reactivating factor (dhaB123, dhaX, orfX, orfY), as well as a gene encoding a fructokinase (scrK).

Strain TTab pSYCO400/AGRO was used as a recipient for P1 transduction. The donor strain was PDO3513, constructed as described in Examples 1-34, and selection for growth was on LB plates with 25 μg/mL kanamycin. A colony resistant to kanamycin and spectinomycin was purified and named PDO2737 [TTab/pSYCO400AGRO yihP::cscKBΔ(61-353)KanR&A].

Various putative sucrose transporters in plasmid pDMWP12 were transformed into strain PDO2737 by electroporation, as shown in Table 4, and the colonies were selected on LB low salt agar plates containing 100 μg/mL carbenillin and 100 μg/mL spectinomycin. One colony for each transporter gene was selected to test the PDO production using sucrose as the carbon source, as described in Example 53 below.

TABLE 4

Recombinant PDO Producing *E. coli* Strains Containing Sucrose Transporters

| Example | Strain | Sucrose Transporter |
|---|---|---|
| 35, Comparative | PDO5134 | none |
| 36 | PDO5101 | scrT1 (SEQ ID NO: 141) |
| 37 | PDO5103 | scrT3 (SEQ ID NO: 142) |
| 38 | PDO5104 | scrT4 (SEQ ID NO: 143) |

TABLE 4-continued

Recombinant PDO Producing *E. coli* Strains Containing Sucrose Transporters

| Example | Strain | Sucrose Transporter |
|---|---|---|
| 39 | PDO5105 | scrT5 (SEQ ID NO: 144) |
| 40 | PDO5106 | scrT6 (SEQ ID NO: 145) |
| 41 | PDO5107 | scrT7 (SEQ ID NO: 146) |
| 42 | PDO5108 | scrT8 (SEQ ID NO: 147) |
| 43 | PDO5109 | scrT9 (SEQ ID NO: 148) |
| 44 | PDO5112 | scrT12 (SEQ ID NO: 149) |
| 45 | PDO5113 | scrT13 (SEQ ID NO: 150) |
| 46 | PDO5114 | scrT14 (SEQ ID NO: 151) |
| 47, Comparative | PDO5119 | scrT19 (SEQ ID NO: 157) |
| 48 | PDO5121 | scrT21 (SEQ ID NO: 152) |
| 49, Comparative | PDO5122 | scrT22 (SEQ ID NO: 159) |
| 50 | PDO5123 | scrT23 (SEQ ID NO: 160) |
| 51 | PDO5125 | scrT25 (SEQ ID NO: 153) |
| 52 | PDO5126 | scrT26 (SEQ ID NO: 154) |

Example 53

Production of Glycerol and 1,3-Propanediol from Sucrose by Recombinant Bacterial Strains Containing Sucrose Transporter Genes The recombinant *E. coli* strains described in Examples 35-52 were grown in 1 mL of LB low salt medium containing carbenicillin (100 μg/mL) to and spectinomycin (100 μg/mL) at 33° C. overnight. A 200 μL sample of each culture was used to inoculate 12.5 mL of MOPS minimal medium with 10 g/L of sucrose, 100 μg/mL of spectinomycin and 100 ng/mL of vitamin B12. Cells were grown at 33° C. with shaking at 250 rpm for 45 hours (strains in Table 5) or 50 hours (strains in Table 6). The control strain PDO5134 with no sucrose transporter gene was grown along with the test strains in each batch. Then, the cultures were centrifuged and the supernatants were added to 0.22 μm Spin-X centrifuge tube filters (Corning Inc., Corning, N.Y.) and centrifuged at 10,000 g for 1 min. The filtrates were analyzed by HPLC using a Waters Alliance 2690 HPLC system (Waters Corp., Milford, Mass.) with an Aminex HPX-87C HPLC carbohydrate analysis column (Bio-Rad Laboratories, Hercules, Calif., Cat #125-0095) heated to 85° C. in a separated Waters TCM heating chamber. A Bio-Rad carbo-C micro-guard column (Bio-Rad, Cat #125-0128) was used before the analysis column. The mobile phase was contained 0.05 mM CaO (Sigma, #208159), 0.5 mM MES (Sigma, #M3671), 0.05 mM $HNO_3$ (EMD Chemicals, Gibbstown, N.J., Cat #NX0409), pH 5.3. The flow rate was 0.5 mL/min. Eluted compounds were quantified by refractive index detection with reference to a standard curve prepared from commercially purchased pure compounds dissolved to known concentrations.

TABLE 5

Production of PDO and Glycerol from Sucrose (45 hours of fermentation)

| Strain | Transporter Gene | PDO (g/L) | Glycerol (g/L) | Remaining Sucrose (g/L) |
|---|---|---|---|---|
| PDO5134 | none | 0.01 | 0.33 | 10.82 |
| PDO5101 | scrT1 | 0.70 | 1.46 | 7.53 |
| PDO5103 | scrT3 | 0.83 | 0.77 | 7.83 |
| PDO5104 | scrT4 | 5.43 | 0.39 | 0.00 |
| PDO5106 | scrT6 | 3.68 | 1.32 | 0.00 |
| PDO5107 | scrT7 | 2.89 | 3.76 | 0.00 |
| PDO5109 | scrT9 | 3.48 | 3.10 | 0.00 |

TABLE 5-continued

Production of PDO and Glycerol from Sucrose (45 hours of fermentation)

| Strain | Transporter Gene | PDO (g/L) | Glycerol (g/L) | Remaining Sucrose (g/L) |
|---|---|---|---|---|
| PDO5113 | scrT13 | 4.35 | 1.88 | 0.00 |
| PDO5114 | scrT14 | 4.71 | 1.34 | 0.00 |

As can be seen from the data in Tables 5 and 6, *E. coli* strains containing sucrose transporters scrT1, scrT3, scrT4, scrT5, scrT6, scrT7, scrT8, scrT9, scrT13, scrT14, scrT21, scrT23, scrT25 and scrT26 were able to use sucrose and produce PDO and glycerol. *E. coli* strains containing scrT19 (Example 47, Comparative) and scrT22 (Example 49, Comparative) didn't use sucrose to produce these products in significant amounts. Allthough scrT12 was shown to be a sucrose transporter (Example 10), the *E. coli* strain containing scrT12 (PDO5112, Example 44), produced small amounts of PDO and glycerol from sucrose.

TABLE 6

Production of PDO and Glycerol from Sucrose (50 hours of fermentation)

| Strain | Transporter Gene | PDO (g/L) | Glycerol (g/L) | Remaining Sucrose (g/L) |
|---|---|---|---|---|
| PDO5134 | none | 0.07 | 0.01 | 10.96 |
| PDO5105 | scrT5 | 1.39 | 0.16 | 8.18 |
| PDO5108 | scrT8 | 1.14 | 0.23 | 8.68 |
| PDO5112 | scrT12 | 0.26 | 0.04 | 10.39 |
| PDO5119 | scrT19 | 0.12 | 0.03 | 10.73 |
| PDO5121 | scrT21 | 1.41 | 0.11 | 8.20 |
| PDO5122 | scrT22 | 0.18 | 0.01 | 10.41 |
| PDO5123 | scrT23 | 0.30 | 0.01 | 8.77 |
| PDO5125 | scrT25 | 4.05 | 0.25 | 3.09 |
| PDO5126 | scrT26 | 0.62 | 0.04 | 9.66 |

What is claimed is:

1. A recombinant bacterium comprising in its genome or in at least one recombinant construct:
    (a) a nucleotide sequence encoding a polypeptide having sucrose transporter activity, said polypeptide having at least 95% sequence identity, based on a Clustal W method of alignment, when compared to an amino acid sequence selected from the group consisting of SEQ ID NO:78 and SEQ ID NO:82; and
    (b) a nucleotide sequence encoding a polypeptide having sucrose hydrolase catalytic activity, wherein the polypeptide having sucrose hydrolase catalytic activity is classified as EC 3.2.1.26 or EC 2.4.1.7;
wherein (a) and (b) are each operably linked to the same or a different promoter, wherein each of (a) and (b): (i) is in a recombinant construct; (ii) encodes a polypeptide comprising a non-native polypeptide; (iii) is a foreign gene; or (iv) is any combination of (i), (ii), or (iii), and further wherein said recombinant bacterium is capable of metabolizing sucrose.

2. The recombinant bacterium of claim 1 further comprising in its genome or in at least one recombinant construct, a nucleotide sequence encoding a polypeptide having fructokinase catalytic activity, wherein the polypeptide having fructokinase catalytic activity is classified as EC 2.7.1.4, EC 2.7.1.3, or EC 2.7.1.1.

3. The recombinant bacterium of claim 1 wherein said bacterium is selected from the group consisting of the genera: *Escherichia*, *Klebsiella*, *Citrobacter*, and *Aerobacter*.

4. The recombinant bacterium of claim 3 wherein said bacterium is *Escherichia coli*.

5. The recombinant bacterium of claim 1 wherein the recombinant bacterium produces 1,3-propanediol, glycerol, and/or 3-hydroxypropionic acid.

6. A process for making glycerol, 1,3-propanediol and/or 3-hydroxypropionic acid from sucrose comprising:
    (a) culturing the recombinant bacterium of claim 5 in the presence of sucrose; and
    (b) optionally, recovering the glycerol, 1,3-propanediol and/or 3-hydroxypropionic acid produced.

* * * * *

SEQUENCE LISTING

<160> NUMBER OF SEQ ID NOS: 177

<210> SEQ ID NO 1
<211> LENGTH: 1176
<212> TYPE: DNA
<213> ORGANISM: Saccharomyces cerevisiae

<400> SEQUENCE: 1

```
atgtctgctg ctgctgatag attaaactta acttccggcc acttgaatgc tggtagaaag    60
agaagttcct cttctgtttc tttgaaggct gccgaaaagc ctttcaaggt tactgtgatt   120
ggatctggta actgggtac tactattgcc aaggtggttg ccgaaaattg taagggatac    180
ccagaagttt tcgctccaat agtacaaatg tgggtgttcg aagaagagat caatggtgaa   240
aaattgactg aaatcataaa tactagacat caaaacgtga atacttgcc tggcatcact    300 ctacccgaca atttggttgc taatccagac ttgattgatt cagtcaagga tgtcgacatc    360
atcgttttca acattccaca tcaattttg ccccgtatct gtagccaatt gaaaggtcat     420
gttgattcac acgtcagagc tatctcctgt ctaaagggtt ttgaagttgg tgctaaaggt    480
gtccaattgc tatcctctta catcactgag gaactaggta ttcaatgtgg tgctctatct    540
ggtgctaaca ttgccaccga agtcgctcaa gaacactggt ctgaaacaac agttgcttac    600
cacattccaa aggatttcag aggcgagggc aaggacgtcg accataaggt tctaaaggcc    660
ttgttccaca gaccttactt ccacgttagt gtcatcgaag atgttgctgg tatctccatc    720
tgtggtgctt tgaagaacgt tgttgcctta ggttgtggtt tcgtcgaagg tctaggctgg    780
ggtaacaacg cttctgctgc catccaaaga gtcggtttgg gtgagatcat cagattcggt    840
caaatgtttt tcccagaatc tagagaagaa acatactacc aagagtctgc tggtgttgct    900
gatttgatca ccacctgcgc tggtggtaga aacgtcaagg ttgctaggct aatggctact    960
tctggtaagg acgcctggga atgtgaaaag gagttgttga atgccaatc cgctcaaggt   1020 ttaattacct gcaaagaagt tcacgaatgg ttggaaacat gtggctctgt cgaagacttc   1080
ccattatttg aagccgtata ccaaatcgtt tacaacaact acccaatgaa gaacctgccg   1140
gacatgattg aagaattaga tctacatgaa gattag                              1176
```

<210> SEQ ID NO 2
<211> LENGTH: 391
<212> TYPE: PRT

<213> ORGANISM: Saccharomyces cerevisiae

<400> SEQUENCE: 2

```
Met Ser Ala Ala Ala Asp Arg Leu Asn Leu Thr Ser Gly His Leu Asn
1               5                   10                  15
Ala Gly Arg Lys Arg Ser Ser Ser Val Ser Leu Lys Ala Ala Glu
            20                  25                  30
Lys Pro Phe Lys Val Thr Val Ile Gly Ser Gly Asn Trp Gly Thr Thr
            35                  40                  45
Ile Ala Lys Val Val Ala Glu Asn Cys Lys Gly Tyr Pro Glu Val Phe
    50                  55                  60
Ala Pro Ile Val Gln Met Trp Val Phe Glu Glu Ile Asn Gly Glu
65                  70                  75                  80
Lys Leu Thr Glu Ile Ile Asn Thr Arg His Gln Asn Val Lys Tyr Leu
                85                  90                  95
Pro Gly Ile Thr Leu Pro Asp Asn Leu Val Ala Asn Pro Asp Leu Ile
            100                 105                 110
Asp Ser Val Lys Asp Val Asp Ile Val Phe Asn Ile Pro His Gln
    115                 120                 125
Phe Leu Pro Arg Ile Cys Ser Gln Leu Lys Gly His Val Asp Ser His
    130                 135                 140
Val Arg Ala Ile Ser Cys Leu Lys Gly Phe Glu Val Gly Ala Lys Gly
145                 150                 155                 160
Val Gln Leu Leu Ser Ser Tyr Ile Thr Glu Glu Leu Gly Ile Gln Cys
                165                 170                 175
Gly Ala Leu Ser Gly Ala Asn Ile Ala Thr Glu Val Ala Gln Glu His
            180                 185                 190
Trp Ser Glu Thr Thr Val Ala Tyr His Ile Pro Lys Asp Phe Arg Gly
    195                 200                 205
Glu Gly Lys Asp Val Asp His Lys Val Leu Lys Ala Leu Phe His Arg
210                 215                 220
Pro Tyr Phe His Val Ser Val Ile Glu Asp Val Ala Gly Ile Ser Ile
225                 230                 235                 240
Cys Gly Ala Leu Lys Asn Val Val Ala Leu Gly Cys Gly Phe Val Glu
                245                 250                 255
Gly Leu Gly Trp Gly Asn Asn Ala Ser Ala Ala Ile Gln Arg Val Gly
            260                 265                 270
Leu Gly Glu Ile Ile Arg Phe Gly Gln Met Phe Phe Pro Glu Ser Arg
    275                 280                 285
Glu Glu Thr Tyr Tyr Gln Glu Ser Ala Gly Val Ala Asp Leu Ile Thr
    290                 295                 300
Thr Cys Ala Gly Gly Arg Asn Val Lys Val Ala Arg Leu Met Ala Thr
305                 310                 315                 320
Ser Gly Lys Asp Ala Trp Glu Cys Glu Lys Glu Leu Leu Asn Gly Gln
                325                 330                 335
Ser Ala Gln Gly Leu Ile Thr Cys Lys Glu Val His Glu Trp Leu Glu
            340                 345                 350
Thr Cys Gly Ser Val Glu Asp Phe Pro Leu Phe Glu Ala Val Tyr Gln
    355                 360                 365
Ile Val Tyr Asn Asn Tyr Pro Met Lys Asn Leu Pro Asp Met Ile Glu
    370                 375                 380
Glu Leu Asp Leu His Glu Asp
385                 390
```

<210> SEQ ID NO 3
<211> LENGTH: 1323
<212> TYPE: DNA
<213> ORGANISM: Saccharomyces cerevisiae

<400> SEQUENCE: 3

| | | | | | |
|---|---|---|---|---|---|
| atgcttgctg | tcagaagatt | aacaagatac | acattcctta | agcgaacgca | tccggtgtta | 60 |
| tatactcgtc | gtgcatataa | aattttgcct | tcaagatcta | ctttcctaag | aagatcatta | 120 |
| ttacaaacac | aactgcactc | aaagatgact | gctcatacta | atatcaaaca | gcacaaacac | 180 |
| tgtcatgagg | accatcctat | cagaagatcg | gactctgccg | tgtcaattgt | acatttgaaa | 240 |
| cgtgcgccct | tcaaggttac | agtgattggt | tctggtaact | gggggaccac | catcgccaaa | 300 |
| gtcattgcgg | aaaacacaga | attgcattcc | catatcttcg | agccagaggt | gagaatgtgg | 360 |
| gtttttgatg | aaaagatcgg | cgacgaaaat | ctgacggata | tcataaatac | aagacaccag | 420 |
| aacgttaaat | atctacccaa | tattgacctg | ccccataatc | tagtggccga | tcctgatctt | 480 |
| ttacactcca | tcaagggtgc | tgacatcctt | gtttcaaca | tccctcatca | attttttacca | 540 |
| aacatagtca | acaattgca | aggccacgtg | gcccctcatg | taagggccat | ctcgtgtcta | 600 |
| aaagggttcg | agttgggctc | caagggtgtg | caattgctat | cctcctatgt | tactgatgag | 660 |
| ttaggaatcc | aatgtggcgc | actatctggt | gcaaacttgg | caccggaagt | ggccaaggag | 720 |
| cattggtccg | aaaccaccgt | ggcttaccaa | ctaccaaagg | attatcaagg | tgatggcaag | 780 |
| gatgtagatc | ataagatttt | gaaattgctg | ttccacagac | cttacttcca | cgtcaatgtc | 840 |
| atcgatgatg | ttgctggtat | atccattgcc | ggtgccttga | agaacgtcgt | ggcacttgca | 900 |
| tgtggtttcg | tagaaggtat | gggatggggt | aacaatgcct | ccgcagccat | tcaaaggctg | 960 |
| ggtttaggtg | aaattatcaa | gttcggtaga | atgttttttcc | cagaatccaa | agtcgagacc | 1020 |
| tactatcaag | aatccgctgg | tgttgcagat | ctgatcacca | cctgctcagg | cggtagaaac | 1080 |
| gtcaaggttg | ccacatacat | ggccaagacc | ggtaagtcag | ccttggaagc | agaaaaggaa | 1140 |
| ttgcttaacg | gtcaatccgc | ccaagggata | atcacatgca | gagaagttca | cgagtggcta | 1200 |
| caaacatgtg | agttgaccca | agaattccca | ttattcgagg | cagtctacca | gatagtctac | 1260 |
| aacaacgtcc | gcatggaaga | cctaccggag | atgattgaag | agctagacat | cgatgacgaa | 1320 |
| tag | | | | | | 1323 |

<210> SEQ ID NO 4
<211> LENGTH: 440
<212> TYPE: PRT
<213> ORGANISM: Saccharomyces cerevisiae

<400> SEQUENCE: 4

Met Leu Ala Val Arg Arg Leu Thr Arg Tyr Thr Phe Leu Lys Arg Thr
1               5                   10                  15

His Pro Val Leu Tyr Thr Arg Arg Ala Tyr Lys Ile Leu Pro Ser Arg
            20                  25                  30

Ser Thr Phe Leu Arg Arg Ser Leu Leu Gln Thr Gln Leu His Ser Lys
        35                  40                  45

Met Thr Ala His Thr Asn Ile Lys Gln His Lys Cys His Glu Asp
    50                  55                  60

His Pro Ile Arg Arg Ser Asp Ser Ala Val Ser Ile Val His Leu Lys
65                  70                  75                  80

Arg Ala Pro Phe Lys Val Thr Val Ile Gly Ser Gly Asn Trp Gly Thr
                85                  90                  95

```
Thr Ile Ala Lys Val Ile Ala Glu Asn Thr Glu Leu His Ser His Ile
            100                 105                 110
Phe Glu Pro Glu Val Arg Met Trp Val Phe Asp Lys Ile Gly Asp
        115                 120                 125
Glu Asn Leu Thr Asp Ile Ile Asn Thr Arg His Gln Asn Val Lys Tyr
        130                 135                 140
Leu Pro Asn Ile Asp Leu Pro His Asn Leu Val Ala Asp Pro Asp Leu
145                 150                 155                 160
Leu His Ser Ile Lys Gly Ala Asp Ile Leu Val Phe Asn Ile Pro His
                165                 170                 175
Gln Phe Leu Pro Asn Ile Val Lys Gln Leu Gln Gly His Val Ala Pro
            180                 185                 190
His Val Arg Ala Ile Ser Cys Leu Lys Gly Phe Glu Leu Gly Ser Lys
        195                 200                 205
Gly Val Gln Leu Leu Ser Ser Tyr Val Thr Asp Glu Leu Gly Ile Gln
        210                 215                 220
Cys Gly Ala Leu Ser Gly Ala Asn Leu Ala Pro Glu Val Ala Lys Glu
225                 230                 235                 240
His Trp Ser Glu Thr Thr Val Ala Tyr Gln Leu Pro Lys Asp Tyr Gln
                245                 250                 255
Gly Asp Gly Lys Asp Val Asp His Lys Ile Leu Lys Leu Leu Phe His
            260                 265                 270
Arg Pro Tyr Phe His Val Asn Val Ile Asp Asp Val Ala Gly Ile Ser
        275                 280                 285
Ile Ala Gly Ala Leu Lys Asn Val Val Ala Leu Ala Cys Gly Phe Val
        290                 295                 300
Glu Gly Met Gly Trp Gly Asn Asn Ala Ser Ala Ala Ile Gln Arg Leu
305                 310                 315                 320
Gly Leu Gly Glu Ile Ile Lys Phe Gly Arg Met Phe Phe Pro Glu Ser
                325                 330                 335
Lys Val Glu Thr Tyr Tyr Gln Glu Ser Ala Gly Val Ala Asp Leu Ile
            340                 345                 350
Thr Thr Cys Ser Gly Gly Arg Asn Val Lys Val Ala Thr Tyr Met Ala
        355                 360                 365
Lys Thr Gly Lys Ser Ala Leu Glu Ala Glu Lys Glu Leu Leu Asn Gly
        370                 375                 380
Gln Ser Ala Gln Gly Ile Ile Thr Cys Arg Glu Val His Glu Trp Leu
385                 390                 395                 400
Gln Thr Cys Glu Leu Thr Gln Glu Phe Pro Leu Phe Glu Ala Val Tyr
                405                 410                 415
Gln Ile Val Tyr Asn Asn Val Arg Met Glu Asp Leu Pro Glu Met Ile
            420                 425                 430
Glu Glu Leu Asp Ile Asp Asp Glu
        435                 440
```

<210> SEQ ID NO 5
<211> LENGTH: 816
<212> TYPE: DNA
<213> ORGANISM: Saccharomyces cerevisiae

<400> SEQUENCE: 5

```
atgaaacgtt tcaatgtttt aaaatatatc agaacaacaa aagcaaatat acaaaccatc    60
gcaatgcctt tgaccacaaa acctttatct ttgaaaatca acgccgctct attcgatgtt   120
```

```
gacggtacca tcatcatctc tcaaccagcc attgctgctt tctggagaga tttcggtaaa      180
gacaagcctt acttcgatgc cgaacacgtt attcacatct ctcacggttg agaacttac      240 gatgccattg ccaagttcgc tccagacttt gctgatgaag aatacgttaa caagctagaa      300
ggtgaaatcc cagaaaagta cggtgaacac tccatcgaag ttccaggtgc tgtcaagttg      360
tgtaatgctt tgaacgcctt gccaaaggaa aaatgggctg tcgccacctc tggtacccgt      420
gacatggcca agaaatggtt cgacattttg aagatcaaga gaccagaata cttcatcacc      480
gccaatgatg tcaagcaagg taagcctcac ccagaaccat acttaaaggg tagaaacggt      540
ttgggtttcc caattaatga acaagaccca tccaaatcta aggttgttgt ctttgaagac      600
gcaccagctg gtattgctgc tggtaaggct gctggctgta aaatcgttgg tattgctacc      660
actttcgatt tggacttctt gaaggaaaag ggttgtgaca tcattgtcaa gaaccacgaa      720
tctatcagag tcggtgaata caacgctgaa accgatgaag tcgaattgat ctttgatgac      780
tacttatacg ctaaggatga cttgttgaaa tggtaa                               816

<210> SEQ ID NO 6
<211> LENGTH: 271
<212> TYPE: PRT
<213> ORGANISM: Saccharomyces cerevisiae

<400> SEQUENCE: 6

Met Lys Arg Phe Asn Val Leu Lys Tyr Ile Arg Thr Thr Lys Ala Asn
1               5                   10                  15

Ile Gln Thr Ile Ala Met Pro Leu Thr Thr Lys Pro Leu Ser Leu Lys
            20                  25                  30

Ile Asn Ala Ala Leu Phe Asp Val Asp Gly Thr Ile Ile Ile Ser Gln
        35                  40                  45

Pro Ala Ile Ala Ala Phe Trp Arg Asp Phe Gly Lys Asp Lys Pro Tyr
    50                  55                  60

Phe Asp Ala Glu His Val Ile His Ile Ser His Gly Trp Arg Thr Tyr
65                  70                  75                  80

Asp Ala Ile Ala Lys Phe Ala Pro Asp Phe Ala Asp Glu Glu Tyr Val
                85                  90                  95

Asn Lys Leu Glu Gly Glu Ile Pro Glu Lys Tyr Gly Glu His Ser Ile
            100                 105                 110

Glu Val Pro Gly Ala Val Lys Leu Cys Asn Ala Leu Asn Ala Leu Pro
        115                 120                 125

Lys Glu Lys Trp Ala Val Ala Thr Ser Gly Thr Arg Asp Met Ala Lys
    130                 135                 140

Lys Trp Phe Asp Ile Leu Lys Ile Lys Arg Pro Glu Tyr Phe Ile Thr
145                 150                 155                 160

Ala Asn Asp Val Lys Gln Gly Lys Pro His Pro Glu Pro Tyr Leu Lys
                165                 170                 175

Gly Arg Asn Gly Leu Gly Phe Pro Ile Asn Glu Gln Asp Pro Ser Lys
            180                 185                 190

Ser Lys Val Val Val Phe Glu Asp Ala Pro Ala Gly Ile Ala Ala Gly
        195                 200                 205

Lys Ala Ala Gly Cys Lys Ile Val Gly Ile Ala Thr Thr Phe Asp Leu
    210                 215                 220

Asp Phe Leu Lys Glu Lys Gly Cys Asp Ile Ile Val Lys Asn His Glu
225                 230                 235                 240

Ser Ile Arg Val Gly Glu Tyr Asn Ala Glu Thr Asp Glu Val Glu Leu
                245                 250                 255
```

Ile Phe Asp Asp Tyr Leu Tyr Ala Lys Asp Asp Leu Leu Lys Trp
            260                 265                 270

<210> SEQ ID NO 7
<211> LENGTH: 753
<212> TYPE: DNA
<213> ORGANISM: Saccharomyces cerevisiae

<400> SEQUENCE: 7

```
atgggattga ctactaaacc tctatctttg aaagttaacg ccgctttgtt cgacgtcgac      60
ggtaccatta tcatctctca accagccatt gctgcattct ggagggattt cggtaaggac     120
aaaccttatt tcgatgctga acacgttatc caagtctcgc atggttggag aacgtttgat     180
gccattgcta agttcgctcc agactttgcc aatgaagagt atgttaacaa attagaagct     240
gaaattccgg tcaagtacgg tgaaaaatcc attgaagtcc aggtgcagt taagctgtgc      300
aacgctttga cgctctacc aaaagagaaa tgggctgtgg caacttccgg tacccgtgat      360
atggcacaaa aatggttcga gcatctggga atcaggagac aaagtacatt cattaccgct     420
aatgatgtca acagggtaa gcctcatcca gaaccatatc tgaagggcag aatggctta      480
ggatatccga tcaatgagca agacccttcc aaatctaagg tagtagtatt tgaagacgct     540
ccagcaggta ttgccgccgg aaaagccgcc ggttgtaaga tcattggtat tgccactact     600
ttcgacttgg acttcctaaa ggaaaaaggc tgtgacatca ttgtcaaaaa ccacgaatcc     660
atcagagttg gcggctacaa tgccgaaaca gacgaagttg aattcatttt tgacgactac     720
ttatatgcta aggacgatct gttgaaatgg taa                                   753
```

<210> SEQ ID NO 8
<211> LENGTH: 250
<212> TYPE: PRT
<213> ORGANISM: Saccharomyces cerevisiae

<400> SEQUENCE: 8

Met Gly Leu Thr Thr Lys Pro Leu Ser Leu Lys Val Asn Ala Ala Leu
1               5                   10                  15

Phe Asp Val Asp Gly Thr Ile Ile Ile Ser Gln Pro Ala Ile Ala Ala
            20                  25                  30

Phe Trp Arg Asp Phe Gly Lys Asp Lys Pro Tyr Phe Asp Ala Glu His
        35                  40                  45

Val Ile Gln Val Ser His Gly Trp Arg Thr Phe Asp Ala Ile Ala Lys
    50                  55                  60

Phe Ala Pro Asp Phe Ala Asn Glu Glu Tyr Val Asn Lys Leu Glu Ala
65                  70                  75                  80

Glu Ile Pro Val Lys Tyr Gly Glu Lys Ser Ile Glu Val Pro Gly Ala
                85                  90                  95

Val Lys Leu Cys Asn Ala Leu Asn Ala Leu Pro Lys Glu Lys Trp Ala
            100                 105                 110

Val Ala Thr Ser Gly Thr Arg Asp Met Ala Gln Lys Trp Phe Glu His
        115                 120                 125

Leu Gly Ile Arg Arg Pro Lys Tyr Phe Ile Thr Ala Asn Asp Val Lys
    130                 135                 140

Gln Gly Lys Pro His Pro Glu Pro Tyr Leu Lys Gly Arg Asn Gly Leu
145                 150                 155                 160

Gly Tyr Pro Ile Asn Glu Gln Asp Pro Ser Lys Ser Lys Val Val Val
                165                 170                 175

```
Phe Glu Asp Ala Pro Ala Gly Ile Ala Ala Gly Lys Ala Ala Gly Cys
            180                 185                 190
Lys Ile Ile Gly Ile Ala Thr Thr Phe Asp Leu Asp Phe Leu Lys Glu
            195                 200                 205
Lys Gly Cys Asp Ile Ile Val Lys Asn His Glu Ser Ile Arg Val Gly
            210                 215                 220
Gly Tyr Asn Ala Glu Thr Asp Glu Val Glu Phe Ile Phe Asp Asp Tyr
225                 230                 235                 240
Leu Tyr Ala Lys Asp Asp Leu Leu Lys Trp
            245                 250

<210> SEQ ID NO 9
<211> LENGTH: 1668
<212> TYPE: DNA
<213> ORGANISM: Klebsiella pneumoniae
<220> FEATURE:
<221> NAME/KEY: CDS
<222> LOCATION: (1)..(1668)

<400> SEQUENCE: 9
```

| | | | | | | | | | | | | | | | | |
|---|---|---|---|---|---|---|---|---|---|---|---|---|---|---|---|---|
| atg | aaa | aga | tca | aaa | cga | ttt | gca | gta | ctg | gcc | cag | cgc | ccc | gtc | aat | 48 |
| Met | Lys | Arg | Ser | Lys | Arg | Phe | Ala | Val | Leu | Ala | Gln | Arg | Pro | Val | Asn | |
| 1 | | | | 5 | | | | | 10 | | | | | 15 | | |
| cag | gac | ggg | ctg | att | ggc | gag | tgg | cct | gaa | gag | ggg | ctg | atc | gcc | atg | 96 |
| Gln | Asp | Gly | Leu | Ile | Gly | Glu | Trp | Pro | Glu | Glu | Gly | Leu | Ile | Ala | Met | |
| | | | 20 | | | | | 25 | | | | | 30 | | | |
| gac | agc | ccc | ttt | gac | ccg | gtc | tct | tca | gta | aaa | gtg | gac | aac | ggt | ctg | 144 |
| Asp | Ser | Pro | Phe | Asp | Pro | Val | Ser | Ser | Val | Lys | Val | Asp | Asn | Gly | Leu | |
| | | 35 | | | | | 40 | | | | | 45 | | | | |
| atc | gtc | gaa | ctg | gac | ggc | aaa | cgc | cgg | gac | cag | ttt | gac | atg | atc | gac | 192 |
| Ile | Val | Glu | Leu | Asp | Gly | Lys | Arg | Arg | Asp | Gln | Phe | Asp | Met | Ile | Asp | |
| | 50 | | | | | 55 | | | | | 60 | | | | | |
| cga | ttt | atc | gcc | gat | tac | gcg | atc | aac | gtt | gag | cgc | aca | gag | cag | gca | 240 |
| Arg | Phe | Ile | Ala | Asp | Tyr | Ala | Ile | Asn | Val | Glu | Arg | Thr | Glu | Gln | Ala | |
| 65 | | | | | 70 | | | | | 75 | | | | | 80 | |
| atg | cgc | ctg | gag | gcg | gtg | gaa | ata | gcc | cgt | atg | ctg | gtg | gat | att | cac | 288 |
| Met | Arg | Leu | Glu | Ala | Val | Glu | Ile | Ala | Arg | Met | Leu | Val | Asp | Ile | His | |
| | | | | 85 | | | | | 90 | | | | | 95 | | |
| gtc | agc | cgg | gag | gag | atc | att | gcc | atc | act | acc | gcc | atc | acg | ccg | gcc | 336 |
| Val | Ser | Arg | Glu | Glu | Ile | Ile | Ala | Ile | Thr | Thr | Ala | Ile | Thr | Pro | Ala | |
| | | | 100 | | | | | 105 | | | | | 110 | | | |
| aaa | gcg | gtc | gag | gtg | atg | gcg | cag | atg | aac | gtg | gtg | gag | atg | atg | atg | 384 |
| Lys | Ala | Val | Glu | Val | Met | Ala | Gln | Met | Asn | Val | Val | Glu | Met | Met | Met | |
| | | 115 | | | | | 120 | | | | | 125 | | | | |
| gcg | ctg | cag | aag | atg | cgt | gcc | cgc | cgg | acc | ccc | tcc | aac | cag | tgc | cac | 432 |
| Ala | Leu | Gln | Lys | Met | Arg | Ala | Arg | Arg | Thr | Pro | Ser | Asn | Gln | Cys | His | |
| | 130 | | | | | 135 | | | | | 140 | | | | | |
| gtc | acc | aat | ctc | aaa | gat | aat | ccg | gtg | cag | att | gcc | gct | gac | gcc | gcc | 480 |
| Val | Thr | Asn | Leu | Lys | Asp | Asn | Pro | Val | Gln | Ile | Ala | Ala | Asp | Ala | Ala | |
| 145 | | | | | 150 | | | | | 155 | | | | | 160 | |
| gag | gcc | ggg | atc | cgc | ggc | ttc | tca | gaa | cag | gag | acc | acg | gtc | ggt | atc | 528 |
| Glu | Ala | Gly | Ile | Arg | Gly | Phe | Ser | Glu | Gln | Glu | Thr | Thr | Val | Gly | Ile | |
| | | | | 165 | | | | | 170 | | | | | 175 | | |
| gcg | cgc | tac | gcg | ccg | ttt | aac | gcc | ctg | gcg | ctg | ttg | gtc | ggt | tcg | cag | 576 |
| Ala | Arg | Tyr | Ala | Pro | Phe | Asn | Ala | Leu | Ala | Leu | Leu | Val | Gly | Ser | Gln | |
| | | | 180 | | | | | 185 | | | | | 190 | | | |
| tgc | ggc | cgc | ccc | ggc | gtg | ttg | acg | cag | tgc | tcg | gtg | gaa | gag | gcc | acc | 624 |
| Cys | Gly | Arg | Pro | Gly | Val | Leu | Thr | Gln | Cys | Ser | Val | Glu | Glu | Ala | Thr | |
| | | 195 | | | | | 200 | | | | | 205 | | | | |
| gag | ctg | gag | ctg | ggc | atg | cgt | ggc | tta | acc | agc | tac | gcc | gag | acg | gtg | 672 |

```
                                                               -continued

Glu Leu Glu Leu Gly Met Arg Gly Leu Thr Ser Tyr Ala Glu Thr Val
    210                 215                 220 tcg gtc tac ggc acc gaa gcg gta ttt acc gac ggc gat gat acg ccg      720
Ser Val Tyr Gly Thr Glu Ala Val Phe Thr Asp Gly Asp Asp Thr Pro
225                 230                 235                 240 tgg tca aag gcg ttc ctc gcc tcg gcc tac gcc tcc cgc ggg ttg aaa      768
Trp Ser Lys Ala Phe Leu Ala Ser Ala Tyr Ala Ser Arg Gly Leu Lys
                    245                 250                 255 atg cgc tac acc tcc ggc acc gga tcc gaa gcg ctg atg ggc tat tcg      816
Met Arg Tyr Thr Ser Gly Thr Gly Ser Glu Ala Leu Met Gly Tyr Ser
                260                 265                 270 gag agc aag tcg atg ctc tac ctc gaa tcg cgc tgc atc ttc att act      864
Glu Ser Lys Ser Met Leu Tyr Leu Glu Ser Arg Cys Ile Phe Ile Thr
            275                 280                 285 aaa ggc gcc ggg gtt cag gga ctg caa aac ggc gcg gtg agc tgt atc      912
Lys Gly Ala Gly Val Gln Gly Leu Gln Asn Gly Ala Val Ser Cys Ile
        290                 295                 300 ggc atg acc ggc gct gtg ccg tcg ggc att cgg gcg gtg ctg gcg gaa      960
Gly Met Thr Gly Ala Val Pro Ser Gly Ile Arg Ala Val Leu Ala Glu
305                 310                 315                 320 aac ctg atc gcc tct atg ctc gac ctc gaa gtg gcg tcc gcc aac gac     1008
Asn Leu Ile Ala Ser Met Leu Asp Leu Glu Val Ala Ser Ala Asn Asp
                325                 330                 335 cag act ttc tcc cac tcg gat att cgc cgc acc gcg cgc acc ctg atg     1056
Gln Thr Phe Ser His Ser Asp Ile Arg Arg Thr Ala Arg Thr Leu Met
                340                 345                 350 cag atg ctg ccg ggc acc gac ttt att ttc tcc ggc tac agc gcg gtg     1104
Gln Met Leu Pro Gly Thr Asp Phe Ile Phe Ser Gly Tyr Ser Ala Val
            355                 360                 365 ccg aac tac gac aac atg ttc gcc ggc tcg aac ttc gat gcg gaa gat     1152
Pro Asn Tyr Asp Asn Met Phe Ala Gly Ser Asn Phe Asp Ala Glu Asp
        370                 375                 380 ttt gat gat tac aac atc ctg cag cgt gac ctg atg gtt gac ggc ggc     1200
Phe Asp Asp Tyr Asn Ile Leu Gln Arg Asp Leu Met Val Asp Gly Gly
385                 390                 395                 400 ctg cgt ccg gtg acc gag gcg gaa acc att gcc att cgc cag aaa gcg     1248
Leu Arg Pro Val Thr Glu Ala Glu Thr Ile Ala Ile Arg Gln Lys Ala
                405                 410                 415 gcg cgg gcg atc cag gcg gtt ttc cgc gag ctg ggg ctg ccg cca atc     1296
Ala Arg Ala Ile Gln Ala Val Phe Arg Glu Leu Gly Leu Pro Pro Ile
                420                 425                 430 gcc gac gag gag gtg gag gcc gcc acc tac gcg cac ggc agc aac gag     1344
Ala Asp Glu Glu Val Glu Ala Ala Thr Tyr Ala His Gly Ser Asn Glu
            435                 440                 445 atg ccg ccg cgt aac gtg gtg gag gat ctg agt gcg gtg gaa gag atg     1392
Met Pro Pro Arg Asn Val Val Glu Asp Leu Ser Ala Val Glu Glu Met
        450                 455                 460 atg aag cgc aac atc acc ggc ctc gat att gtc ggc gcg ctg agc cgc     1440
Met Lys Arg Asn Ile Thr Gly Leu Asp Ile Val Gly Ala Leu Ser Arg
465                 470                 475                 480 agc ggc ttt gag gat atc gcc agc aat att ctc aat atg ctg cgc cag     1488
Ser Gly Phe Glu Asp Ile Ala Ser Asn Ile Leu Asn Met Leu Arg Gln
                485                 490                 495 cgg gtc acc ggc gat tac ctg cag acc tcg gcc att ctc gat cgg cag     1536
Arg Val Thr Gly Asp Tyr Leu Gln Thr Ser Ala Ile Leu Asp Arg Gln
                500                 505                 510 ttc gag gtg gtg agt gcg gtc aac gac atc aat gac tat cag ggg ccg     1584
Phe Glu Val Val Ser Ala Val Asn Asp Ile Asn Asp Tyr Gln Gly Pro
            515                 520                 525
```

```
ggc acc ggc tat cgc atc tct gcc gaa cgc tgg gcg gag atc aaa aat    1632
Gly Thr Gly Tyr Arg Ile Ser Ala Glu Arg Trp Ala Glu Ile Lys Asn
    530                 535                 540 att ccg ggc gtg gtt cag ccc gac acc att gaa taa                    1668
Ile Pro Gly Val Val Gln Pro Asp Thr Ile Glu
545                 550                 555
```

<210> SEQ ID NO 10
<211> LENGTH: 555
<212> TYPE: PRT
<213> ORGANISM: Klebsiella pneumoniae

<400> SEQUENCE: 10

```
Met Lys Arg Ser Lys Arg Phe Ala Val Leu Ala Gln Arg Pro Val Asn
1               5                   10                  15

Gln Asp Gly Leu Ile Gly Glu Trp Pro Glu Glu Gly Leu Ile Ala Met
            20                  25                  30

Asp Ser Pro Phe Asp Pro Val Ser Ser Val Lys Val Asp Asn Gly Leu
        35                  40                  45

Ile Val Glu Leu Asp Gly Lys Arg Arg Asp Gln Phe Asp Met Ile Asp
    50                  55                  60

Arg Phe Ile Ala Asp Tyr Ala Ile Asn Val Glu Arg Thr Glu Gln Ala
65                  70                  75                  80

Met Arg Leu Glu Ala Val Glu Ile Ala Arg Met Leu Val Asp Ile His
                85                  90                  95

Val Ser Arg Glu Glu Ile Ile Ala Ile Thr Thr Ala Ile Thr Pro Ala
            100                 105                 110

Lys Ala Val Glu Val Met Ala Gln Met Asn Val Val Glu Met Met Met
        115                 120                 125

Ala Leu Gln Lys Met Arg Ala Arg Arg Thr Pro Ser Asn Gln Cys His
    130                 135                 140

Val Thr Asn Leu Lys Asp Asn Pro Val Gln Ile Ala Ala Asp Ala Ala
145                 150                 155                 160

Glu Ala Gly Ile Arg Gly Phe Ser Glu Gln Glu Thr Thr Val Gly Ile
                165                 170                 175

Ala Arg Tyr Ala Pro Phe Asn Ala Leu Ala Leu Leu Val Gly Ser Gln
            180                 185                 190

Cys Gly Arg Pro Gly Val Leu Thr Gln Cys Ser Val Glu Glu Ala Thr
        195                 200                 205

Glu Leu Glu Leu Gly Met Arg Gly Leu Thr Ser Tyr Ala Glu Thr Val
    210                 215                 220

Ser Val Tyr Gly Thr Glu Ala Val Phe Thr Asp Gly Asp Asp Thr Pro
225                 230                 235                 240

Trp Ser Lys Ala Phe Leu Ala Ser Ala Tyr Ala Ser Arg Gly Leu Lys
                245                 250                 255

Met Arg Tyr Thr Ser Gly Thr Gly Ser Glu Ala Leu Met Gly Tyr Ser
            260                 265                 270

Glu Ser Lys Ser Met Leu Tyr Leu Glu Ser Arg Cys Ile Phe Ile Thr
        275                 280                 285

Lys Gly Ala Gly Val Gln Gly Leu Gln Asn Gly Ala Val Ser Cys Ile
    290                 295                 300

Gly Met Thr Gly Ala Val Pro Ser Gly Ile Arg Ala Val Leu Ala Glu
305                 310                 315                 320

Asn Leu Ile Ala Ser Met Leu Asp Leu Glu Val Ala Ser Ala Asn Asp
                325                 330                 335
```

```
Gln Thr Phe Ser His Ser Asp Ile Arg Arg Thr Ala Arg Thr Leu Met
            340                 345                 350

Gln Met Leu Pro Gly Thr Asp Phe Ile Phe Ser Gly Tyr Ser Ala Val
        355                 360                 365

Pro Asn Tyr Asp Asn Met Phe Ala Gly Ser Asn Phe Asp Ala Glu Asp
370                 375                 380

Phe Asp Asp Tyr Asn Ile Leu Gln Arg Asp Leu Met Val Asp Gly Gly
385                 390                 395                 400

Leu Arg Pro Val Thr Glu Ala Glu Thr Ile Ala Ile Arg Gln Lys Ala
                405                 410                 415

Ala Arg Ala Ile Gln Ala Val Phe Arg Glu Leu Gly Leu Pro Pro Ile
            420                 425                 430

Ala Asp Glu Glu Val Glu Ala Ala Thr Tyr Ala His Gly Ser Asn Glu
        435                 440                 445

Met Pro Pro Arg Asn Val Val Glu Asp Leu Ser Ala Val Glu Glu Met
450                 455                 460

Met Lys Arg Asn Ile Thr Gly Leu Asp Ile Val Gly Ala Leu Ser Arg
465                 470                 475                 480

Ser Gly Phe Glu Asp Ile Ala Ser Asn Ile Leu Asn Met Leu Arg Gln
                485                 490                 495

Arg Val Thr Gly Asp Tyr Leu Gln Thr Ser Ala Ile Leu Asp Arg Gln
            500                 505                 510

Phe Glu Val Val Ser Ala Val Asn Asp Ile Asn Asp Tyr Gln Gly Pro
        515                 520                 525

Gly Thr Gly Tyr Arg Ile Ser Ala Glu Arg Trp Ala Glu Ile Lys Asn
530                 535                 540

Ile Pro Gly Val Val Gln Pro Asp Thr Ile Glu
545                 550                 555

<210> SEQ ID NO 11
<211> LENGTH: 585
<212> TYPE: DNA
<213> ORGANISM: Klebsiella pneumoniae
<220> FEATURE:
<221> NAME/KEY: CDS
<222> LOCATION: (1)..(585)

<400> SEQUENCE: 11 gtg caa cag aca acc caa att cag ccc tct ttt acc ctg aaa acc cgc    48
Val Gln Gln Thr Thr Gln Ile Gln Pro Ser Phe Thr Leu Lys Thr Arg
1               5                   10                  15 gag ggc ggg gta gct tct gcc gat gaa cgc gcc gat gaa gtg gtg atc    96
Glu Gly Gly Val Ala Ser Ala Asp Glu Arg Ala Asp Glu Val Val Ile
                20                  25                  30 ggc gtc ggc cct gcc ttc gat aaa cac cag cat cac act ctg atc gat   144
Gly Val Gly Pro Ala Phe Asp Lys His Gln His His Thr Leu Ile Asp
            35                  40                  45 atg ccc cat ggc gcg atc ctc aaa gag ctg att gcc ggg gtg gaa gaa   192
Met Pro His Gly Ala Ile Leu Lys Glu Leu Ile Ala Gly Val Glu Glu
        50                  55                  60 gag ggg ctt cac gcc cgg gtg gtg cgc att ctg cgc acg tcc gac gtc   240
Glu Gly Leu His Ala Arg Val Val Arg Ile Leu Arg Thr Ser Asp Val
65                  70                  75                  80 tcc ttt atg gcc tgg gat gcg gcc aac ctg agc ggc tcg ggg atc ggc   288
Ser Phe Met Ala Trp Asp Ala Ala Asn Leu Ser Gly Ser Gly Ile Gly
                85                  90                  95 atc ggt atc cag tcg aag ggg acc acg gtc atc cat cag cgc gat ctg   336
Ile Gly Ile Gln Ser Lys Gly Thr Thr Val Ile His Gln Arg Asp Leu
```

```
ctg ccg ctc agc aac ctg gag ctg ttc tcc cag gcg ccg ctg ctg acg    384
Leu Pro Leu Ser Asn Leu Glu Leu Phe Ser Gln Ala Pro Leu Leu Thr
        115                 120                 125 ctg gag acc tac cgg cag att ggc aaa aac gct gcg cgc tat gcg cgc    432
Leu Glu Thr Tyr Arg Gln Ile Gly Lys Asn Ala Ala Arg Tyr Ala Arg
130                 135                 140 aaa gag tca cct tcg ccg gtg ccg gtg gtg aac gat cag atg gtg cgg    480
Lys Glu Ser Pro Ser Pro Val Pro Val Val Asn Asp Gln Met Val Arg
145                 150                 155                 160 ccg aaa ttt atg gcc aaa gcc gcg cta ttt cat atc aaa gag acc aaa    528
Pro Lys Phe Met Ala Lys Ala Ala Leu Phe His Ile Lys Glu Thr Lys
                165                 170                 175 cat gtg gtg cag gac gcc gag ccc gtc acc ctg cac atc gac tta gta    576
His Val Val Gln Asp Ala Glu Pro Val Thr Leu His Ile Asp Leu Val
            180                 185                 190 agg gag tga                                                        585
Arg Glu
```

<210> SEQ ID NO 12
<211> LENGTH: 194
<212> TYPE: PRT
<213> ORGANISM: Klebsiella pneumoniae

<400> SEQUENCE: 12

```
Val Gln Gln Thr Thr Gln Ile Gln Pro Ser Phe Thr Leu Lys Thr Arg
1               5                   10                  15

Glu Gly Gly Val Ala Ser Ala Asp Glu Arg Ala Asp Glu Val Val Ile
            20                  25                  30

Gly Val Gly Pro Ala Phe Asp Lys His Gln His His Thr Leu Ile Asp
        35                  40                  45

Met Pro His Gly Ala Ile Leu Lys Glu Leu Ile Ala Gly Val Glu Glu
    50                  55                  60

Glu Gly Leu His Ala Arg Val Val Arg Ile Leu Arg Thr Ser Asp Val
65                  70                  75                  80

Ser Phe Met Ala Trp Asp Ala Ala Asn Leu Ser Gly Ser Gly Ile Gly
                85                  90                  95

Ile Gly Ile Gln Ser Lys Gly Thr Thr Val Ile His Gln Arg Asp Leu
            100                 105                 110

Leu Pro Leu Ser Asn Leu Glu Leu Phe Ser Gln Ala Pro Leu Leu Thr
        115                 120                 125

Leu Glu Thr Tyr Arg Gln Ile Gly Lys Asn Ala Ala Arg Tyr Ala Arg
130                 135                 140

Lys Glu Ser Pro Ser Pro Val Pro Val Val Asn Asp Gln Met Val Arg
145                 150                 155                 160

Pro Lys Phe Met Ala Lys Ala Ala Leu Phe His Ile Lys Glu Thr Lys
                165                 170                 175

His Val Val Gln Asp Ala Glu Pro Val Thr Leu His Ile Asp Leu Val
            180                 185                 190

Arg Glu
```

<210> SEQ ID NO 13
<211> LENGTH: 426
<212> TYPE: DNA
<213> ORGANISM: Klebsiella pneumoniae
<220> FEATURE:
<221> NAME/KEY: CDS
<222> LOCATION: (1)..(426)

```
<400> SEQUENCE: 13 atg agc gag aaa acc atg cgc gtg cag gat tat ccg tta gcc acc cgc    48
Met Ser Glu Lys Thr Met Arg Val Gln Asp Tyr Pro Leu Ala Thr Arg
1               5                   10                  15 tgc ccg gag cat atc ctg acg cct acc ggc aaa cca ttg acc gat att    96
Cys Pro Glu His Ile Leu Thr Pro Thr Gly Lys Pro Leu Thr Asp Ile
            20                  25                  30 acc ctc gag aag gtg ctc tct ggc gag gtg ggc ccg cag gat gtg cgg   144
Thr Leu Glu Lys Val Leu Ser Gly Glu Val Gly Pro Gln Asp Val Arg
        35                  40                  45 atc tcc cgc cag acc ctt gag tac cag gcg cag att gcc gag cag atg   192
Ile Ser Arg Gln Thr Leu Glu Tyr Gln Ala Gln Ile Ala Glu Gln Met
    50                  55                  60 cag cgc cat gcg gtg gcg cgc aat ttc cgc cgc gcg gcg gag ctt atc   240
Gln Arg His Ala Val Ala Arg Asn Phe Arg Arg Ala Ala Glu Leu Ile
65                  70                  75                  80 gcc att cct gac gag cgc att ctg gct atc tat aac gcg ctg cgc ccg   288
Ala Ile Pro Asp Glu Arg Ile Leu Ala Ile Tyr Asn Ala Leu Arg Pro
                85                  90                  95 ttc cgc tcc tcg cag gcg gag ctg ctg gcg atc gcc gac gag ctg gag   336
Phe Arg Ser Ser Gln Ala Glu Leu Leu Ala Ile Ala Asp Glu Leu Glu
            100                 105                 110 cac acc tgg cat gcg aca gtg aat gcc gcc ttt gtc cgg gag tcg gcg   384
His Thr Trp His Ala Thr Val Asn Ala Ala Phe Val Arg Glu Ser Ala
        115                 120                 125 gaa gtg tat cag cag cgg cat aag ctg cgt aaa gga agc taa           426
Glu Val Tyr Gln Gln Arg His Lys Leu Arg Lys Gly Ser
    130                 135                 140

<210> SEQ ID NO 14
<211> LENGTH: 141
<212> TYPE: PRT
<213> ORGANISM: Klebsiella pneumoniae

<400> SEQUENCE: 14

Met Ser Glu Lys Thr Met Arg Val Gln Asp Tyr Pro Leu Ala Thr Arg
1               5                   10                  15

Cys Pro Glu His Ile Leu Thr Pro Thr Gly Lys Pro Leu Thr Asp Ile
            20                  25                  30

Thr Leu Glu Lys Val Leu Ser Gly Glu Val Gly Pro Gln Asp Val Arg
        35                  40                  45

Ile Ser Arg Gln Thr Leu Glu Tyr Gln Ala Gln Ile Ala Glu Gln Met
    50                  55                  60

Gln Arg His Ala Val Ala Arg Asn Phe Arg Arg Ala Ala Glu Leu Ile
65                  70                  75                  80

Ala Ile Pro Asp Glu Arg Ile Leu Ala Ile Tyr Asn Ala Leu Arg Pro
                85                  90                  95

Phe Arg Ser Ser Gln Ala Glu Leu Leu Ala Ile Ala Asp Glu Leu Glu
            100                 105                 110

His Thr Trp His Ala Thr Val Asn Ala Ala Phe Val Arg Glu Ser Ala
        115                 120                 125

Glu Val Tyr Gln Gln Arg His Lys Leu Arg Lys Gly Ser
    130                 135                 140

<210> SEQ ID NO 15
<211> LENGTH: 1539
<212> TYPE: DNA
<213> ORGANISM: Escherichia coli
```

```
<220> FEATURE:
<221> NAME/KEY: CDS
<222> LOCATION: (1)..(1539)

<400> SEQUENCE: 15 atg acc aat aat ccc cct tca gca cag att aag ccc ggc gag tat ggt      48
Met Thr Asn Asn Pro Pro Ser Ala Gln Ile Lys Pro Gly Glu Tyr Gly
1               5                   10                  15 ttc ccc ctc aag tta aaa gcc cgc tat gac aac ttt att ggc ggc gaa      96
Phe Pro Leu Lys Leu Lys Ala Arg Tyr Asp Asn Phe Ile Gly Gly Glu
                20                  25                  30 tgg gta gcc cct gcc gac ggc gag tat tac cag aat ctg acg ccg gtg     144
Trp Val Ala Pro Ala Asp Gly Glu Tyr Tyr Gln Asn Leu Thr Pro Val
            35                  40                  45 acc ggg cag ctg ctg tgc gaa gtg gcg tct tcg ggc aaa cga gac atc     192
Thr Gly Gln Leu Leu Cys Glu Val Ala Ser Ser Gly Lys Arg Asp Ile
        50                  55                  60 gat ctg gcg ctg gat gct gcg cac aaa gtg aaa gat aaa tgg gcg cac     240
Asp Leu Ala Leu Asp Ala Ala His Lys Val Lys Asp Lys Trp Ala His
65                  70                  75                  80 acc tcg gtg cag gat cgt gcg gcg att ctg ttt aag att gcc gat cga     288
Thr Ser Val Gln Asp Arg Ala Ala Ile Leu Phe Lys Ile Ala Asp Arg
                85                  90                  95 atg gaa caa aac ctc gag ctg tta gcg aca gct gaa acc tgg gat aac     336
Met Glu Gln Asn Leu Glu Leu Leu Ala Thr Ala Glu Thr Trp Asp Asn
                100                 105                 110 ggc aaa ccc att cgc gaa acc agt gct gcg gat gta ccg ctg gcg att     384
Gly Lys Pro Ile Arg Glu Thr Ser Ala Ala Asp Val Pro Leu Ala Ile
            115                 120                 125 gac cat ttc cgc tat ttc gcc tcg tgt att cgg gcg cag gaa ggt ggg     432
Asp His Phe Arg Tyr Phe Ala Ser Cys Ile Arg Ala Gln Glu Gly Gly
        130                 135                 140 atc agt gaa gtt gat agc gaa acc gtg gcc tat cat ttc cat gaa ccg     480
Ile Ser Glu Val Asp Ser Glu Thr Val Ala Tyr His Phe His Glu Pro
145                 150                 155                 160 tta ggc gtg gtg ggg cag att atc ccg tgg aac ttc ccg ctg ctg atg     528
Leu Gly Val Val Gly Gln Ile Ile Pro Trp Asn Phe Pro Leu Leu Met
                165                 170                 175 gcg agc tgg aaa atg gct ccc gcg ctg gcg gcg ggc aac tgt gtg gtg     576
Ala Ser Trp Lys Met Ala Pro Ala Leu Ala Ala Gly Asn Cys Val Val
                180                 185                 190 ctg aaa ccc gca cgt ctt acc ccg ctt tct gta ctg ctg cta atg gaa     624
Leu Lys Pro Ala Arg Leu Thr Pro Leu Ser Val Leu Leu Leu Met Glu
            195                 200                 205 att gtc ggt gat tta ctg ccg ccg ggc gtg gtg aac gtg gtc aat ggc     672
Ile Val Gly Asp Leu Leu Pro Pro Gly Val Val Asn Val Val Asn Gly
        210                 215                 220 gca ggt ggg gta att ggc gaa tat ctg gcg acc tcg aaa cgc atc gcc     720
Ala Gly Gly Val Ile Gly Glu Tyr Leu Ala Thr Ser Lys Arg Ile Ala
225                 230                 235                 240 aaa gtg gcg ttt acc ggc tca acg gaa gtg ggc caa caa att atg caa     768
Lys Val Ala Phe Thr Gly Ser Thr Glu Val Gly Gln Gln Ile Met Gln
                245                 250                 255 tac gca acg caa aac att att ccg gtg acg ctg gag ttg ggc ggt aag     816
Tyr Ala Thr Gln Asn Ile Ile Pro Val Thr Leu Glu Leu Gly Gly Lys
                260                 265                 270 tcg cca aat atc ttc ttt gct gat gtg atg gat gaa gaa gat gcc ttt     864
Ser Pro Asn Ile Phe Phe Ala Asp Val Met Asp Glu Glu Asp Ala Phe
            275                 280                 285 ttc gat aaa gcg ctg gaa ggc ttt gca ctg ttt gcc ttt aac cag ggc     912
```

```
Phe Asp Lys Ala Leu Glu Gly Phe Ala Leu Phe Ala Phe Asn Gln Gly
            290                 295                 300 gaa gtt tgc acc tgt ccg agt cgt gct tta gtg cag gaa tct atc tac      960
Glu Val Cys Thr Cys Pro Ser Arg Ala Leu Val Gln Glu Ser Ile Tyr
305                 310                 315                 320 gaa cgc ttt atg gaa cgc gcc atc cgc cgt gtc gaa agc att cgt agc     1008
Glu Arg Phe Met Glu Arg Ala Ile Arg Arg Val Glu Ser Ile Arg Ser
                325                 330                 335 ggt aac ccg ctc gac agc gtg acg caa atg ggc gcg cag gtt tct cac     1056
Gly Asn Pro Leu Asp Ser Val Thr Gln Met Gly Ala Gln Val Ser His
            340                 345                 350 ggg caa ctg gaa acc atc ctc aac tac att gat atc ggt aaa aaa gag     1104
Gly Gln Leu Glu Thr Ile Leu Asn Tyr Ile Asp Ile Gly Lys Lys Glu
        355                 360                 365 ggc gct gac gtg ctc aca ggg cgg cgc aag ctg ctg gaa ggt gaa         1152
Gly Ala Asp Val Leu Thr Gly Arg Arg Lys Leu Leu Glu Gly Glu
    370                 375                 380 ctg aaa gac ggc tac tac ctc gaa ccg acg att ctg ttt ggt cag aac     1200
Leu Lys Asp Gly Tyr Tyr Leu Glu Pro Thr Ile Leu Phe Gly Gln Asn
385                 390                 395                 400 aat atg cgg gtg ttc cag gag gag att ttt ggc ccg gtg ctg gcg gtg     1248
Asn Met Arg Val Phe Gln Glu Glu Ile Phe Gly Pro Val Leu Ala Val
                405                 410                 415 acc acc ttc aaa acg atg gaa gaa gcg ctg gag ctg gcg aac gat acg     1296
Thr Thr Phe Lys Thr Met Glu Glu Ala Leu Glu Leu Ala Asn Asp Thr
            420                 425                 430 caa tat ggc ctg ggc gcg ggc gtc tgg agc cgc aac ggt aat ctg gcc     1344
Gln Tyr Gly Leu Gly Ala Gly Val Trp Ser Arg Asn Gly Asn Leu Ala
        435                 440                 445 tat aag atg ggg cgc ggc ata cag gct ggg cgc gtg tgg acc aac tgt     1392
Tyr Lys Met Gly Arg Gly Ile Gln Ala Gly Arg Val Trp Thr Asn Cys
    450                 455                 460 tat cac gct tac ccg gca cat gcg gcg ttt ggt ggc tac aaa caa tca     1440
Tyr His Ala Tyr Pro Ala His Ala Ala Phe Gly Gly Tyr Lys Gln Ser
465                 470                 475                 480 ggt atc ggt cgc gaa acc cac aag atg atg ctg gag cat tac cag caa     1488
Gly Ile Gly Arg Glu Thr His Lys Met Met Leu Glu His Tyr Gln Gln
                485                 490                 495 acc aag tgc ctg ctg gtg agc tac tcg gat aaa ccg ttg ggg ctg ttc     1536
Thr Lys Cys Leu Leu Val Ser Tyr Ser Asp Lys Pro Leu Gly Leu Phe
            500                 505                 510 tga                                                                  1539

<210> SEQ ID NO 16
<211> LENGTH: 512
<212> TYPE: PRT
<213> ORGANISM: Escherichia coli

<400> SEQUENCE: 16

Met Thr Asn Asn Pro Ser Ala Gln Ile Lys Pro Gly Glu Tyr Gly
1               5                   10                  15

Phe Pro Leu Lys Leu Lys Ala Arg Tyr Asp Asn Phe Ile Gly Gly Glu
                20                  25                  30

Trp Val Ala Pro Ala Asp Gly Glu Tyr Tyr Gln Asn Leu Thr Pro Val
            35                  40                  45

Thr Gly Gln Leu Leu Cys Glu Val Ala Ser Ser Gly Lys Arg Asp Ile
        50                  55                  60

Asp Leu Ala Leu Asp Ala Ala His Lys Val Lys Asp Lys Trp Ala His
65                  70                  75                  80
```

```
Thr Ser Val Gln Asp Arg Ala Ala Ile Leu Phe Lys Ile Ala Asp Arg
                85                  90                  95

Met Glu Gln Asn Leu Glu Leu Leu Ala Thr Ala Glu Thr Trp Asp Asn
            100                 105                 110

Gly Lys Pro Ile Arg Glu Thr Ser Ala Ala Asp Val Pro Leu Ala Ile
        115                 120                 125

Asp His Phe Arg Tyr Phe Ala Ser Cys Ile Arg Ala Gln Glu Gly Gly
130                 135                 140

Ile Ser Glu Val Asp Ser Glu Thr Val Ala Tyr His Phe His Glu Pro
145                 150                 155                 160

Leu Gly Val Val Gly Gln Ile Ile Pro Trp Asn Phe Pro Leu Leu Met
                165                 170                 175

Ala Ser Trp Lys Met Ala Pro Ala Leu Ala Ala Gly Asn Cys Val Val
            180                 185                 190

Leu Lys Pro Ala Arg Leu Thr Pro Leu Ser Val Leu Leu Met Glu
        195                 200                 205

Ile Val Gly Asp Leu Leu Pro Pro Gly Val Val Asn Val Val Asn Gly
    210                 215                 220

Ala Gly Gly Val Ile Gly Glu Tyr Leu Ala Thr Ser Lys Arg Ile Ala
225                 230                 235                 240

Lys Val Ala Phe Thr Gly Ser Thr Glu Val Gly Gln Gln Ile Met Gln
                245                 250                 255

Tyr Ala Thr Gln Asn Ile Ile Pro Val Thr Leu Glu Leu Gly Gly Lys
            260                 265                 270

Ser Pro Asn Ile Phe Phe Ala Asp Val Met Asp Glu Asp Ala Phe
        275                 280                 285

Phe Asp Lys Ala Leu Glu Gly Phe Ala Leu Phe Ala Phe Asn Gln Gly
290                 295                 300

Glu Val Cys Thr Cys Pro Ser Arg Ala Leu Val Gln Glu Ser Ile Tyr
305                 310                 315                 320

Glu Arg Phe Met Glu Arg Ala Ile Arg Arg Val Glu Ser Ile Arg Ser
                325                 330                 335

Gly Asn Pro Leu Asp Ser Val Thr Gln Met Gly Ala Gln Val Ser His
            340                 345                 350

Gly Gln Leu Glu Thr Ile Leu Asn Tyr Ile Asp Ile Gly Lys Lys Glu
        355                 360                 365

Gly Ala Asp Val Leu Thr Gly Gly Arg Arg Lys Leu Leu Glu Gly Glu
370                 375                 380

Leu Lys Asp Gly Tyr Tyr Leu Glu Pro Thr Ile Leu Phe Gly Gln Asn
385                 390                 395                 400

Asn Met Arg Val Phe Gln Glu Glu Ile Phe Gly Pro Val Leu Ala Val
                405                 410                 415

Thr Thr Phe Lys Thr Met Glu Glu Ala Leu Glu Leu Ala Asn Asp Thr
            420                 425                 430

Gln Tyr Gly Leu Gly Ala Gly Val Trp Ser Arg Asn Gly Asn Leu Ala
        435                 440                 445

Tyr Lys Met Gly Arg Gly Ile Gln Ala Gly Arg Val Trp Thr Asn Cys
450                 455                 460

Tyr His Ala Tyr Pro Ala His Ala Ala Phe Gly Gly Tyr Lys Gln Ser
465                 470                 475                 480

Gly Ile Gly Arg Glu Thr His Lys Met Met Leu Glu His Tyr Gln Gln
                485                 490                 495
```

```
                Thr Lys Cys Leu Leu Val Ser Tyr Ser Asp Lys Pro Leu Gly Leu Phe
                                500                 505                 510

<210> SEQ ID NO 17
<211> LENGTH: 1440
<212> TYPE: DNA
<213> ORGANISM: Escherichia coli
<220> FEATURE:
<221> NAME/KEY: CDS
<222> LOCATION: (1)..(1440)

<400> SEQUENCE: 17 atg tca gta ccc gtt caa cat cct atg tat atc gat gga cag ttt gtt       48
Met Ser Val Pro Val Gln His Pro Met Tyr Ile Asp Gly Gln Phe Val
1               5                   10                  15 acc tgg cgt gga gac gca tgg att gat gtg gta aac cct gct aca gag       96
Thr Trp Arg Gly Asp Ala Trp Ile Asp Val Val Asn Pro Ala Thr Glu
                20                  25                  30 gct gtc att tcc cgc ata ccc gat ggt cag gcc gag gat gcc cgt aag      144
Ala Val Ile Ser Arg Ile Pro Asp Gly Gln Ala Glu Asp Ala Arg Lys
            35                  40                  45 gca atc gat gca gca gaa cgt gca caa cca gaa tgg gaa gcg ttg cct      192
Ala Ile Asp Ala Ala Glu Arg Ala Gln Pro Glu Trp Glu Ala Leu Pro
        50                  55                  60 gct att gaa cgc gcc agt tgg ttg cgc aaa atc tcc gcc ggg atc cgc      240
Ala Ile Glu Arg Ala Ser Trp Leu Arg Lys Ile Ser Ala Gly Ile Arg
65                  70                  75                  80 gaa cgc gcc agt gaa atc agt gcg ctg att gtt gaa gaa ggg ggc aag      288
Glu Arg Ala Ser Glu Ile Ser Ala Leu Ile Val Glu Glu Gly Gly Lys
                85                  90                  95 atc cag cag ctg gct gaa gtc gaa gtg gct ttt act gcc gac tat atc      336
Ile Gln Gln Leu Ala Glu Val Glu Val Ala Phe Thr Ala Asp Tyr Ile
                100                 105                 110 gat tac atg gcg gag tgg gca cgg cgt tac gag ggc gag att att caa      384
Asp Tyr Met Ala Glu Trp Ala Arg Arg Tyr Glu Gly Glu Ile Ile Gln
            115                 120                 125 agc gat cgt cca gga gaa aat att ctt ttg ttt aaa cgt gcg ctt ggt      432
Ser Asp Arg Pro Gly Glu Asn Ile Leu Leu Phe Lys Arg Ala Leu Gly
        130                 135                 140 gtg act acc ggc att ctg ccg tgg aac ttc ccg ttc ttc ctc att gcc      480
Val Thr Thr Gly Ile Leu Pro Trp Asn Phe Pro Phe Phe Leu Ile Ala
145                 150                 155                 160 cgc aaa atg gct ccc gct ctt ttg acc ggt aat acc atc gtc att aaa      528
Arg Lys Met Ala Pro Ala Leu Leu Thr Gly Asn Thr Ile Val Ile Lys
                165                 170                 175 cct agt gaa ttt acg cca aac aat gcg att gca ttc gcc aaa atc gtc      576
Pro Ser Glu Phe Thr Pro Asn Asn Ala Ile Ala Phe Ala Lys Ile Val
                180                 185                 190 gat gaa ata ggc ctt ccg cgc ggc gtg ttt aac ctt gta ctg ggg cgt      624
Asp Glu Ile Gly Leu Pro Arg Gly Val Phe Asn Leu Val Leu Gly Arg
            195                 200                 205 ggt gaa acc gtt ggg caa gaa ctg gcg ggt aac cca aag gtc gca atg      672
Gly Glu Thr Val Gly Gln Glu Leu Ala Gly Asn Pro Lys Val Ala Met
        210                 215                 220 gtc agt atg aca ggc agc gtc tct gca ggt gag aag atc atg gcg act      720
Val Ser Met Thr Gly Ser Val Ser Ala Gly Glu Lys Ile Met Ala Thr
225                 230                 235                 240 gcg gcg aaa aac atc acc aaa gtg tgt ctg gaa ttg ggg ggt aaa gca      768
Ala Ala Lys Asn Ile Thr Lys Val Cys Leu Glu Leu Gly Gly Lys Ala
                245                 250                 255 cca gct atc gta atg gac gat gcc gat ctt gaa ctg gca gtc aaa gcc      816
Pro Ala Ile Val Met Asp Asp Ala Asp Leu Glu Leu Ala Val Lys Ala
```

```
Pro Ala Ile Val Met Asp Asp Ala Asp Leu Glu Leu Ala Val Lys Ala
                260                 265                 270 atc gtt gat tca cgc gtc att aat agt ggg caa gtg tgt aac tgt gca    864
Ile Val Asp Ser Arg Val Ile Asn Ser Gly Gln Val Cys Asn Cys Ala
            275                 280                 285 gaa cgt gtt tat gta cag aaa ggc att tat gat cag ttc gtc aat cgg    912
Glu Arg Val Tyr Val Gln Lys Gly Ile Tyr Asp Gln Phe Val Asn Arg
    290                 295                 300 ctg ggt gaa gcg atg cag gcg gtt caa ttt ggt aac ccc gct gaa cgc    960
Leu Gly Glu Ala Met Gln Ala Val Gln Phe Gly Asn Pro Ala Glu Arg
305                 310                 315                 320 aac gac att gcg atg ggg ccg ttg att aac gcc gcg gcg ctg gaa agg   1008
Asn Asp Ile Ala Met Gly Pro Leu Ile Asn Ala Ala Ala Leu Glu Arg
                325                 330                 335 gtc gag caa aaa gtg gcg cgc gca gta gaa gaa ggg gcg aga gtg gcg   1056
Val Glu Gln Lys Val Ala Arg Ala Val Glu Glu Gly Ala Arg Val Ala
            340                 345                 350 ttc ggt ggc aaa gcg gta gag ggg aaa gga tat tat tat ccg ccg aca   1104
Phe Gly Gly Lys Ala Val Glu Gly Lys Gly Tyr Tyr Tyr Pro Pro Thr
    355                 360                 365 ttg ctg ctg gat gtt cgc cag gaa atg tcg att atg cat gag gaa acc   1152
Leu Leu Leu Asp Val Arg Gln Glu Met Ser Ile Met His Glu Glu Thr
370                 375                 380 ttt ggc ccg gtg ctg cca gtt gtc gca ttt gac acg ctg gaa gat gct   1200
Phe Gly Pro Val Leu Pro Val Val Ala Phe Asp Thr Leu Glu Asp Ala
385                 390                 395                 400 atc tca atg gct aat gac agt gat tac ggc ctg acc tca tca atc tat   1248
Ile Ser Met Ala Asn Asp Ser Asp Tyr Gly Leu Thr Ser Ser Ile Tyr
                405                 410                 415 acc caa aat ctg aac gtc gcg atg aaa gcc att aaa ggg ctg aag ttt   1296
Thr Gln Asn Leu Asn Val Ala Met Lys Ala Ile Lys Gly Leu Lys Phe
            420                 425                 430 ggt gaa act tac atc aac cgt gaa aac ttc gaa gct atg caa ggc ttc   1344
Gly Glu Thr Tyr Ile Asn Arg Glu Asn Phe Glu Ala Met Gln Gly Phe
    435                 440                 445 cac gcc gga tgg cgt aaa tcc ggt att ggc ggc gca gat ggt aaa cat   1392
His Ala Gly Trp Arg Lys Ser Gly Ile Gly Gly Ala Asp Gly Lys His
450                 455                 460 ggc ttg cat gaa tat ctg cag acc cag gtg gtt tat tta cag tct taa   1440
Gly Leu His Glu Tyr Leu Gln Thr Gln Val Val Tyr Leu Gln Ser
465                 470                 475

<210> SEQ ID NO 18
<211> LENGTH: 479
<212> TYPE: PRT
<213> ORGANISM: Escherichia coli

<400> SEQUENCE: 18

Met Ser Val Pro Val Gln His Pro Met Tyr Ile Asp Gly Gln Phe Val
1               5                   10                  15

Thr Trp Arg Gly Asp Ala Trp Ile Asp Val Val Asn Pro Ala Thr Glu
            20                  25                  30

Ala Val Ile Ser Arg Ile Pro Asp Gly Gln Ala Glu Asp Ala Arg Lys
        35                  40                  45

Ala Ile Asp Ala Ala Glu Arg Ala Gln Pro Glu Trp Glu Ala Leu Pro
    50                  55                  60

Ala Ile Glu Arg Ala Ser Trp Leu Arg Lys Ile Ser Ala Gly Ile Arg
65                  70                  75                  80

Glu Arg Ala Ser Glu Ile Ser Ala Leu Ile Val Glu Gly Gly Gly Lys
```

```
                        85                  90                  95
Ile Gln Gln Leu Ala Glu Val Glu Val Ala Phe Thr Ala Asp Tyr Ile
                100                 105                 110

Asp Tyr Met Ala Glu Trp Ala Arg Arg Tyr Glu Gly Glu Ile Ile Gln
            115                 120                 125

Ser Asp Arg Pro Gly Glu Asn Ile Leu Leu Phe Lys Arg Ala Leu Gly
        130                 135                 140

Val Thr Gly Ile Leu Pro Trp Asn Phe Pro Phe Phe Leu Ile Ala
145                 150                 155                 160

Arg Lys Met Ala Pro Ala Leu Leu Thr Gly Asn Thr Ile Val Ile Lys
                165                 170                 175

Pro Ser Glu Phe Thr Pro Asn Asn Ala Ile Ala Phe Ala Lys Ile Val
                180                 185                 190

Asp Glu Ile Gly Leu Pro Arg Gly Val Phe Asn Leu Val Leu Gly Arg
                195                 200                 205

Gly Glu Thr Val Gly Gln Glu Leu Ala Gly Asn Pro Lys Val Ala Met
            210                 215                 220

Val Ser Met Thr Gly Ser Val Ser Ala Gly Glu Lys Ile Met Ala Thr
225                 230                 235                 240

Ala Ala Lys Asn Ile Thr Lys Val Cys Leu Glu Leu Gly Gly Lys Ala
                245                 250                 255

Pro Ala Ile Val Met Asp Asp Ala Asp Leu Glu Leu Ala Val Lys Ala
                260                 265                 270

Ile Val Asp Ser Arg Val Ile Asn Ser Gly Gln Val Cys Asn Cys Ala
                275                 280                 285

Glu Arg Val Tyr Val Gln Lys Gly Ile Tyr Asp Gln Phe Val Asn Arg
        290                 295                 300

Leu Gly Glu Ala Met Gln Ala Val Gln Phe Gly Asn Pro Ala Glu Arg
305                 310                 315                 320

Asn Asp Ile Ala Met Gly Pro Leu Ile Asn Ala Ala Leu Glu Arg
                325                 330                 335

Val Glu Gln Lys Val Ala Arg Ala Val Glu Glu Gly Ala Arg Val Ala
                340                 345                 350

Phe Gly Gly Lys Ala Val Glu Gly Lys Gly Tyr Tyr Pro Pro Thr
        355                 360                 365

Leu Leu Leu Asp Val Arg Gln Glu Met Ser Ile Met His Glu Thr
        370                 375                 380

Phe Gly Pro Val Leu Pro Val Val Ala Phe Asp Thr Leu Glu Asp Ala
385                 390                 395                 400

Ile Ser Met Ala Asn Asp Ser Asp Tyr Gly Leu Thr Ser Ser Ile Tyr
                405                 410                 415

Thr Gln Asn Leu Asn Val Ala Met Lys Ala Ile Lys Gly Leu Lys Phe
                420                 425                 430

Gly Glu Thr Tyr Ile Asn Arg Glu Asn Phe Glu Ala Met Gln Gly Phe
        435                 440                 445

His Ala Gly Trp Arg Lys Ser Gly Ile Gly Gly Ala Asp Gly Lys His
        450                 455                 460

Gly Leu His Glu Tyr Leu Gln Thr Gln Val Val Tyr Leu Gln Ser
465                 470                 475

<210> SEQ ID NO 19
<211> LENGTH: 1488
<212> TYPE: DNA
<213> ORGANISM: Escherichia coli
```

<220> FEATURE:
<221> NAME/KEY: CDS
<222> LOCATION: (1)..(1488)

<400> SEQUENCE: 19

```
atg aat ttt cat cat ctg gct tac tgg cag gat aaa gcg tta agt ctc      48
Met Asn Phe His His Leu Ala Tyr Trp Gln Asp Lys Ala Leu Ser Leu
1               5                   10                  15 gcc att gaa aac cgc tta ttt att aac ggt gaa tat act gct gcg gcg      96
Ala Ile Glu Asn Arg Leu Phe Ile Asn Gly Glu Tyr Thr Ala Ala Ala
            20                  25                  30 gaa aat gaa acc ttt gaa acc gtt gat ccg gtc acc cag gca ccg ctg     144
Glu Asn Glu Thr Phe Glu Thr Val Asp Pro Val Thr Gln Ala Pro Leu
        35                  40                  45 gcg aaa att gcc cgc ggc aag agc gtc gat atc gac cgt gcg atg agc     192
Ala Lys Ile Ala Arg Gly Lys Ser Val Asp Ile Asp Arg Ala Met Ser
    50                  55                  60 gca gca cgc ggc gta ttt gaa cgc ggc gac tgg tca ctc tct tct ccg     240
Ala Ala Arg Gly Val Phe Glu Arg Gly Asp Trp Ser Leu Ser Ser Pro
65                  70                  75                  80 gct aaa cgt aaa gcg gta ctg aat aaa ctc gcc gat tta atg gaa gcc     288
Ala Lys Arg Lys Ala Val Leu Asn Lys Leu Ala Asp Leu Met Glu Ala
                85                  90                  95 cac gcc gaa gag ctg gca ctg ctg gaa act ctc gac acc ggc aaa ccg     336
His Ala Glu Glu Leu Ala Leu Leu Glu Thr Leu Asp Thr Gly Lys Pro
            100                 105                 110 att cgt cac agt ctg cgt gat gat att ccc ggc gcg gcg cgc gcc att     384
Ile Arg His Ser Leu Arg Asp Asp Ile Pro Gly Ala Ala Arg Ala Ile
        115                 120                 125 cgc tgg tac gcc gaa gcg atc gac aaa gtg tat ggc gaa gtg gcg acc     432
Arg Trp Tyr Ala Glu Ala Ile Asp Lys Val Tyr Gly Glu Val Ala Thr
    130                 135                 140 acc agt agc cat gag ctg gcg atg atc gtg cgt gaa ccg gtc ggc gtg     480
Thr Ser Ser His Glu Leu Ala Met Ile Val Arg Glu Pro Val Gly Val
145                 150                 155                 160 att gcc gcc atc gtg ccg tgg aac ttc ccg ctg ttg ctg act tgc tgg     528
Ile Ala Ala Ile Val Pro Trp Asn Phe Pro Leu Leu Leu Thr Cys Trp
                165                 170                 175 aaa ctc ggc ccg gcg ctg gcg gcg gga aac agc gtg att cta aaa ccg     576
Lys Leu Gly Pro Ala Leu Ala Ala Gly Asn Ser Val Ile Leu Lys Pro
            180                 185                 190 tct gaa aaa tca ccg ctc agt gcg att cgt ctc gcg ggg ctg gcg aaa     624
Ser Glu Lys Ser Pro Leu Ser Ala Ile Arg Leu Ala Gly Leu Ala Lys
        195                 200                 205 gaa gca ggc ttg ccg gat ggt gtg ttg aac gtg gtg acg ggt ttt ggt     672
Glu Ala Gly Leu Pro Asp Gly Val Leu Asn Val Val Thr Gly Phe Gly
    210                 215                 220 cat gaa gcc ggg cag gcg ctg tcg cgt cat aac gat atc gac gcc att     720
His Glu Ala Gly Gln Ala Leu Ser Arg His Asn Asp Ile Asp Ala Ile
225                 230                 235                 240 gcc ttt acc ggt tca acc cgt acc ggg aaa cag ctg ctg aaa gat gcg     768
Ala Phe Thr Gly Ser Thr Arg Thr Gly Lys Gln Leu Leu Lys Asp Ala
                245                 250                 255 ggc gac agc aac atg aaa cgc gtc tgg ctg gaa gcg ggc ggc aaa agc     816
Gly Asp Ser Asn Met Lys Arg Val Trp Leu Glu Ala Gly Gly Lys Ser
            260                 265                 270 gcc aac atc gtt ttc gct gac tgc ccg gat ttg caa cag gcg gca agc     864
Ala Asn Ile Val Phe Ala Asp Cys Pro Asp Leu Gln Gln Ala Ala Ser
        275                 280                 285 gcc acc gca gca ggc att ttc tac aac cag gga cag gtg tgc atc gcc     912
```

```
Ala Thr Ala Ala Gly Ile Phe Tyr Asn Gln Gly Gln Val Cys Ile Ala
    290                 295                 300 gga acg cgc ctg ttg ctg gaa gag agc atc gcc gat gaa ttc tta gcc      960
Gly Thr Arg Leu Leu Leu Glu Glu Ser Ile Ala Asp Glu Phe Leu Ala
305                 310                 315                 320 ctg tta aaa cag cag gcg caa aac tgg cag ccg ggc cat cca ctt gat     1008
Leu Leu Lys Gln Gln Ala Gln Asn Trp Gln Pro Gly His Pro Leu Asp
                325                 330                 335 ccc gca acc acc atg ggc acc tta atc gac tgc gcc cac gcc gac tcg     1056
Pro Ala Thr Thr Met Gly Thr Leu Ile Asp Cys Ala His Ala Asp Ser
        340                 345                 350 gtc cat agc ttt att cgg gaa ggc gaa agc aaa ggg caa ctg ttg ttg     1104
Val His Ser Phe Ile Arg Glu Gly Glu Ser Lys Gly Gln Leu Leu Leu
            355                 360                 365 gat ggc cgt aac gcc ggg ctg gct gcc gcc atc ggc ccg acc atc ttt     1152
Asp Gly Arg Asn Ala Gly Leu Ala Ala Ala Ile Gly Pro Thr Ile Phe
                370                 375                 380 gtg gat gtg gac ccg aat gcg tcc tta agt cgc gaa gag att ttc ggt     1200
Val Asp Val Asp Pro Asn Ala Ser Leu Ser Arg Glu Glu Ile Phe Gly
385                 390                 395                 400 ccg gtg ctg gtg gtc acg cgt ttc aca tca gaa gaa cag gcg cta cag     1248
Pro Val Leu Val Val Thr Arg Phe Thr Ser Glu Glu Gln Ala Leu Gln
                405                 410                 415 ctt gcc aac gac agc cag tac ggc ctt ggc gcg gcg gta tgg acg cgc     1296
Leu Ala Asn Asp Ser Gln Tyr Gly Leu Gly Ala Ala Val Trp Thr Arg
        420                 425                 430 gac ctc tcc cgc gcg cac cgc atg agc cga cgc ctg aaa gcc ggt tcc     1344
Asp Leu Ser Arg Ala His Arg Met Ser Arg Arg Leu Lys Ala Gly Ser
            435                 440                 445 gtc ttc gtc aat aac tac aac gac ggc gat atg acc gtg ccg ttt ggc     1392
Val Phe Val Asn Asn Tyr Asn Asp Gly Asp Met Thr Val Pro Phe Gly
                450                 455                 460 ggc tat aag cag agc ggc aac ggt cgc gac aaa tcc ctg cat gcc ctt     1440
Gly Tyr Lys Gln Ser Gly Asn Gly Arg Asp Lys Ser Leu His Ala Leu
465                 470                 475                 480 gaa aaa ttc act gaa ctg aaa acc atc tgg ata agc ctg gag gcc tga     1488
Glu Lys Phe Thr Glu Leu Lys Thr Ile Trp Ile Ser Leu Glu Ala
                485                 490                 495

<210> SEQ ID NO 20
<211> LENGTH: 495
<212> TYPE: PRT
<213> ORGANISM: Escherichia coli

<400> SEQUENCE: 20

Met Asn Phe His His Leu Ala Tyr Trp Gln Asp Lys Ala Leu Ser Leu
1               5                   10                  15

Ala Ile Glu Asn Arg Leu Phe Ile Asn Gly Glu Tyr Thr Ala Ala Ala
            20                  25                  30

Glu Asn Glu Thr Phe Glu Thr Val Asp Pro Val Thr Gln Ala Pro Leu
        35                  40                  45

Ala Lys Ile Ala Arg Gly Lys Ser Val Asp Ile Asp Arg Ala Met Ser
    50                  55                  60

Ala Ala Arg Gly Val Phe Glu Arg Gly Asp Trp Ser Leu Ser Ser Pro
65                  70                  75                  80

Ala Lys Arg Lys Ala Val Leu Asn Lys Leu Ala Asp Leu Met Glu Ala
                85                  90                  95

His Ala Glu Glu Leu Ala Leu Leu Glu Thr Leu Asp Thr Gly Lys Pro
            100                 105                 110
```

Ile Arg His Ser Leu Arg Asp Asp Ile Pro Gly Ala Ala Arg Ala Ile
            115                 120                 125

Arg Trp Tyr Ala Glu Ala Ile Asp Lys Val Tyr Gly Glu Val Ala Thr
130                 135                 140

Thr Ser Ser His Glu Leu Ala Met Ile Val Arg Glu Pro Val Gly Val
145                 150                 155                 160

Ile Ala Ala Ile Val Pro Trp Asn Phe Pro Leu Leu Leu Thr Cys Trp
                165                 170                 175

Lys Leu Gly Pro Ala Leu Ala Ala Gly Asn Ser Val Ile Leu Lys Pro
            180                 185                 190

Ser Glu Lys Ser Pro Leu Ser Ala Ile Arg Leu Ala Gly Leu Ala Lys
        195                 200                 205

Glu Ala Gly Leu Pro Asp Gly Val Leu Asn Val Thr Gly Phe Gly
210                 215                 220

His Glu Ala Gly Gln Ala Leu Ser Arg His Asn Asp Ile Asp Ala Ile
225                 230                 235                 240

Ala Phe Thr Gly Ser Thr Arg Thr Gly Lys Gln Leu Leu Lys Asp Ala
                245                 250                 255

Gly Asp Ser Asn Met Lys Arg Val Trp Leu Glu Ala Gly Gly Lys Ser
            260                 265                 270

Ala Asn Ile Val Phe Ala Asp Cys Pro Asp Leu Gln Gln Ala Ala Ser
        275                 280                 285

Ala Thr Ala Ala Gly Ile Phe Tyr Asn Gln Gly Gln Val Cys Ile Ala
290                 295                 300

Gly Thr Arg Leu Leu Leu Glu Glu Ser Ile Ala Asp Glu Phe Leu Ala
305                 310                 315                 320

Leu Leu Lys Gln Gln Ala Gln Asn Trp Gln Pro Gly His Pro Leu Asp
                325                 330                 335

Pro Ala Thr Thr Met Gly Thr Leu Ile Asp Cys Ala His Ala Asp Ser
            340                 345                 350

Val His Ser Phe Ile Arg Glu Gly Glu Ser Lys Gly Gln Leu Leu Leu
        355                 360                 365

Asp Gly Arg Asn Ala Gly Leu Ala Ala Ala Ile Gly Pro Thr Ile Phe
370                 375                 380

Val Asp Val Asp Pro Asn Ala Ser Leu Ser Arg Glu Glu Ile Phe Gly
385                 390                 395                 400

Pro Val Leu Val Val Thr Arg Phe Thr Ser Glu Glu Gln Ala Leu Gln
                405                 410                 415

Leu Ala Asn Asp Ser Gln Tyr Gly Leu Gly Ala Ala Val Trp Thr Arg
            420                 425                 430

Asp Leu Ser Arg Ala His Arg Met Ser Arg Arg Leu Lys Ala Gly Ser
        435                 440                 445

Val Phe Val Asn Asn Tyr Asn Asp Gly Asp Met Thr Val Pro Phe Gly
450                 455                 460

Gly Tyr Lys Gln Ser Gly Asn Gly Arg Asp Lys Ser Leu His Ala Leu
465                 470                 475                 480

Glu Lys Phe Thr Glu Leu Lys Thr Ile Trp Ile Ser Leu Glu Ala
                485                 490                 495

<210> SEQ ID NO 21
<211> LENGTH: 1395
<212> TYPE: DNA
<213> ORGANISM: Escherichia coli

<400> SEQUENCE: 21

```
atgcctgacg ctaaaaaaca ggggcggtca acaaggcaa tgacgttttt cgtctgcttc      60
cttgccgctc tggcgggatt actctttggc ctggatatcg gtgtaattgc tggcgcactg     120
ccgtttattg cagatgaatt ccagattact cgcacacgc aagaatgggt cgtaagctcc     180
atgatgttcg gtgcggcagt cggtgcggtg ggcagcggct ggctctcctt taaactcggg     240
cgcaaaaaga gcctgatgat cggcgcaatt ttgtttgttg ccggttcgct gttctctgcg     300
gctgcgccaa acgttgaagt actgattctt tcccgcgttc tactggggct ggcggtgggt     360
gtggcctctt ataccgcacc gctgtacctc tctgaaattg cgccggaaaa aattcgtggc     420
agtatgatct cgatgtatca gttgatgatc actatcggga tcctcggtgc ttatcttcct     480
gataccgcct tcagctacac cggtgcatgg cgctggatgc tgggtgtgat tatcatcccg     540
gcaatttttgc tgctgattgg tgtcttcttc ctgccagaca gcccacgttg gtttgccgcc     600
aaacgccgtt ttgttgatgc cgaacgcgtg ctgctacgcc tgcgtgacac cagcgcggaa     660
gcgaaacgcg aactggatga aatccgtgaa agtttgcagg ttaaacagag tggctgggcg     720
ctgtttaaag agaacagcaa cttccgccgc gcggtgttcc ttggcgtact gttgcaggta     780
atgcagcaat tcaccgggat gaacgtcatc atgtattacg cgccgaaaat cttcgaactg     840
gcgggttata ccaacactac cgagcaaatg tggggaccg tgattgtcgg cctgaccaac     900
gtacttgcca cctttatcgc aatcggcctt gttgaccgct gggacgtaa ccaacgcta     960
acgctgggct tcctggtgat ggctgctggc atgggcgtac tcggtacaat gatgcatatc    1020
ggtattcact ctccgtcggc gcagtatttc gccatcgcca tgctgctgat gtttattgtc    1080
ggttttgcca tgagtgccgg tccgctgatt tgggtactgt gctccgaaat tcagccgctg    1140
aaaggccgcg attttggcat cacctgctcc actgccacca actggattgc caacatgatc    1200
gttggcgcaa cgttcctgac catgctcaac acgctgggta acgccaacac cttctgggtg    1260
tatgcggctc tgaacgtact gtttatcctg ctgacattgt ggctggtacc ggaaaccaaa    1320
cacgtttcgc tggaacatat tgaacgtaat ctgatgaaag gtcgtaaact gcgcgaaata    1380
ggcgctcacg attaa                                                     1395
```

<210> SEQ ID NO 22
<211> LENGTH: 464
<212> TYPE: PRT
<213> ORGANISM: Escherichia coli

<400> SEQUENCE: 22

```
Met Pro Asp Ala Lys Lys Gln Gly Arg Ser Asn Lys Ala Met Thr Phe
1               5                   10                  15

Phe Val Cys Phe Leu Ala Ala Leu Ala Gly Leu Leu Phe Gly Leu Asp
            20                  25                  30

Ile Gly Val Ile Ala Gly Ala Leu Pro Phe Ile Ala Asp Glu Phe Gln
        35                  40                  45

Ile Thr Ser His Thr Gln Glu Trp Val Val Ser Met Met Phe Gly
    50                  55                  60

Ala Ala Val Gly Ala Val Gly Ser Gly Trp Leu Ser Phe Lys Leu Gly
65                  70                  75                  80

Arg Lys Lys Ser Leu Met Ile Gly Ala Ile Leu Phe Val Ala Gly Ser
                85                  90                  95

Leu Phe Ser Ala Ala Ala Pro Asn Val Glu Val Leu Ile Leu Ser Arg
            100                 105                 110
```

```
Val Leu Leu Gly Leu Ala Val Gly Val Ala Ser Tyr Thr Ala Pro Leu
            115                 120                 125
Tyr Leu Ser Glu Ile Ala Pro Glu Lys Ile Arg Gly Ser Met Ile Ser
130                 135                 140
Met Tyr Gln Leu Met Ile Thr Ile Gly Ile Leu Gly Ala Tyr Leu Ser
145                 150                 155                 160
Asp Thr Ala Phe Ser Tyr Thr Gly Ala Trp Arg Trp Met Leu Gly Val
                165                 170                 175
Ile Ile Ile Pro Ala Ile Leu Leu Ile Gly Val Phe Phe Leu Pro
                180                 185                 190
Asp Ser Pro Arg Trp Phe Ala Ala Lys Arg Arg Phe Val Asp Ala Glu
                195                 200                 205
Arg Val Leu Leu Arg Leu Arg Asp Thr Ser Ala Glu Ala Lys Arg Glu
210                 215                 220
Leu Asp Glu Ile Arg Glu Ser Leu Gln Val Lys Gln Ser Gly Trp Ala
225                 230                 235                 240
Leu Phe Lys Glu Asn Ser Asn Phe Arg Arg Ala Val Phe Leu Gly Val
                245                 250                 255
Leu Leu Gln Val Met Gln Gln Phe Thr Gly Met Asn Val Ile Met Tyr
                260                 265                 270
Tyr Ala Pro Lys Ile Phe Glu Leu Ala Gly Tyr Thr Asn Thr Thr Glu
                275                 280                 285
Gln Met Trp Gly Thr Val Ile Val Gly Leu Thr Asn Val Leu Ala Thr
                290                 295                 300
Phe Ile Ala Ile Gly Leu Val Asp Arg Trp Gly Arg Lys Pro Thr Leu
305                 310                 315                 320
Thr Leu Gly Phe Leu Val Met Ala Ala Gly Met Gly Val Leu Gly Thr
                325                 330                 335
Met Met His Ile Gly Ile His Ser Pro Ser Ala Gln Tyr Phe Ala Ile
                340                 345                 350
Ala Met Leu Leu Met Phe Ile Val Gly Phe Ala Met Ser Ala Gly Pro
                355                 360                 365
Leu Ile Trp Val Leu Cys Ser Glu Ile Gln Pro Leu Lys Gly Arg Asp
370                 375                 380
Phe Gly Ile Thr Cys Ser Thr Ala Thr Asn Trp Ile Ala Asn Met Ile
385                 390                 395                 400
Val Gly Ala Thr Phe Leu Thr Met Leu Asn Thr Leu Gly Asn Ala Asn
                405                 410                 415
Thr Phe Trp Val Tyr Ala Ala Leu Asn Val Leu Phe Ile Leu Leu Thr
                420                 425                 430
Leu Trp Leu Val Pro Glu Thr Lys His Val Ser Leu Glu His Ile Glu
                435                 440                 445
Arg Asn Leu Met Lys Gly Arg Lys Leu Arg Glu Ile Gly Ala His Asp
450                 455                 460

<210> SEQ ID NO 23
<211> LENGTH: 1248
<212> TYPE: DNA
<213> ORGANISM: Escherichia coli

<400> SEQUENCE: 23
atggcactga atattccatt cagaaatgcg tactatcgtt ttgcatccag ttactcattt     60
ctctttttta tttcctggtc gctgtggtgg tcgttatacg ctatttggct gaaaggacat    120
ctaggattaa caggacgga attaggtaca ctttattcgg tcaaccagtt taccagcatt    180
```

```
ctatttatga tgttctacgg catcgttcag gataaactcg gtctgaagaa accgctcatc    240
tggtgtatga gtttcattct ggtcttgacc ggaccgttta tgatttacgt ttatgaaccg    300
ttactgcaaa gcaattttc tgtaggtcta attctggggg cgctcttttt tggcctgggg    360
tatctggcgg gatgcggttt gcttgacagc ttcaccgaaa aaatggcgcg aaattttcat    420
ttcgaatatg aacagcgcg cgcctgggga tcttttggct atgctattgg cgcgttcttt    480
gccggtatat tttttagtat cagtccccat atcaacttct ggttggtctc gctatttggc    540
gctgtattta tgatgatcaa catgcgtttt aaagataagg atcaccagtg catagcggcg    600
gatgcgggag gggtaaaaaa agaggatttt atcgcagttt tcaaggatcg aaacttctgg    660
gttttcgtca tatttattgt ggggacgtgg tctttctata acatttttga tcaacaactc    720
tttcctgtct tttatgcagg tttattcgaa tcacacgatg taggaacgcg cctgtatggt    780
tatctcaact cattccaggt ggtactcgaa gcgctgtgca tggcgattat tcctttcttt    840
gtgaatcggg tagggccaaa aaatgcatta cttatcggtg ttgtgattat ggcgttgcgt    900 atccttttcct gcgcgttgtt cgttaacccc tggattattt cattagtgaa gctgttacat    960
gccattgagg ttccactttg tgtcatatcc gtcttcaaat acagcgtggc aaactttgat   1020
aagcgcctgt cgtcgacgat ctttctgatt ggttttcaaa ttgccagttc gcttgggatt   1080
gtgctgcttt caacgccgac tgggatactc tttgaccacg caggctacca gacagttttc   1140
ttcgcaattt cgggtattgt ctgcctgatg ttgctatttg gcattttctt cctgagtaaa   1200
aaacgcgagc aaatagttat ggaaacgcct gtaccttcag caatatag                1248
```

<210> SEQ ID NO 24
<211> LENGTH: 415
<212> TYPE: PRT
<213> ORGANISM: Escherichia coli

<400> SEQUENCE: 24

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
```

```
                180             185             190
Lys Asp His Gln Cys Ile Ala Ala Asp Ala Gly Gly Val Lys Lys Glu
            195                 200                 205

Asp Phe Ile Ala Val Phe Lys Asp Arg Asn Phe Trp Val Phe Val Ile
        210                 215                 220

Phe Ile Val Gly Thr Trp Ser Phe Tyr Asn Ile Phe Asp Gln Gln Leu
225                 230                 235                 240

Phe Pro Val Phe Tyr Ala Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335

Ala Asn Phe Asp Lys Arg Leu Ser Ser Thr Ile Phe Leu Ile Gly Phe
            340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415

<210> SEQ ID NO 25
<211> LENGTH: 1248
<212> TYPE: DNA
<213> ORGANISM: Escherichia coli

<400> SEQUENCE: 25
atggcactga atattccatt cagaaatgcg tactatcgtt ttgcatccag ttactcattt     60 ctcttttta tttcctggtc gctgtggtgg tcgttatacg ctatttggct gaaaggacat    120
ctagggttga cagggacgga attaggtaca ctttattcgg tcaaccagtt taccagcatt    180
ctatttatga tgttctacgg catcgttcag gataaactcg gtctgaagaa accgctcatc    240
tggtgtatga gtttcatcct ggtcttgacc ggaccgttta tgatttacgt ttatgaaccg    300
ttactgcaaa gcaattttc tgtaggtcta attctggggg cgctattttt tggcttgggg    360
tatctggcgg gatgcggttt gcttgatagc ttcaccgaaa aaatggcgcg aaattttcat    420
ttcgaatatg aacagcgcg cgcctgggga tcttttggct atgctattgg cgcgttcttc    480
gccggcatat tttttagtat cagtccccat atcaacttct ggttggtctc gctatttggc    540
gctgtattta tgatgatcaa catgcgtttt aaagataagg atcaccagtg cgtagcggca    600
gatgcgggag gggtaaaaaa agaggatttt atcgcagttt tcaaggatcg aaacttctgg    660
gttttcgtca tatttattgt ggggacgtgg tcttctata acattttga tcaacaactt    720 tttcctgtct tttattcagg tttattcgaa tcacacgatg taggaacgcg cctgtatggt    780
tatctcaact cattccaggt ggtactcgaa gcgctgtgca tggcgattat tccttttctt    840
```

```
gtgaatcggg tagggccaaa aaatgcatta cttatcggag ttgtgattat ggcgttgcgt    900
atcctttcct gcgcgctgtt cgttaacccc tggattattt cattagtgaa gttgttacat    960
gccattgagg ttccactttg tgtcatatcc gtcttcaaat acagcgtggc aaactttgat   1020
aagcgcctgt cgtcgacgat ctttctgatt ggttttcaaa ttgccagttc gcttgggatt   1080
gtgctgcttt caacgccgac tgggatactc tttgaccacg caggctacca gacagttttc   1140
ttcgcaattt cgggtattgt ctgcctgatg ttgctatttg gcattttctt cttgagtaaa   1200
aaacgcgagc aaatagttat ggaaacgcct gtaccttcag caatatag                1248
```

<210> SEQ ID NO 26
<211> LENGTH: 415
<212> TYPE: PRT
<213> ORGANISM: Escherichia coli

<400> SEQUENCE: 26

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Val Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ser Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
    290                 295                 300
```

```
Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
            325                 330                 335

Ala Asn Phe Asp Lys Arg Leu Ser Ser Thr Ile Phe Leu Ile Gly Phe
        340                 345                 350

Gln Ile Ala Ser Ser Leu Gly Ile Val Leu Leu Ser Thr Pro Thr Gly
    355                 360                 365

Ile Leu Phe Asp His Ala Gly Tyr Gln Thr Val Phe Ala Ile Ser
370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
            405                 410                 415
```

<210> SEQ ID NO 27
<211> LENGTH: 1434
<212> TYPE: DNA
<213> ORGANISM: Escherichia coli

<400> SEQUENCE: 27

```
atgacgcaat ctcgattgca tgcggcgcaa aacgcactag caaaacttca cgagcgccga      60
ggtaacactt tctatcccca ttttcacctc gcgcctcctg ccgggtggat gaacgatcca     120
aacggcctga tctggtttaa cgatcgttat cacgcgtttt atcaacatca cccgatgagc     180
gaacactggg ggccaatgca ctggggacat gccaccagcg acgatatgat ccactggcag     240
catgagccta ttgcgctagc gccaggagac gagaatgaca agacgggtg tttttcaggt     300
agtgctgtcg atgacaatgg tgtcctctca cttatctaca ccggacacgt ctggctcgat     360
ggtgcaggta atgacgatgc aattcgcgaa gtacaatgtc tggctaccag tcgggatggt     420
attcatttcg agaaacaggg tgtgatcctc actccaccag aaggcatcat gcacttccgc     480
gatcctaaag tgtggcgtga agccgacaca tggtggatgg tagtcggggc gaaagaccca     540
ggcaacacgg ggcagatcct gctttatcgc ggcagttcat tgcgtgaatg actttcgat     600
cgcgtactgg cccacgctga tgcgggtgaa agctatatgt gggaatgtcc ggacttttc     660
agccttggcg atcagcatta tctgatgttt tccccgcagg gaatgaatgc cgagggatac     720
agttatcgaa atcgctttca agtggcgta ataccggaa tgtggtcgcc aggacgactt     780
tttgcacaat cccgggcattt tactgaactt gataacgggc atgacttta tgcaccacaa     840
agctttgtag cgaaggatgg tcggcgtatt gttatcggct ggatggatat gtgggaatcg     900
ccaatgccct caaaacgtga aggctgggca ggctgcatga cgctggcgcg cgagctatca     960
gagagcaatg gcaaactcct acaacgcccg gtacacgaag ctgagtcgtt acgccagcag    1020
catcaatcta tctctccccg cacaatcagc aataaatatg ttttgcagga aaacgcgcaa    1080
gcagttgaga ttcagttgca gtgggcgctg aagaacagtg atgccgaaca ttacggatta    1140
cagctcggcg ctggaatgcg gctgtatatt gataaccaat ctgagcgact tgttttgtgg    1200
cggtattacc cacacgagaa tttagatggc taccgtagta ttcccctccc gcagggtgac    1260
atgctcgccc taaggatatt tatcgataca tcatccgtgg aagtatttat taacgacggg    1320
gaggcggtga tgagtagccg aatatatccg cagccagaag aacgggaact gtcgctctat    1380
gcctcccacg gagtggctgt gctgcaacat ggagcactct ggcaactggg ttaa           1434
```

```
<210> SEQ ID NO 28
<211> LENGTH: 477
<212> TYPE: PRT
<213> ORGANISM: Escherichia coli

<400> SEQUENCE: 28
```

| Met | Thr | Gln | Ser | Arg | Leu | His | Ala | Ala | Gln | Asn | Ala | Leu | Ala | Lys | Leu |
|---|---|---|---|---|---|---|---|---|---|---|---|---|---|---|---|
| 1 | | | | 5 | | | | | 10 | | | | | 15 | |

| His | Glu | Arg | Arg | Gly | Asn | Thr | Phe | Tyr | Pro | His | Phe | His | Leu | Ala | Pro |
|---|---|---|---|---|---|---|---|---|---|---|---|---|---|---|---|
| | | | 20 | | | | | 25 | | | | | 30 | | |

| Pro | Ala | Gly | Trp | Met | Asn | Asp | Pro | Asn | Gly | Leu | Ile | Trp | Phe | Asn | Asp |
|---|---|---|---|---|---|---|---|---|---|---|---|---|---|---|---|
| | | 35 | | | | | 40 | | | | | 45 | | | |

| Arg | Tyr | His | Ala | Phe | Tyr | Gln | His | His | Pro | Met | Ser | Glu | His | Trp | Gly |
|---|---|---|---|---|---|---|---|---|---|---|---|---|---|---|---|
| | 50 | | | | | 55 | | | | | 60 | | | | |

| Pro | Met | His | Trp | Gly | His | Ala | Thr | Ser | Asp | Asp | Met | Ile | His | Trp | Gln |
|---|---|---|---|---|---|---|---|---|---|---|---|---|---|---|---|
| 65 | | | | | 70 | | | | | 75 | | | | | 80 |

| His | Glu | Pro | Ile | Ala | Leu | Ala | Pro | Gly | Asp | Glu | Asn | Asp | Lys | Asp | Gly |
|---|---|---|---|---|---|---|---|---|---|---|---|---|---|---|---|
| | | | | 85 | | | | | 90 | | | | | 95 | |

| Cys | Phe | Ser | Gly | Ser | Ala | Val | Asp | Asp | Asn | Gly | Val | Leu | Ser | Leu | Ile |
|---|---|---|---|---|---|---|---|---|---|---|---|---|---|---|---|
| | | | 100 | | | | | 105 | | | | | 110 | | |

| Tyr | Thr | Gly | His | Val | Trp | Leu | Asp | Gly | Ala | Gly | Asn | Asp | Ala | Ile |
|---|---|---|---|---|---|---|---|---|---|---|---|---|---|---|
| | | 115 | | | | | 120 | | | | | 125 | | |

| Arg | Glu | Val | Gln | Cys | Leu | Ala | Thr | Ser | Arg | Asp | Gly | Ile | His | Phe | Glu |
|---|---|---|---|---|---|---|---|---|---|---|---|---|---|---|---|
| | 130 | | | | | 135 | | | | | 140 | | | | |

| Lys | Gln | Gly | Val | Ile | Leu | Thr | Pro | Pro | Glu | Gly | Ile | Met | His | Phe | Arg |
|---|---|---|---|---|---|---|---|---|---|---|---|---|---|---|---|
| 145 | | | | | 150 | | | | | 155 | | | | | 160 |

| Asp | Pro | Lys | Val | Trp | Arg | Glu | Ala | Asp | Thr | Trp | Trp | Met | Val | Val | Gly |
|---|---|---|---|---|---|---|---|---|---|---|---|---|---|---|---|
| | | | | 165 | | | | | 170 | | | | | 175 | |

| Ala | Lys | Asp | Pro | Gly | Asn | Thr | Gly | Gln | Ile | Leu | Leu | Tyr | Arg | Gly | Ser |
|---|---|---|---|---|---|---|---|---|---|---|---|---|---|---|---|
| | | | 180 | | | | | 185 | | | | | 190 | | |

| Ser | Leu | Arg | Glu | Trp | Thr | Phe | Asp | Arg | Val | Leu | Ala | His | Ala | Asp | Ala |
|---|---|---|---|---|---|---|---|---|---|---|---|---|---|---|---|
| | | 195 | | | | | 200 | | | | | 205 | | | |

| Gly | Glu | Ser | Tyr | Met | Trp | Glu | Cys | Pro | Asp | Phe | Phe | Ser | Leu | Gly | Asp |
|---|---|---|---|---|---|---|---|---|---|---|---|---|---|---|---|
| 210 | | | | | 215 | | | | | 220 | | | | | |

| Gln | His | Tyr | Leu | Met | Phe | Ser | Pro | Gln | Gly | Met | Asn | Ala | Glu | Gly | Tyr |
|---|---|---|---|---|---|---|---|---|---|---|---|---|---|---|---|
| 225 | | | | | 230 | | | | | 235 | | | | | 240 |

| Ser | Tyr | Arg | Asn | Arg | Phe | Gln | Ser | Gly | Val | Ile | Pro | Gly | Met | Trp | Ser |
|---|---|---|---|---|---|---|---|---|---|---|---|---|---|---|---|
| | | | | 245 | | | | | 250 | | | | | 255 | |

| Pro | Gly | Arg | Leu | Phe | Ala | Gln | Ser | Gly | His | Phe | Thr | Glu | Leu | Asp | Asn |
|---|---|---|---|---|---|---|---|---|---|---|---|---|---|---|---|
| | | | 260 | | | | | 265 | | | | | 270 | | |

| Gly | His | Asp | Phe | Tyr | Ala | Pro | Gln | Ser | Phe | Val | Ala | Lys | Asp | Gly | Arg |
|---|---|---|---|---|---|---|---|---|---|---|---|---|---|---|---|
| | | 275 | | | | | 280 | | | | | 285 | | | |

| Arg | Ile | Val | Ile | Gly | Trp | Met | Asp | Met | Trp | Glu | Ser | Pro | Met | Pro | Ser |
|---|---|---|---|---|---|---|---|---|---|---|---|---|---|---|---|
| | 290 | | | | | 295 | | | | | 300 | | | | |

| Lys | Arg | Glu | Gly | Trp | Ala | Gly | Cys | Met | Thr | Leu | Ala | Arg | Glu | Leu | Ser |
|---|---|---|---|---|---|---|---|---|---|---|---|---|---|---|---|
| 305 | | | | | 310 | | | | | 315 | | | | | 320 |

| Glu | Ser | Asn | Gly | Lys | Leu | Leu | Gln | Arg | Pro | Val | His | Glu | Ala | Glu | Ser |
|---|---|---|---|---|---|---|---|---|---|---|---|---|---|---|---|
| | | | | 325 | | | | | 330 | | | | | 335 | |

| Leu | Arg | Gln | Gln | His | Gln | Ser | Ile | Ser | Pro | Arg | Thr | Ile | Ser | Asn | Lys |
|---|---|---|---|---|---|---|---|---|---|---|---|---|---|---|---|
| | | | 340 | | | | | 345 | | | | | 350 | | |

| Tyr | Val | Leu | Gln | Glu | Asn | Ala | Gln | Ala | Val | Glu | Ile | Gln | Leu | Gln | Trp |
|---|---|---|---|---|---|---|---|---|---|---|---|---|---|---|---|
| | | 355 | | | | | 360 | | | | | 365 | | | |

| Ala | Leu | Lys | Asn | Ser | Asp | Ala | Glu | His | Tyr | Gly | Leu | Gln | Leu | Gly | Ala |
|---|---|---|---|---|---|---|---|---|---|---|---|---|---|---|---|
| 370 | | | | | 375 | | | | | 380 | | | | | |

Gly Met Arg Leu Tyr Ile Asp Asn Gln Ser Glu Arg Leu Val Leu Trp
385                 390                 395                 400

Arg Tyr Tyr Pro His Glu Asn Leu Asp Gly Tyr Arg Ser Ile Pro Leu
            405                 410                 415

Pro Gln Gly Asp Met Leu Ala Leu Arg Ile Phe Ile Asp Thr Ser Ser
        420                 425                 430

Val Glu Val Phe Ile Asn Asp Gly Glu Ala Val Met Ser Ser Arg Ile
        435                 440                 445

Tyr Pro Gln Pro Glu Glu Arg Glu Leu Ser Leu Tyr Ala Ser His Gly
    450                 455                 460

Val Ala Val Leu Gln His Gly Ala Leu Trp Gln Leu Gly
465                 470                 475

<210> SEQ ID NO 29
<211> LENGTH: 1434
<212> TYPE: DNA
<213> ORGANISM: Escherichia coli

<400> SEQUENCE: 29

```
atgacgcaat ctcgattgca tgcggcgcaa acgccctag caaaacttca tgagcaccgg      60
ggtaacactt tctatcccca ttttcacctc gcgcctcctg ccgggtggat gaacgatcca     120
aacggcctga tctggtttaa cgatcgttat cacgcgtttt atcaacatca tccgatgagc     180
gaacactggg ggccaatgca ctggggacat gccaccagcg acgatatgat ccactggcag     240
catgagccta ttgcgctagc gccaggagac gataatgaca agacgggtg tttttcaggt      300
agtgctgtcg atgacaatgg tgtcctctca cttatctaca ccgacacgt ctggctcgat      360
ggtgcaggta atgacgatgc aattcgcgaa gtacaatgtc tggctaccag tcgggatggt     420
attcatttcg agaaacaggg tgtgatcctc actccaccag aaggaatcat gcacttccgc     480
gatcctaaag tgtggcgtga agccgacaca tggtggatgg tagtcggggc gaaagatcca     540
ggcaacacgg ggcagatcct gctttatcgc ggcagttcgt tgcgtgaatg gaccttcgat     600
cgcgtactgg cccacgctga tgcgggtgaa gctatatgt gggaatgtcc ggacttttc     660
agccttggcg atcagcatta tctgatgttt tccccgcagg gaatgaatgc cgagggatac     720
agttaccgaa atcgctttca aagtggcgta ataccggaa tgtggtcgcc aggacgactt     780
tttgcacaat ccgggcattt tactgaactt gataacgggc atgacttta tgcaccacaa     840
agcttttag cgaaggatgg tcggcgtatt gttatcggct ggatggatat gtgggaatcg     900
ccaatgccct caaaacgtga aggatgggca ggctgcatga cgctggcgcg cgagctatca     960
gagagcaatg gcaaacttct acaacgcccg gtacacgaag ctgagtcgtt acgccagcag    1020
catcaatctg tctctccccg cacaatcagc aataaatatg ttttgcagga aaacgcgcaa    1080
gcagttgaga ttcagttgca gtgggcgctg aagaacagtg atgccgaaca ttacggatta    1140
cagctcggca ctggaatgcg gctgtatatt gataaccaat ctgagcgact tgttttgtgg    1200
cggtattacc cacacgagaa tttagacggc taccgtagta ttccctccc gcagcgtgac    1260
acgctcgccc taaggatatt tatcgataca tcatccgtgg aagtatttat aacgacggg    1320
gaagcggtga tgagtagtcg aatctatccg cagccagaag aacgggaact gtcgctttat    1380
gcctcccacg gagtggctgt gctgcaacat ggagcactct ggctactggg ttaa          1434
```

<210> SEQ ID NO 30
<211> LENGTH: 477
<212> TYPE: PRT
<213> ORGANISM: Escherichia coli

<400> SEQUENCE: 30

```
Met Thr Gln Ser Arg Leu His Ala Ala Gln Asn Ala Leu Ala Lys Leu
1               5                   10                  15

His Glu His Arg Gly Asn Thr Phe Tyr Pro His Phe His Leu Ala Pro
            20                  25                  30

Pro Ala Gly Trp Met Asn Asp Pro Asn Gly Leu Ile Trp Phe Asn Asp
        35                  40                  45

Arg Tyr His Ala Phe Tyr Gln His His Pro Met Ser Glu His Trp Gly
    50                  55                  60

Pro Met His Trp Gly His Ala Thr Ser Asp Asp Met Ile His Trp Gln
65                  70                  75                  80

His Glu Pro Ile Ala Leu Ala Pro Gly Asp Asp Asn Asp Lys Asp Gly
                85                  90                  95

Cys Phe Ser Gly Ser Ala Val Asp Asp Asn Gly Val Leu Ser Leu Ile
            100                 105                 110

Tyr Thr Gly His Val Trp Leu Asp Gly Ala Gly Asn Asp Asp Ala Ile
        115                 120                 125

Arg Glu Val Gln Cys Leu Ala Thr Ser Arg Asp Gly Ile His Phe Glu
    130                 135                 140

Lys Gln Gly Val Ile Leu Thr Pro Pro Glu Gly Ile Met His Phe Arg
145                 150                 155                 160

Asp Pro Lys Val Trp Arg Glu Ala Asp Thr Trp Trp Met Val Val Gly
                165                 170                 175

Ala Lys Asp Pro Gly Asn Thr Gly Gln Ile Leu Leu Tyr Arg Gly Ser
            180                 185                 190

Ser Leu Arg Glu Trp Thr Phe Asp Arg Val Leu Ala His Ala Asp Ala
        195                 200                 205

Gly Glu Ser Tyr Met Trp Glu Cys Pro Asp Phe Phe Ser Leu Gly Asp
    210                 215                 220

Gln His Tyr Leu Met Phe Ser Pro Gln Gly Met Asn Ala Glu Gly Tyr
225                 230                 235                 240

Ser Tyr Arg Asn Arg Phe Gln Ser Gly Val Ile Pro Gly Met Trp Ser
                245                 250                 255

Pro Gly Arg Leu Phe Ala Gln Ser Gly His Phe Thr Glu Leu Asp Asn
            260                 265                 270

Gly His Asp Phe Tyr Ala Pro Gln Ser Phe Leu Ala Lys Asp Gly Arg
        275                 280                 285

Arg Ile Val Ile Gly Trp Met Asp Met Trp Glu Ser Pro Met Pro Ser
    290                 295                 300

Lys Arg Glu Gly Trp Ala Gly Cys Met Thr Leu Ala Arg Glu Leu Ser
305                 310                 315                 320

Glu Ser Asn Gly Lys Leu Leu Gln Arg Pro Val His Glu Ala Glu Ser
                325                 330                 335

Leu Arg Gln Gln His Gln Ser Val Ser Pro Arg Thr Ile Ser Asn Lys
            340                 345                 350

Tyr Val Leu Gln Glu Asn Ala Gln Ala Val Glu Ile Gln Leu Gln Trp
        355                 360                 365

Ala Leu Lys Asn Ser Asp Ala Glu His Tyr Gly Leu Gln Leu Gly Thr
    370                 375                 380

Gly Met Arg Leu Tyr Ile Asp Asn Gln Ser Glu Arg Leu Val Leu Trp
385                 390                 395                 400

Arg Tyr Tyr Pro His Glu Asn Leu Asp Gly Tyr Arg Ser Ile Pro Leu
```

```
            405                 410                 415
Pro Gln Arg Asp Thr Leu Ala Leu Arg Ile Phe Ile Asp Thr Ser Ser
                420                 425                 430

Val Glu Val Phe Ile Asn Asp Gly Glu Ala Val Met Ser Ser Arg Ile
            435                 440                 445

Tyr Pro Gln Pro Glu Glu Arg Glu Leu Ser Leu Tyr Ala Ser His Gly
        450                 455                 460

Val Ala Val Leu Gln His Gly Ala Leu Trp Leu Leu Gly
465                 470                 475

<210> SEQ ID NO 31
<211> LENGTH: 1599
<212> TYPE: DNA
<213> ORGANISM: Bifidobacterium lactis

<400> SEQUENCE: 31
atggcaaccc ttcccaccaa tattcccgcc aacggcattc tgaccccga cccggcgctc      60 gaccctgtgc tcacgccgat ctcggaccat gccgagcagc tgtcactcgc cgaagcaggc     120
gtgtcggcac tggaaaccac cgcaacgac cgctggtacc cgaagttcca cattgcctcc     180
aatggcgggt ggatcaacga cccgaacggc ctgtgccgct acaacggacg ctggcacgtg    240
ttctaccagc tgcatcccca cggcacacag tggggcccga tgcattgggg ccacgtctcc    300
tccgacaaca tggtcgactg gcaccgcgaa cccatcgcct tcgcgccaag cctcgaacag    360
gaacgccacg gtgtgttctc cggttccgcc gtgattggcg acgacggcaa gccgtggatt    420
ttctacaccg gccaccgctg gccaacggc aaggacaaca ccggaggcga ctggcaggtg    480
cagatgctcg ccaagccgaa cgacgacgaa ctgaagacct tcacgaagga gggcatgatc    540
atcgactgcc ccaccgacga ggtggaccac cacttccgcg acccgaaggt gtggaagacc    600
ggtgacacct ggtatatgac cttcggtgtc tcgtcgaagg agcatcgtgg ccagatgtgg    660
ctgtacacgt cgagcgacat ggtgcactgg agcttcgatc gggtgctgtt cgagcatccg    720
gatccgaacg tgttcatgct tgaatgcccc gatttcttcc cgatccgcga tgcgcggggc    780
aacgagaaat gggtcatcgg cttctccgcg atgggtgcca agccaaatgg cttcatgaac    840
cgcaacgtga acaatgccgg ctacatggtg ggcacatgga agccaggcga gagcttcaag    900
ccggagaccg agttccgcct gtgggacgaa ggccataact tctatgcacc acagtcgttc    960
aacaccgaag gcgccagat catgtacggc tggatgagcc cgttcgtcgc ccccatcccg   1020
atggaggagg acggctggtg cggcaacctc acccctcccc gcgagatcac gctgggcgat   1080
gacggtgacc tggtcaccgc ccccaccatc gaaatggagg ggctgcgcga ataccata   1140 ggcttcgact cgctcgacct tggtacgaac cagacctcca cgatcctcga cgatgacggc   1200
ggcgccctgg aaatcgagat gagactcgat ctgaacaaaa ccaccgccga acgcgccgga   1260
ctgcatgtgc atgccacaag cgacggccac tacacggcaa tcgtattcga cgcgcagatc   1320
ggcggcgtcg tcatcgaccg gcagaacgtg gcgaacggag acaaaggcta ccgggtggcc   1380
aagctcagcg acaccgagct cgcagccgat acgcttgact tgcgcgtgtt catcgaccgc   1440
ggatgcgtcg aggtctacgt cgacggcggc aagcatgcga tgagctcgta ctcgttccct   1500
ggcgatggcg cacgcgccgt cgaactcgtg agcgaatccg gcaccacgca catcgacacc   1560
ctcaccatgc actcgctcaa gtccatcgga ctcgagtga                         1599

<210> SEQ ID NO 32
<211> LENGTH: 532
```

<212> TYPE: PRT
<213> ORGANISM: Bifidobacterium lactis

<400> SEQUENCE: 32

```
Met Ala Thr Leu Pro Thr Asn Ile Pro Ala Asn Gly Ile Leu Thr Pro
1               5                   10                  15

Asp Pro Ala Leu Asp Pro Val Leu Thr Pro Ile Ser Asp His Ala Glu
            20                  25                  30

Gln Leu Ser Leu Ala Glu Ala Gly Val Ser Ala Leu Glu Thr Thr Arg
        35                  40                  45

Asn Asp Arg Trp Tyr Pro Lys Phe His Ile Ala Ser Asn Gly Gly Trp
50                  55                  60

Ile Asn Asp Pro Asn Gly Leu Cys Arg Tyr Asn Gly Arg Trp His Val
65                  70                  75                  80

Phe Tyr Gln Leu His Pro His Gly Thr Gln Trp Gly Pro Met His Trp
                85                  90                  95

Gly His Val Ser Ser Asp Asn Met Val Asp Trp His Arg Glu Pro Ile
            100                 105                 110

Ala Phe Ala Pro Ser Leu Glu Gln Glu Arg His Gly Val Phe Ser Gly
        115                 120                 125

Ser Ala Val Ile Gly Asp Asp Gly Lys Pro Trp Ile Phe Tyr Thr Gly
130                 135                 140

His Arg Trp Ala Asn Gly Lys Asp Asn Thr Gly Gly Asp Trp Gln Val
145                 150                 155                 160

Gln Met Leu Ala Lys Pro Asn Asp Asp Glu Leu Lys Thr Phe Thr Lys
                165                 170                 175

Glu Gly Met Ile Ile Asp Cys Pro Thr Asp Glu Val Asp His His Phe
            180                 185                 190

Arg Asp Pro Lys Val Trp Lys Thr Gly Asp Thr Trp Tyr Met Thr Phe
        195                 200                 205

Gly Val Ser Ser Lys Glu His Arg Gly Gln Met Trp Leu Tyr Thr Ser
210                 215                 220

Ser Asp Met Val His Trp Ser Phe Asp Arg Val Leu Phe Glu His Pro
225                 230                 235                 240

Asp Pro Asn Val Phe Met Leu Glu Cys Pro Asp Phe Phe Pro Ile Arg
                245                 250                 255

Asp Ala Arg Gly Asn Glu Lys Trp Val Ile Gly Phe Ser Ala Met Gly
            260                 265                 270

Ala Lys Pro Asn Gly Phe Met Asn Arg Asn Val Asn Asn Ala Gly Tyr
        275                 280                 285

Met Val Gly Thr Trp Lys Pro Gly Glu Ser Phe Lys Pro Glu Thr Glu
290                 295                 300

Phe Arg Leu Trp Asp Glu Gly His Asn Phe Tyr Ala Pro Gln Ser Phe
305                 310                 315                 320

Asn Thr Glu Gly Arg Gln Ile Met Tyr Gly Trp Met Ser Pro Phe Val
                325                 330                 335

Ala Pro Ile Pro Met Glu Glu Asp Gly Trp Cys Gly Asn Leu Thr Leu
            340                 345                 350

Pro Arg Glu Ile Thr Leu Gly Asp Asp Gly Asp Leu Val Thr Ala Pro
        355                 360                 365

Thr Ile Glu Met Glu Gly Leu Arg Glu Asn Thr Ile Gly Phe Asp Ser
370                 375                 380

Leu Asp Leu Gly Thr Asn Gln Ser Thr Ile Leu Asp Asp Gly
385                 390                 395                 400
```

```
Gly Ala Leu Glu Ile Glu Met Arg Leu Asp Leu Asn Lys Thr Thr Ala
            405                 410                 415
Glu Arg Ala Gly Leu His Val His Ala Thr Ser Asp Gly His Tyr Thr
        420                 425                 430
Ala Ile Val Phe Asp Ala Gln Ile Gly Gly Val Val Ile Asp Arg Gln
            435                 440                 445
Asn Val Ala Asn Gly Asp Lys Gly Tyr Arg Val Ala Lys Leu Ser Asp
        450                 455                 460
Thr Glu Leu Ala Ala Asp Thr Leu Asp Leu Arg Val Phe Ile Asp Arg
465                 470                 475                 480
Gly Cys Val Glu Val Tyr Val Asp Gly Lys His Ala Met Ser Ser
                485                 490                 495
Tyr Ser Phe Pro Gly Asp Gly Ala Arg Ala Val Glu Leu Val Ser Glu
            500                 505                 510
Ser Gly Thr Thr His Ile Asp Thr Leu Thr Met His Ser Leu Lys Ser
        515                 520                 525
Ile Gly Leu Glu
    530

<210> SEQ ID NO 33
<211> LENGTH: 1599
<212> TYPE: DNA
<213> ORGANISM: Saccharomyces cerevisiae

<400> SEQUENCE: 33
atgcttttgc aagctttcct tttcctttg gctggttttg cagccaaaat atctgcatca      60
atgacaaacg aaactagcga tagacctttg gtccacttca cacccaacaa gggctggatg     120
aatgacccaa tgggttgtg gtacgatgaa aaagatgcca atggcatct gtactttcaa      180 tacaacccaa tgacaccgt atggggtacg ccattgtttt ggggccatgc tacttccgat     240
gatttgacta attgggaaga tcaacccatt gctatcgctc caagcgtaa cgattcaggt     300 gctttctctg ctccatggt ggttgattac aacaacacga gtgggttttt caatgatact    360
attgatccaa gacaaagatg cgttgcgatt tggacttata cactcctga agtgaagag     420 caatacatta gctattctct tgatggtggt tacactttta ctgaatacca aagaaccct    480 gttttagctg ccaactccac tcaattcaga gatccaaagg tgttctggta tgaaccttct    540
caaaaatgga ttatgacggc tgccaaatca aagactaca aaattgaaat ttactcctct     600
gatgacttga gtcctggaa gctagaatct gcatttgcca atgaaggttt cttaggctac    660
caatacgaat gtccaggttt gattgaagtc ccaactgagc aagatccttc caaatcttat    720
tgggtcatgt ttatttctat caacccaggt gcacctgctg gcggttcctt caaccaatat    780
tttgttggat ccttcaatgg tactcatttt gaagcgtttg acaatcaatc tagagtggta    840
gattttggta aggactacta tgccttgcaa actttcttca cactgaccc aacctacggt    900 tcagcattag gtattgcctg gcttcaaac tgggagtaca gtgcctttgt cccaactaac    960
ccatggagat catccatgtc tttggtccgc aagttttctt tgaacactga atatcaagct   1020
aatccagaga ctgaattgat caatttgaaa gccgaaccaa tattgaacat agtaatgct    1080 ggtccctggt ctcgttttgc tactaacaca actctaacta aggccaattc ttacaatgtc   1140
gatttgagca actcgactgg taccctagag tttgagttgg tttacgctgt taacaccaca    1200
caaaccatat ccaaatccgt ctttgccgac ttatcactt ggttcaaggg tttagaagat    1260
cctgaagaat atttgagaat gggttttgaa gtcagtgctt cttccttctt tttggaccgt   1320
```

-continued

```
ggtaactcta aggtcaagtt tgtcaaggag aacccatatt tcacaaacag aatgtctgtc    1380
aacaaccaac cattcaagtc tgagaacgac ctaagttact ataaagtgta cggcctactg    1440
gatcaaaaca tcttggaatt gtacttcaac gatggagatg tggtttctac aaatacctac    1500
ttcatgacca ccggtaacgc tctaggatct gtgaacatga ccactggtgt cgataatttg    1560
ttctacattg acaagttcca agtaagggaa gtaaaatag                           1599
```

<210> SEQ ID NO 34
<211> LENGTH: 532
<212> TYPE: PRT
<213> ORGANISM: Saccharomyces cerevisiae

<400> SEQUENCE: 34

```
Met Leu Leu Gln Ala Phe Leu Phe Leu Leu Ala Gly Phe Ala Ala Lys
1               5                   10                  15

Ile Ser Ala Ser Met Thr Asn Glu Thr Ser Asp Arg Pro Leu Val His
                20                  25                  30

Phe Thr Pro Asn Lys Gly Trp Met Asn Asp Pro Asn Gly Leu Trp Tyr
            35                  40                  45

Asp Glu Lys Asp Ala Lys Trp His Leu Tyr Phe Gln Tyr Asn Pro Asn
        50                  55                  60

Asp Thr Val Trp Gly Thr Pro Leu Phe Trp Gly His Ala Thr Ser Asp
65                  70                  75                  80

Asp Leu Thr Asn Trp Glu Asp Gln Pro Ile Ala Ile Ala Pro Lys Arg
                85                  90                  95

Asn Asp Ser Gly Ala Phe Ser Gly Ser Met Val Val Asp Tyr Asn Asn
            100                 105                 110

Thr Ser Gly Phe Phe Asn Asp Thr Ile Asp Pro Arg Gln Arg Cys Val
        115                 120                 125

Ala Ile Trp Thr Tyr Asn Thr Pro Glu Ser Glu Glu Gln Tyr Ile Ser
    130                 135                 140

Tyr Ser Leu Asp Gly Gly Tyr Thr Phe Thr Glu Tyr Gln Lys Asn Pro
145                 150                 155                 160

Val Leu Ala Ala Asn Ser Thr Gln Phe Arg Asp Pro Lys Val Phe Trp
                165                 170                 175

Tyr Glu Pro Ser Gln Lys Trp Ile Met Thr Ala Ala Lys Ser Gln Asp
            180                 185                 190

Tyr Lys Ile Glu Ile Tyr Ser Ser Asp Asp Leu Lys Ser Trp Lys Leu
        195                 200                 205

Glu Ser Ala Phe Ala Asn Glu Gly Phe Leu Gly Tyr Gln Tyr Glu Cys
    210                 215                 220

Pro Gly Leu Ile Glu Val Pro Thr Glu Gln Asp Pro Ser Lys Ser Tyr
225                 230                 235                 240

Trp Val Met Phe Ile Ser Ile Asn Pro Gly Ala Pro Ala Gly Gly Ser
                245                 250                 255

Phe Asn Gln Tyr Phe Val Gly Ser Phe Asn Gly Thr His Phe Glu Ala
            260                 265                 270

Phe Asp Asn Gln Ser Arg Val Val Asp Phe Gly Lys Asp Tyr Tyr Ala
        275                 280                 285

Leu Gln Thr Phe Phe Asn Thr Asp Pro Thr Tyr Gly Ser Ala Leu Gly
    290                 295                 300

Ile Ala Trp Ala Ser Asn Trp Glu Tyr Ser Ala Phe Val Pro Thr Asn
305                 310                 315                 320
```

```
Pro Trp Arg Ser Ser Met Ser Leu Val Arg Lys Phe Ser Leu Asn Thr
            325                 330                 335
Glu Tyr Gln Ala Asn Pro Glu Thr Glu Leu Ile Asn Leu Lys Ala Glu
            340                 345                 350
Pro Ile Leu Asn Ile Ser Asn Ala Gly Pro Trp Ser Arg Phe Ala Thr
            355                 360                 365
Asn Thr Thr Leu Thr Lys Ala Asn Ser Tyr Asn Val Asp Leu Ser Asn
            370                 375                 380
Ser Thr Gly Thr Leu Glu Phe Glu Leu Val Tyr Ala Val Asn Thr Thr
385                 390                 395                 400
Gln Thr Ile Ser Lys Ser Val Phe Ala Asp Leu Ser Leu Trp Phe Lys
            405                 410                 415
Gly Leu Glu Asp Pro Glu Glu Tyr Leu Arg Met Gly Phe Glu Val Ser
            420                 425                 430
Ala Ser Ser Phe Phe Leu Asp Arg Gly Asn Ser Lys Val Lys Phe Val
            435                 440                 445
Lys Glu Asn Pro Tyr Phe Thr Asn Arg Met Ser Val Asn Asn Gln Pro
450                 455                 460
Phe Lys Ser Glu Asn Asp Leu Ser Tyr Tyr Lys Val Tyr Gly Leu Leu
465                 470                 475                 480
Asp Gln Asn Ile Leu Glu Leu Tyr Phe Asn Asp Gly Asp Val Val Ser
            485                 490                 495
Thr Asn Thr Tyr Phe Met Thr Thr Gly Asn Ala Leu Gly Ser Val Asn
            500                 505                 510
Met Thr Thr Gly Val Asp Asn Leu Phe Tyr Ile Asp Lys Phe Gln Val
            515                 520                 525
Arg Glu Val Lys
    530

<210> SEQ ID NO 35
<211> LENGTH: 1302
<212> TYPE: DNA
<213> ORGANISM: Corynebacterium glutamicum

<400> SEQUENCE: 35
gtgtgtgggg ctatgcacac agaactttcc agtttgcgcc ctgcgtacca tgtgactcct      60
ccgcagggca ggctcaatga tcccaacgga atgtacgtcg atggcgatac cctccacgtc     120
tactaccagc acgatccagg tttcccttc gcaccaaagc gcaccggctg ggctcacacc      180
accacgccgt tgaccggacc gcagcgattg cagtggacgc acctgcccga cgctcttta     240 ccggatgcat cctatgacct ggatggatgc tattccggtg gagccgtatt tactgacggc     300
acacttaaac ttttctacac cggcaaccta aaaattgacg gcaagcgccg cgccacccaa     360
aacctcgtcg aagtcgagga cccaactggg ctgatgggcg gcattcatcg ccgttcgcct     420
aaaaatccgc ttatcgacgg acccgccagc ggtttcacac cccattaccg cgatcccatg     480
atcagccctg atggtgatgg ttggaaaatg gttcttgggg cccaacgcga aaacctcacc     540
ggtgcagcgg ttctataccg ctcgacagat cttgaaaact gggaattctc cggtgaaatc     600 accttttgacc tcagtgatgc acaacctggt tctgctcctg atctcgttcc cggtggctac     660
atgtgggaat gccccaacct ttttacgctt cgcgatgaag aaactggcga agatctcgac     720
gtgctgattt tctgtccaca aggattggac cgaatccacg atgaggttac tcactacgca     780
agctctgacc agtgcggata tgtcgtcggc aagcttgaag gaacgacctt ccgcgtcttg     840
cgaggattca gcgagctgga tttcggccat gaattctacg caccgcaggt tgcagtaaac     900
```

```
ggttctgatg cctggctcgt gggctggatg gggctgcccg cgcaggatga tcacccaaca    960
gttgcacggg aaggatgggt gcactgcctg actgtgcccc gcaagcttca tttgcgcaac   1020
cacgcgatct atcaagagct tcttctccca gaggggagt caggggtaat cagatctgta   1080
ttaggttctg aacctgtccg agtagacatc cgaggcaata tttccctcga gtgggatggt   1140
gtccgtttgt ctgtggatcg tggtggtgat cgtcgcgtag ctgaggtaaa acctggcgaa   1200
ttagtgatcg cggacgataa tacagccatt gagataactg caggtgatgg acaggtttca   1260
ttcgctttcc gggctttcaa aggtgacact attgagagat aa                      1302

<210> SEQ ID NO 36
<211> LENGTH: 433
<212> TYPE: PRT
<213> ORGANISM: Corynebacterium glutamicum

<400> SEQUENCE: 36
```

Met Cys Gly Ala Met His Thr Glu Leu Ser Ser Leu Arg Pro Ala Tyr
1               5                   10                  15

His Val Thr Pro Pro Gln Gly Arg Leu Asn Asp Pro Asn Gly Met Tyr
            20                  25                  30

Val Asp Gly Asp Thr Leu His Val Tyr Tyr Gln His Asp Pro Gly Phe
        35                  40                  45

Pro Phe Ala Pro Lys Arg Thr Gly Trp Ala His Thr Thr Thr Pro Leu
    50                  55                  60

Thr Gly Pro Gln Arg Leu Gln Trp Thr His Leu Pro Asp Ala Leu Tyr
65                  70                  75                  80

Pro Asp Ala Ser Tyr Asp Leu Asp Gly Cys Tyr Ser Gly Gly Ala Val
                85                  90                  95

Phe Thr Asp Gly Thr Leu Lys Leu Phe Tyr Thr Gly Asn Leu Lys Ile
            100                 105                 110

Asp Gly Lys Arg Arg Ala Thr Gln Asn Leu Val Glu Val Glu Asp Pro
        115                 120                 125

Thr Gly Leu Met Gly Gly Ile His Arg Arg Ser Pro Lys Asn Pro Leu
    130                 135                 140

Ile Asp Gly Pro Ala Ser Gly Phe Thr Pro His Tyr Arg Asp Pro Met
145                 150                 155                 160

Ile Ser Pro Asp Gly Asp Gly Trp Lys Met Val Leu Gly Ala Gln Arg
                165                 170                 175

Glu Asn Leu Thr Gly Ala Ala Val Leu Tyr Arg Ser Thr Asp Leu Glu
            180                 185                 190

Asn Trp Glu Phe Ser Gly Glu Ile Thr Phe Asp Leu Ser Asp Ala Gln
        195                 200                 205

Pro Gly Ser Ala Pro Asp Leu Val Pro Gly Gly Tyr Met Trp Glu Cys
    210                 215                 220

Pro Asn Leu Phe Thr Leu Arg Asp Glu Glu Thr Gly Glu Asp Leu Asp
225                 230                 235                 240

Val Leu Ile Phe Cys Pro Gln Gly Leu Asp Arg Ile His Asp Glu Val
                245                 250                 255

Thr His Tyr Ala Ser Ser Asp Gln Cys Gly Tyr Val Val Gly Lys Leu
            260                 265                 270

Glu Gly Thr Thr Phe Arg Val Leu Arg Gly Phe Ser Glu Leu Asp Phe
        275                 280                 285

Gly His Glu Phe Tyr Ala Pro Gln Val Ala Val Asn Gly Ser Asp Ala
    290                 295                 300

```
Trp Leu Val Gly Trp Met Gly Leu Pro Ala Gln Asp Asp His Pro Thr
305                 310                 315                 320

Val Ala Arg Glu Gly Trp Val His Cys Leu Thr Val Pro Arg Lys Leu
            325                 330                 335

His Leu Arg Asn His Ala Ile Tyr Gln Glu Leu Leu Pro Glu Gly
        340                 345                 350

Glu Ser Gly Val Ile Arg Ser Val Leu Gly Ser Glu Pro Val Arg Val
        355                 360                 365

Asp Ile Arg Gly Asn Ile Ser Leu Glu Trp Asp Gly Val Arg Leu Ser
    370                 375                 380

Val Asp Arg Gly Gly Asp Arg Arg Val Ala Glu Val Lys Pro Gly Glu
385                 390                 395                 400

Leu Val Ile Ala Asp Asp Asn Thr Ala Ile Glu Ile Thr Ala Gly Asp
                405                 410                 415

Gly Gln Val Ser Phe Ala Phe Arg Ala Phe Lys Gly Asp Thr Ile Glu
            420                 425                 430

Arg

<210> SEQ ID NO 37
<211> LENGTH: 1473
<212> TYPE: DNA
<213> ORGANISM: Leuconostoc mesenteroides

<400> SEQUENCE: 37
```

| | | | | | |
|---|---|---|---|---|---|
| atggaaattc | aaaacaaagc | aatgttgatc | acttatgctg | attcgttggg | caaaaactta | 60 |
| aaagatgttc | atcaagtctt | gaaagaagat | attggagatg | cgattggtgg | ggttcatttg | 120 |
| ttgcctttct | tcccttcaac | aggtgatcgc | ggttttgcgc | cagccgatta | tactcgtgtt | 180 |
| gatgccgcat | ttggtgattg | gcagatgtc | gaagcattgg | gtgaagaata | ctatttgatg | 240 |
| tttgacttca | tgattaacca | tatttctcgt | gaatcagtga | tgtatcaaga | ttttaagaag | 300 |
| aatcatgacg | attcaaagta | taagatttc | tttattcgtt | gggaaaagtt | ctgggcaaag | 360 |
| gccggcgaaa | accgtccaac | acaagccgat | gttgacttaa | tttacaagcg | taaagataag | 420 |
| gcaccaacgc | aagaaatcac | ttttgatgat | ggcacaacag | aaaacttgtg | gaatactttt | 480 |
| ggtgaagaac | aaattgacat | tgatgttaat | tcagccattg | ccaaggaatt | tattaagaca | 540 |
| acccttgaag | acatggtaaa | acatggtgct | aacttgattc | gtttggatgc | ctttgcgtat | 600 |
| gcagttaaaa | aagttgacac | aaatgacttc | ttcgttgagc | cagaaatctg | ggcactttg | 660 |
| aatgaagtac | gtgaaatttt | gacaccatta | aaggctgaaa | ttttaccaga | aattcatgaa | 720 |
| cattactcaa | tccctaaaaa | gatcaatgat | catggttact | tcacctatga | ctttgcatta | 780 |
| ccaatgacaa | cgcttacac | attgtattca | ggtaagacaa | atcaattggc | aaagtggttg | 840 |
| aagatgtcac | caatgaagca | attcacaaca | ttggacacgc | atgatggtat | tggtgtcgtt | 900 |
| gatgcccgtg | atattctaac | tgatgatgaa | attgactacg | cttctgaaca | actttacaag | 960 |
| gttggcgcga | atgtcaaaaa | gacatattca | tctgcttcat | acaacaacct | tgatatttac | 1020 |
| caaattaact | caacttatta | ttcagcattg | ggaaatgatg | atgcagcata | cttgttgagt | 1080 |
| cgtgtcttcc | aagtctttgc | gcctggaatt | ccacaaattt | attacgttgg | tttgttggca | 1140 |
| ggtgaaaacg | atatcgcgct | tttggagtca | actaagaag | gtcgtaatat | taaccgtcat | 1200 |
| tactatacgc | gtgaagaagt | taagtcgaaa | gttaagcgac | cagttgttgc | taacttattg | 1260 |
| aagctattgt | catggcgtaa | tgaaagccct | gcatttgatt | tggctggctc | aatcacagtt | 1320 |

```
gacacgccaa ctgatacaac aattgtggtg acacgtcaag atgaaaatgg tcaaaacaaa    1380
gctgtattaa cagccgatgc ggccaacaaa acttttgaaa tcgttgagaa tggtcaaact    1440
gttatgagca gtgataattt gactcagaac taa                                 1473
```

<210> SEQ ID NO 38
<211> LENGTH: 490
<212> TYPE: PRT
<213> ORGANISM: Leuconostoc mesenteroides

<400> SEQUENCE: 38

```
Met Glu Ile Gln Asn Lys Ala Met Leu Ile Thr Tyr Ala Asp Ser Leu
1               5                   10                  15

Gly Lys Asn Leu Lys Asp Val His Gln Val Leu Lys Glu Asp Ile Gly
            20                  25                  30

Asp Ala Ile Gly Gly Val His Leu Leu Pro Phe Phe Pro Ser Thr Gly
        35                  40                  45

Asp Arg Gly Phe Ala Pro Ala Asp Tyr Thr Arg Val Asp Ala Ala Phe
    50                  55                  60

Gly Asp Trp Ala Asp Val Glu Ala Leu Gly Glu Tyr Tyr Leu Met
65                  70                  75                  80

Phe Asp Phe Met Ile Asn His Ile Ser Arg Glu Ser Val Met Tyr Gln
                85                  90                  95

Asp Phe Lys Lys Asn His Asp Asp Ser Lys Tyr Lys Asp Phe Phe Ile
            100                 105                 110

Arg Trp Glu Lys Phe Trp Ala Lys Ala Gly Glu Asn Arg Pro Thr Gln
        115                 120                 125

Ala Asp Val Asp Leu Ile Tyr Lys Arg Lys Asp Lys Ala Pro Thr Gln
    130                 135                 140

Glu Ile Thr Phe Asp Asp Gly Thr Thr Glu Asn Leu Trp Asn Thr Phe
145                 150                 155                 160

Gly Glu Glu Gln Ile Asp Ile Asp Val Asn Ser Ala Ile Ala Lys Glu
                165                 170                 175

Phe Ile Lys Thr Thr Leu Glu Asp Met Val Lys His Gly Ala Asn Leu
            180                 185                 190

Ile Arg Leu Asp Ala Phe Ala Tyr Ala Val Lys Lys Val Asp Thr Asn
        195                 200                 205

Asp Phe Phe Val Glu Pro Glu Ile Trp Asp Thr Leu Asn Glu Val Arg
    210                 215                 220

Glu Ile Leu Thr Pro Leu Lys Ala Glu Ile Leu Pro Glu Ile His Glu
225                 230                 235                 240

His Tyr Ser Ile Pro Lys Lys Ile Asn Asp His Gly Tyr Phe Thr Tyr
                245                 250                 255

Asp Phe Ala Leu Pro Met Thr Thr Leu Tyr Thr Leu Tyr Ser Gly Lys
            260                 265                 270

Thr Asn Gln Leu Ala Lys Trp Leu Lys Met Ser Pro Met Lys Gln Phe
        275                 280                 285

Thr Thr Leu Asp Thr His Asp Gly Ile Gly Val Val Asp Ala Arg Asp
    290                 295                 300

Ile Leu Thr Asp Asp Glu Ile Asp Tyr Ala Ser Glu Gln Leu Tyr Lys
305                 310                 315                 320

Val Gly Ala Asn Val Lys Lys Thr Tyr Ser Ser Ala Ser Tyr Asn Asn
                325                 330                 335

Leu Asp Ile Tyr Gln Ile Asn Ser Thr Tyr Tyr Ser Ala Leu Gly Asn
            340                 345                 350
```

```
Asp Asp Ala Ala Tyr Leu Leu Ser Arg Val Phe Gln Val Phe Ala Pro
            355                 360                 365
Gly Ile Pro Gln Ile Tyr Tyr Val Gly Leu Leu Ala Gly Glu Asn Asp
        370                 375                 380
Ile Ala Leu Leu Glu Ser Thr Lys Glu Gly Arg Asn Ile Asn Arg His
385                 390                 395                 400
Tyr Tyr Thr Arg Glu Glu Val Lys Ser Glu Val Lys Arg Pro Val Val
                405                 410                 415
Ala Asn Leu Leu Lys Leu Leu Ser Trp Arg Asn Glu Ser Pro Ala Phe
            420                 425                 430
Asp Leu Ala Gly Ser Ile Thr Val Asp Thr Pro Thr Asp Thr Thr Ile
            435                 440                 445
Val Val Thr Arg Gln Asp Glu Asn Gly Gln Asn Lys Ala Val Leu Thr
        450                 455                 460
Ala Asp Ala Ala Asn Lys Thr Phe Glu Ile Val Glu Asn Gly Gln Thr
465                 470                 475                 480
Val Met Ser Ser Asp Asn Leu Thr Gln Asn
                485                 490

<210> SEQ ID NO 39
<211> LENGTH: 1515
<212> TYPE: DNA
<213> ORGANISM: Bifidobacterium adolescentis

<400> SEQUENCE: 39
```

| | | | |
|---|---|---|---|
| atgaaaaaca aggtgcagct catcacttac gccgaccgcc ttggcgacgg caccatcaag | 60 |
| tcgatgaccg acattctgcg cacccgcttc gacggcgtgt acgacggcgt tcacatcctg | 120 |
| ccgttcttca ccccgttcga cggcgccgac gcaggcttcg acccgatcga ccacaccaag | 180 |
| gtcgacgaac gtctcggcag ctgggacgac gtcgccgaac tctccaagac ccacaacatc | 240 |
| atggtcgacg ccatcgtcaa ccacatgagt tgggaatcca agcagttcca ggacgtgctg | 300 |
| gccaagggcg aggagtccga atactatccg atgttcctca ccatgagctc cgtgttcccg | 360 |
| aacgcgccca ccgaagagga cctggccggc atctaccgtc cgtcccgggg cctgccgttc | 420 |
| acccactaca agttcgccgg caagacccgc ctcgtgtggg tcagcttcac cccgcagcag | 480 |
| gtggacatcg acaccgattc cgacaagggt tgggaatacc tcatgtcgat tttcgaccag | 540 |
| atggccgcct ctcacgtcag ctacatccgc ctcgacgccg tcggctatgg cgccaaggaa | 600 |
| gccggcacca gctgcttcat gacccgaag accttcaagc tgatctcccg tctgcgtgag | 660 |
| gaaggcgtca agcgcggtct ggaaatcctc atcgaagtgc actcctacta caagaagcag | 720 |
| gtcgaaatcg catccaaggt ggaccgcgtc tacgacttcg ccctgcctcc gctgctgctg | 780 |
| cacgcgctga gcaccggcca cgtcgagccc gtcgcccact ggaccgacat acgcccgaac | 840 |
| aacgccgtca ccgtgctcga tacgcacgac ggcatcggcg tgatcgacat cggctccgac | 900 |
| cagctcgacc gctcgctcaa gggtctcgtg ccggatgagg acgtggacaa cctcgtcaac | 960 |
| accatccacg ccaacaccca cggcgaatcc caggcagcca ctggcgccgc cgcatccaat | 1020 |
| ctcgacctct accaggtcaa cagcacctac tattcggcgc tcgggtgcaa cgaccagcac | 1080 |
| tacatcgccg cccgcgcggt gcagttcttc ctgccgggcg tgccgcaagt ctactacgtc | 1140 |
| ggcgcgctcg ccggcaagaa cgacatggag ctgctgcgta agacgaataa cggccgcgac | 1200 |
| atcaatcgcc attactactc caccgcggaa atcgacgaga acctcaagcg tccggtcgtc | 1260 |
| aaggccctga cgcgctcgc caagttccgc aacgagctcg acgcgttcga cggcacgttc | 1320 |

```
tcgtacacca ccgatgacga cacgtccatc agcttcacct ggcgcggcga aaccagccag    1380
gccacgctga cgttcgagcc gaagcgcggt ctcggtgtgg acaacactac gccggtcgcc    1440
atgttggaat gggaggattc cgcgggagac caccgttcgg atgatctgat cgccaatccg    1500
cctgtcgtcg cctga                                                    1515

<210> SEQ ID NO 40
<211> LENGTH: 504
<212> TYPE: PRT
<213> ORGANISM: Bifidobacterium adolescentis

<400> SEQUENCE: 40

Met Lys Asn Lys Val Gln Leu Ile Thr Tyr Ala Asp Arg Leu Gly Asp
1               5                   10                  15

Gly Thr Ile Lys Ser Met Thr Asp Ile Leu Arg Thr Arg Phe Asp Gly
                20                  25                  30

Val Tyr Asp Gly Val His Ile Leu Pro Phe Phe Thr Pro Phe Asp Gly
            35                  40                  45

Ala Asp Ala Gly Phe Asp Pro Ile Asp His Thr Lys Val Asp Glu Arg
        50                  55                  60

Leu Gly Ser Trp Asp Asp Val Ala Glu Leu Ser Lys Thr His Asn Ile
65                  70                  75                  80

Met Val Asp Ala Ile Val Asn His Met Ser Trp Glu Ser Lys Gln Phe
                85                  90                  95

Gln Asp Val Leu Ala Lys Gly Glu Glu Ser Glu Tyr Tyr Pro Met Phe
            100                 105                 110

Leu Thr Met Ser Ser Val Phe Pro Asn Gly Ala Thr Glu Glu Asp Leu
        115                 120                 125

Ala Gly Ile Tyr Arg Pro Arg Pro Gly Leu Pro Phe Thr His Tyr Lys
    130                 135                 140

Phe Ala Gly Lys Thr Arg Leu Val Trp Val Ser Phe Thr Pro Gln Gln
145                 150                 155                 160

Val Asp Ile Asp Thr Asp Ser Asp Lys Gly Trp Glu Tyr Leu Met Ser
                165                 170                 175

Ile Phe Asp Gln Met Ala Ala Ser His Val Ser Tyr Ile Arg Leu Asp
            180                 185                 190

Ala Val Gly Tyr Gly Ala Lys Glu Ala Gly Thr Ser Cys Phe Met Thr
        195                 200                 205

Pro Lys Thr Phe Lys Leu Ile Ser Arg Leu Arg Glu Glu Gly Val Lys
    210                 215                 220

Arg Gly Leu Glu Ile Leu Ile Glu Val His Ser Tyr Tyr Lys Lys Gln
225                 230                 235                 240

Val Glu Ile Ala Ser Lys Val Asp Arg Val Tyr Asp Phe Ala Leu Pro
                245                 250                 255

Pro Leu Leu Leu His Ala Leu Ser Thr Gly His Val Glu Pro Val Ala
            260                 265                 270

His Trp Thr Asp Ile Arg Pro Asn Asn Ala Val Thr Val Leu Asp Thr
        275                 280                 285

His Asp Gly Ile Gly Val Ile Asp Ile Gly Ser Asp Gln Leu Asp Arg
    290                 295                 300

Ser Leu Lys Gly Leu Val Pro Asp Glu Asp Val Asp Asn Leu Val Asn
305                 310                 315                 320

Thr Ile His Ala Asn Thr His Gly Glu Ser Gln Ala Ala Thr Gly Ala
                325                 330                 335
```

```
Ala Ala Ser Asn Leu Asp Leu Tyr Gln Val Asn Ser Thr Tyr Tyr Ser
            340                 345                 350

Ala Leu Gly Cys Asn Asp Gln His Tyr Ile Ala Ala Arg Ala Val Gln
        355                 360                 365

Phe Phe Leu Pro Gly Val Pro Gln Val Tyr Tyr Val Gly Ala Leu Ala
    370                 375                 380

Gly Lys Asn Asp Met Glu Leu Leu Arg Lys Thr Asn Asn Gly Arg Asp
385                 390                 395                 400

Ile Asn Arg His Tyr Tyr Ser Thr Ala Glu Ile Asp Glu Asn Leu Lys
                405                 410                 415

Arg Pro Val Val Lys Ala Leu Asn Ala Leu Ala Lys Phe Arg Asn Glu
            420                 425                 430

Leu Asp Ala Phe Asp Gly Thr Phe Ser Tyr Thr Thr Asp Asp Asp Thr
                435                 440                 445

Ser Ile Ser Phe Thr Trp Arg Gly Glu Thr Ser Gln Ala Thr Leu Thr
        450                 455                 460

Phe Glu Pro Lys Arg Gly Leu Gly Val Asp Asn Thr Thr Pro Val Ala
465                 470                 475                 480

Met Leu Glu Trp Glu Asp Ser Ala Gly Asp His Arg Ser Asp Asp Leu
                485                 490                 495

Ile Ala Asn Pro Pro Val Val Ala
            500

<210> SEQ ID NO 41
<211> LENGTH: 927
<212> TYPE: DNA
<213> ORGANISM: Agrobacterium tumefaciens

<400> SEQUENCE: 41
atgatcctgt gttgtggtga agccctgatc gacatgctgc cccggcagac gacgctgggt      60
gaggcgggct tgcccctta cgcaggcgga gcggtcttca acacggcaat tgcgctgggg      120
cgtcttggcg tcccttcagc cttttttacc ggtctttccg acgacatgat gggcgatatc     180
ctgcgggaga ccctgcgggc cagcaaggtg gatttcagct attgcgccac cctgtcgcgc     240
cccaccacca ttgcgttcgt taagctggtt gatggccatg cgacctacgc tttttacgac     300
gagaacaccg ccgccggat gatcaccgag gccgaacttc cggccttggg agcggattgc      360
gaagcgctgc atttcggcgc catcagcctt attccgaac cctgcggcag cacctatgag      420 cgctgatga cgcgcgagca tgagacccgc gtcatctcgc tcgatccgaa cattcgtccc      480
ggcttcatcc agaacaagca gtcgcacatg cccgcatcc gccgcatggc ggcgatgtct      540
gacatcgtca gttctcgga tgaggacctg gcgtggttcg gtctggaagg cgacgaggac      600
acgcttgccc gccactggct gcaccacggt gcaaaactcg tcgttgtcac ccgtggcgcc      660
aagggtgccg tgggttacag cgccaatctc aaggtggaag tggcctccga gcgcgtcgaa      720
gtggtcgata cggtcggcgc cggcgatacg ttcgatgccg gcattcttgc ttcgctgaaa      780
atgcagggcc tgctgaccaa agcgcaggtg gcttcgctga gcgaagagca gatcagaaaa      840
gctttggcgc ttggcgcgaa agccgctgcg gtcactgtct cgcgggctgg cgcaaatccg      900
cctttcgcgc atgaaatcgg tttgtga                                          927

<210> SEQ ID NO 42
<211> LENGTH: 308
<212> TYPE: PRT
<213> ORGANISM: Agrobacterium tumefaciens
```

<400> SEQUENCE: 42

| | | | | | | | | | | | | | | |
|---|---|---|---|---|---|---|---|---|---|---|---|---|---|---|
|Met|Ile|Leu|Cys|Cys|Gly|Glu|Ala|Leu|Ile|Asp|Met|Leu|Pro|Arg|Gln|
|1| | | |5| | | | |10| | | | |15|

Met Ile Leu Cys Cys Gly Glu Ala Leu Ile Asp Met Leu Pro Arg Gln
1               5                   10                  15

Thr Thr Leu Gly Glu Ala Gly Phe Ala Pro Tyr Ala Gly Gly Ala Val
            20                  25                  30

Phe Asn Thr Ala Ile Ala Leu Gly Arg Leu Gly Val Pro Ser Ala Phe
        35                  40                  45

Phe Thr Gly Leu Ser Asp Asp Met Met Gly Asp Ile Leu Arg Glu Thr
    50                  55                  60

Leu Arg Ala Ser Lys Val Asp Phe Ser Tyr Cys Ala Thr Leu Ser Arg
65                  70                  75                  80

Pro Thr Thr Ile Ala Phe Val Lys Leu Val Asp Gly His Ala Thr Tyr
                85                  90                  95

Ala Phe Tyr Asp Glu Asn Thr Ala Gly Arg Met Ile Thr Glu Ala Glu
            100                 105                 110

Leu Pro Ala Leu Gly Ala Asp Cys Glu Ala Leu His Phe Gly Ala Ile
        115                 120                 125

Ser Leu Ile Pro Glu Pro Cys Gly Ser Thr Tyr Glu Ala Leu Met Thr
    130                 135                 140

Arg Glu His Glu Thr Arg Val Ile Ser Leu Asp Pro Asn Ile Arg Pro
145                 150                 155                 160

Gly Phe Ile Gln Asn Lys Gln Ser His Met Ala Arg Ile Arg Arg Met
                165                 170                 175

Ala Ala Met Ser Asp Ile Val Lys Phe Ser Asp Glu Asp Leu Ala Trp
            180                 185                 190

Phe Gly Leu Glu Gly Asp Glu Asp Thr Leu Ala Arg His Trp Leu His
        195                 200                 205

His Gly Ala Lys Leu Val Val Thr Arg Gly Ala Lys Gly Ala Val
    210                 215                 220

Gly Tyr Ser Ala Asn Leu Lys Val Glu Val Ala Ser Glu Arg Val Glu
225                 230                 235                 240

Val Val Asp Thr Val Gly Ala Gly Asp Thr Phe Asp Ala Gly Ile Leu
                245                 250                 255

Ala Ser Leu Lys Met Gln Gly Leu Leu Thr Lys Ala Gln Val Ala Ser
            260                 265                 270

Leu Ser Glu Glu Gln Ile Arg Lys Ala Leu Ala Leu Gly Ala Lys Ala
        275                 280                 285

Ala Ala Val Thr Val Ser Arg Ala Gly Ala Asn Pro Pro Phe Ala His
290                 295                 300

Glu Ile Gly Leu
305

<210> SEQ ID NO 43
<211> LENGTH: 1404
<212> TYPE: DNA
<213> ORGANISM: Streptococcus mutans

<400> SEQUENCE: 43

```
cagctgatta tgcgtcagtt gaaaccctcg cttcttcagg aactgttgct gtaggtgata      60
gcttacttga agttaaaaaa taagaaatat tatcagaaag accgtaaggt ctttttgact     120
gcttaaaaga ttcagtaaca atagtattaa agccttttgg ctaactaata cttgaaattt     180
agcaaattat gatataatgt taagtagtcc ttaagggtag attaagggta ttcaaatcca     240
```

-continued

```
aaaattgatt tggtaagtta agtaaaatat aagaggttta ttatgtctaa attatatggc      300
agcatcgaag ctggcggaac aaaatttgtc tgtgctgtag gtgatgaaaa ttttcaaatt      360
ttagaaaaag ttcagttccc aacaacaaca ccttatgaaa caatagaaaa aacagttgct      420
ttctttaaaa aatttgaagc tgatttagcc agtgttgcca ttggttcttt tggccctatt      480
gatattgatc aaaattcaga cacttatggt tacattactt caacaccaaa gccaaactgg      540
gctaacgttg attttgtcgg cttaatttct aaagatttta aaattccatt ttactttacg      600
acagatgtta attcttctgc ttatggggaa acaattgctc gttcaaatgt taaaagtctg      660
gtttattata ctattggaac aggcattgga gcagggctta ttcaaaatgg cgaattcatt      720
ggcggtatgg gacatacgga agctggacac gtttacatgg ctccgcatcc caatgatgtt      780
catcatggtt ttgtaggcac ctgtcctttc cataaaggct gtttagaagg acttgcagcg      840
ggtcctagct tagaggctcg tactggtatt cgtggtgagt taattgagca aaactcagaa      900
gtttgggata ttcaggcata ctacattgct caggcggcta ttcaagcgac tgtcctttat      960
cgtccgcaag tcattgtatt tggcggaggc gttatggcac aagaacatat gctcaatcgg     1020
gttcgtgaaa aatttacttc acttttgaat gactatcttc cagttccaga tgttaaagat     1080
tatattgtga caccagctgt tgcagaaaat ggttcagcaa cattgggaaa tctcgcttta     1140
gctaaaaaga tagcagcgcg ttaattaaaa atgaattgga agattaaagc accttctaat     1200
attcaatatt aaactgttag aatttacgtg aacgaaattt tcattttatg aggataatga     1260
agtgaatata attactcttg atttcctctg aaactagata gtggtatatt gaaaaacaga     1320
aaggagaaca ctatggaagg acctttgttt ttacaatcac aaatgcataa aaaaatctgg     1380
ggcggcaatc ggctcagaaa agaa                                             1404
```

<210> SEQ ID NO 44
<211> LENGTH: 293
<212> TYPE: PRT
<213> ORGANISM: Streptococcus mutans

<400> SEQUENCE: 44

```
Met Ser Lys Leu Tyr Gly Ser Ile Glu Ala Gly Gly Thr Lys Phe Val
1               5                   10                  15

Cys Ala Val Gly Asp Glu Asn Phe Gln Ile Leu Glu Lys Val Gln Phe
            20                  25                  30

Pro Thr Thr Thr Pro Tyr Glu Thr Ile Glu Lys Thr Val Ala Phe Phe
        35                  40                  45

Lys Lys Phe Glu Ala Asp Leu Ala Ser Val Ala Ile Gly Ser Phe Gly
    50                  55                  60

Pro Ile Asp Ile Asp Gln Asn Ser Asp Thr Tyr Gly Tyr Ile Thr Ser
65                  70                  75                  80

Thr Pro Lys Pro Asn Trp Ala Asn Val Asp Phe Val Gly Leu Ile Ser
                85                  90                  95

Lys Asp Phe Lys Ile Pro Phe Tyr Phe Thr Thr Asp Val Asn Ser Ser
            100                 105                 110

Ala Tyr Gly Glu Thr Ile Ala Arg Ser Asn Val Lys Ser Leu Val Tyr
        115                 120                 125

Tyr Thr Ile Gly Thr Gly Ile Gly Ala Gly Ala Ile Gln Asn Gly Glu
    130                 135                 140

Phe Ile Gly Gly Met Gly His Thr Glu Ala Gly His Val Tyr Met Ala
145                 150                 155                 160

Pro His Pro Asn Asp Val His His Gly Phe Val Gly Thr Cys Pro Phe
```

```
                     165                 170                 175
His Lys Gly Cys Leu Glu Gly Leu Ala Ala Gly Pro Ser Leu Glu Ala
            180                 185                 190

Arg Thr Gly Ile Arg Gly Glu Leu Ile Glu Gln Asn Ser Glu Val Trp
        195                 200                 205

Asp Ile Gln Ala Tyr Tyr Ile Ala Gln Ala Ala Ile Gln Ala Thr Val
    210                 215                 220

Leu Tyr Arg Pro Gln Val Ile Val Phe Gly Gly Val Met Ala Gln
225                 230                 235                 240

Glu His Met Leu Asn Arg Val Arg Glu Lys Phe Thr Ser Leu Leu Asn
                245                 250                 255

Asp Tyr Leu Pro Val Pro Asp Val Lys Asp Tyr Ile Val Thr Pro Ala
            260                 265                 270

Val Ala Glu Asn Gly Ser Ala Thr Leu Gly Asn Leu Ala Leu Ala Lys
        275                 280                 285

Lys Ile Ala Ala Arg
    290
```

<210> SEQ ID NO 45
<211> LENGTH: 915
<212> TYPE: DNA
<213> ORGANISM: Escherichia coli

<400> SEQUENCE: 45

```
atgtcagcca aagtatgggt tttaggggat gcggtcgtag atctcttgcc agaatcagac    60
gggcgcctac tgccttgtcc tggcggcgcg ccagctaacg ttgcggtggg aatcgccaga   120
ttaggcggaa caagtgggtt tataggtcgg gtggggatg atccttttgg tgcgttaatg   180
caaagaacgc tgctaactga gggagtcgat atcacgtatc tgaagcaaga tgaatggcac   240
cggacatcca cggtgcttgt cgatctgaac gatcaagggg aacgttcatt tacgtttatg   300
gtccgcccca gtgccgatct tttttagag acgacagact tgccctgctg gcgacatggc   360
gaatggttac atctctgttc aattgcgttg tctgccgagc cttcgcgtac cagcgcattt   420
actgcgatga cggcgatccg gcatgccgga ggttttgtca gcttcgatcc taatattcgt   480
gaagatctat ggcaagacga gcatttgctc cgcttgtgtt tgcggcaggc gctacaactg   540
gcggatgtcg tcaagctctc ggaagaagaa tggcgactta cagtggaaaa acacagaaac   600
gatcaggata tatgcgccct ggcaaaagag tatgagatcg ccatgctgtt ggtgactaaa   660
ggtgcagaag gggtggtggt ctgttatcga ggacaagttc accattttgc tggaatgtct   720
gtgaattgtg tcgatagcac gggggcggga gatgcgttcg ttgccgggtt actcacaggt   780
ctgtcctcta cgggattatc tacagatgag agagaaatgc gacgaattat cgatctcgct   840
caacgttgcg gagcgcttgc agtaacggcg aaaggggcaa tgacagcgct gccatgtcga   900
caagaactgg aatag                                                    915
```

<210> SEQ ID NO 46
<211> LENGTH: 304
<212> TYPE: PRT
<213> ORGANISM: Escherichia coli

<400> SEQUENCE: 46

```
Met Ser Ala Lys Val Trp Val Leu Gly Asp Ala Val Val Asp Leu Leu
1               5                   10                  15

Pro Glu Ser Asp Gly Arg Leu Leu Pro Cys Pro Gly Gly Ala Pro Ala
            20                  25                  30
```

Asn Val Ala Val Gly Ile Ala Arg Leu Gly Gly Thr Ser Gly Phe Ile
              35                  40                  45

Gly Arg Val Gly Asp Asp Pro Phe Gly Ala Leu Met Gln Arg Thr Leu
 50                  55                  60

Leu Thr Glu Gly Val Asp Ile Thr Tyr Leu Lys Gln Asp Glu Trp His
 65                  70                  75                  80

Arg Thr Ser Thr Val Leu Val Asp Leu Asn Asp Gln Gly Glu Arg Ser
                 85                  90                  95

Phe Thr Phe Met Val Arg Pro Ser Ala Asp Leu Phe Leu Glu Thr Thr
                100                 105                 110

Asp Leu Pro Cys Trp Arg His Gly Glu Trp Leu His Leu Cys Ser Ile
            115                 120                 125

Ala Leu Ser Ala Glu Pro Ser Arg Thr Ser Ala Phe Thr Ala Met Thr
        130                 135                 140

Ala Ile Arg His Ala Gly Gly Phe Val Ser Phe Asp Pro Asn Ile Arg
145                 150                 155                 160

Glu Asp Leu Trp Gln Asp Glu His Leu Leu Arg Leu Cys Leu Arg Gln
                165                 170                 175

Ala Leu Gln Leu Ala Asp Val Val Lys Leu Ser Glu Glu Trp Arg
                180                 185                 190

Leu Ile Ser Gly Lys Thr Gln Asn Asp Gln Asp Ile Cys Ala Leu Ala
            195                 200                 205

Lys Glu Tyr Glu Ile Ala Met Leu Leu Val Thr Lys Gly Ala Glu Gly
210                 215                 220

Val Val Val Cys Tyr Arg Gly Gln Val His His Phe Ala Gly Met Ser
225                 230                 235                 240

Val Asn Cys Val Asp Ser Thr Gly Ala Gly Asp Ala Phe Val Ala Gly
                245                 250                 255

Leu Leu Thr Gly Leu Ser Ser Thr Gly Leu Ser Thr Asp Glu Arg Glu
            260                 265                 270

Met Arg Arg Ile Ile Asp Leu Ala Gln Arg Cys Gly Ala Leu Ala Val
        275                 280                 285

Thr Ala Lys Gly Ala Met Thr Ala Leu Pro Cys Arg Gln Glu Leu Glu
    290                 295                 300

<210> SEQ ID NO 47
<211> LENGTH: 924
<212> TYPE: DNA
<213> ORGANISM: Klebsiella pneumoniae

<400> SEQUENCE: 47
atgaatggaa aaatctgggt actcggcgat gcggtcgtcg atctcctgcc cgatggagag      60
ggccgcctgc tgcaatgccc cggcggcgcg ccggccaacg tggcggtcgg cgtggcgcgg     120
ctcggcggtg acagcgggtt tatcggccgc gtcggcgacg atcccttcgg ccgttttatg     180
cgtcacaccc tggcgcagga gcaagtggat gtgaactata tgcgcctcga tgcggcgcag     240
cgcacctcca cggtggtggt cgatctcgat agccacgggg agcgcacctt tacctttatg     300
gtccgtccga gcgccgacct gttccttcag cccgaggatc tccgccgtt tgccgccggt      360 cagtggctgc acgtctgctc catcgctctc agcgcggagc cgagccgcag cacgacattc     420
gcggcgatgg aggcgataaa gcgcgccggg gctatgtca gcttcgaccc caatatccgc      480
agcgacctgt ggcaggatcc gcaggacctt cgcgactgtc tcgaccgggc gctgccctc      540 gccgacgcca taaaactttc ggaagaggag ctggcgttta tcagcggcag cgacgacatc     600

```
gtcagcggca ccgcccggct gaacgcccgc ttccagccga cgctactgct ggtgacccag    660
ggtaaagcgg gggtccaggc cgccctgcgc gggcaggtta gccacttccc tgcccgcccg    720
gtggtggccg tcgataccac cggcgccggc gatgcctttg tcgccgggct actcgccggc    780
ctcgccgccc acgtatccc ggacaacctc gcagccctgg ctcccgacct cgcgctggcg    840
caaacctgcg cgccctggc accaccgcc aaaggcgcca tgaccgccct gccctacagg    900
gacgatcttc agcgctcgct gtga                                            924
```

<210> SEQ ID NO 48
<211> LENGTH: 307
<212> TYPE: PRT
<213> ORGANISM: Klebsiella pneumoniae

<400> SEQUENCE: 48

```
Met Asn Gly Lys Ile Trp Val Leu Gly Asp Ala Val Val Asp Leu Leu
1               5                   10                  15

Pro Asp Gly Glu Gly Arg Leu Leu Gln Cys Pro Gly Gly Ala Pro Ala
            20                  25                  30

Asn Val Ala Val Gly Val Ala Arg Leu Gly Gly Asp Ser Gly Phe Ile
        35                  40                  45

Gly Arg Val Gly Asp Asp Pro Phe Gly Arg Phe Met Arg His Thr Leu
    50                  55                  60

Ala Gln Glu Gln Val Asp Val Asn Tyr Met Arg Leu Asp Ala Ala Gln
65                  70                  75                  80

Arg Thr Ser Thr Val Val Asp Leu Asp Ser His Gly Glu Arg Thr
                85                  90                  95

Phe Thr Phe Met Val Arg Pro Ser Ala Asp Leu Phe Leu Gln Pro Glu
            100                 105                 110

Asp Leu Pro Pro Phe Ala Ala Gly Gln Trp Leu His Val Cys Ser Ile
        115                 120                 125

Ala Leu Ser Ala Glu Pro Ser Arg Ser Thr Thr Phe Ala Ala Met Glu
    130                 135                 140

Ala Ile Lys Arg Ala Gly Gly Tyr Val Ser Phe Asp Pro Asn Ile Arg
145                 150                 155                 160

Ser Asp Leu Trp Gln Asp Pro Gln Asp Leu Arg Asp Cys Leu Asp Arg
                165                 170                 175

Ala Leu Ala Leu Ala Asp Ala Ile Lys Leu Ser Glu Glu Glu Leu Ala
            180                 185                 190

Phe Ile Ser Gly Ser Asp Asp Ile Val Ser Gly Thr Ala Arg Leu Asn
        195                 200                 205

Ala Arg Phe Gln Pro Thr Leu Leu Leu Val Thr Gln Gly Lys Ala Gly
    210                 215                 220

Val Gln Ala Ala Leu Arg Gly Gln Val Ser His Phe Pro Ala Arg Pro
225                 230                 235                 240

Val Val Ala Val Asp Thr Thr Gly Ala Gly Asp Ala Phe Val Ala Gly
                245                 250                 255

Leu Leu Ala Gly Leu Ala Ala His Gly Ile Pro Asp Asn Leu Ala Ala
            260                 265                 270

Leu Ala Pro Asp Leu Ala Leu Ala Gln Thr Cys Gly Ala Leu Ala Thr
        275                 280                 285

Thr Ala Lys Gly Ala Met Thr Ala Leu Pro Tyr Arg Asp Asp Leu Gln
    290                 295                 300

Arg Ser Leu
```

<210> SEQ ID NO 49
<211> LENGTH: 915
<212> TYPE: DNA
<213> ORGANISM: Escherichia coli

<400> SEQUENCE: 49

```
atgtcagcca aagtatgggt tttaggggat gcggtcgtag atctcttgcc agaatcagac      60
gggcgcctac tgccttgtcc tggcggcgcg ccagctaacg ttgcggtggg aatcgccaga     120
ttaggcggaa caagtgggtt tataggtcgg gtggggatg atccttttgg tgcgttaatg      180
caaagaacgc tgctaactga gggagtcgat atcacgtatc tgaagcaaga tgaatggcac     240
cggacatcca cggtgcttgt cgatctgaac gatcaagggg aacgttcatt tacgtttatg     300
gtccgcccca gtgccgatct ttttttagag acgacagact tgccctgctg gcgacatggc     360
gaatggttac atctctgttc aattgcgttg tctgccgagc cttcgcgtac cagcgcattt     420
actgcgatga cggcgatccg gcatgccgga ggttttgtca gcttcgatcc taatattcgt     480
gaagatctat ggcaagacga gcatttgctc cgcttgtgtt tgcggcaggc gctacaactg     540
gcggatgtcg tcaagctctc ggaagaagaa tggcgactta cagtggaaaa acacagaac      600
gatcaggata tatgcgccct ggcaaaagag tatgagatcg ccatgctgtt ggtgactaaa     660
ggtgcagaag gggtggtggt ctgttatcga ggacaagttc accattttgc tggaatgtct     720
gtgaattgtg tcgatagcac gggggcggga gatgcgttcg ttgccgggtt actcacaggt     780
ctgtcctcta cgggattatc tacagatgag agagaaatgc gacgaattat cgatctcgct     840
caacgttgcg gagcgcttgc agtaacggcg aaagggcaa tgacagcgct gccatgtcga      900
caagaactgg aatag                                                      915
```

<210> SEQ ID NO 50
<211> LENGTH: 304
<212> TYPE: PRT
<213> ORGANISM: Escherichia coli

<400> SEQUENCE: 50

```
Met Ser Ala Lys Val Trp Val Leu Gly Asp Ala Val Val Asp Leu Leu
1               5                   10                  15

Pro Glu Ser Asp Gly Arg Leu Leu Pro Cys Pro Gly Gly Ala Pro Ala
            20                  25                  30

Asn Val Ala Val Gly Ile Ala Arg Leu Gly Gly Thr Ser Gly Phe Ile
        35                  40                  45

Gly Arg Val Gly Asp Asp Pro Phe Gly Ala Leu Met Gln Arg Thr Leu
    50                  55                  60

Leu Thr Glu Gly Val Asp Ile Thr Tyr Leu Lys Gln Asp Glu Trp His
65                  70                  75                  80

Arg Thr Ser Thr Val Leu Val Asp Leu Asn Asp Gln Gly Glu Arg Ser
                85                  90                  95

Phe Thr Phe Met Val Arg Pro Ser Ala Asp Leu Phe Leu Glu Thr Thr
            100                 105                 110

Asp Leu Pro Cys Trp Arg His Gly Glu Trp Leu His Leu Cys Ser Ile
        115                 120                 125

Ala Leu Ser Ala Glu Pro Ser Arg Thr Ser Ala Phe Thr Ala Met Thr
    130                 135                 140

Ala Ile Arg His Ala Gly Gly Phe Val Ser Phe Asp Pro Asn Ile Arg
145                 150                 155                 160
```

```
Glu Asp Leu Trp Gln Asp Glu His Leu Leu Arg Leu Cys Leu Arg Gln
            165                 170                 175

Ala Leu Gln Leu Ala Asp Val Val Lys Leu Ser Glu Glu Trp Arg
        180                 185                 190

Leu Ile Ser Gly Lys Thr Gln Asn Asp Gln Asp Ile Cys Ala Leu Ala
            195                 200                 205

Lys Glu Tyr Glu Ile Ala Met Leu Leu Val Thr Lys Gly Ala Glu Gly
            210                 215                 220

Val Val Val Cys Tyr Arg Gly Gln Val His His Phe Ala Gly Met Ser
225                 230                 235                 240

Val Asn Cys Val Asp Ser Thr Gly Ala Gly Asp Ala Phe Val Ala Gly
                245                 250                 255

Leu Leu Thr Gly Leu Ser Ser Thr Gly Leu Ser Thr Asp Glu Arg Glu
            260                 265                 270

Met Arg Arg Ile Ile Asp Leu Ala Gln Arg Cys Gly Ala Leu Ala Val
            275                 280                 285

Thr Ala Lys Gly Ala Met Thr Ala Leu Pro Cys Arg Gln Glu Leu Glu
            290                 295                 300
```

<210> SEQ ID NO 51
<211> LENGTH: 879
<212> TYPE: DNA
<213> ORGANISM: Enterococcus faecalis

<400> SEQUENCE: 51

```
atgacagaaa aacttttagg aagtatcgaa gccggtggca caaaatttgt atgtggcgtt      60
gggacagatg atttgaccat cgtagaacgt gtcagttttc ccacaacaac cccagaagaa     120
acaatgaaaa aagtaataga attttttccaa caatatcctt taaaagcgat tgggattggt     180
tcatttggtc cgattgatat tcacgttgat tctcctacgt atggttatat cacttctaca     240
ccaaaattag cttggcgtaa cttgacttg ttaggaacta tgaaacaaca ttttgatgtg      300
ccaatggctt ggacaacgga tgtgaatgct gcggcatatg tgagtatgt tgctggaaat      360
gggcaacata catctagttg tgtatattat acaattggaa ctggtgttgg cgctggagcg     420
attcaaaacg gtgagtttat tgaaggctt agccacccag aaatggggca tgcgttagtt      480
cgtcgtcatc ctgaagatac gtatgcagga aattgtcctt atcatggaga ttgtttagaa     540
gggattgcag caggaccagc agttgaaggt cgttctggta aaaaaggaca tttattggaa     600
gaggatcata aaactgggga attagaagct tattatttag cgcaagcggc gtacaatacg     660
actttattat tagcgccaga agtgatcatt ttaggtggcg gcgtcatgaa acaacgtcat     720
ttgatgccga agttcgtga aaaatttgct gaattagtca atggatatgt ggaaacaccg     780
cctttagaaa aatacttggt gacgcctctt ttagaagata tccaggaac aatcggttgc     840
tttgccttgg caaaaaagc tttaatggct caaaaataa                             879
```

<210> SEQ ID NO 52
<211> LENGTH: 292
<212> TYPE: PRT
<213> ORGANISM: Enterococcus faecalis

<400> SEQUENCE: 52

```
Met Thr Glu Lys Leu Leu Gly Ser Ile Glu Ala Gly Gly Thr Lys Phe
1               5                   10                  15

Val Cys Gly Val Gly Thr Asp Asp Leu Thr Ile Val Glu Arg Val Ser
            20                  25                  30
```

```
Phe Pro Thr Thr Thr Pro Glu Glu Thr Met Lys Lys Val Ile Glu Phe
            35                  40                  45

Phe Gln Gln Tyr Pro Leu Lys Ala Ile Gly Ile Gly Ser Phe Gly Pro
        50                  55                  60

Ile Asp Ile His Val Asp Ser Pro Thr Tyr Gly Tyr Ile Thr Ser Thr
 65                  70                  75                  80

Pro Lys Leu Ala Trp Arg Asn Phe Asp Leu Leu Gly Thr Met Lys Gln
                85                  90                  95

His Phe Asp Val Pro Met Ala Trp Thr Thr Asp Val Asn Ala Ala Ala
               100                 105                 110

Tyr Gly Glu Tyr Val Ala Gly Asn Gly Gln His Thr Ser Ser Cys Val
           115                 120                 125

Tyr Tyr Thr Ile Gly Thr Gly Val Gly Ala Gly Ala Ile Gln Asn Gly
       130                 135                 140

Glu Phe Ile Glu Gly Phe Ser His Pro Glu Met Gly His Ala Leu Val
145                 150                 155                 160

Arg Arg His Pro Glu Asp Thr Tyr Ala Gly Asn Cys Pro Tyr His Gly
               165                 170                 175

Asp Cys Leu Glu Gly Ile Ala Ala Gly Pro Ala Val Glu Gly Arg Ser
           180                 185                 190

Gly Lys Lys Gly His Leu Leu Glu Glu Asp His Lys Thr Trp Glu Leu
       195                 200                 205

Glu Ala Tyr Tyr Leu Ala Gln Ala Ala Tyr Asn Thr Thr Leu Leu Leu
210                 215                 220

Ala Pro Glu Val Ile Ile Leu Gly Gly Val Met Lys Gln Arg His
225                 230                 235                 240

Leu Met Pro Lys Val Arg Glu Lys Phe Ala Glu Leu Val Asn Gly Tyr
               245                 250                 255

Val Glu Thr Pro Pro Leu Glu Lys Tyr Leu Val Thr Pro Leu Leu Glu
           260                 265                 270

Asp Asn Pro Gly Thr Ile Gly Cys Phe Ala Leu Ala Lys Lys Ala Leu
       275                 280                 285

Met Ala Gln Lys
    290

<210> SEQ ID NO 53
<211> LENGTH: 1458
<212> TYPE: DNA
<213> ORGANISM: Saccharomyces cerevisiae

<400> SEQUENCE: 53
atggttcatt taggtccaaa gaaaccacag gctagaaagg gttccatggc tgatgtgccc        60
aaggaattga tggatgaaat tcatcagttg aagatatgt ttacagttga cagcgagacc       120
ttgagaaagg ttgttaagca ctttatcgac gaattgaata aaggtttgac aaagaaggga       180
ggtaacattc aatgattcc cggttgggtc atggaattcc caacaggtaa agaatctggt       240
aactatttgg ccattgattt gggtggtact aacttaagag tcgtgttggt caagttgagc       300
ggtaaccata cctttgacac cactcaatcc aagtataaac taccacatga catgagaacc       360
actaagcacc aagaggagtt atggtccttt attgccgact ctttgaagga ctttatggtc       420
gagcaagaat tgctaaacac caaggacacc ttaccattag gtttcacctt ctcgtaccca       480
gcttcccaaa acaagattaa cgaaggtatt ttgcaaagat ggaccaaggg tttcgatatt       540
ccaaatgtcg aaggccacga tgtcgtccca ttgctacaaa acgaaatttc caagagagag       600
```

-continued

```
ttgcctattg aaattgtagc attgattaat gatactgttg gtactttaat tgcctcatac    660
tacactgacc cagagactaa gatgggtgtg attttcggta ctggtgtcaa cggtgctttc    720
tatgatgttg tttccgatat cgaaaagttg gagggcaaat tagcagacga tattccaagt    780
aactctccaa tggctatcaa ttgtgaatat ggttccttcg ataatgaaca tttggtcttg    840
ccaagaacca agtacgatgt tgctgtcgac gaacaatctc aagacctggt caacaagct    900
tttgaaaaga tgacctccgg ttactacttg ggtgaattgt tgcgtctagt gttacttgaa    960
ttaaacgaga agggcttgat gttgaaggat caagatctaa gcaagttgaa acaaccatac   1020
atcatggata cctcctaccc agcaagaatc gaggatgatc catttgaaaa cttggaagat   1080
actgatgaca tcttccaaaa ggactttggt gtcaagacca ctctgccaga acgtaagttg   1140
attagaaagac tttgtgaatt gatcggtacc agagctgcta gattagctgt ttgtggtatt   1200
gccgctattt gccaaaagag aggttacaag actggtcaca ttgccgctga cggttctgtc   1260
tataacaaat acccaggttt caaggaagcc gccgctaagg gtttgagaga tatctatgga   1320
tggactggtg acgcaagcaa agatccaatt acgattgttc cagctgagga tggttcaggt   1380
gcaggtgctg ctgttattgc tgcattgtcc gaaaaaagaa ttgccgaagg taagtctctt   1440
ggtatcattg gcgcttaa                                                 1458
```

<210> SEQ ID NO 54
<211> LENGTH: 485
<212> TYPE: PRT
<213> ORGANISM: Saccharomyces cerevisiae

<400> SEQUENCE: 54

```
Met Val His Leu Gly Pro Lys Lys Pro Gln Ala Arg Lys Gly Ser Met
1               5                   10                  15

Ala Asp Val Pro Lys Glu Leu Met Asp Glu Ile His Gln Leu Glu Asp
                20                  25                  30

Met Phe Thr Val Asp Ser Glu Thr Leu Arg Lys Val Val Lys His Phe
            35                  40                  45

Ile Asp Glu Leu Asn Lys Gly Leu Thr Lys Lys Gly Gly Asn Ile Pro
        50                  55                  60

Met Ile Pro Gly Trp Val Met Glu Phe Pro Thr Gly Lys Glu Ser Gly
65                  70                  75                  80

Asn Tyr Leu Ala Ile Asp Leu Gly Gly Thr Asn Leu Arg Val Val Leu
                85                  90                  95

Val Lys Leu Ser Gly Asn His Thr Phe Asp Thr Thr Gln Ser Lys Tyr
            100                 105                 110

Lys Leu Pro His Asp Met Arg Thr Thr Lys His Gln Glu Glu Leu Trp
        115                 120                 125

Ser Phe Ile Ala Asp Ser Leu Lys Asp Phe Met Val Glu Gln Glu Leu
    130                 135                 140

Leu Asn Thr Lys Asp Thr Leu Pro Leu Gly Phe Thr Phe Ser Tyr Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Val Glu Gly His Asp Val Val Pro Leu Leu
            180                 185                 190

Gln Asn Glu Ile Ser Lys Arg Glu Leu Pro Ile Glu Ile Val Ala Leu
        195                 200                 205

Ile Asn Asp Thr Val Gly Thr Leu Ile Ala Ser Tyr Tyr Thr Asp Pro
```

Glu Thr Lys Met Gly Val Ile Phe Gly Thr Gly Val Asn Gly Ala Phe
225                 230                 235                 240

Tyr Asp Val Val Ser Asp Ile Glu Lys Leu Glu Gly Lys Leu Ala Asp
            245                 250                 255

Asp Ile Pro Ser Asn Ser Pro Met Ala Ile Asn Cys Glu Tyr Gly Ser
        260                 265                 270

Phe Asp Asn Glu His Leu Val Leu Pro Arg Thr Lys Tyr Asp Val Ala
        275                 280                 285

Val Asp Glu Gln Ser Pro Arg Pro Gly Gln Gln Ala Phe Glu Lys Met
290                 295                 300

Thr Ser Gly Tyr Tyr Leu Gly Glu Leu Leu Arg Leu Val Leu Leu Glu
305                 310                 315                 320

Leu Asn Glu Lys Gly Leu Met Leu Lys Asp Gln Asp Leu Ser Lys Leu
                325                 330                 335

Lys Gln Pro Tyr Ile Met Asp Thr Ser Tyr Pro Ala Arg Ile Glu Asp
                340                 345                 350

Asp Pro Phe Glu Asn Leu Glu Asp Thr Asp Ile Phe Gln Lys Asp
        355                 360                 365

Phe Gly Val Lys Thr Thr Leu Pro Glu Arg Lys Leu Ile Arg Arg Leu
        370                 375                 380

Cys Glu Leu Ile Gly Thr Arg Ala Ala Arg Leu Ala Val Cys Gly Ile
385                 390                 395                 400

Ala Ala Ile Cys Gln Lys Arg Gly Tyr Lys Thr Gly His Ile Ala Ala
                405                 410                 415

Asp Gly Ser Val Tyr Asn Lys Tyr Pro Gly Phe Lys Glu Ala Ala Ala
                420                 425                 430

Lys Gly Leu Arg Asp Ile Tyr Gly Trp Thr Gly Asp Ala Ser Lys Asp
                435                 440                 445

Pro Ile Thr Ile Val Pro Ala Glu Asp Gly Ser Gly Ala Gly Ala Ala
            450                 455                 460

Val Ile Ala Ala Leu Ser Glu Lys Arg Ile Ala Glu Gly Lys Ser Leu
465                 470                 475                 480

Gly Ile Ile Gly Ala
                485

<210> SEQ ID NO 55
<211> LENGTH: 1461
<212> TYPE: DNA
<213> ORGANISM: Saccharomyces cerevisiae

<400> SEQUENCE: 55
atggttcatt taggtccaaa aaaaccacaa gccagaaagg gttccatggc cgatgtgcca      60
aaggaattga tgcaacaaat tgagaatttt gaaaaatttt tcactgttcc aactgaaact     120
ttacaagccg ttaccaagca cttcatttcc gaattggaaa agggtttgtc caagaagggt     180
ggtaacattc caatgattcc aggttgggtt atggatttcc caactggtaa ggaatccggt     240
gatttcttgg ccattgattt gggtggtacc aacttgagag ttgtcttagt caagttgggc     300
ggtgaccgta cctttgacac cactcaatct aagtacagat accagatgc tatgagaact     360 actcaaaatc cagacgaatt gtgggaattt attgccgact ctttgaaagc ttttattgat     420
gagcaattcc cacaaggtat ctctgagcca attccattgg gttcaccctt ttctttccca     480
gcttctcaaa acaaaatcaa tgaaggtatc ttgcaaagat ggactaaagg ttttgatatt     540

```
ccaaacattg aaaaccacga tgttgttcca atgttgcaaa agcaaatcac taagaggaat    600
atcccaattg aagttgttgc tttgataaac gacactaccg gtactttggt tgcttcttac    660
tacactgacc cagaaactaa gatgggtgtt atcttcggta ctggtgtcaa tggtgcttac    720
tacgatgttt gttccgatat cgaaaagcta caaggaaaac tatctgatga cattccacca    780
tctgctccaa tggccatcaa ctgtgaatac ggttccttcg ataatgaaca tgtcgttttg    840
ccaagaacta aatacgatat caccattgat gaagaatctc caagaccagg ccaacaaacc    900
tttgaaaaaa tgtcttctgg ttactactta ggtgaaattt gcgtttggc cttgatggac     960 atgtacaaac aaggtttcat cttcaagaac caagacttgt ctaagttcga caagcctttc   1020
gtcatggaca cttcttaccc agccagaatc gaggaagatc cattcgagaa cctagaagat   1080
accgatgact tgttccaaaa tgagttcggt atcaacacta ctgttcaaga acgtaaattg   1140
atcagacgtt tatctgaatt gattggtgct agagctgcta gattgtccgt tgtggtatt    1200 gctgctatct gtcaaaagag aggttacaag accggtcaca tcgctgcaga cggttccgtt   1260
tacaacagat acccaggttt caagaaaaag gctgccaatg ctttgaagga catttacggc   1320
tggactcaaa cctcactaga cgactaccca atcaagattg ttcctgctga agatggttcc   1380
ggtgctggtg ccgctgttat tgctgctttg gcccaaaaaa gaattgctga aggtaagtcc   1440
gttggtatca tcggtgctta a                                              1461

<210> SEQ ID NO 56
<211> LENGTH: 486
<212> TYPE: PRT
<213> ORGANISM: Saccharomyces cerevisiae

<400> SEQUENCE: 56

Met Val His Leu Gly Pro Lys Lys Pro Gln Ala Arg Lys Gly Ser Met
1               5                   10                  15

Ala Asp Val Pro Lys Glu Leu Met Gln Gln Ile Glu Asn Phe Glu Lys
            20                  25                  30

Ile Phe Thr Val Pro Thr Glu Thr Leu Gln Ala Val Thr Lys His Phe
        35                  40                  45

Ile Ser Glu Leu Glu Lys Gly Leu Ser Lys Lys Gly Gly Asn Ile Pro
    50                  55                  60

Met Ile Pro Gly Trp Val Met Asp Phe Pro Thr Gly Lys Glu Ser Gly
65                  70                  75                  80

Asp Phe Leu Ala Ile Asp Leu Gly Gly Thr Asn Leu Arg Val Val Leu
                85                  90                  95

Val Lys Leu Gly Gly Asp Arg Thr Phe Asp Thr Thr Gln Ser Lys Tyr
            100                 105                 110

Arg Leu Pro Asp Ala Met Arg Thr Thr Gln Asn Pro Asp Glu Leu Trp
        115                 120                 125

Glu Phe Ile Ala Asp Ser Leu Lys Ala Phe Ile Asp Glu Gln Phe Pro
    130                 135                 140

Gln Gly Ile Ser Glu Pro Ile Pro Leu Gly Phe Thr Phe Ser Phe Pro
145                 150                 155                 160

Ala Ser Gln Asn Lys Ile Asn Glu Gly Ile Leu Gln Arg Trp Thr Lys
                165                 170                 175

Gly Phe Asp Ile Pro Asn Ile Glu Asn His Asp Val Val Pro Met Leu
            180                 185                 190

Gln Lys Gln Ile Thr Lys Arg Asn Ile Pro Ile Glu Val Val Ala Leu
        195                 200                 205
```

```
Ile Asn Asp Thr Thr Gly Thr Leu Val Ala Ser Tyr Tyr Thr Asp Pro
    210                 215                 220
Glu Thr Lys Met Gly Val Ile Phe Gly Thr Gly Val Asn Gly Ala Tyr
225                 230                 235                 240
Tyr Asp Val Cys Ser Asp Ile Glu Lys Leu Gln Gly Lys Leu Ser Asp
                245                 250                 255
Asp Ile Pro Pro Ser Ala Pro Met Ala Ile Asn Cys Glu Tyr Gly Ser
            260                 265                 270
Phe Asp Asn Glu His Val Val Leu Pro Arg Thr Lys Tyr Asp Ile Thr
        275                 280                 285
Ile Asp Glu Glu Ser Pro Arg Pro Gly Gln Gln Thr Phe Glu Lys Met
    290                 295                 300
Ser Ser Gly Tyr Tyr Leu Gly Glu Ile Leu Arg Leu Ala Leu Met Asp
305                 310                 315                 320
Met Tyr Lys Gln Gly Phe Ile Phe Lys Asn Gln Asp Leu Ser Lys Phe
                325                 330                 335
Asp Lys Pro Phe Val Met Asp Thr Ser Tyr Pro Ala Arg Ile Glu Glu
            340                 345                 350
Asp Pro Phe Glu Asn Leu Glu Asp Thr Asp Asp Leu Phe Gln Asn Glu
        355                 360                 365
Phe Gly Ile Asn Thr Thr Val Gln Glu Arg Lys Leu Ile Arg Arg Leu
    370                 375                 380
Ser Glu Leu Ile Gly Ala Arg Ala Ala Arg Leu Ser Val Cys Gly Ile
385                 390                 395                 400
Ala Ala Ile Cys Gln Lys Arg Gly Tyr Lys Thr Gly His Ile Ala Ala
                405                 410                 415
Asp Gly Ser Val Tyr Asn Arg Tyr Pro Gly Phe Lys Glu Lys Ala Ala
            420                 425                 430
Asn Ala Leu Lys Asp Ile Tyr Gly Trp Thr Gln Thr Ser Leu Asp Asp
        435                 440                 445
Tyr Pro Ile Lys Ile Val Pro Ala Glu Asp Gly Ser Gly Ala Gly Ala
    450                 455                 460
Ala Val Ile Ala Ala Leu Ala Gln Lys Arg Ile Ala Glu Gly Lys Ser
465                 470                 475                 480
Val Gly Ile Ile Gly Ala
                485

<210> SEQ ID NO 57
<211> LENGTH: 1164
<212> TYPE: DNA
<213> ORGANISM: Klebsiella pneumoniae

<400> SEQUENCE: 57
atgagctatc gtatgtttga ttatctggtg ccaaacgtta acttttttgg ccccaacgcc    60
atttccgtag tcggcgaacg ctgccagctg ctggggggga aaaagcccct gctggtcacc   120
gacaaaggcc tgcgggcaat taagatggc gcagtggaca aaaccctgca ttatctgcgg    180
gaggccggga tcgaggtggc gatctttgac ggcgtcgagc cgaacccgaa agacaccaac   240
gtgcgcgacg gcctcgccgt gtttcgccgc gaacagtgcg acatcatcgt caccgtgggc   300
ggcggcagcc gcacgattg cggcaaaggc atcggcatcg ccgccaccca tgagggcgat   360
ctgtaccagt atgccggaat cgagaccctg accaacccgc tgccgcctat cgtcgcggtc   420
aataccaccg ccggcaccgc cagcgaggtc accgccact gcgtcctgac caacaccgaa   480
accaaagtga agtttgtgat cgtcagctgg cgcaacctgc cgtcggtctc tatcaacgat   540
```

-continued

```
ccgctgctga tgatcggtaa accggccgcc ctgaccgcgg cgaccgggat ggatgccctg    600
acccacgccg tagaggccta tatctccaaa gacgctaacc cggtgacgga cgccgccgcc    660
atgcaggcga tccgcctcat cgcccgcaac ctgcgccagg ccgtggccct cggcagcaat    720
ctgcaggcgc gggaaaacat ggcctatgcc tctctgctgg ccgggatggc tttcaataac    780
gccaacctcg gctacgtgca cgccatggcg caccagctgg cggcctgta cgacatgccg    840 cacggcgtgg ccaacgctgt cctgctgccg catgtggccc gctacaacct gatcgccaac    900
ccggagaaat cgccgatat cgctgaactg atgggcgaaa atatcaccgg actgtccact    960 ctcgacgcg cggaaaaagc catcgccgct atcacgcgtc tgtcgatgga tatcggtatt   1020
ccgcagcatc tgcgcgatct gggagtaaaa gaggccgact tcccctacat ggcggagatg   1080
gctctgaaag acggcaatgc gttctcgaac ccgcgtaaag caacgagca ggagattgcc   1140 gcgattttcc gccaggcatt ctga                                         1164
```

<210> SEQ ID NO 58
<211> LENGTH: 387
<212> TYPE: PRT
<213> ORGANISM: Klebsiella pneumoniae

<400> SEQUENCE: 58

```
Met Ser Tyr Arg Met Phe Asp Tyr Leu Val Pro Asn Val Asn Phe Phe
1               5                   10                  15

Gly Pro Asn Ala Ile Ser Val Val Gly Glu Arg Cys Gln Leu Leu Gly
                20                  25                  30

Gly Lys Lys Ala Leu Leu Val Thr Asp Lys Gly Leu Arg Ala Ile Lys
            35                  40                  45

Asp Gly Ala Val Asp Lys Thr Leu His Tyr Leu Arg Glu Ala Gly Ile
        50                  55                  60

Glu Val Ala Ile Phe Asp Gly Val Glu Pro Asn Pro Lys Asp Thr Asn
65                  70                  75                  80

Val Arg Asp Gly Leu Ala Val Phe Arg Arg Glu Gln Cys Asp Ile Ile
                85                  90                  95

Val Thr Val Gly Gly Gly Ser Pro His Asp Cys Gly Lys Gly Ile Gly
            100                 105                 110

Ile Ala Ala Thr His Glu Gly Asp Leu Tyr Gln Tyr Ala Gly Ile Glu
        115                 120                 125

Thr Leu Thr Asn Pro Leu Pro Pro Ile Val Ala Val Asn Thr Thr Ala
    130                 135                 140

Gly Thr Ala Ser Glu Val Thr Arg His Cys Val Leu Thr Asn Thr Glu
145                 150                 155                 160

Thr Lys Val Lys Phe Val Ile Val Ser Trp Arg Asn Leu Pro Ser Val
                165                 170                 175

Ser Ile Asn Asp Pro Leu Leu Met Ile Gly Lys Pro Ala Ala Leu Thr
            180                 185                 190

Ala Ala Thr Gly Met Asp Ala Leu Thr His Ala Val Glu Ala Tyr Ile
        195                 200                 205

Ser Lys Asp Ala Asn Pro Val Thr Asp Ala Ala Met Gln Ala Ile
    210                 215                 220

Arg Leu Ile Ala Arg Asn Leu Arg Gln Ala Val Ala Leu Gly Ser Asn
225                 230                 235                 240

Leu Gln Ala Arg Glu Asn Met Ala Tyr Ala Ser Leu Leu Ala Gly Met
                245                 250                 255
```

```
                    Ala Phe Asn Asn Ala Asn Leu Gly Tyr Val His Ala Met Ala His Gln
                                    260                 265                 270

Leu Gly Gly Leu Tyr Asp Met Pro His Gly Val Ala Asn Ala Val Leu
                                275                 280                 285

Leu Pro His Val Ala Arg Tyr Asn Leu Ile Ala Asn Pro Glu Lys Phe
                            290                 295                 300

Ala Asp Ile Ala Glu Leu Met Gly Glu Asn Ile Thr Gly Leu Ser Thr
                    305                 310                 315                 320

Leu Asp Ala Ala Glu Lys Ala Ile Ala Ile Thr Arg Leu Ser Met
                                        325                 330                 335

Asp Ile Gly Ile Pro Gln His Leu Arg Asp Leu Gly Val Lys Glu Ala
                                    340                 345                 350

Asp Phe Pro Tyr Met Ala Glu Met Ala Leu Lys Asp Gly Asn Ala Phe
                                355                 360                 365

Ser Asn Pro Arg Lys Gly Asn Glu Gln Glu Ile Ala Ala Ile Phe Arg
                            370                 375                 380

Gln Ala Phe
                    385

<210> SEQ ID NO 59
                    <211> LENGTH: 1824
                    <212> TYPE: DNA
                    <213> ORGANISM: Klebsiella pneumoniae
                    <220> FEATURE:
                    <221> NAME/KEY: CDS
                    <222> LOCATION: (1)..(1824)

<400> SEQUENCE: 59 atg ccg tta ata gcc ggg att gat atc ggc aac gcc acc acc gag gtg       48
                    Met Pro Leu Ile Ala Gly Ile Asp Ile Gly Asn Ala Thr Thr Glu Val
                    1               5                   10                  15 gcg ctg gcg tcc gac tac ccg cag gcg agg gcg ttt gtt gcc agc ggg       96
                    Ala Leu Ala Ser Asp Tyr Pro Gln Ala Arg Ala Phe Val Ala Ser Gly
                                    20                  25                  30 atc gtc gcg acg acg ggc atg aaa ggg acg cgg gac aat atc gcc ggg      144
                    Ile Val Ala Thr Thr Gly Met Lys Gly Thr Arg Asp Asn Ile Ala Gly
                                35                  40                  45 acc ctc gcc gcg ctg gag cag gcc ctg gcg aaa aca ccg tgg tcg atg      192
                    Thr Leu Ala Ala Leu Glu Gln Ala Leu Ala Lys Thr Pro Trp Ser Met
                            50                  55                  60 agc gat gtc tct cgc atc tat ctt aac gaa gcc gcg ccg gtg att ggc      240
                    Ser Asp Val Ser Arg Ile Tyr Leu Asn Glu Ala Ala Pro Val Ile Gly
                    65                  70                  75                  80 gat gtg gcg atg gag acc atc acc gag acc att atc acc gaa tcg acc      288
                    Asp Val Ala Met Glu Thr Ile Thr Glu Thr Ile Ile Thr Glu Ser Thr
                                    85                  90                  95 atg atc ggt cat aac ccg cag acg ccg ggg gtg ggc gtt ggc gtg      336
                    Met Ile Gly His Asn Pro Gln Thr Pro Gly Val Gly Val Gly Val
                                100                 105                 110 ggg acg act atc gcc ctc ggg cgg ctg gcg acg ctg ccg gcg gcg cag      384
                    Gly Thr Thr Ile Ala Leu Gly Arg Leu Ala Thr Leu Pro Ala Ala Gln
                                115                 120                 125 tat gcc gag ggg tgg atc gta ctg att gac gac gcc gtc gat ttc ctt      432
                    Tyr Ala Glu Gly Trp Ile Val Leu Ile Asp Asp Ala Val Asp Phe Leu
                            130                 135                 140 gac gcc gtg tgg tgg ctc aat gag gcg ctc gac cgg ggg atc aac gtg      480
                    Asp Ala Val Trp Trp Leu Asn Glu Ala Leu Asp Arg Gly Ile Asn Val
                    145                 150                 155                 160 gtg gcg gcg atc ctc aaa aag gac gac ggc gtg ctg gtg aac aac cgc      528
```

```
                Val Ala Ala Ile Leu Lys Lys Asp Asp Gly Val Leu Val Asn Asn Arg
                            165                 170                 175 ctg cgt aaa acc ctg ccg gtg gtg gat gaa gtg acg ctg ctg gag cag      576
Leu Arg Lys Thr Leu Pro Val Val Asp Glu Val Thr Leu Leu Glu Gln
            180                 185                 190 gtc ccc gag ggg gta atg gcg gcg gtg gaa gtg gcc gcg ccg ggc cag      624
Val Pro Glu Gly Val Met Ala Ala Val Glu Val Ala Ala Pro Gly Gln
        195                 200                 205 gtg gtg cgg atc ctg tcg aat ccc tac ggg atc gcc acc ttc ttc ggg      672
Val Val Arg Ile Leu Ser Asn Pro Tyr Gly Ile Ala Thr Phe Phe Gly
    210                 215                 220 cta agc ccg gaa gag acc cag gcc atc gtc ccc atc gcc cgc gcc ctg      720
Leu Ser Pro Glu Glu Thr Gln Ala Ile Val Pro Ile Ala Arg Ala Leu
225                 230                 235                 240 att ggc aac cgt tcc gcg gtg gtg ctc aag acc ccg cag ggg gat gtg      768
Ile Gly Asn Arg Ser Ala Val Val Leu Lys Thr Pro Gln Gly Asp Val
            245                 250                 255 cag tcg cgg gtg atc ccg gcg ggc aac ctc tac att agc ggc gaa aag      816
Gln Ser Arg Val Ile Pro Ala Gly Asn Leu Tyr Ile Ser Gly Glu Lys
        260                 265                 270 cgc cgc gga gag gcc gat gtc gcc gag ggc gcg gaa gcc atc atg cag      864
Arg Arg Gly Glu Ala Asp Val Ala Glu Gly Ala Glu Ala Ile Met Gln
    275                 280                 285 gcg atg agc gcc tgc gct ccg gta cgc gac atc cgc ggc gaa ccg ggc      912
Ala Met Ser Ala Cys Ala Pro Val Arg Asp Ile Arg Gly Glu Pro Gly
290                 295                 300 acc cac gcc ggc ggc atg ctt gag cgg gtg cgc aag gta atg gcg tcc      960
Thr His Ala Gly Gly Met Leu Glu Arg Val Arg Lys Val Met Ala Ser
305                 310                 315                 320 ctg acc ggc cat gag atg agc gcg ata tac atc cag gat ctg ctg gcg     1008
Leu Thr Gly His Glu Met Ser Ala Ile Tyr Ile Gln Asp Leu Leu Ala
            325                 330                 335 gtg gat acg ttt att ccg cgc aag gtg cag ggc ggg atg gcc ggc gag     1056
Val Asp Thr Phe Ile Pro Arg Lys Val Gln Gly Gly Met Ala Gly Glu
        340                 345                 350 tgc gcc atg gag aat gcc gtc ggg atg gcg gcg atg gtg aaa gcg gat     1104
Cys Ala Met Glu Asn Ala Val Gly Met Ala Ala Met Val Lys Ala Asp
    355                 360                 365 cgt ctg caa atg cag gtt atc gcc cgc gaa ctg agc gcc cga ctg cag     1152
Arg Leu Gln Met Gln Val Ile Ala Arg Glu Leu Ser Ala Arg Leu Gln
370                 375                 380 acc gag gtg gtg gtg ggc ggc gtg gag gcc aac atg gcc atc gcc ggg     1200
Thr Glu Val Val Val Gly Gly Val Glu Ala Asn Met Ala Ile Ala Gly
385                 390                 395                 400 gcg tta acc act ccc ggc tgt gcg gcg ccg ctg gcg atc ctc gac ctc     1248
Ala Leu Thr Thr Pro Gly Cys Ala Ala Pro Leu Ala Ile Leu Asp Leu
            405                 410                 415 ggc gcc ggc tcg acg gat gcg gcg atc gtc aac gcg gag ggg cag ata     1296
Gly Ala Gly Ser Thr Asp Ala Ala Ile Val Asn Ala Glu Gly Gln Ile
        420                 425                 430 acg gcg gtc cat ctc gcc ggg gcg ggg aat atg gtc agc ctg ttg att     1344
Thr Ala Val His Leu Ala Gly Ala Gly Asn Met Val Ser Leu Leu Ile
    435                 440                 445 aaa acc gag ctg ggc ctc gag gat ctt tcg ctg gcg gaa gcg ata aaa     1392
Lys Thr Glu Leu Gly Leu Glu Asp Leu Ser Leu Ala Glu Ala Ile Lys
450                 455                 460 aaa tac ccg ctg gcc aaa gtg gaa agc ctg ttc agt att cgt cac gag     1440
Lys Tyr Pro Leu Ala Lys Val Glu Ser Leu Phe Ser Ile Arg His Glu
465                 470                 475                 480
```

| | | | | | | | | | | | | | | | |
|---|---|---|---|---|---|---|---|---|---|---|---|---|---|---|---|
| aat | ggc | gcg | gtg | gag | ttc | ttt | cgg | gaa | gcc | ctc | agc | ccg | gcg | gtg | ttc | 1488
| Asn | Gly | Ala | Val | Glu | Phe | Phe | Arg | Glu | Ala | Leu | Ser | Pro | Ala | Val | Phe |
| | | | 485 | | | | | 490 | | | | | 495 | | |

| | | | | | | | | | | | | | | | |
|---|---|---|---|---|---|---|---|---|---|---|---|---|---|---|---|
| gcc | aaa | gtg | gtg | tac | atc | aag | gag | ggc | gaa | ctg | gtg | ccg | atc | gat | aac | 1536
| Ala | Lys | Val | Val | Tyr | Ile | Lys | Glu | Gly | Glu | Leu | Val | Pro | Ile | Asp | Asn |
| | 500 | | | | | 505 | | | | | 510 | | | | |

| | | | | | | | | | | | | | | | |
|---|---|---|---|---|---|---|---|---|---|---|---|---|---|---|---|
| gcc | agc | ccg | ctg | gaa | aaa | att | cgt | ctc | gtg | cgc | cgg | cag | gcg | aaa | gag | 1584
| Ala | Ser | Pro | Leu | Glu | Lys | Ile | Arg | Leu | Val | Arg | Arg | Gln | Ala | Lys | Glu |
| | | 515 | | | | | 520 | | | | | 525 | | | |

| | | | | | | | | | | | | | | | |
|---|---|---|---|---|---|---|---|---|---|---|---|---|---|---|---|
| aaa | gtg | ttt | gtc | acc | aac | tgc | ctg | cgc | gcg | ctg | cgc | cag | gtc | tca | ccc | 1632
| Lys | Val | Phe | Val | Thr | Asn | Cys | Leu | Arg | Ala | Leu | Arg | Gln | Val | Ser | Pro |
| 530 | | | | | 535 | | | | | 540 | | | | | |

| | | | | | | | | | | | | | | | |
|---|---|---|---|---|---|---|---|---|---|---|---|---|---|---|---|
| ggc | ggt | tcc | att | cgc | gat | atc | gcc | ttt | gtg | gtg | ctg | gtg | ggc | ggc | tca | 1680
| Gly | Gly | Ser | Ile | Arg | Asp | Ile | Ala | Phe | Val | Val | Leu | Val | Gly | Gly | Ser |
| 545 | | | | 550 | | | | | 555 | | | | | | 560 |

| | | | | | | | | | | | | | | | |
|---|---|---|---|---|---|---|---|---|---|---|---|---|---|---|---|
| tcg | ctg | gac | ttt | gag | atc | ccg | cag | ctt | atc | acg | gaa | gcc | ttg | tcg | cac | 1728
| Ser | Leu | Asp | Phe | Glu | Ile | Pro | Gln | Leu | Ile | Thr | Glu | Ala | Leu | Ser | His |
| | | | 565 | | | | | 570 | | | | | 575 | | |

| | | | | | | | | | | | | | | | |
|---|---|---|---|---|---|---|---|---|---|---|---|---|---|---|---|
| tat | ggc | gtg | gtc | gcc | ggg | cag | ggc | aat | att | cgg | gga | aca | gaa | ggg | ccg | 1776
| Tyr | Gly | Val | Val | Ala | Gly | Gln | Gly | Asn | Ile | Arg | Gly | Thr | Glu | Gly | Pro |
| | | | 580 | | | | | 585 | | | | | 590 | | |

| | | | | | | | | | | | | | | | |
|---|---|---|---|---|---|---|---|---|---|---|---|---|---|---|---|
| cgc | aat | gcg | gtc | gcc | acc | ggg | ctg | cta | ctg | gcc | ggt | cag | gcg | aat | taa | 1824
| Arg | Asn | Ala | Val | Ala | Thr | Gly | Leu | Leu | Leu | Ala | Gly | Gln | Ala | Asn | |
| | 595 | | | | 600 | | | | | 605 | | | | | |

<210> SEQ ID NO 60
<211> LENGTH: 607
<212> TYPE: PRT
<213> ORGANISM: Klebsiella pneumoniae

<400> SEQUENCE: 60

Met Pro Leu Ile Ala Gly Ile Asp Ile Gly Asn Ala Thr Thr Glu Val
1               5                   10                  15

Ala Leu Ala Ser Asp Tyr Pro Gln Ala Arg Ala Phe Val Ala Ser Gly
            20                  25                  30

Ile Val Ala Thr Thr Gly Met Lys Gly Thr Arg Asp Asn Ile Ala Gly
        35                  40                  45

Thr Leu Ala Ala Leu Glu Gln Ala Leu Ala Lys Thr Pro Trp Ser Met
    50                  55                  60

Ser Asp Val Ser Arg Ile Tyr Leu Asn Glu Ala Ala Pro Val Ile Gly
65                  70                  75                  80

Asp Val Ala Met Glu Thr Ile Thr Glu Thr Ile Ile Thr Glu Ser Thr
                85                  90                  95

Met Ile Gly His Asn Pro Gln Thr Pro Gly Gly Val Gly Val Gly Val
            100                 105                 110

Gly Thr Thr Ile Ala Leu Gly Arg Leu Ala Thr Leu Pro Ala Ala Gln
        115                 120                 125

Tyr Ala Glu Gly Trp Ile Val Leu Ile Asp Asp Ala Val Asp Phe Leu
    130                 135                 140

Asp Ala Val Trp Trp Leu Asn Glu Ala Leu Asp Arg Gly Ile Asn Val
145                 150                 155                 160

Val Ala Ala Ile Leu Lys Lys Asp Asp Gly Val Leu Val Asn Asn Arg
                165                 170                 175

Leu Arg Lys Thr Leu Pro Val Val Asp Glu Val Thr Leu Leu Glu Gln
            180                 185                 190

Val Pro Glu Gly Val Met Ala Ala Val Glu Val Ala Ala Pro Gly Gln
        195                 200                 205

```
Val Val Arg Ile Leu Ser Asn Pro Tyr Gly Ile Ala Thr Phe Phe Gly
    210                 215                 220
Leu Ser Pro Glu Glu Thr Gln Ala Ile Val Pro Ile Ala Arg Ala Leu
225                 230                 235                 240
Ile Gly Asn Arg Ser Ala Val Val Leu Lys Thr Pro Gln Gly Asp Val
                245                 250                 255
Gln Ser Arg Val Ile Pro Ala Gly Asn Leu Tyr Ile Ser Gly Glu Lys
                260                 265                 270
Arg Arg Gly Glu Ala Asp Val Ala Glu Gly Ala Glu Ala Ile Met Gln
            275                 280                 285
Ala Met Ser Ala Cys Ala Pro Val Arg Asp Ile Arg Gly Glu Pro Gly
290                 295                 300
Thr His Ala Gly Gly Met Leu Glu Arg Val Arg Lys Val Met Ala Ser
305                 310                 315                 320
Leu Thr Gly His Glu Met Ser Ala Ile Tyr Ile Gln Asp Leu Leu Ala
                325                 330                 335
Val Asp Thr Phe Ile Pro Arg Lys Val Gln Gly Gly Met Ala Gly Glu
                340                 345                 350
Cys Ala Met Glu Asn Ala Val Gly Met Ala Ala Met Val Lys Ala Asp
            355                 360                 365
Arg Leu Gln Met Gln Val Ile Ala Arg Glu Leu Ser Ala Arg Leu Gln
370                 375                 380
Thr Glu Val Val Val Gly Val Glu Ala Asn Met Ala Ile Ala Gly
385                 390                 395                 400
Ala Leu Thr Thr Pro Gly Cys Ala Ala Pro Leu Ala Ile Leu Asp Leu
                405                 410                 415
Gly Ala Gly Ser Thr Asp Ala Ala Ile Val Asn Ala Glu Gly Gln Ile
                420                 425                 430
Thr Ala Val His Leu Ala Gly Ala Gly Asn Met Val Ser Leu Leu Ile
            435                 440                 445
Lys Thr Glu Leu Gly Leu Glu Asp Leu Ser Leu Ala Glu Ala Ile Lys
450                 455                 460
Lys Tyr Pro Leu Ala Lys Val Glu Ser Leu Phe Ser Ile Arg His Glu
465                 470                 475                 480
Asn Gly Ala Val Glu Phe Phe Arg Glu Ala Leu Ser Pro Ala Val Phe
                485                 490                 495
Ala Lys Val Val Tyr Ile Lys Glu Gly Glu Leu Val Pro Ile Asp Asn
                500                 505                 510
Ala Ser Pro Leu Glu Lys Ile Arg Leu Val Arg Arg Gln Ala Lys Glu
            515                 520                 525
Lys Val Phe Val Thr Asn Cys Leu Arg Ala Leu Arg Gln Val Ser Pro
530                 535                 540
Gly Gly Ser Ile Arg Asp Ile Ala Phe Val Val Leu Val Gly Gly Ser
545                 550                 555                 560
Ser Leu Asp Phe Glu Ile Pro Gln Leu Ile Thr Glu Ala Leu Ser His
                565                 570                 575
Tyr Gly Val Val Ala Gly Gln Gly Asn Ile Arg Gly Thr Glu Gly Pro
                580                 585                 590
Arg Asn Ala Val Ala Thr Gly Leu Leu Leu Ala Gly Gln Ala Asn
            595                 600                 605

<210> SEQ ID NO 61
<211> LENGTH: 4146
<212> TYPE: DNA
```

<213> ORGANISM: Escherichia coli

<400> SEQUENCE: 61

```
ggatcccttg cccgctgttg atccgttgtt ccacctgata ttatgttaac ccagtagcca      60
gagtgctcca tgttgcagca cagccactcc gtgggaggca taaagcgaca gttcccgttc     120
ttctggctgc ggatagattc gactactcat caccgcttcc ccgtcgttaa taaatacttc     180
cacggatgat gtatcgataa atatccttag ggcgagcgtg tcacgctgcg ggaggggaat     240
actacggtag ccgtctaaat tctcgtgtgg gtaataccgc cacaaaacaa gtcgctcaga     300
ttggttatca atatacagcc gcattccagt gccgagctgt aatccgtaat gttcggcatc     360
actgttcttc agcgcccact gcaactgaat ctcaactgct tgcgcgtttt cctgcaaaac     420
atatttattg ctgattgtgc ggggagagac agattgatgc tgctggcgta acgactcagc     480
ttcgtgtacc gggcgttgta gaagtttgcc attgctctct gatagctcgc gcgccagcgt     540
catgcagcct gcccatcctt cacgttttga gggcattggc gattcccaca tatccatcca     600
gccgataaca atacgccgac catccttcgc taaaaagctt tgtggtgcat aaaagtcatg     660
cccgttatca agttcagtaa aatgcccgga ttgtgcaaaa agtcgtcctg gcgaccacat     720
tccgggtatt acgccacttt gaaagcgatt tcggtaactg tatccctcgg cattcattcc     780
ctgcggggaa acatcagat aatgctgatc gccaaggctg aaaaagtccg gacattccca     840
catatagctt tcacccgcat cagcgtgggc cagtacgcga tcgaaggtcc attcacgcaa     900
cgaactgccg cgataaagca ggatctgccc cgtgttgcct ggatctttcg ccccgactac     960
catccaccat gtgtcggctt cacgccacac tttaggatcg cggaagtgca tgattccttc    1020
tggtggagtg aggatcacac cctgtttctc gaaatgaata ccatcccgac tggtagccag    1080
acattgtact tcgcgaattg catcgtcatt acctgcacca tcgagccaga cgtgtccggt    1140
gtagataagt gagaggacac cattgtcatc gacagcacta cctgaaaaac acccgtcttt    1200
gtcattatcg tctcctggcg ctagcgcaat aggctcatgc tgccagtgga tcatatcgtc    1260
gctggtggca tgtccccagt gcattggccc ccagtgttcg ctcatcggat gatgttgata    1320
aaacgcgtga taacgatcgt taaccagat caggccgttt ggatcgttca tccacccggc    1380
aggaggcgcg aggtgaaaat ggggatagaa agtgttaccc cggtgctcat gaagttttgc    1440
tagggcgttt tgcgccgcat gcaatcgaga ttgcgtcatt ttaatcatcc tggttaagca    1500
aatttggtga attgttaacg ttaacttta taaaaataaa gtcccttact ttcataaatg    1560
cgatgaatat cacaaatgtt aacgttaact atgacgtttt gtgatcgaat atgcatgttt    1620
tagtaaatcc atgacgattt tgcgaaaaag aggtttatca ctatgcgtaa ctcagatgaa    1680
tttaagggaa aaaatgtca gccaaagtat gggttttagg ggatgcggtc gtagatctct    1740
tgccagaatc agacgggcgc ctactgcctt gtcctggcgg cgcgccagct aacgttgcgg    1800
tgggaatcgc cagattaggc ggaacaagtg ggtttatagg tcgggtgggg gatgatcctt    1860
ttggtgcgtt aatgcaaaga acgctgctaa ctgagggagt cgatatcacg tatctgaagc    1920
aagatgaatg gcaccggaca tccacggtgc ttgtcgatct gaacgatcaa ggggaacgtt    1980
catttacgtt tatggtccgc cccagtgccg atcttttttt agagacgaca gacttgccct    2040
gctggcgaca tggcgaatgg ttacatctct gttcaattgc gttgtctgcc gagccttcgc    2100
gtaccagcgc atttactgcg atgacggcga tccggcatgc cggaggtttt gtcagcttcg    2160
atcctaatat tcgtgaagat ctatggcaag acgagcattt gctccgcttg tgtttgcggc    2220
aggcgctaca actggcggat gtcgtcaagc tctcggaaga agaatggcga cttatcagtg    2280
```

```
gaaaaacaca gaacgatcag gatatatgcg ccctggcaaa agagtatgag atcgccatgc    2340
tgttggtgac taaaggtgca gaaggggtgg tggtctgtta tcgaggacaa gttcaccatt    2400
ttgctggaat gtctgtgaat tgtgtcgata gcacggggc gggagatgcg ttcgttgccg     2460
ggttactcac aggtctgtcc tctacgggat tatctacaga tgagagagaa atgcgacgaa    2520
ttatcgatct cgctcaacgt tgcggagcgc ttgcagtaac ggcgaaaggg gcaatgacag    2580
cgctgccatg tcgacaagaa ctggaatagt gagaagtaaa cggcgaagtc gctcttatct    2640
ctaaatagga cgtgaatttt taacgacag gcaggtaatt atggcactga atattccatt     2700
cagaaatgcg tactatcgtt ttgcatccag ttactcattt ctctttttta tttcctggtc    2760
gctgtggtgg tcgttatacg ctatttggct gaaaggacat ctaggggttga cagggacgga   2820 attaggtaca cttttattcgg tcaaccagtt taccagcatt ctatttatga tgttctacgg   2880
catcgttcag gataaactcg gtctgaagaa accgctcatc tggtgtatga gtttcatcct    2940
ggtcttgacc ggaccgttta tgatttacgt ttatgaaccg ttactgcaaa gcaatttttc    3000
tgtaggtcta attctggggg cgctattttt tggcttgggg tatctggcgg gatgcggttt    3060
gcttgatagc ttcaccgaaa aaatggcgcg aaatttttcat ttcgaatatg gaacagcgcg   3120
cgcctgggga tcttttggct atgctattgg cgcgttcttt gccggcatat ttttttagtat   3180 cagtccccat atcaacttct ggttggtctc gctatttggc gctgtattta tgatgatcaa    3240
catgcgtttt aaagataagg atcaccagtg cgtagcggca gatgcgggag gggtaaaaaa    3300
agaggatttt atcgcagttt tcaaggatcg aaacttctgg gttttcgtca tatttattgt    3360
ggggacgtgg tctttctata acatttttga tcaacaactt tttcctgtct tttattcagg    3420
tttattcgaa tcacacgatg taggaacgcg cctgtatggt tatctcaact cattccaggt    3480
ggtactcgaa gcgctgtgca tggcgattat tccttctctt gtgaatcggg taggggccaaa    3540 aaatgcatta cttatcggag ttgtgattat ggcgttgcgt atcctttcct gcgcgctgtt     3600
cgttaacccc tggattattt cattagtgaa gttgttacat gccattgagg ttccactttg     3660
tgtcatatcc gtcttcaaat acagcgtggc aaactttgat aagcgcctgt cgtcgacgat     3720 cttttctgatt ggttttcaaa ttgccagttc gcttgggatt gtgctgcttt caacgccgac    3780
tgggatactc tttgaccacg caggctacca gacagtttc ttcgcaattt cgggtattgt      3840
ctgcctgatg ttgctattg gcattttctt cttgagtaaa aaacgcgagc aaatagttat      3900
ggaaacgcct gtaccttcag caatatagac gtaaacttt tccggttgtt gtcgatagct      3960
ctatatccct caaccggaaa ataataatag taaaatgctt agccctgcta ataatcgcct     4020
aatccaaacg cctcattcat gttctggtac agtcgctcaa atgtacttca gatgcgcggt     4080
tcgctgattt ccaggacatt gtcgtcattc agtgacctgt cccgtgtatc acggtcctgc     4140
gaattc                                                                4146
```

<210> SEQ ID NO 62
<211> LENGTH: 13669
<212> TYPE: DNA
<213> ORGANISM: Artificial Sequence
<220> FEATURE:
<223> OTHER INFORMATION: Plasmid

<400> SEQUENCE: 62

```
tagtaaagcc ctcgctagat tttaatgcgg atgttgcgat tacttcgcca actattgcga     60
taacaagaaa aagccagcct ttcatgatat atctcccaat ttgtgtaggg cttattatgc    120
```

```
acgcttaaaa ataataaaag cagacttgac ctgatagttt ggctgtgagc aattatgtgc     180
ttagtgcatc taacgcttga gttaagccgc gccgcgaagc ggcgtcggct tgaacgaatt     240
gttagacatt atttgccgac taccttggtg atctcgcctt tcacgtagtg acaaattct     300
tccaactgat ctgcgcgcga ggccaagcga tcttcttctt gtccaagata agcctgtcta     360
gcttcaagta tgacgggctg atactgggcc ggcaggcgct ccattgccca gtcggcagcg     420
acatccttcg gcgcgatttt gccggttact gcgctgtacc aaatgcggga caacgtaagc     480
actacatttc gctcatcgcc agcccagtcg ggcggcgagt tccatagcgt taaggtttca     540
tttagcgcct caaatagatc ctgttcagga accggatcaa agagttcctc cgccgctgga     600
cctaccaagg caacgctatg ttctcttgct tttgtcagca agatagccag atcaatgtcg     660
atcgtggctg gctcgaagat acctgcaaga atgtcattgc gctgccattc tccaaattgc     720
agttcgcgct tagctggata acgccacgga atgatgtcgt cgtgcacaac aatggtgact     780
tctacagcgc ggagaatctc gctctctcca ggggaagccg aagtttccaa aaggtcgttg     840
atcaaagctc gccgcgttgt tcatcaagcc cttacgtcca ccgtaaccag caaatcaata     900
tcactgtgtg gcttcaggcc gccatccact gcggagccgt acaaatgtac ggccagcaac     960
gtcggttcga gatggcgctc gatgacgcca actacctctg atagttgagt cgatacttcg    1020
gcgatcaccg cttccctcat gatgtttaac tttgttttag ggcgactgcc ctgctgcgta    1080
acatcgttgc tgctccataa catcaaacat cgacccacgg cgtaacgcgc ttgctgcttg    1140
gatgcccgag gcatagactg taccccaaaa aaacagtcat aacaagccat gaaaaccgcc    1200
actgcgccgt taccaccgct gcgttcggtc aaggttctgg accagttgcg tgagcgcata    1260
cgctacttgc attacagctt acgaaccgaa caggcttatg tccactgggt tcgtgccttc    1320
atccgtttcc acggtgtgcg tcacccggca accttgggca gcagcgaagt cgaggcattt    1380
ctgtcctggc tggcgaacga gcgcaaggtt tcggtctcca cgcatcgtca ggcattggcg    1440
gccttgctgt tcttctacgg caaggtgctg tgcacggatc tgccctggct tcaggagatc    1500
ggaagacctc ggccgtcgcg gcgcttgccg gtggtgctga ccccggatga agtggttcgc    1560
atcctcggtt ttctggaagg cgagcatcgt ttgttcgccc agcttctgta tggaacgggc    1620
atgcggatca gtgagggttt gcaactgcgg gtcaaggatc tggatttcga tcacggcacg    1680
atcatcgtgc gggagggcaa gggctccaag gatcgggcct tgatgttacc cgagagcttg    1740
gcacccagcc tgcgcgagca ggggaattaa ttcccacggg ttttgctgcc cgcaaacggg    1800
ctgttctggt gttgctagtt tgttatcaga atcgcagatc cggcttcagc cggtttgccg    1860
gctgaaagcg ctatttcttc cagaattgcc atgatttttt ccccacggga ggcgtcactg    1920
gctcccgtgt tgtcggcagc tttgattcga taagcagcat cgcctgtttc aggctgtcta    1980
tgtgtgactg ttgagctgta acaagttgtc tcaggtgttc aatttcatgt tctagttgct    2040
ttgtttttact ggtttcacct gttctattag gtgttacatg ctgttcatct gttacattgt    2100
cgatctgttc atggtgaaca gctttgaatg caccaaaaac tcgtaaaagc tctgatgtat    2160
ctatcttttt tacaccgttt tcatctgtgc atatggacag ttttcccttt gatatgtaac    2220
ggtgaacagt tgttctactt tgttttgtta gtcttgatgc ttcactgata gatacaagag    2280
ccataagaac ctcagatcct tccgtattta gccagtatgt tctctagtgt ggttcgttgt    2340
ttttgcgtga gccatgagaa cgaaccattg agatcatact tactttgcat gtcactcaaa    2400
aattttgcct caaaactggt gagctgaatt tttgcagtta aagcatcgtg tagtgttttt    2460
cttagtccgt tatgtaggta ggaatctgat gtaatggttg ttggtatttt gtcaccattc    2520
```

```
attttttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta aatctttact tattggtttc aaaacccatt ggttaagcct tttaaactca   2700
tggtagttat tttcaagcat taacatgaac ttaaattcat caaggctaat ctctatattt   2760
gccttgtgag ttttcttttg tgttagttct tttaataacc actcataaat cctcatagag   2820
tatttgtttt caaaagactt aacatgttcc agattatatt ttatgaattt ttttaactgg   2880
aaaagataag gcaatatctc ttcactaaaa actaattcta attttttcgct tgagaacttg   2940
gcatagtttg tccactggaa aatctcaaag cctttaacca aaggattcct gatttccaca   3000
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgattttaa tcactatacc aattgagatg ggctagtcaa   3300
tgataattac tagtcctttt cctttgagtt gtgggtatct gtaaattctg ctagacccttt   3360
gctggaaaac ttgtaaattc tgctagaccc tctgtaaatt ccgctagacc tttgtgtgtt   3420
ttttttgttt atattcaagt ggttataatt tatagaataa agaaagaata aaaaagata    3480
aaagaatag atcccagccc tgtgtataac tcactacttt agtcagttcc gcagtattac    3540
aaaggatgt cgcaaacgct gtttgctcct ctacaaaaca gaccttaaaa ccctaaaggc    3600
ttaagtagca ccctcgcaag ctcgggcaaa tcgctgaata ttcctttttgt ctccgaccat  3660
caggcacctg agtcgctgtc ttttcgtga cattcagttc gctgcgctca cggctctggc    3720
agtgaatggg ggtaaatggc actacaggcg ccttttatgg attcatgcaa ggaaactacc   3780
cataatacaa gaaagcccg tcacgggctt ctcagggcgt tttatggcgg gtctgctatg    3840
tggtgctatc tgactttttg ctgttcagca gttcctgccc tctgattttc cagtctgacc   3900
acttcggatt atcccgtgac aggtcattca gactggctaa tgcacccagt aaggcagcgg   3960
tatcatcaac aggcttaccc gtcttactgt cgggaattca tttaaatagt caaaagcctc   4020
cgaccggagg cttttgactg ctaggcgatc tgtgctgttt gccacggtat gcagcaccag   4080
cgcgagatta tgggctcgca cgctcgactg tcggacgggg gcactggaac gagaagtcag   4140
gcgagccgtc acgcccttga caatgccaca tcctgagcaa ataattcaac cactaaacaa   4200
atcaaccgcg tttcccggag gtaaccaagc ttgcgggaga gaatgatgaa caagagccaa   4260
caagttcaga caatcaccct ggccgccgcc cagcaaatgg cggcggcggt ggaaaaaaaa   4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac caacagcgaa ttattatttt tggcggcggc   4560
ctgccagtta tttttaatga gcaggtaatt ggcgccgtcg cgttagcgg cggtacggtc    4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800
atgccggcgc catcaatgag ctgtgctggg ggctggagga gcaggggtc ccctgccaga    4860
```

```
ccataaccta tgacggaggc ggtgacgccg ctgcgctggg cgccctggcg gccagaagct    4920
cgccctgcg ggtgggtatc gggctcagcg cgtccggcga gatagccctc actcatgccc    4980
agctgccggc ggacgcgccg ctggctaccg gacacgtcac cgatagcgac gatcaactgc    5040
gtacgctcgg cgccaacgcc gggcagctgg ttaaagtcct gccgttaagt gagagaaact    5100
gaatgtatcg tatctatacc cgcaccgggg ataaaggcac caccgccctg tacggcggca    5160
gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
ctgcccagct gcacgtggcg cgcacccagt cccgtcggct cgaacgcctg ctgacggcca    5520
tggaccgcgc gcatccgctg cgcgacgcgc tcaaacgcta cagcaatcgc ctgtcggatg    5580
ccctgttctc catggcgcga atcgaagaga ctaggcctga tgcttgcgct tgaactggcc    5640
tagcaaacac agaaaaaagc ccgcacctga cagtgcgggc ttttttttc ctaggcgatc    5700
tgtgctgttt gccacggtat gcagcaccag cgcgagatta tgggctcgca cgctcgactg    5760
tcggacgggg gcactggaac gagaagtcag gcgagccgtc acgcccttga caatgccaca    5820
tcctgagcaa ataattcaac cactaaacaa atcaaccgcg tttcccggag gtaaccaagc    5880
ttcacctttt gagccgatga acaatgaaaa gatcaaaacg atttgcagta ctggcccagc    5940
gcccgtcaa tcaggacggg ctgattggcg agtggcctga agaggggctg atcgccatgg    6000
acagcccctt tgacccggtc tcttcagtaa aagtggacaa cggtctgatc gtcgaactgg    6060
acggcaaacg ccgggaccag tttgacatga tcgaccgatt tatcgccgat tacgcgatca    6120
acgttgagcg cacagagcag gcaatgcgcc tggaggcggt ggaaatagcc cgtatgctgg    6180
tggatattca cgtcagccgg gaggagatca ttgccatcac taccgccatc acgccggcca    6240
aagcggtcga ggtgatggcg cagatgaacg tggtggagat gatgatggcg ctgcagaaga    6300
tgcgtgcccg ccggaccccc tccaaccagt gccacgtcac caatctcaaa gataatccgg    6360
tgcagattgc cgctgacgcc gccgaggccg ggatccgcgg cttctcagaa caggagacca    6420
cggtcggtat cgcgcgctac gcgccgttta acgccctggc gctgttggtc ggttcgcagt    6480
gcggccgccc cggcgtgttg acgcagtgct cggtggaaga ggccaccgag ctggagctgg    6540
gcatgcgtgg cttaaccagc tacgccgaga cggtgtcggt ctacggcacc gaagcggtat    6600
ttaccgacgg cgatgatacg ccgtggtcaa aggcgttcct cgcctcggcc tacgcctccc    6660
gcgggttgaa aatgcgctac acctccggca ccggatccga agcgctgatg gctattcgg    6720
agagcaagtc gatgctctac ctcgaatcgc gctgcatctt cattactaaa ggcgccgggg    6780
ttcagggact gcaaaacggc gcggtgagct gtatcggcat gaccggcgct gtgccgtcgg    6840
gcattcgggc ggtgctggcg gaaaacctga tcgcctctat gctcgacctc gaagtggcgt    6900
ccgccaacga ccagactttc tcccactcgg atattcgccg caccgcgcgc acctgatgc    6960
agatgctgcc gggcaccgac tttatttct ccggctacag cgcggtgccg aactacgaca    7020
acatgttcgc cggctcgaac ttcgatgcgg aagattttga tgattacaac atcctgcagc    7080
gtgacctgat ggttgacggc ggcctgcgtc cggtgaccga gcggaaaacc attgccattc    7140
gccagaaagc ggcgcgggcg atccaggcgg tttttccgcg agctggggctg ccgccaatcg    7200
ccgacgagga ggtggaggcc gccacctacg cgcacggcag caacgagatg ccgccgcgta    7260
```

```
acgtggtgga ggatctgagt gcggtggaag agatgatgaa gcgcaacatc accggcctcg    7320
atattgtcgg cgcgctgagc cgcagcggct ttgaggatat cgccagcaat attctcaata    7380
tgctgcgcca gcgggtcacc ggcgattacc tgcagacctc ggccattctc gatcggcagt    7440
tcgaggtggt gagtgcggtc aacgacatca atgactatca ggggccgggc accggctatc    7500
gcatctctgc cgaacgctgg gcggagatca aaatattcc gggcgtggtt cagcccgaca    7560
ccattgaata aggcggtatt cctgtgcaac agacaaccca aattcagccc tcttttaccc    7620 tgaaacccg cgagggcggg gtagcttctg ccgatgaacg cgccgatgaa gtggtgatcg    7680
gcgtcggccc tgccttcgat aaacaccagc atcacactct gatcgatatg ccccatggcg    7740
cgatcctcaa agagctgatt gccggggtgg aagaagaggg gcttcacgcc cgggtggtgc    7800
gcattctgcg cacgtccgac gtctccttta tggcctggga tgcggccaac ctgagcggct    7860
cggggatcgg catcggtatc cagtcgaagg ggaccacggt catccatcag cgcgatctgc    7920
tgccgctcag caacctggag ctgttctccc aggcgccgct gctgacgctg gagacctacc    7980
ggcagattgg caaaaacgct gcgcgctatg cgcgcaaaga gtcaccttcg ccggtgccgg    8040
tggtgaacga tcagatggtg cggccgaaat ttatggccaa agccgcgcta tttcatatca    8100 agagaccaa acatgtggtg caggacgccg agcccgtcac cctgcacatc gacttagtaa    8160
gggagtgacc atgagcgaga aaaccatgcg cgtgcaggat tatccgttag ccacccgctg    8220
cccggagcat atcctgacgc ctaccggcaa accattgacc gatattaccc tcgagaaggt    8280
gctctctggc gaggtgggcc cgcaggatgt gcggatctcc cgccagaccc ttgagtacca    8340
ggcgcagatt gccgagcaga tgcagcgcca tgcggtggcg cgcaatttcc gccgcgcggc    8400
ggagcttatc gccattcctg acgagcgcat tctggctatc tataacgcgc tgcgcccgtt    8460
ccgctcctcg caggcggagc tgctggcgat cgccgacgag ctggagcaca cctggcatgc    8520
gacagtgaat gccgcctttg tccgggagtc ggcggaagtg tatcagcagc ggcataagct    8580
gcgtaaagga agctaagcgg aggtcagcat gccgttaata gccgggattg atatcggcaa    8640
cgccaccacc gaggtggcgc tggcgtccga ctacccgcag gcgagggcgt ttgttgccag    8700
cgggatcgtc gcgacgacgg gcatgaaagg gacgcgggac aatatcgccg ggaccctcgc    8760
cgcgctggag caggccctgg cgaaaacacc gtggtcgatg agcgatgtct ctcgcatcta    8820
tcttaacgaa gccgcgccgg tgattggcga tgtggcgatg gagaccatca ccgagaccat    8880
tatcaccgaa tcgaccatga tcggtcataa cccgcagacg ccgggcgggg tgggcgttgg    8940 cgtgggggacg actatcgccc tcgggcggct ggcgacgctg ccggcggcgc agtatgccga    9000
ggggtggatc gtactgattg acgacgccgt cgatttcctt gacgccgtgt ggtggctcaa    9060
tgaggcgctc gaccggggga tcaacgtggt ggcggcgatc ctcaaaaagg acgacggcgt    9120
gctggtgaac aaccgcctgc gtaaaaccct gccggtggtg gatgaagtga cgctgctgga    9180
gcaggtcccc gagggggtaa tggcggcggt ggaagtggcc gcgccgggcc aggtggtgcg    9240
gatcctgtcg aatccctacg ggatcgccac cttcttcggg ctaagcccgg aagagaccca    9300
ggccatcgtc cccatcgccc gcgccctgat tggcaaccgt tccgcggtgg tgctcaagac    9360
cccgcagggg gatgtgcagt cgcgggtgat cccggcgggc aacctctaca ttagcggcga    9420
aaagcgccgc ggagaggccg atgtcgccga gggcgcggaa gccatcatgc aggcgatgag    9480
cgcctgcgct ccggtacgcg acatccgcgg cgaaccgggc acccacgccg gcggcatgct    9540
tgagcgggtg cgcaaggtaa tggcgtccct gaccggccat gagatgagcg cgatatacat    9600
```

| | |
|---|---|
| ccaggatctg ctggcggtgg atacgtttat tccgcgcaag gtgcagggcg ggatggccgg | 9660 |
| cgagtgcgcc atggagaatg ccgtcgggat ggcggcgatg gtgaaagcgg atcgtctgca | 9720 |
| aatgcaggtt atcgcccgcg aactgagcgc ccgactgcag accgaggtgg tggtgggcgg | 9780 |
| cgtggaggcc aacatggcca tcgccggggc gttaaccact cccggctgtg cggcgccgct | 9840 |
| ggcgatcctc gacctcggcg ccggctcgac ggatgcggcg atcgtcaacg cggaggggca | 9900 |
| gataacggcg gtccatctcg ccggggcggg gaatatggtc agcctgttga ttaaaaccga | 9960 |
| gctgggcctc gaggatcttt cgctggcgga agcgataaaa aaatacccgc tggccaaagt | 10020 |
| ggaaagcctg ttcagtattc gtcacgagaa tggcgcggtg gagttctttc gggaagccct | 10080 |
| cagcccggcg gtgttcgcca agtggtgta catcaaggag ggcgaactgg tgccgatcga | 10140 |
| taacgccagc ccgctggaaa aaattcgtct cgtgcgccgg caggcgaaag agaaagtgtt | 10200 |
| tgtcaccaac tgcctgcgcg cgctgcgcca ggtctcaccc ggcggttcca ttcgcgatat | 10260 |
| cgcctttgtg gtgctggtgg gcggctcatc gctggacttt gagatcccgc agcttatcac | 10320 |
| ggaagccttg tcgcactatg gcgtggtcgc cgggcagggc aatattcggg gaacagaagg | 10380 |
| gccgcgcaat gcggtcgcca ccgggctgct actggccggt caggcgaatt aaacgggcgc | 10440 |
| tcgcgccagc ctctaggtac aaataaaaaa ggcacgtcag atgacgtgcc tttttcttg | 10500 |
| tctagagtac tggcgaaagg gggatgtgct gcaaggcgat taagttgggt aacgccaggg | 10560 |
| ttttcccagt cacgacgttg taaaacgacg gccagtgaat tcgagctcgg tacccggggc | 10620 |
| ggccgcgcta gcgcccgatc cagctggagt ttgtagaaac gcaaaaaggc catccgtcag | 10680 |
| gatgccttc tgcttaattt gatgcctggc agtttatggc gggcgtcctg cccgccaccc | 10740 |
| tccgggccgt tgcttcgcaa cgttcaaatc cgctcccggc ggatttgtcc tactcaggag | 10800 |
| agcgttcacc gacaaacaac agataaaacg aaaggcccag tctttcgact gagccttcg | 10860 |
| ttttatttga tgcctggcag ttccctactc tcgcatgggg agaccccaca ctaccatcgg | 10920 |
| cgctacggcg tttcacttct gagttcggca tggggtcagg tgggaccacc gcgctactgc | 10980 |
| cgccaggcaa attctgtttt atcagaccgc ttctgcgttc tgatttaatc tgtatcaggc | 11040 |
| tgaaaatctt ctctcatccg ccaaaacagc caagcttgca tgcctgcagc ccgggttacc | 11100 |
| atttcaacag atcgtcctta gcatataagt agtcgtcaaa aatgaattca acttcgtctg | 11160 |
| tttcggcatt gtagccgcca actctgatgg attcgtggtt tttgacaatg atgtcacagc | 11220 |
| cttttttcctt taggaagtcc aagtcgaaag tagtggcaat accaatgatc ttacaaccgg | 11280 |
| cggcttttcc ggcggcaata cctgctgag cgtcttcaaa tactactacc ttagatttgg | 11340 |
| aagggtcttg ctcattgatc ggatatccta agccattcct gcccttcaga tatggttctg | 11400 |
| gatgaggctt accctgtttg acatcattag cggtaatgaa gtactttggt ctcctgattc | 11460 |
| ccagatgctc gaaccatttt tgtgccatat cacgggtacc ggaagttgcc acagcccatt | 11520 |
| tctcttttgg tagagcgttc aaagcgttgc acagcttaac tgcacctggg acttcaatgg | 11580 |
| atttttcacc gtacttgacc ggaatttcag cttctaattt gttaacatac tcttcattgg | 11640 |
| caaagtctgg agcgaactta gcaatggcat caaacgttct ccaaccatgc gagacttgga | 11700 |
| taacgtgttc agcatcgaaa taaggtttgt ccttaccgaa atccctccag aatgcagcaa | 11760 |
| tggctggttg agagatgata atggtaccgt cgacgtcgaa caaagcggcg ttaactttca | 11820 |
| aagatagagg tttagtagtc aatcccataa ttcagtctg tttcctggat ccaataaatc | 11880 |
| taatcttcat gtagatctaa ttcttcaatc atgtccggca ggtcttcat tgggtagttg | 11940 |
| ttgtaaacga tttggtatac ggcttcaaat aatgggaagt cttcgacaga gccacatgtt | 12000 |

```
tccaaccatt cgtgaacttc tttgcaggta attaaacctt gagcggattg gccattcaac    12060
aactcctttt cacattccca ggcgtcctta ccagaagtag ccattagcct agcaaccttg    12120
acgtttctac caccagcgca ggtggtgatc aaatcagcaa caccagcaga ctcttggtag    12180
tatgtttctt ctctagattc tgggaaaaac atttgaccga atctgatgat ctcacccaaa    12240
ccgactcttt ggatggcagc agaagcgttg ttaccccagc ctagaccttc gacgaaacca    12300
caacctaagg caacaacgtt cttcaaagca ccacagatgg agataccagc aacatcttcg    12360
atgacactaa cgtggaagta aggtctgtgg aacaaggcct ttagaacctt atggtcgacg    12420
tccttgccct cgcctctgaa atcctttgga atgtggtaag caactgttgt ttcagaccag    12480
tgttcttgag cgacttcggt ggcaatgtta gcaccagata gagcaccaca ttgaatacct    12540
agttcctcag tgatgtaaga ggatagcaat tggacacctt tagcaccaac ttcaaaaccc    12600
tttagacagg agatagctct gacgtgtgaa tcaacatgac ctttcaattg ctacagata    12660 cggggcaaaa attgatgtgg aatgttgaaa acgatgatgt cgacatcctt gactgaatca    12720
atcaagtctg gattagcaac caaattgtcg ggtagagtga tgccaggcaa gtatttcacg    12780
ttttgatgtc tagtatttat gatttcagtc aattttttcac cattgatctc ttcttcgaac    12840
acccacattt gtactattgg agcgaaaact tctgggtatc ccttacaatt tcggcaacc    12900 accttggcaa tagtagtacc ccagttacca gatccaatca cagtaaccttt gaaaggcttt    12960 tcggcagcct tcaaagaaac agaagaggaa cttctcttc taccagcatt caagtggccg    13020
gaagttaagt ttaatctatc agcagcagca gccatggaat tgtcctcctt actagtcatg    13080
gtctgtttcc tgtgtgaaat tgttatccgc tcacaattcc acacattata cgagccggat    13140
gattaattgt caacagctca tttcagaata tttgccagaa ccgttatgat gtcggcgcaa    13200
aaaacattat ccagaacggg agtgcgcctt gagcgacacg aattatgcag tgatttacga    13260
cctgcacagc cataccacag cttccgatgg ctgcctgacg ccagaagcat tggtgcacgc    13320
tagccagtac atttaaatgg taccctctag tcaaggcctt aagtgagtcg tattacggac    13380
tggccgtcgt tttacaacgt cgtgactggg aaaaccctgg cgttacccaa cttaatcgcc    13440
ttgcagcaca tccccctttc gccagctggc gtaatagcga agaggcccgc accgatcgcc    13500
cttcccaaca gttgcgcagc ctgaatggcg aatggcgcct gatgcggtat tttctcctta    13560
cgcatctgtg cggtatttca caccgcatat ggtgcactct cagtacaatc tgctctgatg    13620
ccgcatagtt aagccagccc cgacacccgc caacacccgc tgacgagct               13669
```

<210> SEQ ID NO 63
<211> LENGTH: 13543
<212> TYPE: DNA
<213> ORGANISM: Artificial Sequence
<220> FEATURE:
<223> OTHER INFORMATION: Plasmid

<400> SEQUENCE: 63

```
tagtaaagcc ctcgctagat tttaatgcgg atgttgcgat tacttcgcca actattgcga      60
taacaagaaa aagccagcct ttcatgatat atctcccaat ttgtgtaggg cttattatgc     120
acgcttaaaa ataataaaag cagacttgac ctgatagttt ggctgtgagc aattatgtgc     180
ttagtgcatc taacgcttga gttaagccgc gccgcgaagc ggcgtcggct tgaacgaatt     240
gttagacatt atttgccgac taccttggtg atctcgcctt tcacgtagtg gacaaattct     300
tccaactgat ctgcgcgcga ggccaagcga tcttcttctt gtccaagata agcctgtcta     360
```

-continued

```
gcttcaagta tgacgggctg atactgggcc ggcaggcgct ccattgccca gtcggcagcg    420
acatccttcg gcgcgatttt gccggttact gcgctgtacc aaatgcggga caacgtaagc    480
actacatttc gctcatcgcc agcccagtcg ggcggcgagt tccatagcgt taaggtttca    540
tttagcgcct caaatagatc ctgttcagga accggatcaa agagttcctc cgccgctgga    600
cctaccaagg caacgctatg ttctcttgct tttgtcagca agatagccag atcaatgtcg    660
atcgtggctg gctcgaagat acctgcaaga atgtcattgc gctgccattc tccaaattgc    720
agttcgcgct tagctggata cgccacgga tgatgtcgt cgtgcacaac aatggtgact     780 tctacacgc ggagaatctc gctctctcca ggggaagccg aagtttccaa aaggtcgttg    840
atcaaagctc gccgcgttgt tcatcaagc cttacggtca ccgtaaccag caaatcaata    900
tcactgtgtg gcttcaggcc gccatccact gcggagccgt acaaatgtac ggccagcaac    960
gtcggttcga gatggcgctc gatgacgcca actacctctg atagttgagt cgatacttcg    1020
gcgatcaccg cttccctcat gatgtttaac tttgttttag ggcgactgcc ctgctgcgta    1080
acatcgttgc tgctccataa catcaaacat cgacccacgg cgtaacgcgc ttgctgcttg    1140
gatgcccgag gcatagactg tacccccaaaa aaacagtcat aacaagccat gaaaaccgcc    1200
actgcgccgt taccaccgct gcgttcggtc aaggttctgg accagttgcg tgagcgcata    1260
cgctacttgc attacagctt acgaaccgaa caggcttatg tccactgggt tcgtgccttc    1320
atccgtttcc acggtgtgcg tcacccggca accttgggca gcagcgaagt cgaggcattt    1380
ctgtcctggc tggcgaacga gcgcaaggtt tcggtctcca cgcatcgtca ggcattggcg    1440
gccttgctgt tcttctacgg caaggtgctg tgcacggatc tgccctggct tcaggagatc    1500
ggaagacctc ggccgtcgcg gcgcttgccg gtggtgctga ccccggatga agtggttcgc    1560
atcctcggtt ttctggaagg cgagcatcgt ttgttcgccc agcttctgta tggaacgggc    1620
atgcggatca gtgagggttt gcaactgcgg gtcaaggatc tggatttcga tcacggcacg    1680
atcatcgtgc gggagggcaa gggctccaag gatcgggcct tgatgttacc cgagagcttg    1740
gcacccagcc tgcgcgagca ggggaattaa ttcccacggg ttttgctgcc cgcaaacggg    1800
ctgttctggt gttgctagtt tgttatcaga atcgcagatc cggcttcagc cggttttgccg    1860 gctgaaagcg ctatttcttc cagaattgcc atgatttttt ccccacggga ggcgtcactg    1920
gctcccgtgt tgtcggcagc tttgattcga taagcagcat cgcctgtttc aggctgtcta    1980
tgtgtgactg ttgagctgta acaagttgtc tcaggtgttc aatttcatgt tctagttgct    2040
ttgttttact ggtttcacct gttctattag gtgttacatg ctgttcatct gttacattgt    2100
cgatctgttc atggtgaaca gctttgaatg caccaaaaac tcgtaaaagc tctgatgtat    2160 ctatctttt tacaccgttt tcatctgtgc atatggacag ttttccctt gatatgtaac    2220 ggtgaacagt tgttctactt tgtttgtta gtcttgatgc ttcactgata gatacaagag    2280
ccataagaac ctcagatcct tccgtattta gccagtatgt tctctagtgt ggttcgttgt    2340
ttttgcgtga gccatgagaa cgaaccattg agatcatact tactttgcat gtcactcaaa    2400
aattttgcct caaaactggt gagctgaatt tttgcagtta aagcatcgtg tagtgttttt    2460
cttagtccgt tatgtaggta ggaatctgat gtaatggttg ttggtatttt gtcaccattc    2520 attttatct ggttgttctc aagttcggtt acgagatcca tttgtctatc tagttcaact    2580
tggaaaatca acgtatcagt cgggcggcct cgcttatcaa ccaccaattt catattgctg    2640
taagtgttta aatctttact tattggtttc aaaacccatt ggttaagcct tttaaactca    2700
tggtagttat tttcaagcat taacatgaac ttaaattcat caaggctaat ctctatattt    2760
```

```
gccttgtgag ttttcttttg tgttagttct tttaataacc actcataaat cctcatagag   2820
tatttgtttt caaaagactt aacatgttcc agattatatt ttatgaattt ttttaactgg   2880
aaaagataag gcaatatctc ttcactaaaa actaattcta atttttcgct tgagaacttg   2940
gcatagtttg tccactggaa aatctcaaag cctttaacca aaggattcct gatttccaca   3000
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgattttaa tcactatacc aattgagatg gctagtcaa    3300 tgataattac tagtccttt cctttgagtt gtgggtatct gtaaattctg ctagacctt     3360 gctggaaaac ttgtaaattc tgctagaccc tctgtaaatt ccgctagacc tttgtgtgtt   3420
ttttttgttt atattcaagt ggttataatt tatagaataa agaaagaata aaaaagata    3480 aaagaatag atcccagccc tgtgtataac tcactacttt agtcagttcc gcagtattac    3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat   3660
caggcacctg agtcgctgtc tttttcgtga cattcagttc gctgcgctca cggctctggc   3720
agtgaatggg ggtaaatggc actacaggcg ccttttatgg attcatgcaa ggaaactacc   3780
cataatacaa gaaaagcccg tcacgggctt ctcagggcgt tttatggcgg gtctgctatg   3840
tggtgctatc tgactttttg ctgttcagca gttcctgccc tctgattttc cagtctgacc   3900
acttcggatt atcccgtgac aggtcattca gactggctaa tgcacccagt aaggcagcgg   3960
tatcatcaac aggcttaccc gtcttactgt cgggaattca tttaaatagt caaaagcctc   4020
cgaccggagg cttttgactg ctaggcgatc tgtgctgttt gccacggtat gcagcaccag   4080
cgcgagatta tgggctcgca cgctcgactg tcggacgggg gcactggaac gagaagtcag   4140
gcgagccgtc acgcccttga ctatgccaca tcctgagcaa ataattcaac cactaaacaa   4200
atcaaccgcg tttcccggag gtaaccaagc ttgcgggaga gaatgatgaa caagagccaa   4260
caagttcaga caatcaccct ggccgccgcc cagcaaatgg cggcggcggt ggaaaaaaaa   4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac caacagcgaa ttattatttt tggcggcggc   4560
ctgccagtta ttttttaatga gcaggtaatt ggcgccgtcg gcgttagcgg cggtacggtc   4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800
atgccggcgc catcaatgag ctgtgctggg ggctggagga gcaggggtc ccctgccaga    4860 ccataaccta tgacggaggc ggtgacgccg ctgcgctggg cgcctggcg ccagaagct     4920 cgccctgcg ggtgggtatc gggctcagcg cgtccggcga gatagccctc actcatgccc    4980
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
```

```
gaatgtatcg tatctatacc cgcaccgggg ataaaggcac caccgccctg tacggcggca    5160
gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
ctgcccagct gcacgtggcg cgcacccagt cccgtcggct cgaacgcctg ctgacggcca    5520
tggaccgcgc gcatccgctg cgcgacgcgc tcaaacgcta cagcaatcgc ctgtcggatg    5580
ccctgttctc catggcgcga atcgaagaga ctaggcctga tgcttgcgct tgaactggcc    5640
tagcaaacac agaaaaaagc ccgcacctga cagtgcgggc ttttttttc  ctaggcgatc    5700 tgtgctgttt gccacggtat gcagcaccag cgcgagatta tgggctcgca cgctcgactg    5760
tcggacgggg gcactggaac gagaagtcag gcgagccgtc acgcccttga ctatgccaca    5820
tcctgagcaa ataattcaac cactaaacaa atcaaccgcg tttcccggag gtaaccaagc    5880 ttcaccttt  gagccgatga acaatgaaaa gatcaaaacg atttgcagta ctggcccagc    5940
gccccgtcaa tcaggacggg ctgattggcg agtggcctga agaggggctg atcgccatgg    6000
acagccccTT tgacccggtc tcttcagtaa aagtggacaa cggtctgatc gtcgaactgg    6060
acggcaaacg ccgggaccag tttgacatga tcgaccgatt tatcgccgat tacgcgatca    6120
acgttgagcg cacagagcag gcaatgcgcc tggaggcggt ggaaatagcc cgtatgctgg    6180
tggatattca cgtcagccgg gaggagatca ttgccatcac taccgccatc acgccggcca    6240
aagcggtcga ggtgatggcg cagatgaacg tggtggagat gatgatggcg ctgcagaaga    6300
tgcgtgcccg ccgacccccc tccaaccagt gccacgtcac caatctcaaa gataatccgg    6360
tgcagattgc cgctgacgcc gccgaggccg ggatccgcgg cttctcagaa caggagacca    6420
cggtcggtat cgcgcgctac gcgccgttta acgccctggc gctgttggtc ggttcgcagt    6480
gcggccgccc cggcgtgttg acgcagtgct cggtggaaga ggccaccgag ctggagctgg    6540
gcatgcgtgt cttaaccagc tacgccgaga cggtgtcggt ctacggcacc gaagcggtat    6600
ttaccgacgg cgatgatacg ccgtggtcaa aggcgttcct cgcctcggcc tacgcctccc    6660
gcgggttgaa aatgcgctac acctccggca ccggatccga agcgctgatg ggctattcgg    6720
agagcaagtc gatgctctac ctcgaatcgc gctgcatctt cattactaaa ggcgccgggg    6780
ttcagggact gcaaaacggc gcggtgagct gtatcggcat gaccggcgct gtgccgtcgg    6840
gcattcgggc ggtgctggcg gaaaacctga tcgcctctat gctcgacctc gaagtggcgt    6900
ccgccaacga ccagactttc tcccactcgg atattcgccg caccgcgcgc acctgatgc    6960 agatgctgcc gggcaccgac tttatttttct ccggctacag cgcggtgccg aactacgaca    7020
acatgttcgc cggctcgaac ttcgatgcgg aagattttga tgattacaac atcctgcagc    7080
gtgacctgat ggttgacggc ggcctgcgtc cggtgaccga ggcggaaacc attgccattc    7140
gccagaaagc ggcgcgggcg atccaggcgg ttttccgcga gctggggctg ccgccaatcg    7200
ccgacgagga ggtggaggcc gccacctacg cgcacggcag caacgagatg ccgccgcgta    7260
acgtggtgga ggatctgagt gcggtggaag agatgatgaa gcgcaacatc accggcctcg    7320
atattgtcgg cgcgctgagc cgcagcggct ttgaggatat cgccagcaat attctcaata    7380
tgctgcgcca gcgggtcacc ggcgattacc tgcagacctc ggccattctc gatcggcagt    7440
tcgaggtggt gagtgcggtc aacgacatca atgactatca ggggccgggc accggctatc    7500
```

```
gcatctctgc cgaacgctgg gcggagatca aaaatattcc gggcgtggtt cagcccgaca   7560
ccattgaata aggcggtatt cctgtgcaac agacaaccca aattcagccc tcttttaccc   7620
tgaaaacccg cgagggcggg gtagcttctg ccgatgaacg cgccgatgaa gtggtgatcg   7680
gcgtcggccc tgccttcgat aaacaccagc atcacactct gatcgatatg ccccatggcg   7740
cgatcctcaa agagctgatt gccggggtgg aagaagaggg gcttcacgcc cgggtggtgc   7800
gcattctgcg cacgtccgac gtctccttta tggcctggga tgcggccaac ctgagcggct   7860
cggggatcgg catcggtatc cagtcgaagg ggaccacggt catccatcag cgcgatctgc   7920
tgccgctcag caacctggag ctgttctccc aggcgccgct gctgacgctg gagacctacc   7980
ggcagattgg caaaaacgct gcgcgctatg cgcgcaaaga gtcaccttcg ccggtgccgg   8040
tggtgaacga tcagatggtg cggccgaaat ttatggccaa agccgcgcta tttcatatca   8100
aagagaccaa acatgtggtg caggacgccg agcccgtcac cctgcacatc gacttagtaa   8160
gggagtgacc atgagcgaga aaaccatgcg cgtgcaggat tatccgttag ccacccgctg   8220
cccggagcat atcctgacgc ctaccggcaa accattgacc gatattaccc tcgagaaggt   8280
gctctctggc gaggtgggcc gcaggatgt gcggatctcc cgccagaccc ttgagtacca   8340
ggcgcagatt gccgagcaga tgcagcgcca tgcggtggcg cgcaatttcc gccgcgcggc   8400
ggagcttatc gccattcctg acgagcgcat tctggctatc tataacgcgc tgcgcccgtt   8460
ccgctcctcg caggcggagc tgctggcgat cgccgacgag ctggagcaca cctggcatgc   8520
gacagtgaat gccgcctttg tccgggagtc ggcggaagtg tatcagcagc ggcataagct   8580
gcgtaaagga agctaagcgg aggtcagcat gccgttaata gccgggattg atatcggcaa   8640
cgccaccacc gaggtggcgc tggcgtccga ctacccgcag gcgagggcgt tgttgccag   8700 cgggatcgtc gcgacgacgg gcatgaaagg gacgcgggac aatatcgccg ggaccctcgc   8760
cgcgctggag caggccctgg cgaaaacacc gtggtcgatg agcgatgtct ctcgcatcta   8820
tcttaacgaa gccgcgccgg tgattggcga tgtggcgatg gagaccatca ccgagaccat   8880
tatcaccgaa tcgaccatga tcggtcataa cccgcagacg ccgggcgggg tgggcgttgg   8940
cgtggggacg actatcgccc tcgggcggct ggcgacgctg ccgcggcgc agtatgccga   9000 ggggtggatc gtactgattg acgacgccgt cgattccttt gacgccgtgt ggtggctcaa   9060
tgaggcgctc gaccgggga tcaacgtggt ggcggcgatc ctcaaaaagg acgacggcgt   9120
gctggtgaac aaccgcctgc gtaaaaccct gccggtggtg gatgaagtga cgctgctgga   9180
gcaggtcccc gaggggtaa tggcggcggt ggaagtggcc gcgccgggcc aggtggtgcg   9240
gatcctgtcg aatccctacg ggatcgccac cttcttcggg ctaagcccgg aagagaccca   9300
ggccatcgtc cccatcgccc gcgccctgat tggcaaccgt tccgcggtgg tgctcaagac   9360
cccgcagggg gatgtgcagt cgcgggtgat cccggcgggc aacctctaca ttagcggcga   9420
aaagcgccgc ggagaggccg atgtcgccga gggcgcggaa gccatcatgc aggcgatgag   9480
cgcctgcgct ccggtacgcg acatccgcgg cgaaccgggc acccacgccg gcggcatgct   9540
tgagcgggtg cgcaaggtaa tggcgtccct gaccggccat gagatgagcg cgatatacat   9600
ccaggatctg ctggcggtgg atacgtttat tccgcgcaag gtgcagggcg ggatggccgg   9660
cgagtgcgcc atggagaatg ccgtcggat ggcggcgatg gtgaaagcgg atcgtctgca   9720
aatgcaggtt atcgcccgcg aactgagcgc ccgactgcag accgaggtgg tggtgggcgg   9780
cgtggaggcc aacatggcca tcgccggggc gttaaccact cccggctgtg cggcgccgct   9840
```

```
ggcgatcctc gacctcggcg ccggctcgac ggatgcggcg atcgtcaacg cggaggggca    9900
gataacggcg gtccatctcg ccggggcggg aatatggtc agcctgttga ttaaaaccga     9960
gctgggcctc gaggatcttt cgctggcgga agcgataaaa aaatacccgc tggccaaagt   10020
ggaaagcctg ttcagtattc gtcacgagaa tggcgcggtg gagttctttc gggaagccct   10080
cagcccggcg gtgttcgcca agtggtgta catcaaggag ggcgaactgg tgccgatcga    10140
taacgccagc ccgctggaaa aaattcgtct cgtgcgccgg caggcgaaag agaaagtgtt   10200
tgtcaccaac tgcctgcgcg cgctgcgcca ggtctcaccc ggcggttcca ttcgcgatat   10260
cgcctttgtg gtgctggtgg gcggctcatc gctggacttt gagatcccgc agcttatcac   10320
ggaagccttg tcgcactatg gcgtggtcgc cgggcagggc aatattcggg aacagaagg    10380
gccgcgcaat gcggtcgcca ccgggctgct actggccggt caggcgaatt aaacgggcgc   10440
tcgcgccagc ctctaggtac aaataaaaaa ggcacgtcag atgacgtgcc ttttttcttg   10500
tctagcgtgc accatgctt ctggcgtcag gcagccatcg gaagctgtgg tatggctgtg    10560
caggtcgtaa atcactgcat aattcgtgtc gctcaaggcg cactcccgtt ctggataatg   10620
ttttttgcgc cgacatcata acggttctgg caaatattct gaaatgagct gttgacaatt   10680
aatcatccgg ctcgtataat gtgtggaatt gtgagcggat aacaatttca cacaggaaac   10740
agaccatgac tagtaaggag gacaattcca tggctgctgc tgctgataga ttaaacttaa   10800
cttccggcca cttgaatgct ggtagaaaga gaagttcctc ttctgtttct ttgaaggctg   10860
ccgaaaagcc tttcaaggtt actgtgattg gatctggtaa ctggggtact actattgcca   10920
aggtggttgc cgaaaattgt aagggatacc agaagttttt cgctccaata gtacaaatgt   10980
gggtgttcga agaagagatc aatggtgaaa aattgactga atcataaat actagacatc    11040
aaaacgtgaa atacttgcct ggcatcactc tacccgacaa tttggttgct aatccagact   11100
tgattgattc agtcaaggat gtcgacatca tcgtttcaa cattccacat caattttgc     11160
cccgtatctg tagccaattg aaaggtcatg ttgattcaca cgtcagagct atctcctgtc   11220
taaagggttt tgaagttggt gctaaaggtg tccaattgct atcctcttac atcactgagg   11280
aactaggtat tcaatgtggt gctctatctg gtgctaacat tgccaccgaa gtcgctcaag   11340
aacactggtc tgaaacaaca gttgcttacc acattccaaa ggatttcaga ggcgagggca   11400
aggacgtcga ccataaggtt ctaaaggcct tgttccacag accttacttc cacgttagtg   11460
tcatcgaaga tgttgctggt atctccatct gtggtgcttt gaagaacgtt gttgccttag   11520
gttgtggttt cgtcgaaggt ctaggctggg gtaacaacgc ttctgctgcc atccaaagag   11580
tcggtttggg tgagatcatc agattcggtc aaatgttttt cccagaatct agagaagaaa   11640
catactacca agagtctgct ggtgttgctg atttgatcac cacctgcgct ggtggtagaa   11700
acgtcaaggt tgctaggcta atggctactt ctggtaagga cgcctgggaa tgtgaaaagg   11760
agttgttgaa tggccaatcc gctcaaggtt taattacctg caaagaagtt cacgaatggt   11820
tggaaacatg tggctctgtc gaagacttcc cattatttga agccgtatac caaatcgttt   11880
acaacaacta cccaatgaag aacctgccgg acatgattga agaattagat ctacatgaag   11940
attagattta ttggatccag gaaacagact agaattatgg gattgactac taaacctcta   12000
tctttgaaag ttaacgccgc tttgttcgac gtcgacggta ccattatcat ctctcaacca   12060
gccattgctg cattctggag ggatttcggt aaggacaaac cttatttcga tgctgaacac   12120
gttatccaag tctcgcatgg ttggagaacg tttgatgcca ttgctaagtt cgctccagac   12180
tttgccaatg aagagtatgt taacaaatta gaagctgaaa ttccggtcaa gtacggtgaa   12240
```

```
aaatccattg aagtcccagg tgcagttaag ctgtgcaacg ctttgaacgc tctaccaaaa      12300
gagaaatggg ctgtggcaac ttccggtacc cgtgatatgg cacaaaaatg gttcgagcat      12360
ctgggaatca ggagaccaaa gtacttcatt accgctaatg atgtcaaaca gggtaagcct      12420
catccagaac catatctgaa gggcaggaat ggcttaggat atccgatcaa tgagcaagac      12480
ccttccaaat ctaaggtagt agtatttgaa gacgctccag caggtattgc cgccggaaaa      12540
gccgccggtt gtaagatcat tggtattgcc actactttcg acttggactt cctaaaggaa      12600
aaaggctgtg acatcattgt caaaaaccac gaatccatca gagttggcgg ctacaatgcc      12660
gaaacagacg aagttgaatt catttttgac gactacttat atgctaagga cgatctgttg      12720
aaatggtaac ccgggctgca ggcatgcaag cttggctgtt ttggcggatg agagaagatt      12780
ttcagcctga tacagattaa atcagaacgc agaagcggtc tgataaaaca gaatttgcct      12840
ggcggcagta gcgcggtggt cccacctgac cccatgccga actcagaagt gaaacgccgt      12900
agcgccgatg gtagtgtggg gtctccccat gcgagagtag ggaactgcca ggcatcaaat      12960
aaaacgaaag gctcagtcga agactgggcc ttttcgtttt atctgttgtt tgtcggtgaa      13020
cgctctcctg agtaggacaa atccgccggg agcggatttg aacgttgcga agcaacggcc      13080
cggagggtgg cgggcaggac gcccgccata aactgccagg catcaaatta agcagaaggc      13140
catcctgacg gatggccttt ttgcgtttct acaaactcca gctggatcgg cgctagagt       13200 atacatttaa atggtacccct ctagtcaagg ccttaagtga gtcgtattac ggactggccg     13260
tcgttttaca acgtcgtgac tgggaaaacc ctggcgttac ccaacttaat cgccttgcag      13320
cacatccccc tttcgccagc tggcgtaata gcgaagaggc ccgcaccgat cgcccttccc      13380
aacagttgcg cagcctgaat ggcgaatggc gcctgatgcg gtattttctc cttacgcatc      13440
tgtgcggtat ttcacaccgc atatggtgca ctctcagtac aatctgctct gatgccgcat      13500
agttaagcca gccccgacac ccgccaacac ccgctgacga gct                        13543
```

<210> SEQ ID NO 64
<211> LENGTH: 13543
<212> TYPE: DNA
<213> ORGANISM: Artificial Sequence
<220> FEATURE:
<223> OTHER INFORMATION: Plasmid

<400> SEQUENCE: 64

```
tagtaaagcc ctcgctagat tttaatgcgg atgttgcgat tacttcgcca actattgcga        60
taacaagaaa aagccagcct ttcatgatat atctcccaat ttgtgtaggg cttattatgc       120
acgcttaaaa ataataaaag cagacttgac ctgatagttt ggctgtgagc aattatgtgc       180
ttagtgcatc taacgcttga gttaagccgc gccgcgaagc ggcgtcggct tgaacgaatt       240
gttagacatt atttgccgac taccttggtg atctcgcctt tcacgtagtg gacaaattct       300
tccaactgat ctgcgcgcga ggccaagcga tcttcttctt gtccaagata agcctgtcta       360
gcttcaagta tgacgggctg atactgggcc ggcaggcgct ccattgccca gtcggcagcg       420
acatccttcg gcgcgatttt gccggttact gcgctgtacc aaatgcggga caacgtaagc       480
actacatttc gctcatcgcc agcccagtcg ggcggcgagt tccatagcgt taaggtttca       540
tttagcgcct caaatagatc ctgttcagga accggatcaa agagttcctc cgccgctgga       600
cctaccaagg caacgctatg ttctcttgct tttgtcagca agatagccag atcaatgtcg       660
atcgtggctg gctcgaagat acctgcaaga atgtcattgc gctgccattc tccaaattgc       720
```

```
agttcgcgct tagctggata acgccacgga atgatgtcgt cgtgcacaac aatggtgact    780
tctacagcgc ggagaatctc gctctctcca ggggaagccg aagtttccaa aaggtcgttg    840
atcaaagctc gccgcgttgt ttcatcaagc cttacggtca ccgtaaccag caaatcaata    900
tcactgtgtg gcttcaggcc gccatccact gcggagccgt acaaatgtac ggccagcaac    960
gtcggttcga gatggcgctc gatgacgcca actacctctg atagttgagt cgatacttcg   1020
gcgatcaccg cttccctcat gatgtttaac tttgttttag ggcgactgcc ctgctgcgta   1080
acatcgttgc tgctccataa catcaaacat cgacccacgg cgtaacgcgc ttgctgcttg   1140
gatgcccgag gcatagactg tacccaaaa aaacagtcat aacaagccat gaaaaccgcc   1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320
atccgtttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga ccccggatga agtggttcgc   1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgattttt ccccacggga ggcgtcactg   1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040
ttgttttact ggtttcacct gttctattag gtgttacatg ctgttcatct gttacattgt   2100
cgatctgttc atggtgaaca gctttgaatg caccaaaaac tcgtaaaagc tctgatgtat   2160
ctatcttttt tacaccgttt tcatctgtgc atatggacag ttttcccttt gatatgtaac   2220
ggtgaacagt tgttctactt tgtttgtta gtcttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520
attttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta aatctttact tattggtttc aaaacccatt ggttaagcct tttaaactca   2700
tggtagttat tttcaagcat taacatgaac ttaaattcat caaggctaat ctctatattt   2760
gccttgtgag ttttcttttg tgttagttct tttaataacc actcataaat cctcatagag   2820
tatttgtttt caaagacttt aacatgttcc agattatatt ttatgaattt ttttaactgg   2880
aaaagataag gcaatatctc ttcactaaaa actaattcta attttcgct tgagaacttg   2940
gcatagtttg tccactggaa aatctcaaag cctttaacca aaggattcct gatttccaca   3000
gttctcgtca tcagctctct ggttgcttta gctaatacac cataagcatt ttccctactg   3060
atgttcatca tctgagcgta ttggttataa gtgaacgata ccgtccgttc tttccttgta   3120
```

```
gggttttcaa tcgtgggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg ggctagtcaa    3300
tgataattac tagtccttttt cctttgagtt gtgggtatct gtaaattctg ctagaccttt    3360
gctggaaaac ttgtaaattc tgctagaccc tctgtaaatt ccgctagacc tttgtgtgtt    3420 tttttttgttt atattcaagt ggttataatt tatagaataa agaaagaata aaaaagata    3480 aaaagaatag atcccagccc tgtgtataac tcactacttt agtcagttcc gcagtattac    3540
aaaaggatgt cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc ttttttcgtga cattcagttc gctgcgctca cggctctggc    3720
agtgaatggg ggtaaatggc actacaggcg cctttttatgg attcatgcaa ggaaactacc    3780
cataatacaa gaaaagcccg tcacgggctt ctcagggcgt tttatggcgg gtctgctatg    3840
tggtgctatc tgacttttttg ctgttcagca gttcctgccc tctgattttc cagtctgacc    3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagc cttttgactg ctaggcgatc tgtgctgttt ccacggtat gcagcaccag    4080 cgcgagatta tgggctcgca cgctcgactg tcggacgggg gcactggaac gagaagtcag    4140
gcgagccgtc acgcccttga caatgccaca tcctgagcaa ataattcaac cactaaacaa    4200
atcaaccgcg tttccccggag gtaaccaagc ttgcgggaga gaatgatgaa caagagccaa    4260
caagttcaga caatcaccct ggccgccgcc cagcaaatgg cggcggcggt ggaaaaaaaa    4320
gccactgaga tcaacgtggc ggtggtgttt tccgtagttg accgcggagg caacacgctg    4380
cttatccagc ggatggacga ggccttcgtc tccagctgcg atatttccct gaataaagcc    4440
tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
ctgccagtta tttttaatga gcaggtaatt ggcgccgtcg cgttagcgg cggtacggtc    4620 gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga gcaggggtc ccctgccaga    4860 ccataaccta tgacggaggc ggtgacgccg ctgcgctggg cgccctggcg gccagaagct    4920 cgccctgcg ggtgggtatc gggctcagcg cgtccggcga gatagccctc actcatgccc    4980
agctgccggc ggacgcgccg ctggctaccg gacacgtcac cgatagcgac gatcaactgc    5040
gtacgctcgc cgccaacgcc gggcagctgg ttaaagtcct gccgttaagt gagagaaact    5100
gaatgtatcg tatctatacc cgcaccgggg ataaaggcac caccgccctg tacggcggca    5160
gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
```

-continued

```
ctgcccagct gcacgtggcg cgcacccagt cccgtcggct cgaacgcctg ctgacggcca    5520
tggaccgcgc gcatccgctg cgcgacgcgc tcaaacgcta cagcaatcgc ctgtcggatg    5580
ccctgttctc catggcgcga atcgaagaga ctaggcctga tgcttgcgct tgaactggcc    5640
tagcaaacac agaaaaaagc ccgcacctga cagtgcgggc ttttttttc ctaggcgatc     5700 tgtgctgttt gccacggtat gcagcaccag cgcgagatta tgggctcgca cgctcgactg    5760
tcggacgggg gcactggaac gagaagtcag gcgagccgtc acgcccttga caatgccaca    5820
tcctgagcaa ataattcaac cactaaacaa atcaaccgcg tttcccggag gtaaccaagc    5880
ttcacctttt gagccgatga acaatgaaaa gatcaaaacg atttgcagta ctggcccagc    5940
gccccgtcaa tcaggacggg ctgattggcg agtggcctga gaggggctg atcgccatgg     6000 acagcccctt tgaccggtc tcttcagtaa aagtggacaa cggtctgatc gtcgaactgg    6060
acggcaaacg ccgggaccag tttgacatga tcgaccgatt tatcgccgat tacgcgatca    6120
acgttgagcg cacagagcag gcaatgcgcc tggaggcggt ggaaatagcc cgtatgctgg    6180
tggatattca cgtcagccgg gaggagatca ttgccatcac taccgccatc acgccggcca    6240
aagcggtcga ggtgatggcg cagatgaacg tggtggagat gatgatgcg ctgcagaaga     6300 tgcgtgcccg ccgaccccc tccaaccagt gccacgtcac caatctcaaa gataatccgg     6360
tgcagattgc cgctgacgcc gccgaggccg ggatccgcgg cttctcagaa caggagacca    6420
cggtcggtat cgcgcgctac gcgccgttta acgccctggc gctgttggtc ggttcgcagt    6480
gcggccgccc cggcgtgttg acgcagtgct cggtggaaga ggccaccgag ctggagctgg    6540
gcatgcgtgg cttaaccagc tacgccgaga cggtgtcggt ctacggcacc gaagcggtat    6600
ttaccgacgg cgatgatacg ccgtggtcaa aggcgttcct cgcctcggcc tacgcctccc    6660
gcgggttgaa aatgcgctac acctccggca ccggatccga agcgctgatg gctattcgg     6720 agagcaagtc gatgctctac ctcgaatcgc gctgcatctt cattactaaa ggcgccgggg    6780
ttcagggact gcaaaacggc gcggtgagct gtatcggcat gaccggcgct gtgccgtcgg    6840
gcattcgggc ggtgctggcg gaaaaacctga tcgcctctat gctcgacctc gaagtggcgt    6900
ccgccaacga ccagactttc tcccactcgg atattcgccg caccgcgcgc accctgatgc    6960
agatgctgcc gggcaccgac tttattttct ccggctacag cgcggtgccg aactacgaca    7020
acatgttcgc cggctcgaac ttcgatgcgg aagattttga tgattacaac atcctgcagc    7080
gtgacctgat ggttgacggc ggcctgcgtc cggtgaccga ggcggaaacc attgccattc    7140
gccagaaagc ggcgcgggcg atccaggcgg tttccgcga gctggggctg ccgccaatcg     7200
ccgacgagga ggtggaggcc gccacctacg cgcacggcag caacgagatg ccgccgcgta    7260
acgtggtgga ggatctgagt gcggtggaag agatgatgaa gcgcaacatc accgcctcg    7320 atattgtcgg cgcgctgagc cgcagcggct ttgaggatat cgccagcaat attctcaata    7380
tgctgcgcca gcgggtcacc ggcgattacc tgcagacctc ggccattctc gatcggcagt    7440
tcgaggtggt gagtgcggtc aacgacatca atgactatca ggggccgggc accggctatc    7500
gcatctctgc cgaacgctgg gcggagatca aaaatattcc gggcgtggtt cagcccgaca    7560
ccattgaata aggcggtatt cctgtgcaac agacaaccca aattcagccc tcttttaccc    7620 tgaaacccg cgagggcggg gtagcttctg ccgatgaacg cgccgatgaa gtggtgatcg    7680
gcgtcggccc tgccttcgat aaacaccagc atcacactct gatcgatatg ccccatggcg    7740
cgatcctcaa agagctgatt gccggggtgg aagaagaggg gcttcacgcc cggtggtgc    7800 gcattctgcg cacgtccgac gtctccttta tggcctggga tgcggccaac ctgagcggct    7860
```

```
cggggatcgg catcggtatc cagtcgaagg ggaccacggt catccatcag cgcgatctgc   7920
tgccgctcag caacctggag ctgttctccc aggcgccgct gctgacgctg gagacctacc   7980
ggcagattgg caaaaacgct gcgcgctatg cgcgcaaaga gtcaccttcg ccggtgccgg   8040
tggtgaacga tcagatggtg cggccgaaat ttatggccaa agccgcgcta tttcatatca   8100
aagagaccaa acatgtggtg caggacgccg agcccgtcac cctgcacatc gacttagtaa   8160
gggagtgacc atgagcgaga aaaccatgcg cgtgcaggat tatccgttag ccacccgctg   8220
cccggagcat atcctgacgc ctaccggcaa accattgacc gatattaccc tcgagaaggt   8280
gctctctggc gaggtgggcc cgcaggatgt gcggatctcc cgccagaccc ttgagtacca   8340
ggcgcagatt gccgagcaga tgcagcgcca tgcggtggcg cgcaatttcc gccgcgcggc   8400
ggagcttatc gccattcctg acgagcgcat tctggctatc tataacgcgc tgcgcccgtt   8460
ccgctcctcg caggcggagc tgctggcgat cgccgacgag ctggagcaca cctggcatgc   8520
gacagtgaat gccgccttttg tccgggagtc ggcggaagtg tatcagcagc ggcataagct   8580
gcgtaaagga agctaagcgg aggtcagcat gccgttaata gccgggattg atatcggcaa   8640
cgccaccacc gaggtggcgc tggcgtccga ctacccgcag gcgagggcgt ttgttgccag   8700
cgggatcgtc gcgacgacgg gcatgaaagg gacgcgggac aatatcgccg ggaccctcgc   8760
cgcgctggag caggccctgg cgaaaacacc gtggtcgatg agcgatgtct ctcgcatcta   8820
tcttaacgaa gccgcgccgg tgattggcga tgtggcgatg gagaccatca ccgagaccat   8880
tatcaccgaa tcgaccatga tcggtcataa cccgcagacg ccgggcgggg tgggcgttgg   8940
cgtggggacg actatcgccc tcgggcggct ggcgacgctg ccggcggcgc agtatgccga   9000
ggggtggatc gtactgattg acgacgccgt cgatttcctt gacgccgtgt ggtggctcaa   9060
tgaggcgctc gaccggggga tcaacgtggt ggcggcgatc ctcaaaaagg acgacggcgt   9120
gctggtgaac aaccgcctgc gtaaaaccct gccggtggtg gatgaagtga cgctgctgga   9180
gcaggtcccc gagggggtaa tggcggcggt ggaagtggcc gcgccgggcc aggtggtgcg   9240
gatcctgtcg aatccctacg ggatcgccac cttcttcggg ctaagcccgg aagagaccca   9300
ggccatcgtc cccatcgccc gcgccctgat tggcaaccgt tccgcggtgg tgctcaagac   9360
cccgcagggg gatgtgcagt cgcgggtgat cccggcgggc aacctctaca ttagcggcga   9420
aaagcgccgc ggagaggccg atgtcgccga gggcgcggaa gccatcatgc aggcgatgag   9480
cgcctgcgct ccggtacgcg acatccgcgg cgaaccgggc acccacgccg gcggcatgct   9540
tgagcgggtg cgcaaggtaa tggcgtccct gaccggccat gagatgagcg cgatatacat   9600
ccaggatctg ctggcggtgg atacgtttat tccgcgcaag gtgcagggcg ggatggccgg   9660
cgagtgcgcc atggagaatg ccgtcgggat ggcggcgatg gtgaaagcgg atcgtctgca   9720
aatgcaggtt atcgcccgcg aactgagcgc ccgactgcag accgaggtgg tggtgggcgg   9780
cgtggaggcc aacatggcca tcgccggggc gttaaccact cccggctgtg cggcgccgct   9840
ggcgatcctc gacctcggcg ccggctcgac ggatgcggcg atcgtcaacg cggaggggca   9900
gataacggcg gtccatctcg ccggggcggg gaatatggtc agcctgttga ttaaaaccga   9960
gctgggcctc gaggatcttt cgctggcgga agcgataaaa aaatacccgc tggccaaagt  10020
ggaaagcctg ttcagtattc gtcacgagaa tggcgcggtg gagttctttc gggaagccct  10080
cagcccggcg gtgttcgcca aagtggtgta catcaaggag ggcgaactgg tgccgatcga  10140
taacgccagc ccgctggaaa aaattcgtct cgtgcgccgg caggcgaaag agaaagtgtt  10200
```

```
tgtcaccaac tgcctgcgcg cgctgcgcca ggtctcaccc ggcggttcca ttcgcgatat    10260
cgcctttgtg gtgctggtgg gcggctcatc gctggacttt gagatcccgc agcttatcac    10320
ggaagccttg tcgcactatg gcgtggtcgc cgggcagggc aatattcggg gaacagaagg    10380
gccgcgcaat gcggtcgcca ccgggctgct actggccggt caggcgaatt aaacgggcgc    10440
tcgcgccagc ctctaggtac aaataaaaaa ggcacgtcag atgacgtgcc ttttttcttg    10500
tctagcgtgc accaatgctt ctggcgtcag gcagccatcg gaagctgtgg tatggctgtg    10560
caggtcgtaa atcactgcat aattcgtgtc gctcaaggcg cactcccgtt ctggataatg    10620 tttttttgcgc cgacatcata acggttctgg caaatattct gaaatgagct gttgacaatt    10680
aatcatccgg ctcgtataat gtgtggaatt gtgagcggat aacaatttca cacaggaaac    10740
agaccatgac tagtaaggag gacaattcca tggctgctgc tgctgataga ttaaacttaa    10800
cttccggcca cttgaatgct ggtagaaaga gaagttcctc ttctgttttct ttgaaggctg    10860 ccgaaaagcc tttcaaggtt actgtgattg gatctggtaa ctggggtact actattgcca    10920
aggtggttgc cgaaaattgt aagggatacc cagaagtttt cgctccaata gtacaaatgt    10980
gggtgttcga agaagagatc aatggtgaaa aattgactga atcataaat actagacatc    11040 aaaacgtgaa atacttgcct ggcatcactc tacccgacaa tttggttgct aatccagact    11100
tgattgattc agtcaaggat gtcgacatca tcgtttttcaa cattccacat caattttttgc    11160 cccgtatctg tagccaattg aaaggtcatg ttgattcaca cgtcagagct atctcctgtc    11220
taaagggttt tgaagttggt gctaaaggtg tccaattgct atcctcttac atcactgagg    11280
aactaggtat tcaatgtggt gctctatctg gtgctaacat tgccaccgaa gtcgctcaag    11340
aacactggtc tgaaacaaca gttgcttacc acattccaaa ggatttcaga ggcgagggca    11400
aggacgtcga ccataaggtt ctaaaggcct tgttccacag accttacttc cacgttagtg    11460
tcatcgaaga tgttgctggt atctccatct gtggtgcttt gaagaacgtt gttgccttag    11520 gttgtgggtttt cgtcgaaggt ctaggctggg gtaacaacgc ttctgctgcc atccaaagag    11580
tcggtttggg tgagatcatc agattcggtc aaatgttttt cccagaatct agagaagaaa    11640
catactacca agagtctgct ggtgttgctg atttgatcac cacctgcgct ggtggtagaa    11700
acgtcaaggt tgctaggcta atggctactt ctggtaagga cgcctgggaa tgtgaaaagg    11760
agttgttgaa tggccaatcc gctcaaggtt taattacctg caaagaagtt cacgaatggt    11820
tggaaacatg tggctctgtc gaagacttcc cattatttga agccgtatac caaatcgttt    11880
acaacaacta cccaatgaag aacctgccgg acatgattga agaattagat ctacatgaag    11940
attagattta ttggatccag gaaacagact agaattatgg gattgactac taaacctcta    12000
tctttgaaag ttaacgccgc tttgttcgac gtcgacggta ccattatcat ctctcaacca    12060
gccattgctg cattctggag ggatttcggt aaggacaaac cttatttcga tgctgaacac    12120
gttatccaag tctcgcatgg ttggagaacg tttgatgcca ttgctaagtt cgctccagac    12180
tttgccaatg aagagtatgt taacaaatta gaagctgaaa ttccggtcaa gtacggtgaa    12240
aaatccattg aagtcccagg tgcagttaag ctgtgcaacg ctttgaacgc tctaccaaaa    12300
gagaaatggg ctgtggcaac ttccggtacc cgtgatatgg cacaaaaatg gttcgagcat    12360
ctgggaatca ggagaccaaa gtacttcatt accgctaatg atgtcaaaca gggtaagcct    12420
catccagaac catatctgaa gggcaggaat ggcttaggat atccgatcaa tgagcaagac    12480
ccttccaaat ctaaggtagt agtatttgaa gacgctccag caggtattgc cgccggaaaa    12540
gccgccggtt gtaagatcat tggtattgcc actactttcg acttggactt cctaaaggaa    12600
```

```
aaaggctgtg acatcattgt caaaaaccac gaatccatca gagttggcgg ctacaatgcc    12660
gaaacagacg aagttgaatt cattttttgac gactacttat atgctaagga cgatctgttg    12720
aaatggtaac ccgggctgca ggcatgcaag cttggctgtt ttggcggatg agagaagatt    12780
ttcagcctga tacagattaa atcagaacgc agaagcggtc tgataaaaca gaatttgcct    12840
ggcggcagta gcgcggtggt cccacctgac cccatgccga actcagaagt gaaacgccgt    12900
agcgccgatg gtagtgtggg gtctccccat gcgagagtag ggaactgcca ggcatcaaat    12960
aaaacgaaag gctcagtcga agactgggcc ttttcgtttt atctgttgtt tgtcggtgaa    13020
cgctctcctg agtaggacaa atccgccggg agcggatttg aacgttgcga agcaacggcc    13080
cggagggtgg cgggcaggac gcccgccata aactgccagg catcaaatta agcagaaggc    13140
catcctgacg gatggccttt ttgcgtttct acaaactcca gctggatcgg cgctagagt    13200 atacatttaa atggtaccct ctagtcaagg ccttaagtga gtcgtattac ggactggccg    13260
tcgttttaca acgtcgtgac tgggaaaacc ctggcgttac ccaacttaat cgccttgcag    13320
cacatccccc tttcgccagc tggcgtaata gcgaagaggc ccgcaccgat cgcccttccc    13380
aacagttgcg cagcctgaat ggcgaatggc gcctgatgcg gtatttttctc cttacgcatc    13440 tgtgcggtat ttcacaccgc atatggtgca ctctcagtac aatctgctct gatgccgcat    13500
agttaagcca gccccgacac ccgccaacac ccgctgacga gct                       13543
```

<210> SEQ ID NO 65
<211> LENGTH: 13402
<212> TYPE: DNA
<213> ORGANISM: Artificial Sequence
<220> FEATURE:
<223> OTHER INFORMATION: Plamid

<400> SEQUENCE: 65

```
tagtaaagcc ctcgctagat tttaatgcgg atgttgcgat tacttcgcca actattgcga      60
taacaagaaa aagccagcct ttcatgatat atctcccaat ttgtgtaggg cttattatgc     120
acgcttaaaa ataataaaag cagacttgac ctgatagttt ggctgtgagc aattatgtgc     180
ttagtgcatc taacgcttga gttaagccgc gccgcgaagc ggcgtcggct tgaacgaatt     240
gttagacatt atttgccgac taccttggtg atctcgcctt tcacgtagtg gacaaattct     300
tccaactgat ctgcgcgcga ggccaagcga tcttcttctt gtccaagata agcctgtcta     360
gcttcaagta tgacgggctg atactgggcc ggcaggcgct ccattgccca gtcggcagcg     420
acatccttcg gcgcgatttt gccggttact gcgctgtacc aaatgcggga caacgtaagc     480
actacatttc gctcatcgcc agcccagtcg ggcggcgagt tccatagcgt taaggtttca     540
tttagcgcct caaatagatc ctgttcagga accggatcaa agagttcctc cgccgctgga     600
cctaccaagg caacgctatg ttctcttgct tttgtcagca agatagccag atcaatgtcg     660
atcgtggctg gctcgaagat acctgcaaga atgtcattgc gctgccattc tccaaattgc     720
agttcgcgct tagctggata acgccacgga atgatgtcgt cgtgcacaac aatggtgact     780
tctacagcgc ggagaatctc gctctctcca ggggaagccg aagtttccaa aaggtcgttg     840
atcaaagctc gccgcgttgt ttcatcaagc cttacggtca ccgtaaccag caaatcaata     900
tcactgtgtg gcttcaggcc gccatccact gcggagccgt acaaatgtac ggccagcaac     960
gtcggttcga gatggcgctc gatgacgcca actacctctg atagttgagt cgatacttcg    1020
gcgatcaccg cttccctcat gatgtttaac tttgttttag ggcgactgcc ctgctgcgta    1080
```

```
acatcgttgc tgctccataa catcaaacat cgacccacgg cgtaacgcgc ttgctgcttg   1140
gatgcccgag gcatagactg tacccaaaa aaacagtcat aacaagccat gaaaaccgcc    1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320
atccgtttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga ccccggatga agtggttcgc   1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggttttgccg  1860 gctgaaagcg ctatttcttc cagaattgcc atgattttt ccccacggga ggcgtcactg    1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040
ttgttttact ggtttcacct gttctattag gtgttacatg ctgttcatct gttacattgt   2100
cgatctgttc atggtgaaca gctttgaatg caccaaaaac tcgtaaaagc tctgatgtat   2160 ctatctttt tacaccgttt tcatctgtgc atatggacag ttttccctt gatatgtaac     2220 ggtgaacagt tgttctactt ttgtttgtta gtcttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520
atttttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta atctttact tattggtttc aaaaccatt ggttaagcct tttaaactca    2700
tggtagttat tttcaagcat taacatgaac ttaaattcat caaggctaat ctctatattt   2760
gccttgtgag ttttcttttg tgttagttct tttaataacc actcataaat cctcatagag   2820
tatttgtttt caaaagactt aacatgttcc agattatatt ttatgaattt ttttaactgg   2880
aaaagataag gcaatatctc ttcactaaaa actaattcta attttcgct tgagaacttg    2940 gcatagtttg tccactggaa aatctcaaag cctttaacca aaggattcct gatttccaca   3000
gttctcgtca tcagctctct ggttgcttta gctaatacac cataagcatt tccctactg    3060 atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgattttaa tcactatacc aattgagatg ggctagtcaa   3300
tgataattac tagtcctttt cctttgagtt gtgggtatct gtaaattctg ctagacctt    3360 gctggaaaac ttgtaaattc tgctagaccc tctgtaaatt ccgctagacc tttgtgtgtt   3420 tttttgttt atattcaagt ggttataatt tatagaataa agaaagaata aaaaagata     3480
```

```
aaaagaatag atcccagccc tgtgtataac tcactacttt agtcagttcc gcagtattac   3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat   3660
caggcacctg agtcgctgtc tttttcgtga cattcagttc gctgcgctca cggctctggc   3720
agtgaatggg ggtaaatggc actacaggcg cctttttatgg attcatgcaa ggaaactacc   3780
cataatacaa gaaaagcccg tcacgggctt ctcagggcgt tttatggcgg gtctgctatg   3840
tggtgctatc tgactttttg ctgttcagca gttcctgccc tctgattttc cagtctgacc   3900
acttcggatt atcccgtgac aggtcattca gactggctaa tgcacccagt aaggcagcgg   3960
tatcatcaac aggcttaccc gtcttactgt cgggaattca tttaaatagt caaaagcctc   4020
cgaccggagg cttttgactg ctaggcgatc tgtgctgttt gccacggtat gcagcaccag   4080
cgcgagatta tgggctcgca cgctcgactg tcggacgggg gcactggaac gagaagtcag   4140
gcgagccgtc acgcccttga caatgccaca tcctgagcaa ataattcaac cactaaacaa   4200
atcaaccgcg tttcccggag gtaaccaagc ttgcgggaga gaatgatgaa caagagccaa   4260
caagttcaga caatcaccct ggccgccgcc cagcaaatgg cggcggcggt ggaaaaaaaa   4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac aacagcgaa ttattatttt tggcggcggc   4560
ctgccagtta tttttaatga gcaggtaatt ggcgccgtcg gcgttagcgg cggtacggtc   4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800
atgccggcgc catcaatgag ctgtgctggg ggctggagga gcaggggggtc ccctgccaga   4860 ccataaccta tgacggaggc ggtgacgccg ctgcgctggg cgccctggcg ccagaagct   4920 cgccccctgcg ggtgggtatc gggctcagcg cgtccggcga gatagccctc actcatgccc   4980
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
gaatgtatcg tatctatacc cgcaccgggg ataaaggcac caccgccctg tacggcggca   5160
gccgcatcga gaaagaccat attgcgctcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatcaccgc cctggagcgg cttatcgacc   5400
gcaatatggc cgagagcggc ccgttaaaac agttcgtgat cccggggagg aatctcgcct   5460
ctgcccagct gcaccctgat gcttgcgctt gaactggcct agcaaacaca gaaaaaagcc   5520
cgcacctgac agtgcgggct tttttttttcc taggcgatct gtgctgtttg ccacggtatg   5580
cagcaccagc gcgagattat gggctcgcac gctcgactgt cggacggggg cactggaacg   5640
agaagtcagg cgagccgtca cgcccttgac aatgccacat cctgagcaaa taattcaacc   5700
actaaacaaa tcaaccgcgt ttcccggagg taaccaagct tcacctttg agccgatgaa   5760 caatgaaaag atcaaaacga tttgcagtac tggcccagcg ccccgtcaat caggacgggc   5820
```

```
tgattggcga gtggcctgaa gaggggctga tcgccatgga cagccccttt gacccggtct    5880
cttcagtaaa agtggacaac ggtctgatcg tcgaactgga cggcaaacgc cgggaccagt    5940
ttgacatgat cgaccgattt atcgccgatt acgcgatcaa cgttgagcgc acagagcagg    6000
caatgcgcct ggaggcggtg gaaatagccc gtatgctggt ggatattcac gtcagccggg    6060
aggagatcat tgccatcact accgccatca cgccggccaa agcggtcgag gtgatggcgc    6120
agatgaacgt ggtggagatg atgatggcgc tgcagaagat gcgtgcccgc cggacccccct   6180
ccaaccagtg ccacgtcacc aatctcaaag ataatccggt gcagattgcc gctgacgccg    6240
ccgaggccgg gatccgcggc ttctcagaac aggagaccac ggtcggtatc gcgcgctacg    6300
cgccgtttaa cgccctggcg ctgttggtcg gttcgcagtg cggccgcccc ggcgtgttga    6360
cgcagtgctc ggtggaagag gccaccgagc tggagctggg catgcgtggc ttaaccagct    6420
acgccgagac ggtgtcggtc tacggcaccg aagcggtatt taccgacggc gatgatacgc    6480
cgtggtcaaa ggcgttcctc gcctcggcct acgcctcccg cgggttgaaa atgcgctaca    6540
cctccggcac cggatccgaa gcgctgatgg gctattcgga gagcaagtcg atgctctacc    6600
tcgaatcgcg ctgcatcttc attactaaag gcgccggggt tcagggactg caaaacggcg    6660
cggtgagctg tatcggcatg accggcgctg tgccgtcggg cattcgggcg gtgctggcgg    6720
aaaacctgat cgcctctatg ctcgacctcg aagtggcgtc cgccaacgac cagactttct    6780
cccactcgga tattcgccgc accgcgcgca ccctgatgca gatgctgccg ggcaccgact    6840
ttatttctc cggctacagc gcggtgccga actacgacaa catgttcgcc ggctcgaact    6900
tcgatgcgga agattttgat gattacaaca tcctgcagcg tgacctgatg gttgacggcg    6960
gcctgcgtcc ggtgaccgag gcggaaacca ttgccattcg ccagaaagcg cgcgggcga    7020
tccaggcggt tttccgcgag ctggggctgc cgccaatcgc cgacgaggag gtggaggccg    7080
ccacctacgc gcacggcagc aacgagatgc cgccgcgtaa cgtggtggag gatctgagtg    7140
cggtggaaga gatgatgaag cgcaacatca ccggcctcga tattgtcggc gcgctgagcc    7200
gcagcggctt tgaggatatc gccagcaata ttctcaatat gctgcgccag cgggtcaccg    7260
gcgattacct gcagacctcg gccattctcg atcggcagtt cgaggtggtg agtgcggtca    7320
acgacatcaa tgactatcag gggccgggca ccggctatcg catctctgcc gaacgctggg    7380
cggagatcaa aaatattccg ggcgtggttc agcccgacac cattgaataa ggcggtattc    7440
ctgtgcaaca gacaacccaa attcagccct cttttaccct gaaaacccgc gagggcgggg    7500
tagcttctgc cgatgaacgc gccgatgaag tggtgatcgg cgtcggccct gccttcgata    7560
aacaccagca tcacactctg atcgatatgc cccatggcgc gatcctcaaa gagctgattg    7620
ccggggtgga agaagagggg cttcacgccc ggtggtgcg cattctgcgc acgtccgacg    7680
tctccttat ggcctgggat gcggccaacc tgagcggctc ggggatcggc atcggtatcc    7740
agtcgaaggg gaccacggtc atccatcagc gcgatctgct gccgctcagc aacctggagc    7800
tgttctccca ggcgccgctg ctgacgctgg agacctaccg gcagattggc aaaaacgctg    7860
cgcgctatgc gcgcaaagag tcaccttcgc cggtgccggt ggtgaacgat cagatggtgc    7920
ggccgaaatt tatggccaaa gccgcgctat ttcatatcaa agagaccaaa catgtggtgc    7980
aggacgccga gcccgtcacc ctgcacatcg acttagtaag ggagtgacca tgagcgagaa    8040
aaccatgcgc gtgcaggatt atccgttagc caccgctgc ccggagcata tcctgacgcc    8100
taccggcaaa ccattgaccg atattaccct cgagaaggtg ctctctgcg aggtgggccc    8160
gcaggatgtg cggatctccc gccagaccct tgagtaccag gcgcagattg ccgagcagat    8220
```

```
gcagcgccat gcggtggcgc gcaatttccg ccgcgcggcg gagcttatcg ccattcctga    8280
cgagcgcatt ctggctatct ataacgcgct gcgcccgttc cgctcctcgc aggcggagct    8340
gctggcgatc gccgacgagc tggagcacac ctggcatgcg acagtgaatg ccgcctttgt    8400
ccgggagtcg gcggaagtgt atcagcagcg gcataagctg cgtaaaggaa gctaagcgga    8460
ggtcagcatg ccgttaatag ccgggattga tatcggcaac gccaccaccg aggtggcgct    8520
ggcgtccgac tacccgcagg cgagggcgtt tgttgccagc gggatcgtcg cgacgacggg    8580
catgaaaggg acgcgggaca atatcgccgg gaccctcgcc gcgctggagc aggccctggc    8640
gaaaacaccg tggtcgatga gcgatgtctc tcgcatctat cttaacgaag ccgcgccggt    8700
gattggcgat gtggcgatgg agaccatcac cgagaccatt atcaccgaat cgaccatgat    8760
cggtcataac ccgcagacgc cgggcggggt gggcgttggc gtggggacga ctatcgccct    8820
cgggcggctg gcgacgctgc cggcggcgca gtatgccgag gggtggatcg tactgattga    8880
cgacgccgtc gatttccttg acgccgtgtg gtggctcaat gaggcgctcg accgggggat    8940
caacgtggtg gcggcgatcc tcaaaaagga cgacggcgtg ctggtgaaca accgcctgcg    9000
taaaaccctg ccggtggtgg atgaagtgac gctgctggag caggtccccg agggggtaat    9060
ggcggcggtg gaagtggccg cgccgggcca ggtggtgcgg atcctgtcga atccctacgg    9120
gatcgccacc ttcttcgggc taagcccgga agagacccag gccatcgtcc ccatcgcccg    9180
cgccctgatt ggcaaccgtt ccgcggtggt gctcaagacc ccgcagggg atgtgcagtc    9240 gcgggtgatc ccgcgggca acctctacat tagcggcgaa aagcgccgcg agaggccga    9300 tgtcgccgag ggcgcggaag ccatcatgca ggcgatgagc gcctgcgctc cggtacgcga    9360
catccgcggc gaaccgggca cccacgccgg cggcatgctt gagcgggtgc gcaaggtaat    9420
ggcgtccctg accggccatg agatgagcgc gatatacatc caggatctgc tggcggtgga    9480
tacgtttatt ccgcgcaagg tgcagggcgg gatggccggc gagtgcgcca tggagaatgc    9540
cgtcgggatg gcggcgatgg tgaaagcgga tcgtctgcaa atgcaggtta tcgcccgcga    9600
actgagcgcc cgactgcaga ccgaggtggt ggtgggcggc gtggaggcca acatggccat    9660
cgccggggcg ttaaccactc ccggctgtgc ggcgccgctg gcgatcctcg acctcggcgc    9720
cggctcgacg gatgcggcga tcgtcaacgc ggaggggcag ataacggcgg tccatctcgc    9780
cggggcgggg aatatggtca gcctgttgat taaaaccgag ctgggcctcg aggatctttc    9840
gctggcggaa gcgataaaaa atacccgct ggccaaagtg gaaagcctgt tcagtattcg    9900
tcacgagaat ggcgcggtgg agttctttcg gaagccctc agcccggcgg tgttcgccaa    9960
agtggtgtac atcaaggagg cgaactggt gccgatcgat aacgccagcc gctggaaaa    10020 aattcgtctc gtgcgccggc aggcgaaaga gaaagtgttt gtcaccaact gcctgcgcgc    10080
gctgcgccag gtctcacccg gcggttccat tcgcgatatc gcctttgtgg tgctggtggg    10140
cggctcatcg ctggactttg agatcccgca gcttatcacg gaagccttgt cgcactatgg    10200
cgtggtcgcc gggcagggca atattcgggg aacagaaggg ccgcgcaatg cggtcgccac    10260
cgggctgcta ctggccggtc aggcgaatta acgggcgct cgcgccagcc tctaggtaca    10320
aataaaaaag gcacgtcaga tgacgtgcct tttttcttgt ctagcgtgca ccaatgcttc    10380
tggcgtcagg cagccatcgg aagctgtggt atggctgtgc aggtcgtaaa tcactgcata    10440
attcgtgtcg ctcaaggcgc actcccgttc tggataatgt ttttttgcgcc gacatcataa    10500 cggttctggc aaatattctg aaatgagctg ttgacaatta atcatccggc tcgtataatg    10560
```

```
tgtggaattg tgagcggata caatttcac acaggaaaca gaccatgact agtaaggagg    10620
acaattccat ggctgctgct gctgatagat taaacttaac ttccggccac ttgaatgctg    10680
gtagaaagag aagttcctct tctgtttctt tgaaggctgc cgaaaagcct ttcaaggtta    10740
ctgtgattgg atctggtaac tggggtacta ctattgccaa ggtggttgcc gaaaattgta    10800
agggataccc agaagttttc gctccaatag tacaaatgtg ggtgttcgaa gaagagatca    10860
atggtgaaaa attgactgaa atcataaata ctagacatca aaacgtgaaa tacttgcctg    10920
gcatcactct acccgacaat ttggttgcta atccagactt gattgattca gtcaaggatg    10980
tcgacatcat cgttttcaac attccacatc aattttttgcc ccgtatctgt agccaattga    11040
aaggtcatgt tgattcacac gtcagagcta tctcctgtct aaagggtttt gaagttggtg    11100
ctaaaggtgt ccaattgcta tcctcttaca tcactgagga actaggtatt caatgtggtg    11160
ctctatctgg tgctaacatt gccaccgaag tcgctcaaga acactggtct gaaacaacag    11220
ttgcttacca cattccaaag gatttcagag gcgagggcaa ggacgtcgac cataaggttc    11280
taaaggcctt gttccacaga ccttacttcc acgttagtgt catcgaagat gttgctggta    11340
tctccatctg tggtgctttg aagaacgttg ttgccttagg ttgtggtttc gtcgaaggtc    11400
taggctgggg taacaacgct tctgctgcca tccaaagagt cggtttgggt gagatcatca    11460
gattcggtca aatgttttc ccagaatcta gagaagaaac atactaccaa gagtctgctg    11520
gtgttgctga tttgatcacc acctgcgctg gtggtagaaa cgtcaaggtt gctaggctaa    11580
tggctacttc tggtaaggac gcctgggaat gtgaaaagga gttgttgaat ggccaatccg    11640
ctcaaggttt aattacctgc aaagaagttc acgaatggtt ggaaacatgt ggctctgtcg    11700
aagacttccc attatttgaa gccgtatacc aaatcgttta caacaactac ccaatgaaga    11760
acctgccgga catgattgaa gaattagatc tacatgaaga ttagatttat tggatccagg    11820
aaacagacta gaattatggg attgactact aaacctctat ctttgaaagt taacgccgct    11880
ttgttcgacg tcgacggtac cattatcatc tctcaaccag ccattgctgc attctggagg    11940
gatttcggta aggacaaacc ttatttcgat gctgaacacg ttatccaagt ctcgcatggt    12000
tggagaacgt tgatgccat tgctaagttc gctccagact ttgccaatga agagtatgtt    12060
aacaaattag aagctgaaat tccggtcaag tacggtgaaa aatccattga agtcccaggt    12120
gcagttaagc tgtgcaacgc tttgaacgct ctaccaaaag agaaatgggc tgtggcaact    12180
tccggtaccc gtgatatggc acaaaaatgg ttcgagcatc tgggaatcag gagaccaaag    12240
tacttcatta ccgctaatga tgtcaaacag ggtaagcctc atccagaacc atatctgaag    12300
ggcaggaatg gcttaggata tccgatcaat gagcaagacc cttccaaatc taaggtagta    12360
gtatttgaag acgctccagc aggtattgcc gccggaaaag ccgccggttg taagatcatt    12420
ggtattgcca ctactttcga cttggacttc ctaaaggaaa aaggctgtga catcattgtc    12480
aaaaaccacg aatccatcag agttggcggc tacaatgccg aaacagacga agttgaattc    12540
atttttgacg actacttata tgctaaggac gatctgttga atggtaacc cgggctgcag    12600 gcatgcaagc ttggctgttt tggcggatga gaagagattt cagcctgat acagattaaa    12660 tcagaacgca gaagcggtct gataaaacag aatttgcctg gcggcagtag cgcggtggtc    12720
ccacctgacc ccatgccgaa ctcagaagtg aaacgccgta gcgccgatgg tagtgtgggg    12780
tctccccatg cgagagtagg gaactgccag gcatcaaata aaacgaaagg ctcagtcgaa    12840
agactgggcc tttcgtttta tctgttgttt gtcggtgaac gctctcctga gtaggacaaa    12900
tccgccggga gcggatttga acgttgcgaa gcaacggccc ggagggtggc gggcaggacg    12960
```

| | |
|---|---:|
| cccgccataa actgccaggc atcaaattaa gcagaaggcc atcctgacgg atggccttt | 13020 |
| tgcgtttcta caaactccag ctggatcggg cgctagagta tacatttaaa tggtaccctc | 13080 |
| tagtcaaggc cttaagtgag tcgtattacg gactggccgt cgttttacaa cgtcgtgact | 13140 |
| gggaaaaccc tggcgttacc caacttaatc gccttgcagc acatccccct ttcgccagct | 13200 |
| ggcgtaatag cgaagaggcc cgcaccgatc gcccttccca acagttgcgc agcctgaatg | 13260 |
| gcgaatggcg cctgatgcgg tattttctcc ttacgcatct gtgcggtatt tcacaccgca | 13320 |
| tatggtgcac tctcagtaca atctgctctg atgccgcata gttaagccag ccccgacacc | 13380 |
| cgccaacacc cgctgacgag ct | 13402 |

<210> SEQ ID NO 66
<211> LENGTH: 14443
<212> TYPE: DNA
<213> ORGANISM: Artificial Sequence
<220> FEATURE:
<223> OTHER INFORMATION: Plasmid

<400> SEQUENCE: 66

| | |
|---|---:|
| ttctgataac aaactagcaa caccagaaca gcccgtttgc gggcagcaaa acccgtggga | 60 |
| attaattccc ctgctcgcgc aggctgggtg ccaagctctc gggtaacatc aaggcccgat | 120 |
| ccttggagcc cttcttacag agatgaaaaa caaaccgcga cgccaggcgg catcgcggtc | 180 |
| tcagagatat gtttacgtag atcgaagagc accggtgttt aaacgccctt gacgatgcca | 240 |
| catcctgagc aaataattca accactaaac aaatcaaccg cgtttcccgg aggtaaccga | 300 |
| gctcatgatc ctgtgttgtg gtgaagccct gatcgacatg ctgccccggc agacgacgct | 360 |
| gggtgaggcg ggctttgccc cttacgcagg cggagcggtc ttcaacacgg caattgcgct | 420 |
| ggggcgtctt ggcgtccctt cagccttttt taccggtctt tccgacgaca tgatgggcga | 480 |
| tatcctgcgg gagaccctgc gggccagcaa ggtggatttc agctattgcg ccaccctgtc | 540 |
| gcgccccacc accattgcgt tcgttaagct ggttgatggc catgcgacct acgctttta | 600 |
| cgacgagaac accgccggcc ggatgatcac cgaggccgaa cttccggcct tgggagcgga | 660 |
| ttgcgaagcg ctgcatttcg gcgccatcag ccttattccc gaaccctgcg gcagcaccta | 720 |
| tgaggcgctg atgacgcgcg agcatgagac ccgcgtcatc tcgctcgatc cgaacattcg | 780 |
| tcccggcttc atccagaaca gcagtcgca catggcccgc atccgccgca tggcggcgat | 840 |
| gtctgacatc gtcaagttct cggatgagga cctggcgtgg ttcggtctgg aaggcgacga | 900 |
| ggacacgctt gcccgccact ggctgcacca cggtgcaaaa ctcgtcgttg tcaccccgtgg | 960 |
| cgccaagggt gccgtgggtt acagcgccaa tctcaaggtg gaagtggcct ccgagcgcgt | 1020 |
| cgaagtggtc gatacggtcg gcgccggcga tacgttcgat gccggcattc ttgcttcgct | 1080 |
| gaaaatgcag ggcctgctga ccaaagcgca ggtggcttcg ctgagcgaag agcagatcag | 1140 |
| aaaagctttg gcgcttggcg cgaaagccgc tgcggtcact gtctcgcggg ctggcgcaaa | 1200 |
| tccgcctttc gcgcatgaaa tcggtttgtg attaattaaa gcacgcagtc aaacaaaaaa | 1260 |
| cccgcgccat tgcgcgggtt ttttatgcc cgaaggcgcg ccagcacgca gtcaaacaaa | 1320 |
| aaacccgcgc cattgcgcgg gtttttttat gcccgaacgg ccgaggtctt ccgatctcct | 1380 |
| gaagccaggg cagatccgtg cacagcacct tgccgtagaa gaacagcaag gccgccaatg | 1440 |
| cctgacgatg cgtggagacc gaaaccttgc gctcgttcgc cagccaggac agaaatgcct | 1500 |
| cgacttcgct gctgcccaag gttgccgggt gacgcacacc gtggaaacgg atgaaggcac | 1560 |

-continued

```
gaacccagtg gacataagcc tgttcggttc gtaagctgta atgcaagtag cgtatgcgct   1620
cacgcaactg gtccagaacc ttgaccgaac gcagcggtgg taacggcgca gtggcggttt   1680
tcatggcttg ttatgactgt ttttttgggg tacagtctat gcctcgggca tccaagcagc   1740
aagcgcgtta cgccgtgggt cgatgtttga tgttatggag cagcaacgat gttacgcagc   1800
agggcagtcg ccctaaaaca aagttaaaca tcatgaggga agcggtgatc gccgaagtat   1860
cgactcaact atcagaggta gttggcgtca tcgagcgcca tctcgaaccg acgttgctgg   1920
ccgtacattt gtacggctcc gcagtggatg gcggcctgaa gccacacagt gatattgatt   1980
tgctggttac ggtgaccgta aggcttgatg aaacaacgcg gcgagctttg atcaacgacc   2040
ttttggaaac ttcggcttcc cctggagaga gcgagattct ccgcgctgta gaagtcacca   2100
ttgttgtgca cgacgacatc attccgtggc gttatccagc taagcgcgaa ctgcaatttg   2160
gagaatggca gcgcaatgac attcttgcag gtatcttcga gccagccacg atcgacattg   2220
atctggctat cttgctgaca aaagcaagag aacatagcgt tgccttggta ggtccagcgg   2280
cggaggaact ctttgatccg gttcctgaac aggatctatt tgaggcgcta aatgaaacct   2340
taacgctatg gaactcgccg cccgactggg ctggcgatga gcgaaatgta gtgcttacgt   2400
tgtcccgcat ttggtacagc gcagtaaccg gcaaaatcgc gccgaaggat gtcgctgccg   2460
actgggcaat ggagcgcctg ccggcccagt atcagcccgt catacttgaa gctagacagg   2520
cttatcttgg acaagaagaa gatcgcttgg cctcgcgcgc agatcagttg gaagaatttg   2580
tccactacgt gaaaggcgag atcaccaagg tagtcggcaa ataatgtcta acaattcgtt   2640
caagccgacg ccgcttcgcg gcgcggctta actcaagcgt tagatgcact aagcacataa   2700
ttgctcacag ccaaactatc aggtcaagtc tgcttttatt ttttttaagc gtgcataata   2760
agccctacac aaattgggag atatatcatg aaaggctggc ttttcttgt tatcgcaata   2820
gttggcgaag taatcgcaac atccgcatta aaatctagcg agggctttac taagctcgtc   2880
agcgggtgtt ggcgggtgtc ggggctggct taactatgcg gcatcagagc agattgtact   2940
gagagtgcac catatgcggt gtgaaatacc gcacagatgc gtaaggagaa aataccgcat   3000
caggcgccat tcgccattca ggctgcgcaa ctgttgggaa gggcgatcgg tgcgggcctc   3060
ttcgctatta cgccagctgg cgaaaggggg atgtgctgca aggcgattaa gttgggtaac   3120
gccagggttt tcccagtcac gacgttgtaa aacgacggcc agtccgtaat acgactcact   3180
taaggccttg actagagggt accatttaaa tgtatactct agcgcccgat ccagctggag   3240
tttgtagaaa cgcaaaaagg ccatccgtca ggatggcctt ctgcttaatt tgatgcctgg   3300
cagtttatgg cgggcgtcct gcccgccacc ctccgggccg ttgcttcgca acgttcaaat   3360
ccgctcccgg cggatttgtc ctactcagga gagcgttcac cgacaaacaa cagataaaac   3420
gaaaggccca gtctttcgac tgagcctttc gttttatttg atgcctggca gttccctact   3480
ctcgcatggg gagaccccac actaccatcg gcgctacggc gtttcacttc tgagttcggc   3540
atggggtcag gtgggaccac cgcgctactg ccgccaggca aattctgttt tatcagaccg   3600
cttctgcgtt ctgatttaat ctgtatcagg ctgaaaatct tctctcatcc gccaaaacag   3660
ccaagcttgc atgcctgcag cccgggttac catttcaaca gatcgtcctt agcatataag   3720
tagtcgtcaa aaatgaattc aacttcgtct gtttcggcat tgtagccgcc aactctgatg   3780
gattcgtggt ttttgacaat gatgtcacag cctttttcct ttaggaagtc caagtcgaaa   3840
gtagtggcaa taccaatgat cttacaaccg gcggcttttc cggcggcaat acctgctgga   3900
gcgtcttcaa atactactac cttagatttg gaagggtctt gctcattgat cggatatcct   3960
```

```
aagccattcc tgcccttcag atatggttct ggatgaggct taccctgttt gacatcatta    4020
gcggtaatga agtactttgg tctcctgatt cccagatgct cgaaccattt ttgtgccata    4080
tcacgggtac cggaagttgc cacagcccat ttctcttttg gtagagcgtt caaagcgttg    4140
cacagcttaa ctgcacctgg gacttcaatg gattttttcac cgtacttgac cggaatttca   4200
gcttctaatt tgttaacata ctcttcattg gcaaagtctg gagcgaactt agcaatggca    4260
tcaaacgttc tccaaccatg cgagacttgg ataacgtgtt cagcatcgaa ataaggtttg    4320
tccttaccga aatccctcca gaatgcagca atggctggtt gagagatgat aatggtaccg    4380
tcgacgtcga acaaagcggc gttaactttc aaagatagag gtttagtagt caatcccata    4440
attctagtct gtttcctgga tccaataaat ctaatcttca tgtagatcta attcttcaat    4500
catgtccggc aggttcttca ttgggtagtt gttgtaaacg atttggtata cggcttcaaa    4560
taatgggaag tcttcgacag agccacatgt ttccaaccat tcgtgaactt ctttgcaggt    4620
aattaaacct tgagcggatt ggccattcaa caactccttt tcacattccc aggcgtcctt    4680
accagaagta gccattagcc tagcaacctt gacgtttcta ccaccagcgc aggtggtgat    4740
caaatcagca acaccagcag actcttggta gtatgtttct tctctagatt ctgggaaaaa    4800
catttgaccg aatctgatga tctcacccaa accgactctt tggatggcag cagaagcgtt    4860
gttaccccag cctagacctt cgacgaaacc acaacctaag gcaacaacgt tcttcaaagc    4920
accacagatg gagataccag caacatcttc gatgacacta acgtggaagt aaggtctgtg    4980
gaacaaggcc tttagaacct tatggtcgac gtccttgccc tcgcctctga atcctttgg     5040
aatgtggtaa gcaactgttg tttcagacca gtgttcttga gcgacttcgg tggcaatgtt    5100
agcaccagat agagcaccac attgaatacc tagttcctca gtgatgtaag aggatagcaa    5160
ttggacacct ttagcaccaa cttcaaaacc ctttagacag gagatagctc tgacgtgtga    5220
atcaacatga cctttcaatt ggctacagat acggggcaaa aattgatgtg gaatgttgaa    5280
aacgatgatg tcgacatcct tgactgaatc aatcaagtct ggattagcaa ccaaattgtc    5340
gggtagagtg atgccaggca agtatttcac gttttgatgt ctagtattta tgatttcagt    5400
caatttttca ccattgatct cttcttcgaa cacccacatt tgtactattg gagcgaaaac    5460
ttctgggtat cccttacaat tttcggcaac caccttggca atagtagtac cccagttacc    5520
agatccaatc acagtaacct tgaaaggctt ttcggcagcc ttcaaagaaa cagaagagga    5580
acttctcttt ctaccagcat tcaagtggcc ggaagttaag tttaatctat cagcagcagc    5640
agccatggaa ttgtcctcct tactagtcat ggtctgtttc ctgtgtgaaa ttgttatccg    5700
ctcacaattc cacacattat acgagccgga tgattaattg tcaacagctc atttcagaat    5760
atttgccaga accgttatga tgtcggcgca aaaacatta tccagaacgg gagtgcgcct    5820
tgagcgacac gaattatgca gtgatttacg acctgcacag ccataccaca gcttccgatg    5880
gctgcctgac gccagaagca ttggtgcacg ctagacaaga aaaaggcac gtcatctgac    5940
gtgccttttt tatttgtacc tagaggctgg cgcgagcgcc cgtttaattc gcctgaccgg    6000
ccagtagcag cccggtggcg accgcattgc gcggcccttc tgttcccga atattgccct     6060
gcccggcgac cacgccatag tgcgacaagg cttccgtgat aagctgcggg atctcaaagt    6120
ccagcgatga gccgcccacc agcaccacaa aggcgatatc gcgaatggaa ccgccgggtg    6180
agacctggcg cagcgcgcgc aggcagttgg tgacaaacac tttctctttc gcctgccggc    6240
gcacgagacg aatttttttcc agcgggctgg cgttatcgat cggcaccagt tcgccctcct    6300
```

```
tgatgtacac cactttggcg aacaccgccg ggctgagggc ttcccgaaag aactccaccg    6360
cgccattctc gtgacgaata ctgaacaggc tttccacttt ggccagcggg tattttttta    6420
tcgcttccgc cagcgaaaga tcctcgaggc ccagctcggt tttaatcaac aggctgacca    6480
tattccccgc cccggcgaga tggaccgccg ttatctgccc ctccgcgttg acgatcgccg    6540
catccgtcga gccggcgccg aggtcgagga tcgccagcgg cgccgcacag ccgggagtgg    6600
ttaacgcccc ggcgatggcc atgttggcct ccacgccgcc caccaccacc tcggtctgca    6660
gtcgggcgct cagttcgcgg gcgataacct gcatttgcag acgatccgct ttcaccatcg    6720
ccgccatccc gacggcattc tccatggcgc actccgccgc catcccgccc tgcaccttgc    6780
gcggaataaa cgtatccacc gccagcagat cctggatgta tatcgcgctc atctcatggc    6840
cggtcaggga cgccattacc ttgcgcaccc gctcaagcat gccgccgcg tgggtgcccg     6900
gttcgccgcg gatgtcgcgt accggagcgc aggcgctcat cgcctgcatg atggcttccg    6960
cgccctcggc gacatcggcc tctccgcggc gcttttcgcc gctaatgtag aggttgcccg    7020
ccgggatcac ccgcgactgc acatcccct gcggggtctt gagcaccacc gcggaacggt     7080
tgccaatcag ggcgcgggcg atggggacga tggcctgggt ctcttccggg cttagcccga    7140
agaaggtggc gatcccgtag ggattcgaca ggatccgcac cacctggccc ggcgcggcca    7200
cttccaccgc cgccattacc ccctcgggga cctgctccag cagcgtcact tcatccacca    7260
ccggcagggt tttacgcagg cggttgttca ccagcacgcc gtcgtccttt ttgaggatcg    7320
ccgccaccac gttgatcccc cggtcgagcg cctcattgag ccaccacacg gcgtcaagga    7380
aatcgacggg gtcgtcaatc agtacgatcc acccctcggc atactgcgcc gccggcagcg    7440
tcgccagccg cccgagggcg atagtcgtcc ccacgccaac gcccacccg cccggcgtct     7500
gcgggttatg accgatcatg gtcgattcgg tgataatggt ctcggtgatg gtctccatcg    7560
ccacatcgcc aataccggc gcggcttcgt taagatagat gcgagagaca tcgctcatcg     7620
accacggtgt tttcgccagg gcctgctcca gcgcggcgag ggtccggcg atattgtccc     7680
gcgtcccttt catgcccgtc gtcgcgacga tcccgctggc aacaaacgcc ctcgcctgcg    7740
ggtagtcgga cgccagcgcc acctcggtgg tggcgttgcc gatatcaatc ccggctatta    7800
acggcatgct gacctccgct tagcttcctt tacgcagctt atgccgctgc tgatacactt    7860
ccgccgactc ccggacaaag gcggcattca ctgtcgcatg ccaggtgtgc tccagctcgt    7920
cggcgatcgc cagcagctcc gcctgcgagg agcggaacgg gcgcagcgcg ttatagatag    7980
ccagaatgcg ctcgtcagga atggcgataa gctccgccgc gcggcggaaa ttgcgcgcca    8040
ccgcatggcg ctgcatctgc tcggcaatct gcgcctggta ctcaagggtc tggcgggaga    8100
tccgcacatc ctgcgggccc acctcgccag agagcacctt ctcgagggta atatcggtca    8160
atggtttgcc ggtaggcgtc aggatatgct ccgggcagcg ggtggctaac ggataatcct    8220
gcacgcgcat ggttttctcg ctcatggtca ctcccttact aagtcgatgt gcagggtgac    8280
gggctcggcg tcctgcacca catgtttggt ctctttgata tgaaatagcg cggctttggc    8340
cataaatttc ggccgcacca tctgatcgtt caccaccggc accggcgaag gtgactcttt    8400
gcgcgcatag cgcgcagcgt ttttgccaat ctgccggtag gtctccagcg tcagcagcgg    8460
cgcctgggag aacagctcca ggttgctgag cggcagcaga tcgcgctgat ggatgaccgt    8520
ggtcccttc gactggatac cgatgccgat ccccgagccg ctcaggttgg ccgcatccca     8580
ggccataaag gagacgtcgg acgtgcgcag aatgcgcacc acccgggcgt gaagcccctc    8640
ttcttccacc ccggcaatca gctctttgag gatcgcgcca tggggcatat cgatcagagt    8700
```

```
gtgatgctgg tgtttatcga aggcagggcc gacgccgatc accacttcat cggcgcgttc    8760
atcggcagaa gctacccgc cctcgcgggt tttcagggta aaagagggct gaatttgggt    8820
tgtctgttgc acaggaatac cgccttgttc aatggtgtcg ggctgaacca cgcccggaat    8880 attttgatc tccgcccagc gttcggcaga gatgcgatag ccggtgcccg gcccctgata    8940
gtcattgatg tcgttgaccg cactcaccac ctcgaactgc cgatcgaaaa tggccgaggt    9000
ctgcaggtaa tcgccggtga cccgctggcg cagcatattg agaatattgc tggcgatatc    9060
ctcaaagccg ctgcggctca gcgcgccgac aatatcgagg ccggtgatgt tgcgcttcat    9120
catctcttcc accgcactca gatcctccac cacgttacgc ggcggcatct cgttgctgcc    9180
gtgcgcgtag gtggcggcct ccacctcctc gtcggcgatt ggcggcagcc ccagctcgcg    9240
gaaaaccgcc tggatcgccc gcgccgcttt ctggcgaatg gcaatggttt ccgcctcggt    9300
caccggacgc aggccgccgt caaccatcag gtcacgctgc aggatgttgt aatcatcaaa    9360
atcttccgca tcgaagttcg agccggcgaa catgttgtcg tagttcggca ccgcgctgta    9420
gccggagaaa ataaagtcgg tgcccggcag catctgcatc agggtgcgcg cggtgcggcg    9480
aatatccgag tgggagaaag tctggtcgtt ggcggacgcc acttcgaggt cgagcataga    9540
ggcgatcagg ttttccgcca gcaccgcccg aatgcccgac ggcacagcgc cggtcatgcc    9600
gatacagctc accgcgccgt tttgcagtcc ctgaaccccg cgcctttag taatgaagat    9660 gcagcgcgat tcgaggtaga gcatcgactt gctctccgaa tagcccatca gcgcttcgga    9720
tccggtgccg gaggtgtagc gcattttcaa cccgcgggag gcgtaggccg aggcgaggaa    9780
cgcctttgac cacggcgtat catcgccgtc ggtaaatacc gcttcggtgc cgtagaccga    9840
caccgtctcg gcgtagctgg ttaagccacg catgcccagc tccagctcgg tggcctcttc    9900
caccgagcac tgcgtcaaca cgccggggcg gccgcactgc gaaccgacca acagcgccag    9960
ggcgttaaac ggcgcgtagc gcgcgatacc gaccgtggtc tcctgttctg agaagccgcg   10020
gatcccggcc tcgcggcgt cagcggcaat ctgcaccgga ttatctttga gattggtgac   10080
gtggcactgg ttggaggggg tccggcgggc acgcatcttc tgcagcgcca tcatcatctc   10140
caccacgttc atctgcgcca tcacctcgac cgctttggcc ggcgtgatgg cggtagtgat   10200
ggcaatgatc tcctcccggc tgacgtgaat atccaccagc atacgggcta tttccaccgc   10260
ctccaggcgc attgcctgct ctgtgcgctc aacgttgatc gcgtaatcgg cgataaatcg   10320
gtcgatcatg tcaaactggt cccggcgttt gccgtccagt tcgacgatca gaccgttgtc   10380
cacttttact gaagagaccg ggtcaaaggg gctgtccatg gcgatcagcc cctcttcagg   10440
ccactcgcca atcagcccgt cctgattgac ggggcgctgg gccagtactg caaatcgttt   10500
tgatcttttc attgttcatc ggctcaaaag gtgaagcttg gttacctccg ggaaacgcgg   10560
ttgatttgtt tagtggttga attatttgct caggatgtgg cattgtcaag ggcgtgacgg   10620
ctcgcctgac ttctcgttcc agtgcccccg tccgacagtc gagcgtgcga gcccataatc   10680
tcgcgctggt gctgcatacc gtggcaaaca gcacagatcg cctaggaaaa aaaaagcccg   10740
cactgtcagg tgcgggcttt tttctgtgtt tgctaggcca gttcaagcgc aagcatcagg   10800
gtgcagctgg gcagaggcga gattcctccc cgggatcacg aactgtttta acgggccgct   10860
ctcggccata ttgcggtcga taagccgctc cagggcggtg atctcctctt cgccgatcgt   10920
ctggctcagg cgggtcaggc cccgcgcatc gctggccagt tcagcccccca gcacgaacag   10980 cgtctgctga atatggtgca ggctttcccg cagcccggcg tcgcgggtcg tggcgtagca   11040
```

```
gacgcccagc tgggatatca gttcatcgac ggtgccgtag gcctcgacgc gaatatggtc  11100
tttctcgatg cggctgccgc cgtacagggc ggtggtgcct ttatccccgg tgcgggtata  11160
gatacgatac attcagtttc tctcacttaa cggcaggact ttaaccagct gcccggcgtt  11220
ggcgccgagc gtacgcagtt gatcgtcgct atcggtgacg tgtccggtag ccagcggcgc  11280
gtccgccggc agctgggcat gagtgagggc tatctcgccg gacgcgctga gcccgatacc  11340
cacccgcagg ggcgagcttc tggccgccag ggcgcccagc gcagcggcgt caccgcctcc  11400
gtcataggtt atggtctggc aggggacccc ctgctcctcc agccccagc acagctcatt  11460 gatggcgccg gcatggtgcc cgcgcggatc gtaaaacagg cgtacgcctg gcggtgaaag  11520
cgacatgacg gtcccctcgt taacactcag aatgcctggc ggaacatacg atagctcata  11580
atataccttc tcgcttcagg ttataatgcg gaaaaacaat ccaggcgca ctgggctaat  11640 aattgatcct gctcgaccgt accgccgcta acgccgacgg cgccaattac ctgctcatta  11700
aaaataactg gcaggccgcc gccaaaaata taattcgct gttggttggt tagctgcaga  11760
ccgtacagag attgtcctgg ctggaccgct gacgtaattt catgggtacc ttgcttcagg  11820
ctgcaggcgc tccaggcttt attcaggaa atatcgcagc tggagacgaa ggcctcgtcc  11880
atccgctgga taagcagcgt gttgcctccg cggtcaacta cggaaaacac caccgccacg  11940
ttgatctcag tggcttttttt ttccaccgcc gccgccattt gctgggcggc ggccagggtg  12000
attgtctgaa cttgttggct cttgttcatc attctctccc gcaagcttgg ttacctccgg  12060
gaaacgcggt tgatttgttt agtggttgaa ttatttgctc aggatgtggc attgtcaagg  12120
gcgtgacggc tcgcctgact tctcgttcca gtgcccccgt ccgacagtcg agcgtgcgag  12180
cccataatct cgcgctggtg ctgcataccg tggcaaacag cacagatcgc ctagcagtca  12240
aaagcctccg gtcggaggct tttgactatt taaatgaatt cccgacagta agacgggtaa  12300
gcctgttgat gataccgctg ccttactggg tgcattagcc agtctgaatg acctgtcacg  12360
ggataatccg aagtggtcag actggaaaat cagagggcag gaactgctga acagcaaaaa  12420
gtcagatagc accacatagc agacccgcca taaaacgccc tgagaagccc gtgacgggct  12480
tttcttgtat tatgggtagt ttccttgcat gaatccataa aaggcgcctg tagtgccatt  12540
tacccccatt cactgccaga gccgtgagcg cagcgaactg aatgtcacga aaaagacagc  12600
gactcaggtg cctgatggtc ggagacaaaa ggaatattca gcgatttgcc cgagcttgcg  12660
agggtgctac ttaagccttt agggttttaa ggtctgtttt gtagaggagc aaacagcgtt  12720
tgcgacatcc ttttgtaata ctgcggaact gactaaagta gtgagttata cacagggctg  12780
ggatctattc tttttatctt tttttattct ttctttattc tataaattat aaccacttga  12840
atataaacaa aaaaaacaca caaaggtcta gcggaattta cagagggtct agcagaattt  12900
acaagttttc cagcaaaggt ctagcagaat ttacagatac ccacaactca aggaaaagg  12960 actagtaatt atcattgact agcccatctc aattggtata gtgattaaaa tcacctagac  13020
caattgagat gtatgtctga attagttgtt ttcaaagcaa atgaactagc gattagtcgc  13080
tatgacttaa cggagcatga accaagcta attttatgct gtgtggcact actcaacccc  13140
acgattgaaa accctacaag gaaagaacgg acgtatcgt tcacttataa ccaatacgct  13200
cagatgatga acatcagtag ggaaaatgct tatggtgtat tagctaaagc aaccagagag  13260
ctgatgacga gaactgtgga aatcaggaat ccttttggta aaggctttga gattttccag  13320
tggacaaact atgccaagtt ctcaagcgaa aaattagaat tagtttttag tgaagagata  13380
ttgccttatc ttttccagtt aaaaaaattc ataaaatata atctggaaca tgttaagtct  13440
```

-continued

```
tttgaaaaca aatactctat gaggatttat gagtggttat taaaagaact aacacaaaag   13500
aaaactcaca aggcaaatat agagattagc cttgatgaat ttaagttcat gttaatgctt   13560
gaaaataact accatgagtt taaaaggctt aaccaatggg ttttgaaacc aataagtaaa   13620
gatttaaaca cttacagcaa tatgaaattg gtggttgata agcgaggccg cccgactgat   13680
acgttgattt tccaagttga actagataga caaatggatc tcgtaaccga acttgagaac   13740
aaccagataa aaatgaatgg tgacaaaata ccaacaacca ttacatcaga ttcctaccta   13800
cataacggac taagaaaaac actacacgat gctttaactg caaaaattca gctcaccagt   13860
tttgaggcaa aattttttgag tgacatgcaa agtaagtatg atctcaatgg ttcgttctca   13920
tggctcacgc aaaaacaacg aaccacacta gagaacatac tggctaaata cggaaggatc   13980
tgaggttctt atggctcttg tatctatcag tgaagcatca agactaacaa acaaagtag    14040 aacaactgtt caccgttaca tatcaaaggg aaaactgtcc atatgcacag atgaaaacgg   14100
tgtaaaaaag atagatacat cagagctttt acgagttttt ggtgcattca agctgttca    14160 ccatgaacag atcgacaatg taacagatga acagcatgta acacctaata gaacaggtga   14220
aaccagtaaa acaaagcaac tagaacatga aattgaacac ctgagacaac ttgttacagc   14280
tcaacagtca cacatagaca gcctgaaaca ggcgatgctg cttatcgaat caaagctgcc   14340
gacaacacgg gagccagtga cgcctcccgt ggggaaaaaa tcatggcaat tctggaagaa   14400
atagcgcttt cagccggcaa accggctgaa gccggatctg cga                    14443
```

<210> SEQ ID NO 67
<211> LENGTH: 1260
<212> TYPE: DNA
<213> ORGANISM: Citrobacter sp

<400> SEQUENCE: 67

```
atgaagataa atatgccgtt cagtaatgac aaatatcggt actcgtccgg gtatctgctt     60 ttttttctttg ccgcctggtc gttgtggtgg tcttttatg cgatatggct aaaaaataaa    120
cttggcctgt ccggaacgga gctgggaatg ctgtatgccg taaaccagtt ctttagcatg    180
ctgtttatgc tggtctacgg ttttctgcag gataagctcg gcacccgtaa acaccttatc    240
tggctgatgg ggatagtcat cacgctcagc ggcccgttcc tgatttatgt ttacgaaccg    300
ctgctgacct ccaacttcaa acttggtatg gcgctgggag ccattttctt tggccttggc    360
tacctcgcgg ttgtggtct ggtagaaagc ttcgtcgaaa aagtgagccg caaattcaac    420
tttgaattcg gcaccgcccg cttgtgggga tcgcttggct acgccgcagg acatttgtt    480 ggcggtatct tcttcagcat caacccacac attaacttct ggtgcgtatc ggtaatgggg    540
gtgttattcc tgttgattaa cgtgttgttc aaaaccaact caccgcccc atcttctgta    600 aaaacgcgtt ctcctgaacc tgacgcgctg acccgaaagg atttctcac tatctttaaa    660 gatacgcagt tctggttttt cgttatcttt gtcgtcggta cctggtcgtt ctatagcatc    720
tacgatcagc agatgttccc ggtgttttac gccagcttat ttgacgatcc cgaactggca    780
ccacgcgtat acggctacct caactcggta caggtcttta tggaagccgt cggtatggcg    840
ctggttccat tcctgattaa ccgcatcggg cctaaatccg cattgctgct gggtggcaca    900
atcatggcct gtcgaatcct gggttcagca ctgttcaccg atatctatat tatctccttg    960
attaaaatgc ttcatgcgct ggaagtccca ctgtttgtta tttcagtgtt taaattcagc   1020
gtagcgaatt ttgataaacg cctgtcatca acgatatatc tcattggctt caatatcgcc   1080
```

```
agttccattg gcattatcgt gctgtcactg cctgtcggta agttgtttga taaagtgggc    1140
tatcaggaaa tcttcctgat tatggccagc attgtgataa taacactaat atttggctat    1200
ttctcgttga gcaaaaagca tcatcagcag aagatgggaa atgaactggt gacagagtag    1260
```

<210> SEQ ID NO 68
<211> LENGTH: 419
<212> TYPE: PRT
<213> ORGANISM: Citrobacter sp

<400> SEQUENCE: 68

```
Met Lys Ile Asn Met Pro Phe Ser Asn Asp Lys Tyr Arg Tyr Ser Ser
1               5                   10                  15

Gly Tyr Leu Leu Phe Phe Phe Ala Ala Trp Ser Leu Trp Trp Ser Phe
            20                  25                  30

Tyr Ala Ile Trp Leu Lys Asn Lys Leu Gly Leu Ser Gly Thr Glu Leu
        35                  40                  45

Gly Met Leu Tyr Ala Val Asn Gln Phe Phe Ser Met Leu Phe Met Leu
    50                  55                  60

Val Tyr Gly Phe Leu Gln Asp Lys Leu Gly Thr Arg Lys His Leu Ile
65                  70                  75                  80

Trp Leu Met Gly Ile Val Ile Thr Leu Ser Gly Pro Phe Leu Ile Tyr
                85                  90                  95

Val Tyr Glu Pro Leu Leu Thr Ser Asn Phe Lys Leu Gly Met Ala Leu
            100                 105                 110

Gly Ala Ile Phe Phe Gly Leu Gly Tyr Leu Ala Gly Cys Gly Leu Val
        115                 120                 125

Glu Ser Phe Val Glu Lys Val Ser Arg Lys Phe Asn Phe Glu Phe Gly
    130                 135                 140

Thr Ala Arg Leu Trp Gly Ser Leu Gly Tyr Ala Ala Gly Thr Phe Val
145                 150                 155                 160

Gly Gly Ile Phe Phe Ser Ile Asn Pro His Ile Asn Phe Trp Cys Val
                165                 170                 175

Ser Val Met Gly Val Leu Phe Leu Ile Asn Val Leu Phe Lys Thr
            180                 185                 190

Asn Ser Pro Ala Pro Ser Ser Val Lys Thr Arg Ser Pro Glu Pro Asp
        195                 200                 205

Ala Leu Thr Arg Lys Asp Phe Leu Thr Ile Phe Lys Asp Thr Gln Phe
    210                 215                 220

Trp Phe Phe Val Ile Phe Val Val Gly Thr Trp Ser Phe Tyr Ser Ile
225                 230                 235                 240

Tyr Asp Gln Gln Met Phe Pro Val Phe Tyr Ala Ser Leu Phe Asp Asp
                245                 250                 255

Pro Glu Leu Ala Pro Arg Val Tyr Gly Tyr Leu Asn Ser Val Gln Val
            260                 265                 270

Phe Met Glu Ala Val Gly Met Ala Leu Val Pro Phe Leu Ile Asn Arg
        275                 280                 285

Ile Gly Pro Lys Ser Ala Leu Leu Leu Gly Gly Thr Ile Met Ala Cys
    290                 295                 300

Arg Ile Leu Gly Ser Ala Leu Phe Thr Asp Ile Tyr Ile Ile Ser Leu
305                 310                 315                 320

Ile Lys Met Leu His Ala Leu Glu Val Pro Leu Phe Val Ile Ser Val
                325                 330                 335

Phe Lys Phe Ser Val Ala Asn Phe Asp Lys Arg Leu Ser Ser Thr Ile
            340                 345                 350
```

```
Tyr Leu Ile Gly Phe Asn Ile Ala Ser Ser Ile Gly Ile Ile Val Leu
        355                 360                 365

Ser Leu Pro Val Gly Lys Leu Phe Asp Lys Val Gly Tyr Gln Glu Ile
    370                 375                 380

Phe Leu Ile Met Ala Ser Ile Val Ile Ile Thr Leu Ile Phe Gly Tyr
385                 390                 395                 400

Phe Ser Leu Ser Lys Lys His His Gln Gln Lys Met Gly Asn Glu Leu
                405                 410                 415

Val Thr Glu
```

<210> SEQ ID NO 69
<211> LENGTH: 1314
<212> TYPE: DNA
<213> ORGANISM: Enterococcus faecium

<400> SEQUENCE: 69

```
atgaaagggg atacaaatat atcgttggag gataaaaata tgtcaaaagt taacgtattt      60
aaaaatcaat cttatttaca aagttcagct acattattac tattttttgc ttcttggggt     120
gtttggtggt cattttttca actttggcta acatctgaat caaatggttt agggttatct     180
ggcagtgctg taggaacagt attctcggca aattcgttag ttaccttaat tttgatgttt     240
atttatggaa cattacaaga taaattgtat attaaacgaa atttattaat ttttgcttct     300
gtattagcga cacttgttgg accatttttt atatggatat atgggccatt gctagataac     360
aattttaatt taggcattat tatgggagcg ctattttttgt cagctggata tttagcttct     420
gtaggagttt ttgaagctgt gtcagaaagg tttagtcgtt tatttggctt tgaatatgga     480
caagcaaggg cgtggggatc atttggttat gccttggtag cgcttttggc aggattttta     540
tttgtaaaaa atcctcattt aaactttggg gcgggatctt tctttggttc tttactattg     600
ttaaatttat tattttggaa ccctaaagtt gaacgggaag caaatcaaaa ttttaatcaa     660
gaacaagctg aatcaaatag tattccttct ttaaaagaaa tgtttgatct aatgaaactg     720
cctcaattat ggacgataat catctttatt gttttttacat ggacattttta tacggtattc     780
gatcaacaaa tgtttccggg atttatact ggtttgtttt caacatcagc taatggtgaa     840
aaaatatatg ggacattgaa tgctattcaa gtattttgtg aagcgttaat gatgggaatt     900
gttccaatca ttatgagaaa attaggggtt cgaaatactt tgttattagg tgtaaccatt     960
atgtgtgtac gaattggatt gtgcgggttt gcctcgacac cattatctgt ttcatgcata    1020
aaatgttgc atgctttaga agtaccatta tttacattac aatgtttcg ctattttaca    1080
cttcattttg atacaaagct atcagcaacc ctctatatga taggatttca gatagctgct    1140
caaattgggc aagtgatttt atcaacacca ttgggaatat aagagacaa cgttggctat    1200
caaccaacat ttaaaattat ttctcttatt gtattactag caggcatata tgcattcttt    1260
attcttaaac aagatgatag agatgttcaa ggggatccat ttattcgagg ataa         1314
```

<210> SEQ ID NO 70
<211> LENGTH: 437
<212> TYPE: PRT
<213> ORGANISM: Enterococcus faecium

<400> SEQUENCE: 70

```
Met Lys Gly Asp Thr Asn Ile Ser Leu Glu Asp Lys Asn Met Ser Lys
1               5                   10                  15

Val Asn Val Phe Lys Asn Gln Ser Tyr Leu Gln Ser Ser Ala Thr Leu
```

-continued

```
                20                  25                  30
Leu Leu Phe Phe Ala Ser Trp Gly Val Trp Ser Phe Gln Leu
                35                  40                  45
Trp Leu Thr Ser Glu Ser Asn Gly Leu Gly Leu Ser Gly Ala Val
 50                  55                  60
Gly Thr Val Phe Ser Ala Asn Ser Leu Val Thr Leu Ile Leu Met Phe
 65                  70                  75                  80
Ile Tyr Gly Thr Leu Gln Asp Lys Leu Tyr Ile Lys Arg Asn Leu Leu
                 85                  90                  95
Ile Phe Ala Ser Val Leu Ala Thr Leu Val Gly Pro Phe Phe Ile Trp
                100                 105                 110
Ile Tyr Gly Pro Leu Leu Asp Asn Asn Phe Asn Leu Gly Ile Ile Met
                115                 120                 125
Gly Ala Leu Phe Leu Ser Ala Gly Tyr Leu Ala Ser Val Gly Val Phe
                130                 135                 140
Glu Ala Val Ser Glu Arg Phe Ser Arg Leu Phe Gly Phe Glu Tyr Gly
145                 150                 155                 160
Gln Ala Arg Ala Trp Gly Ser Phe Gly Tyr Ala Leu Val Ala Leu Leu
                165                 170                 175
Ala Gly Phe Leu Phe Val Lys Asn Pro His Leu Asn Phe Trp Ala Gly
                180                 185                 190
Ser Phe Phe Gly Ser Leu Leu Leu Asn Leu Leu Phe Trp Asn Pro
                195                 200                 205
Lys Val Glu Arg Glu Ala Asn Gln Asn Phe Asn Gln Glu Gln Ala Glu
                210                 215                 220
Ser Asn Ser Ile Pro Ser Leu Lys Glu Met Phe Asp Leu Met Lys Leu
225                 230                 235                 240
Pro Gln Leu Trp Thr Ile Ile Ile Phe Ile Val Phe Thr Trp Thr Phe
                245                 250                 255
Tyr Thr Val Phe Asp Gln Gln Met Phe Pro Gly Phe Tyr Thr Gly Leu
                260                 265                 270
Phe Ser Thr Ser Ala Asn Gly Glu Lys Ile Tyr Gly Thr Leu Asn Ala
                275                 280                 285
Ile Gln Val Phe Cys Glu Ala Leu Met Met Gly Ile Val Pro Ile Ile
                290                 295                 300
Met Arg Lys Leu Gly Val Arg Asn Thr Leu Leu Leu Gly Val Thr Ile
305                 310                 315                 320
Met Cys Val Arg Ile Gly Leu Cys Gly Phe Ala Ser Thr Pro Leu Ser
                325                 330                 335
Val Ser Cys Ile Lys Met Leu His Ala Leu Glu Val Pro Leu Phe Thr
                340                 345                 350
Leu Pro Met Phe Arg Tyr Phe Thr Leu His Phe Asp Thr Lys Leu Ser
                355                 360                 365
Ala Thr Leu Tyr Met Ile Gly Phe Gln Ile Ala Ala Gln Ile Gly Gln
                370                 375                 380
Val Ile Leu Ser Thr Pro Leu Gly Ile Leu Arg Asp Asn Val Gly Tyr
385                 390                 395                 400
Gln Pro Thr Phe Lys Ile Ile Ser Leu Ile Val Leu Leu Ala Gly Ile
                405                 410                 415
Tyr Ala Phe Phe Ile Leu Lys Gln Asp Asp Arg Asp Val Gln Gly Asp
                420                 425                 430
Pro Phe Ile Arg Gly
                435
```

<210> SEQ ID NO 71
<211> LENGTH: 1299
<212> TYPE: DNA
<213> ORGANISM: Corynebacterium glucuronolyticum

<400> SEQUENCE: 71

```
atgtcaaaat tcatgcagca gctgaaaaac actgcgtatc agcagtcatc agcgcaactc      60
ctgctcttct tcatgtcctg gggcatctgg tggtccttct tccagctttg gctctccagc     120
gaaacccgcg gtctcggctt caacggcagt gagatcggca ccatctactc ggtgaactcc     180
gccgtcacgc tcgtcctcat gctcgtctac ggaactgccc aagataagct tcgtactcgc     240
cgtaatttgg tgatcggtat tgcagttcta atgagcttga ccggcccgtt cttcatgtgg     300
gtctactggc cactgctgca gagcgagtcg ctctatgtcc tcggtgttgg acttggcgca     360
atcttcatcg gtacggcttt tgtggggtca tgcccgctgt tcgaggcgct tgccgagcgc     420
atgtcccgaa acacaacttt cgaatatggc caggcccgcg cgtggggttc ctttggctac     480
gccatcgtcg cactcctcgc cggcttcaac ttcaccatca cccggcgat  taacttctgg     540
atggcctcgg ccttcggcgt tctgttgctt ctcatcctcg ttttctggaa ggaaccggta     600
gcgcctcgta acgaaattgc agaggaggaa gtggaaaaca ccacacctag cgtcaaggaa     660
atggtgtctg ttctcaaagt gcccgccctc tgggtcgtca ttgtcctcgt gttcttcacg     720
tggacgttct acacggtctt cgaccagcag atgttcccgc agttctacac ctcactttt     780
agtgactccg ccaccggcga gcgaacctat ggcgtgctca actccgtcca agtgttcgtc     840
gaggcgttga tgatgggaat cgtgcccatc tacatgcgga aggtcggcgt gaagaacacc     900
ctcatgacgg gcttcgccgt catggcactg cgcatcctag gttgcgcggt cttcgcggac     960
ccagtcacca tctcctttgt caagatgttc cacgctctcg aggtaccact gtgcatcctc    1020
cccatcttcc gctacttcac cctgcacttc cccacgaaga tctcggccac cttgtacatg    1080
gtcggcttcc agattgcctc gcaggtgggt aacgtcgtca tgtccccgat cctcggttcg    1140
ctgcgtgacc gcctcggttt ccagccgacc ttctatgtca tctcgggaat cgtccttgtc    1200
tccgctatct tcgcctggtt ggctctcaag ggcgataagg aacaagtgga gggcgatccc    1260
ttctaccgcg attcggaact taaggagata caccaatga                         1299
```

<210> SEQ ID NO 72
<211> LENGTH: 432
<212> TYPE: PRT
<213> ORGANISM: Corynebacterium glucuronolyticum

<400> SEQUENCE: 72

```
Met Ser Lys Phe Met Gln Gln Leu Lys Asn Thr Ala Tyr Gln Gln Ser
1               5                   10                  15

Ser Ala Gln Leu Leu Phe Phe Met Ser Trp Gly Ile Trp Trp Ser
            20                  25                  30

Phe Phe Gln Leu Trp Leu Ser Ser Glu Thr Arg Gly Leu Gly Phe Asn
        35                  40                  45

Gly Ser Glu Ile Gly Thr Ile Tyr Ser Val Asn Ser Ala Val Thr Leu
    50                  55                  60

Val Leu Met Leu Val Tyr Gly Thr Ala Gln Asp Lys Leu Arg Thr Arg
65                  70                  75                  80

Arg Asn Leu Val Ile Gly Ile Ala Val Leu Met Ser Leu Thr Gly Pro
                85                  90                  95
```

Phe Phe Met Trp Val Tyr Trp Pro Leu Leu Gln Ser Glu Ser Leu Tyr
            100                 105                 110

Val Leu Gly Val Gly Leu Gly Ala Ile Phe Ile Gly Thr Ala Phe Val
            115                 120                 125

Gly Ser Cys Pro Leu Phe Glu Ala Leu Ala Glu Arg Met Ser Arg Lys
130                 135                 140

His Asn Phe Glu Tyr Gly Gln Ala Arg Ala Trp Gly Ser Phe Gly Tyr
145                 150                 155                 160

Ala Ile Val Ala Leu Leu Ala Gly Phe Asn Phe Thr Ile Asn Pro Ala
                165                 170                 175

Ile Asn Phe Trp Met Ala Ser Ala Phe Gly Val Leu Leu Leu Leu Ile
            180                 185                 190

Leu Val Phe Trp Lys Glu Pro Val Ala Pro Arg Asn Glu Ile Ala Glu
            195                 200                 205

Glu Glu Val Glu Asn Thr Thr Pro Ser Val Lys Glu Met Val Ser Val
210                 215                 220

Leu Lys Val Pro Ala Leu Trp Val Val Ile Val Leu Val Phe Phe Thr
225                 230                 235                 240

Trp Thr Phe Tyr Thr Val Phe Asp Gln Gln Met Phe Pro Gln Phe Tyr
                245                 250                 255

Thr Ser Leu Phe Ser Asp Ser Ala Thr Gly Glu Arg Thr Tyr Gly Val
            260                 265                 270

Leu Asn Ser Val Gln Val Phe Val Glu Ala Leu Met Met Gly Ile Val
            275                 280                 285

Pro Ile Tyr Met Arg Lys Val Gly Val Lys Asn Thr Leu Met Thr Gly
290                 295                 300

Phe Ala Val Met Ala Leu Arg Ile Leu Gly Cys Ala Val Phe Ala Asp
305                 310                 315                 320

Pro Val Thr Ile Ser Phe Val Lys Met Phe His Ala Leu Glu Val Pro
                325                 330                 335

Leu Cys Ile Leu Pro Ile Phe Arg Tyr Phe Thr Leu His Phe Pro Thr
            340                 345                 350

Lys Ile Ser Ala Thr Leu Tyr Met Val Gly Phe Gln Ile Ala Ser Gln
            355                 360                 365

Val Gly Asn Val Val Met Ser Pro Ile Leu Gly Ser Leu Arg Asp Arg
            370                 375                 380

Leu Gly Phe Gln Pro Thr Phe Tyr Val Ile Ser Gly Ile Val Leu Val
385                 390                 395                 400

Ser Ala Ile Phe Ala Trp Leu Ala Leu Lys Gly Asp Lys Glu Gln Val
                405                 410                 415

Glu Gly Asp Pro Phe Tyr Arg Asp Ser Glu Leu Lys Glu Ile His Gln
            420                 425                 430

<210> SEQ ID NO 73
<211> LENGTH: 1326
<212> TYPE: DNA
<213> ORGANISM: Bifidobacterium animalis

<400> SEQUENCE: 73
atggcaacaa ccacgaaggt gtggaggaac ccctcctacc tgcaaagctc aaccggcatc      60
ttcctgttct tctgctcctg gggcatctgg tggtcgttct tccagcgctg gctcaactcg     120
atgggactca acggcgcgga agtgggcacg atctattcga tcaactcgct ggccacgctc     180
atcctcatgt tcgggtacgg cctcatccag gacaatctcg gactcaagcg ccgtcttgtg     240

```
ctcgtcatct cggcgatcgc cgcactcgtc ggacccttcg tgcagttcgt gtacgcgccg      300
ctgatgagga cgaacatgat ggccgccgca ctcgtgggct ccgtcgttct ctccgcgggc      360
ttcatggcag gctgctcgct catcgaggcc gtgaccgaac ggtacagccg ccgtttcaac      420
ttcgagtacg gccaatcccg cgcatggggt tccttcggct atgccattgt ggcgcttgtc      480
gccggcttcg tgttcaacat caacccgatg atcaacttct ggctcggctc cgcattcggc      540
gtgggcatgc tcatcgtgta cctcacctgg tatccggccg agcagcgcga agcgctcaag      600
gaagccgccg atccgaatgc cgcgccaact aacccgacca tcaaagacat gctcggcgtg      660
ctcaagatgc ccacgctgtg ggtgctcatc gtgttcatgc tgctcaccaa cacgttctac      720
accgtattcg accagcagat gttccccacc tactacgcct cgctcttccc gaatgaggcc      780
accggcaacg ccgtctacgg cacgctcaac tcggtgcagg tgttctgcga atccgcgatg      840
atgggcgtcg tgccgatcat catgcgcaag gtaggtgtgc gcaacgcgtt gctgctcgga      900
tccacggtga tgttccttcg catcgggctg tgcggcatct tccacgatcc ggtgtccatc      960
tcgatcgtca aaatgttcca cgccattgaa gttccgctgt tctgcctgcc ggcgttccgc     1020
tacttcacgc tccacttcaa tccgaagctc tccgcgacgc tctacatggt cggcttccag     1080
attgcctcac agatcggcca ggtcgtcttc tccaccccgc tcggcatgct gcatgaccgc     1140
atgggcgacc gcacgacgtt cctgacgatc tccgccatcg tgcttgctgc accgtctac      1200 ggattcttcg tgatcaagcg cgacgacgag caggtggatg cgatccgtt catccgcgat      1260 tcgaagaagc tgccgtcgct cgccaccgac gaggcgatcc tctccgcgga ttccgaggat     1320
atgtaa                                                                1326
```

<210> SEQ ID NO 74
<211> LENGTH: 441
<212> TYPE: PRT
<213> ORGANISM: Bifidobacterium animalis

<400> SEQUENCE: 74

```
Met Ala Thr Thr Thr Lys Val Trp Arg Asn Pro Ser Tyr Leu Gln Ser
1               5                   10                  15

Ser Thr Gly Ile Phe Leu Phe Phe Cys Ser Trp Gly Ile Trp Trp Ser
            20                  25                  30

Phe Phe Gln Arg Trp Leu Asn Ser Met Gly Leu Asn Gly Ala Glu Val
        35                  40                  45

Gly Thr Ile Tyr Ser Ile Asn Ser Leu Ala Thr Leu Ile Leu Met Phe
    50                  55                  60

Gly Tyr Gly Leu Ile Gln Asp Asn Leu Gly Leu Lys Arg Arg Leu Val
65                  70                  75                  80

Leu Val Ile Ser Ala Ile Ala Ala Leu Val Gly Pro Phe Val Gln Phe
                85                  90                  95

Val Tyr Ala Pro Leu Met Arg Thr Asn Met Met Ala Ala Leu Val
            100                 105                 110

Gly Ser Val Val Leu Ser Ala Gly Phe Met Ala Gly Cys Ser Leu Ile
        115                 120                 125

Glu Ala Val Thr Glu Arg Tyr Ser Arg Arg Phe Asn Phe Glu Tyr Gly
    130                 135                 140

Gln Ser Arg Ala Trp Gly Ser Phe Gly Tyr Ala Ile Val Ala Leu Val
145                 150                 155                 160

Ala Gly Phe Val Phe Asn Ile Asn Pro Met Ile Asn Phe Trp Leu Gly
                165                 170                 175
```

```
Ser Ala Phe Gly Val Gly Met Leu Ile Val Tyr Leu Thr Trp Tyr Pro
            180                 185                 190
Ala Glu Gln Arg Glu Ala Leu Lys Glu Ala Ala Asp Pro Asn Ala Ala
        195                 200                 205
Pro Thr Asn Pro Thr Ile Lys Asp Met Leu Gly Val Leu Lys Met Pro
    210                 215                 220
Thr Leu Trp Val Leu Ile Val Phe Met Leu Leu Thr Asn Thr Phe Tyr
225                 230                 235                 240
Thr Val Phe Asp Gln Gln Met Phe Pro Thr Tyr Tyr Ala Ser Leu Phe
                245                 250                 255
Pro Asn Glu Ala Thr Gly Asn Ala Val Tyr Gly Thr Leu Asn Ser Val
            260                 265                 270
Gln Val Phe Cys Glu Ser Ala Met Met Gly Val Val Pro Ile Ile Met
        275                 280                 285
Arg Lys Val Gly Val Arg Asn Ala Leu Leu Leu Gly Ser Thr Val Met
    290                 295                 300
Phe Leu Arg Ile Gly Leu Cys Gly Ile Phe His Asp Pro Val Ser Ile
305                 310                 315                 320
Ser Ile Val Lys Met Phe His Ala Ile Glu Val Pro Leu Phe Cys Leu
                325                 330                 335
Pro Ala Phe Arg Tyr Phe Thr Leu His Phe Asn Pro Lys Leu Ser Ala
            340                 345                 350
Thr Leu Tyr Met Val Gly Phe Gln Ile Ala Ser Gln Ile Gly Gln Val
        355                 360                 365
Val Phe Ser Thr Pro Leu Gly Met Leu His Asp Arg Met Gly Asp Arg
    370                 375                 380
Thr Thr Phe Leu Thr Ile Ser Ala Ile Val Leu Ala Ala Thr Val Tyr
385                 390                 395                 400
Gly Phe Phe Val Ile Lys Arg Asp Asp Glu Gln Val Asp Gly Asp Pro
                405                 410                 415
Phe Ile Arg Asp Ser Lys Lys Leu Pro Ser Leu Ala Thr Asp Glu Ala
            420                 425                 430
Ile Leu Ser Ala Asp Ser Glu Asp Met
        435                 440

<210> SEQ ID NO 75
<211> LENGTH: 1398
<212> TYPE: DNA
<213> ORGANISM: Bifidobacterium gallicum

<400> SEQUENCE: 75
atggtgaata aaccgaagac cgcaaaaatc tggtccaacc cgtcctattt gcagagctcg      60
tttggcattt tcctgttctt ctgctcatgg ggcatctggt ggtccttctt ccagcgctgg     120
ctcaatacca ttggcctgaa cggcgcggaa gtcggcaccg tctattccat caactcgctg     180
gccacgctga tcctcatgtt cggctacgga atcatccagg acaacctggg catcaagcgc     240
cgtctcgtgg tcgtcatcgc caccatcgcg gcactgatcg gccccttcgt ccagttcgtg     300
tacgcgccgc tcatgcagac gaacatcatg gccgccgccc tgatcggctc cgtggtgctc     360
tccgccggct tcatgtccgg atgctcgctg attgaagcgc ttaccgaacg ctacagccgc     420
aagttcggct cgaatacgg ccagtcccgc gcatggggct ccttcggcta cgccattgtg     480
gccctgatcg ccgcattgt cttcaacatc aacccgatga tcaacttctg gctcggctcc     540
gcattcggcg tgggcatgct catcgtgtac ctcacgtggt acccggccga gcagcgccag     600
```

```
gccctcaagg aagcggccga cccgaacgcc gagaagtcca acccgtcctt caaggacatg    660
gtcaacgtgc tcaagatgcc gacgctgtgg gtgctcatca tcttcatgct gctgaccaac    720
acgttctaca cggtcttcga ccagcagatg ttcccgacct actacgcctc gctgttcccg    780
agcattgaaa cgggcaacac ggtctacggc gtgctcaact ccatccaggt cttctgcgaa    840
tccgcgatga tgggcgtcgt cccgatcatc atgcgcaaga tcggcgtgcg caacgcgctg    900
ctgctgggcg ccaccgtcat gttcctgcgc atcggcctgt gcggcatctt ccacgacccg    960
gtagccatct ccatcgtcaa gatgttccac gccatcgaag ttccactgtt ctgcctgccg   1020
gcgttccgct acttcacgct gcacttcaac ccgaagctct cggccacgct gtacatggtg   1080
ggcttccaga tcgcctcaca gatcggccag gttatcttct ccaccccgct gggcatgctg   1140
cacgaccgct tcggcgaccg caccaccttc ctgtccatca gcggcatcgt gctgctggca   1200
acgatctacg gcttcttcgt catcaagcgc gacgacgagc acgtggacgg cgatccgttc   1260
ctgcgtgacc gcgaccgcaa ggaaatggaa ctcatcgaag agaacctgca gccagacgcc   1320
gagctggaaa cgagccccgt aggcgtcgca gcacaggtgc gcgacaaccg cgcggtccag   1380
ccggaatacg caagctga                                                 1398
```

<210> SEQ ID NO 76
<211> LENGTH: 465
<212> TYPE: PRT
<213> ORGANISM: Bifidobacterium gallicum

<400> SEQUENCE: 76

```
Met Val Asn Lys Pro Lys Thr Ala Lys Ile Trp Ser Asn Pro Ser Tyr
1               5                   10                  15

Leu Gln Ser Ser Phe Gly Ile Phe Leu Phe Cys Ser Trp Gly Ile
            20                  25                  30

Trp Trp Ser Phe Phe Gln Arg Trp Leu Asn Thr Ile Gly Leu Asn Gly
        35                  40                  45

Ala Glu Val Gly Thr Val Tyr Ser Ile Asn Ser Leu Ala Thr Leu Ile
    50                  55                  60

Leu Met Phe Gly Tyr Gly Ile Ile Gln Asp Asn Leu Gly Ile Lys Arg
65                  70                  75                  80

Arg Leu Val Val Ile Ala Thr Ile Ala Ala Leu Ile Gly Pro Phe
                85                  90                  95

Val Gln Phe Val Tyr Ala Pro Leu Met Gln Thr Asn Ile Met Ala Ala
            100                 105                 110

Ala Leu Ile Gly Ser Val Val Leu Ser Ala Gly Phe Met Ser Gly Cys
        115                 120                 125

Ser Leu Ile Glu Ala Leu Thr Glu Arg Tyr Ser Arg Lys Phe Gly Phe
    130                 135                 140

Glu Tyr Gly Gln Ser Arg Ala Trp Gly Ser Phe Gly Tyr Ala Ile Val
145                 150                 155                 160

Ala Leu Ile Ala Gly Ile Val Phe Asn Ile Asn Pro Met Ile Asn Phe
                165                 170                 175

Trp Leu Gly Ser Ala Phe Gly Val Gly Met Leu Ile Val Tyr Leu Thr
            180                 185                 190

Trp Tyr Pro Ala Glu Gln Arg Gln Ala Leu Lys Glu Ala Ala Asp Pro
        195                 200                 205

Asn Ala Glu Lys Ser Asn Pro Ser Phe Lys Asp Met Val Asn Val Leu
    210                 215                 220

Lys Met Pro Thr Leu Trp Val Leu Ile Ile Phe Met Leu Leu Thr Asn
```

| | | | | 225 | | | | 230 | | | | 235 | | | | 240 |
|---|---|---|---|---|---|---|---|---|---|---|---|---|---|---|---|---|
Thr Phe Tyr Thr Val Phe Asp Gln Gln Met Phe Pro Thr Tyr Tyr Ala
                         245                         250                         255

Ser Leu Phe Pro Ser Ile Glu Thr Gly Asn Thr Val Tyr Gly Val Leu
                260                 265                 270

Asn Ser Ile Gln Val Phe Cys Glu Ser Ala Met Met Gly Val Val Pro
                275                 280                 285

Ile Ile Met Arg Lys Ile Gly Val Arg Asn Ala Leu Leu Leu Gly Ala
                290                 295                 300

Thr Val Met Phe Leu Arg Ile Gly Leu Cys Gly Ile Phe His Asp Pro
305                 310                 315                 320

Val Ala Ile Ser Ile Val Lys Met Phe His Ala Ile Glu Val Pro Leu
                325                 330                 335

Phe Cys Leu Pro Ala Phe Arg Tyr Phe Thr Leu His Phe Asn Pro Lys
                340                 345                 350

Leu Ser Ala Thr Leu Tyr Met Val Gly Phe Gln Ile Ala Ser Gln Ile
                355                 360                 365

Gly Gln Val Ile Phe Ser Thr Pro Leu Gly Met Leu His Asp Arg Phe
                370                 375                 380

Gly Asp Arg Thr Thr Phe Leu Ser Ile Ser Gly Ile Val Leu Leu Ala
385                 390                 395                 400

Thr Ile Tyr Gly Phe Phe Val Ile Lys Arg Asp Asp Glu His Val Asp
                405                 410                 415

Gly Asp Pro Phe Leu Arg Asp Arg Asp Arg Lys Glu Met Glu Leu Ile
                420                 425                 430

Glu Glu Asn Leu Gln Pro Asp Ala Glu Leu Glu Thr Ser Pro Val Gly
                435                 440                 445

Val Ala Ala Gln Val Arg Asp Asn Arg Ala Val Gln Pro Glu Tyr Ala
                450                 455                 460

Ser
465

<210> SEQ ID NO 77
<211> LENGTH: 1338
<212> TYPE: DNA
<213> ORGANISM: Bifidobacterium longum

<400> SEQUENCE: 77

```
atggcaagtg caaccaagtc tgcatggaag aatccttcct atctgcagag ctctttcggc      60
atcttcatgt tcttctgctc ctggggcatc tggtggtcct tcttccagcg ctggctcatc     120
tcaggcgttg gattgaccaa tgctgaagtc ggcaccatct actccatcaa ctcgctggcc     180
accctggtca tcatgtttgt gtacggcgtg attcaggatc agctcggcat caagcgcaag     240
ctcgtcatcg tagtctcggt aatcgccgcc tgcgttggcc cattcgtcca attcgtttac     300
gccccgatga tcctcgccgg tgcaccacc cgctggatcg cgcactcat cggctccatc      360
gttctgtctg ccggcttcat gtccggctgc tccctgttcg aggccgtcac cgaacgctac     420
tcccgtaaat tcggtttcga atatggccag tcccgtgctt ggggctcctt cggttacgcc     480
atcgtggcgc tgtgcgccgg cttcctgttc aacatcaacc cgctgatcaa cttctgggtc     540
ggctccgcat tcggccctgg catgctcctc gtgtacgcct ctgggtcccg gccgagcag      600
aaggaagagc tcaagaagga aaccgacccg aacgcagccc ccaccaaccc gtccctcaag     660
gaaatggtcg ccgttctcaa gatgccgacc ctgtgggtgc tcatcgtctt catgctgctg     720
```

```
accaacacct tctacaccgt gttcgatcag cagatgttcc cgacctacta cgccaacctc    780
ttccccactg aagaaatcgg caacgccacc tacggcaccc tgaacggttt ccaggtcttc    840
cttgagtccg caatgatggg cgtggtcccg atcatcatga agaagatcgg cgtgcgcaac    900
gctctgctgc tcggcgctac cgtgatgttc ctgcgcatcg gcttgtgcgg cgtgttccac    960
gacccggtca ccatctccat cgtcaagctg ttccactcca tcgaagtgcc gctgttctgc   1020
ctgccggcat ccgctacttt cactctgcac ttcgacacca gctctctgc cacgctgtac    1080 atggtgggct tccagatcgc ttcccaagtg ggtcaggtca tcttctcgac ccctctgggt   1140
gccttccacg acaagatggc tcagattctg ccgaacaacg acatgggatc ccgcgtgacc   1200
ttctgggtca tctctgccat cgtgctgtgc gcactgattt acggcttctt cgtcatcaag   1260
catgatgatc aggaagtcgg cggcgacccg ttctacaccg acaagcagct tcgccagatg   1320
gaagccgcca aggcctga                                                 1338
```

<210> SEQ ID NO 78
<211> LENGTH: 445
<212> TYPE: PRT
<213> ORGANISM: Bifidobacterium longum

<400> SEQUENCE: 78

```
Met Ala Ser Ala Thr Lys Ser Ala Trp Lys Asn Pro Ser Tyr Leu Gln
1               5                   10                  15

Ser Ser Phe Gly Ile Phe Met Phe Phe Cys Ser Trp Gly Ile Trp Trp
            20                  25                  30

Ser Phe Phe Gln Arg Trp Leu Ile Ser Gly Val Gly Leu Thr Asn Ala
        35                  40                  45

Glu Val Gly Thr Ile Tyr Ser Ile Asn Ser Leu Ala Thr Leu Val Ile
    50                  55                  60

Met Phe Val Tyr Gly Val Ile Gln Asp Gln Leu Gly Ile Lys Arg Lys
65                  70                  75                  80

Leu Val Ile Val Ser Val Ile Ala Ala Cys Val Gly Pro Phe Val
                85                  90                  95

Gln Phe Val Tyr Ala Pro Met Ile Leu Ala Gly Gly Thr Thr Arg Trp
            100                 105                 110

Ile Gly Ala Leu Ile Gly Ser Ile Val Leu Ser Ala Gly Phe Met Ser
        115                 120                 125

Gly Cys Ser Leu Phe Glu Ala Val Thr Glu Arg Tyr Ser Arg Lys Phe
    130                 135                 140

Gly Phe Glu Tyr Gly Gln Ser Arg Ala Trp Gly Ser Phe Gly Tyr Ala
145                 150                 155                 160

Ile Val Ala Leu Cys Ala Gly Phe Leu Phe Asn Ile Asn Pro Leu Ile
                165                 170                 175

Asn Phe Trp Val Gly Ser Ala Phe Gly Pro Gly Met Leu Leu Val Tyr
            180                 185                 190

Ala Phe Trp Val Pro Ala Glu Gln Lys Glu Leu Lys Lys Glu Thr
        195                 200                 205

Asp Pro Asn Ala Ala Pro Thr Asn Pro Ser Leu Lys Glu Met Val Ala
    210                 215                 220

Val Leu Lys Met Pro Thr Leu Trp Val Leu Ile Val Phe Met Leu Leu
225                 230                 235                 240

Thr Asn Thr Phe Tyr Thr Val Phe Asp Gln Gln Met Phe Pro Thr Tyr
                245                 250                 255

Tyr Ala Asn Leu Phe Pro Thr Glu Glu Ile Gly Asn Ala Thr Tyr Gly
```

```
            260                 265                 270
Thr Leu Asn Gly Phe Gln Val Phe Leu Glu Ser Ala Met Met Gly Val
            275                 280                 285
Val Pro Ile Ile Met Lys Lys Ile Gly Val Arg Asn Ala Leu Leu Leu
            290                 295                 300
Gly Ala Thr Val Met Phe Leu Arg Ile Gly Leu Cys Gly Val Phe His
305                 310                 315                 320
Asp Pro Val Thr Ile Ser Ile Val Lys Leu Phe His Ser Ile Glu Val
                    325                 330                 335
Pro Leu Phe Cys Leu Pro Ala Phe Arg Tyr Phe Thr Leu His Phe Asp
                    340                 345                 350
Thr Lys Leu Ser Ala Thr Leu Tyr Met Val Gly Phe Gln Ile Ala Ser
            355                 360                 365
Gln Val Gly Gln Val Ile Phe Ser Thr Pro Leu Gly Ala Phe His Asp
            370                 375                 380
Lys Met Ala Gln Ile Leu Pro Asn Asn Asp Met Gly Ser Arg Val Thr
385                 390                 395                 400
Phe Trp Val Ile Ser Ala Ile Val Leu Cys Ala Leu Ile Tyr Gly Phe
                    405                 410                 415
Phe Val Ile Lys His Asp Asp Gln Glu Val Gly Gly Asp Pro Phe Tyr
                    420                 425                 430
Thr Asp Lys Gln Leu Arg Gln Met Glu Ala Ala Lys Ala
            435                 440                 445

<210> SEQ ID NO 79
<211> LENGTH: 1422
<212> TYPE: DNA
<213> ORGANISM: Bifidobacterium adolescentis

<400> SEQUENCE: 79
ctgaaatcag agcaggcgca agccaaaaca acatcggaag cgatcgctgc cgcgcggcag      60
cggcagcgcg aagagaaaaa gagaatcaaa atggcaagca aaacacgttc tgtatggaag     120
aatccttcct atctgcagag ctccttcggc attttcatgt tcttctgttc ctggggcatc     180
tggtggtcct tcttctcccg ctggctcact gacccgaccc acggtctggg catgagctcc     240
gcggaacagg gccagatcta ctccatcaac tccttggcca ccctggtcat catgttcgtt     300
tacggcacca ttcaggacca gctgggcatt aagcgtaagc tcgtgatctt catctctgcg     360
gtcgctgcat gcgttggccc gttcgtgcag ttcgtgtacc agccgatgct gaccgccggc     420
ggcaccaccc gattcatcgg cgtgcttctc ggctccatcg tgctgtccgc aggcttcatg     480
gccggctgct ccctgttcga agccatcacc gaacgttact cccgtaagtt cggcttcgaa     540
tacgccagtc ccgcgcttg gggctccttc ggctacgctg tcgtggcact gtgcgcaggc     600
ttcctgttca acatcaaccc gctgctgaac ttctggggttg gttccatctg cggcctcagc     660
atgctgtgcg tctatgcttt ctgggttccg gccgagcaga aggaagaact caagaaggaa     720
gctgatccga acgcaactcc gaccaacccg tccttcaagg aaatggtctc cgtcctgaag     780
atgccgaccc tgtgggtgct catcgtcttc atgctgttca ccaacacctt ctacaccgtg     840
ttcgatcagc agatgttccc gaactactac gcctccctct cccgaccac cgaaatcggc     900
aacgccacct acggcaccct gaactccttc caggtgttcc ttgagtccgc catgatgggc     960
gtcgtcccga tcatcatgaa gaagatcggc gtgcgtaact ccctgctgct cggcgccacc    1020
gtgatgttcg cccgtatcgg tctgtgcggc gtgttccatg acccggtctc cgtctccatc    1080
```

```
gtcaagctgt tccactccat cgaggtaccg ctgttctgcc tgccggcgtt ccgctacttc    1140
accctgcact cgacacgaa gctgtctgcc accctgtaca tggttggttt ccagatcgct     1200
tcccaggtcg gccaggtgat tttctccacc ccgatgggtg ctctgcatga tgccatgggc    1260
gaccgtccga ccttcttcac catctctgcc atcgtgtttg cggctctggt ctacggcttc    1320
ttcgtcatca agaaggatga tcaggaagtc ggcggcgatc cgttctacac tgacaagcag    1380
ctcaaggcca tgaaggccgc tgatgcggaa gtgaaggcct ga                       1422

<210> SEQ ID NO 80
<211> LENGTH: 473
<212> TYPE: PRT
<213> ORGANISM: Bifidobacterium adolescentis

<400> SEQUENCE: 80
```

Met Lys Ser Glu Gln Ala Gln Ala Lys Thr Thr Ser Glu Ala Ile Ala
1               5                   10                  15

Ala Ala Arg Gln Arg Gln Arg Glu Gly Lys Lys Arg Ile Lys Met Ala
                20                  25                  30

Ser Lys Thr Arg Ser Val Trp Lys Asn Pro Ser Tyr Leu Gln Ser Ser
            35                  40                  45

Phe Gly Ile Phe Met Phe Phe Cys Ser Trp Gly Ile Trp Trp Ser Phe
    50                  55                  60

Phe Ser Arg Trp Leu Thr Asp Pro Thr His Gly Leu Gly Met Ser Ser
65                  70                  75                  80

Ala Glu Gln Gly Gln Ile Tyr Ser Ile Asn Ser Leu Ala Thr Leu Val
                85                  90                  95

Ile Met Phe Val Tyr Gly Thr Ile Gln Asp Gln Leu Gly Ile Lys Arg
                100                 105                 110

Lys Leu Val Ile Phe Ile Ser Ala Val Ala Ala Cys Val Gly Pro Phe
            115                 120                 125

Val Gln Phe Val Tyr Gln Pro Met Leu Thr Ala Gly Gly Thr Thr Arg
        130                 135                 140

Phe Ile Gly Val Leu Leu Gly Ser Ile Val Leu Ser Ala Gly Phe Met
145                 150                 155                 160

Ala Gly Cys Ser Leu Phe Glu Ala Ile Thr Glu Arg Tyr Ser Arg Lys
                165                 170                 175

Phe Gly Phe Glu Tyr Gly Gln Ser Arg Ala Trp Gly Ser Phe Gly Tyr
            180                 185                 190

Ala Val Val Ala Leu Cys Ala Gly Phe Leu Phe Asn Ile Asn Pro Leu
        195                 200                 205

Leu Asn Phe Trp Val Gly Ser Ile Cys Gly Leu Ser Met Leu Cys Val
    210                 215                 220

Tyr Ala Phe Trp Val Pro Ala Glu Gln Lys Glu Leu Lys Lys Glu
225                 230                 235                 240

Ala Asp Pro Asn Ala Thr Pro Thr Asn Pro Ser Phe Lys Glu Met Val
                245                 250                 255

Ser Val Leu Lys Met Pro Thr Leu Trp Val Leu Ile Val Phe Met Leu
            260                 265                 270

Phe Thr Asn Thr Phe Tyr Thr Val Phe Asp Gln Gln Met Phe Pro Asn
        275                 280                 285

Tyr Tyr Ala Ser Leu Phe Pro Thr Glu Ile Gly Asn Ala Thr Tyr
    290                 295                 300

Gly Thr Leu Asn Ser Phe Gln Val Phe Leu Glu Ser Ala Met Met Gly
305                 310                 315                 320

```
Val Val Pro Ile Ile Met Lys Lys Ile Gly Val Arg Asn Ser Leu Leu
            325                 330                 335

Leu Gly Ala Thr Val Met Phe Ala Arg Ile Gly Leu Cys Gly Val Phe
            340                 345                 350

His Asp Pro Val Ser Val Ser Ile Val Lys Leu Phe His Ser Ile Glu
            355                 360                 365

Val Pro Leu Phe Cys Leu Pro Ala Phe Arg Tyr Phe Thr Leu His Phe
            370                 375                 380

Asp Thr Lys Leu Ser Ala Thr Leu Tyr Met Val Gly Phe Gln Ile Ala
385                 390                 395                 400

Ser Gln Val Gly Gln Val Ile Phe Ser Thr Pro Met Gly Ala Leu His
                405                 410                 415

Asp Ala Met Gly Asp Arg Pro Thr Phe Phe Thr Ile Ser Ala Ile Val
            420                 425                 430

Phe Ala Ala Leu Val Tyr Gly Phe Phe Val Ile Lys Lys Asp Asp Gln
            435                 440                 445

Glu Val Gly Gly Asp Pro Phe Tyr Thr Asp Lys Gln Leu Lys Ala Met
    450                 455                 460

Lys Ala Ala Asp Ala Glu Val Lys Ala
465                 470

<210> SEQ ID NO 81
<211> LENGTH: 1503
<212> TYPE: DNA
<213> ORGANISM: Bifidobacterium longum

<400> SEQUENCE: 81
ttgcgtgtcg aacaggtacg acacgccgat ttacgtcaat cgattgacgt aaatcgattg      60
acgtcgcata ataattacta cataacaact tctacaaagg cacggccgcc cgagcagaag     120
cgttacataa ccaataacca accaagtagt aatcaaagga tgattatggc aagtgcaacc     180
aagtctgcat ggaagaatcc ttcctatctg cagagctctt tcggcatctt catgttcttc     240
tgctcctggg gcatctggtg gtccttcttc cagcgctggc tcatctcagg cgttggattg     300
accaatgctg aagtcggcac catctactcc atcaactcgc tggccaccct ggtcatcatg     360
tttgtgtacg gcgtgattca ggatcagctc ggcatcaagc gcaagctcgt catcgtagtc     420
tcggtaatcg ccgcctgcgt tggcccattc gtccaattcg tttacgcccc gatgatcctc     480
gccggtggca ccacccgctg gatcggcgca ctcatcggct ccatcgttct gtctgccggc     540
ttcatgtccg gctgctccct gttcgaggcc gtcaccgaac gctactcccg taaattcggt     600
ttcgaatatg gccagtcccg tgcttggggc tccttcggtt acgccatcgt ggcgctgtgc     660
gccggcttcc tgttcaacat caacccgctg atcaacttct gggtcggctc cgcattcggc     720
cctggcatgc tcctcgtgta cgccttctgg gtcccggccg agcagaagga agagctcaag     780
aaggaaaccg acccgaacgc agcccccacc aacccgtccc tcaaggaaat ggtcgccgtt     840
ctcaagatgc cgaccctgtg ggtgctcatc gtcttcatgc tgctgaccaa caccttctac     900
accgtgttcg atcagcagat gttcccgacc tactacgcca acctcttccc cactgaagaa     960
atcggcaacg ccacctacgg cacccctgaac ggtttccagg tcttccttga gtccgcaatg    1020
atgggcgtgg tcccgatcat catgaagaag atcggcgtgc gcaacgctct gctgctcggc    1080
gctaccgtga tgttcctgcg catcggcttg tgcggcgtgt tccacgaccc ggtcaccatc    1140
tccatcgtca agctgttcca ctccatcgaa gtgccgctgt tctgcctgcc ggcattccgc    1200
```

-continued

```
tacttcactc tgcacttcga caccaagctc tctgccacgc tgtacatggt gggcttccag   1260
atcgcttccc aagtgggtca ggtcatcttc tcgacccctc tgggtgcctt ccacgacaag   1320
atggctcaga ttctgccgaa caacgacatg ggatcccgcg tgaccttctg ggtcatctct   1380
gccatcgtgc tgtgcgcact gatttacggc ttcttcgtca tcaagcatga tgatcaggaa   1440
gtcggcggcg acccgttcta caccgacaag cagcttcgcc agatggaagc cgccaaggcc   1500
tga                                                                 1503
```

<210> SEQ ID NO 82
<211> LENGTH: 500
<212> TYPE: PRT
<213> ORGANISM: Bifidobacterium longum

<400> SEQUENCE: 82

```
Met Arg Val Glu Gln Val Arg His Ala Asp Leu Arg Gln Ser Ile Asp
1               5                   10                  15

Val Asn Arg Leu Thr Ser His Asn Asn Tyr Tyr Ile Thr Thr Ser Thr
            20                  25                  30

Lys Ala Arg Pro Pro Glu Gln Lys Arg Tyr Ile Thr Asn Asn Gln Pro
        35                  40                  45

Ser Ser Asn Gln Arg Met Ile Met Ala Ser Ala Thr Lys Ser Ala Trp
    50                  55                  60

Lys Asn Pro Ser Tyr Leu Gln Ser Ser Phe Gly Ile Phe Met Phe Phe
65                  70                  75                  80

Cys Ser Trp Gly Ile Trp Trp Ser Phe Phe Gln Arg Trp Leu Ile Ser
                85                  90                  95

Gly Val Gly Leu Thr Asn Ala Glu Val Gly Thr Ile Tyr Ser Ile Asn
            100                 105                 110

Ser Leu Ala Thr Leu Val Ile Met Phe Val Tyr Gly Val Ile Gln Asp
        115                 120                 125

Gln Leu Gly Ile Lys Arg Lys Leu Val Ile Val Ser Val Ile Ala
    130                 135                 140

Ala Cys Val Gly Pro Phe Val Gln Phe Val Tyr Ala Pro Met Ile Leu
145                 150                 155                 160

Ala Gly Gly Thr Thr Arg Trp Ile Gly Ala Leu Ile Gly Ser Ile Val
                165                 170                 175

Leu Ser Ala Gly Phe Met Ser Gly Cys Ser Leu Phe Glu Ala Val Thr
            180                 185                 190

Glu Arg Tyr Ser Arg Lys Phe Gly Phe Glu Tyr Gly Gln Ser Arg Ala
        195                 200                 205

Trp Gly Ser Phe Gly Tyr Ala Ile Val Ala Leu Cys Ala Gly Phe Leu
    210                 215                 220

Phe Asn Ile Asn Pro Leu Ile Asn Phe Trp Val Gly Ser Ala Phe Gly
225                 230                 235                 240

Pro Gly Met Leu Leu Val Tyr Ala Phe Val Pro Ala Glu Gln Lys
                245                 250                 255

Glu Glu Leu Lys Lys Glu Thr Asp Pro Asn Ala Ala Pro Thr Asn Pro
            260                 265                 270

Ser Leu Lys Glu Met Val Ala Val Leu Lys Met Pro Thr Leu Trp Val
        275                 280                 285

Leu Ile Val Phe Met Leu Leu Thr Asn Thr Phe Tyr Thr Val Phe Asp
    290                 295                 300

Gln Gln Met Phe Pro Thr Tyr Tyr Ala Asn Leu Phe Pro Thr Glu Glu
305                 310                 315                 320
```

Ile Gly Asn Ala Thr Tyr Gly Thr Leu Asn Gly Phe Gln Val Phe Leu
                325                 330                 335

Glu Ser Ala Met Met Gly Val Val Pro Ile Ile Met Lys Lys Ile Gly
            340                 345                 350

Val Arg Asn Ala Leu Leu Leu Gly Ala Thr Val Met Phe Leu Arg Ile
        355                 360                 365

Gly Leu Cys Gly Val Phe His Asp Pro Val Thr Ile Ser Ile Val Lys
    370                 375                 380

Leu Phe His Ser Ile Glu Val Pro Leu Phe Cys Leu Pro Ala Phe Arg
385                 390                 395                 400

Tyr Phe Thr Leu His Phe Asp Thr Lys Leu Ser Ala Thr Leu Tyr Met
                405                 410                 415

Val Gly Phe Gln Ile Ala Ser Gln Val Gly Gln Val Ile Phe Ser Thr
            420                 425                 430

Pro Leu Gly Ala Phe His Asp Lys Met Ala Gln Ile Leu Pro Asn Asn
        435                 440                 445

Asp Met Gly Ser Arg Val Thr Phe Trp Val Ile Ser Ala Ile Val Leu
    450                 455                 460

Cys Ala Leu Ile Tyr Gly Phe Phe Val Ile Lys His Asp Asp Gln Glu
465                 470                 475                 480

Val Gly Gly Asp Pro Phe Tyr Thr Asp Lys Gln Leu Arg Gln Met Glu
                485                 490                 495

Ala Ala Lys Ala
            500

<210> SEQ ID NO 83
<211> LENGTH: 1266
<212> TYPE: DNA
<213> ORGANISM: Mitsuokella multacida

<400> SEQUENCE: 83

```
atgggaaatc tcttgaaggc attttcgaat ccgttctaca ggacgagctc gcttgagatc    60
ctgctgttct tcgcgggctg gggcatctgg tggtcgttct ttcagatctg gctgacgacg   120
aagcagggct tcacgggcgc gcaggtcggc acgattact ccttcggcag cgcggtcgcg   180
ctcgtcctga tgttcgtcta cggctccctg caggacaagc tcggcatgaa gaagacgatg   240
ctgaagttct tcgccgtctg ccagatcctc gtcggcccgt tcttcacctg gtctacgtg   300
ccgatgctcg ccgcgaactt ctacgtcggc gctgtcgtcg gtgccgtcta cctcgcggtg   360
gcgttcctcg cggcctgccc tgtctttgag gcggtcacag agcgcctgag ccgccgctac   420
tcctttgagt acggccaggc cagagcctgg ggctcgttcg gctatgccgt ggcagcgctc   480
tgcgcaggct tcctcttcac gatgaacccg aacctgatct tctggacggg ctccgctgtg   540
gcggcggtgc agcttatcgt cttggtctcg atgacgccgg agaacgacgc ttcgcttacg   600
gcgcagtacg aggtcaaggc agagagcatc aaggagagca agacgccgtc gttcggcgag   660
atcgtcggcg tgttcaagct catcgaggtc tggaagatga tcgtcttcgt catcatgagc   720
tggacgttct acaccgtctt tgaccagcag atgttcccgg agttcttcac gcgcttcttc   780
gcgacgccag aagcaggcca gcaggcttac ggcgtgctca actccatcga agtcttcctc   840
gaattcctca tgatgggcct cgtgccgatc ctcatgcgcc gtatcggcgt cgcaaggcc   900
atcctgctcg gctgcgccat catgatcgtc gcatcggcg gctgcggcct cgtcacgaat   960
cctcttggcg tcgccgtcat caagctcttg cacgcaccgg aaacgcgcgt cttcatcctc  1020
```

-continued

```
gctgtcttcc gctacttcac gctgcactttgacacgcgca tctcggcgac gctctacatg    1080
gtcggtttcc agatcgctgc acaggtcggc cagattatct tctcgacgcc gctcggcgcc    1140
ctgcatgaca gcatcggcta ccagagcact ttcctcgtca tctccggcat cgtctgtgtg    1200
gccagcctct acgctttcgt catcctcaag aaagacgacc agcaggtcga cggccagccg    1260
ctttga                                                              1266
```

<210> SEQ ID NO 84
<211> LENGTH: 421
<212> TYPE: PRT
<213> ORGANISM: Mitsuokella multacida

<400> SEQUENCE: 84

Met Gly Asn Leu Leu Lys Ala Phe Ser Asn Pro Phe Tyr Arg Thr Ser
1               5                   10                  15

Ser Leu Glu Ile Leu Leu Phe Phe Ala Gly Trp Gly Ile Trp Trp Ser
            20                  25                  30

Phe Phe Gln Ile Trp Leu Thr Thr Lys Gln Gly Phe Thr Gly Ala Gln
        35                  40                  45

Val Gly Thr Ile Tyr Ser Phe Gly Ser Ala Val Ala Leu Val Leu Met
    50                  55                  60

Phe Val Tyr Gly Ser Leu Gln Asp Lys Leu Gly Met Lys Lys Thr Met
65                  70                  75                  80

Leu Lys Phe Phe Ala Val Cys Gln Ile Leu Val Gly Pro Phe Phe Thr
                85                  90                  95

Trp Val Tyr Val Pro Met Leu Ala Ala Asn Phe Tyr Val Gly Ala Val
            100                 105                 110

Val Gly Ala Val Tyr Leu Ala Val Ala Phe Leu Ala Ala Cys Pro Val
        115                 120                 125

Phe Glu Ala Val Thr Glu Arg Leu Ser Arg Arg Tyr Ser Phe Glu Tyr
    130                 135                 140

Gly Gln Ala Arg Ala Trp Gly Ser Phe Gly Tyr Ala Val Ala Ala Leu
145                 150                 155                 160

Cys Ala Gly Phe Leu Phe Thr Met Asn Pro Asn Leu Ile Phe Trp Thr
                165                 170                 175

Gly Ser Ala Val Ala Ala Val Gln Leu Ile Val Leu Val Ser Met Thr
            180                 185                 190

Pro Glu Asn Asp Ala Ser Leu Thr Ala Gln Tyr Glu Val Lys Ala Glu
        195                 200                 205

Ser Ile Lys Glu Ser Lys Thr Pro Ser Phe Gly Glu Ile Val Gly Val
    210                 215                 220

Phe Lys Leu Ile Glu Val Trp Lys Met Ile Val Phe Val Ile Met Ser
225                 230                 235                 240

Trp Thr Phe Tyr Thr Val Phe Asp Gln Gln Met Phe Pro Glu Phe Phe
                245                 250                 255

Thr Arg Phe Phe Ala Thr Pro Glu Ala Gly Gln Gln Ala Tyr Gly Val
            260                 265                 270

Leu Asn Ser Ile Glu Val Phe Leu Glu Phe Leu Met Met Gly Leu Val
        275                 280                 285

Pro Ile Leu Met Arg Arg Gly Val Arg Lys Ala Ile Leu Leu Gly
    290                 295                 300

Cys Ala Ile Met Ile Val Arg Ile Gly Gly Cys Gly Leu Val Thr Asn
305                 310                 315                 320

Pro Leu Gly Val Ala Val Ile Lys Leu Leu His Ala Pro Glu Thr Ala

```
                    325                 330                 335
Leu Phe Ile Leu Ala Val Phe Arg Tyr Phe Thr Leu His Phe Asp Thr
            340                 345                 350

Arg Ile Ser Ala Thr Leu Tyr Met Val Gly Phe Gln Ile Ala Ala Gln
            355                 360                 365

Val Gly Gln Ile Ile Phe Ser Thr Pro Leu Gly Ala Leu His Asp Ser
        370                 375                 380

Ile Gly Tyr Gln Ser Thr Phe Leu Val Ile Ser Gly Ile Val Cys Val
385                 390                 395                 400

Ala Ser Leu Tyr Ala Phe Val Ile Leu Lys Lys Asp Asp Gln Gln Val
                405                 410                 415

Asp Gly Gln Pro Leu
            420
```

<210> SEQ ID NO 85
<211> LENGTH: 1275
<212> TYPE: DNA
<213> ORGANISM: Lactobacillus antri

<400> SEQUENCE: 85

```
atgaaaaata gcaagttatc agcgtttaaa aacagctttt acctggagag ttcgcttagt      60
ctgctgctgt tcttcgccgc gtggggaatc tggtggtcgt tcttccaaat ctggctcacc    120
aatgacctcg gcttctctgg ggccaaggtc gggatgatct atactttcga ttcggcaatt    180
acgctggtct taatgttcat ctacgggtca gtgcaagaca agctcggcat taaacgccgg    240
ctgctgattg gggttaccat cctggaaatg ctccttgggc ccttctttac ctggatttac    300
gcgccactgc tgcactctaa ctttatcctc ggcgccttct taggttccct ctacctctcc    360
tttgcctttc tggcggcgtc cccgaccttc gaggccctcg cagaacggat gagccggcgg    420
tacagctttg aatacggtcg ggcccgggcc tggggtcat ttggttacgc cgtttcggca    480
ttgtgtgccg gctacctctt caccatcagt ccctacatcg tcttttggct cagcagcggg    540
attagcttgc taaccttcct cctgctctgc tttggccgga ctaagagccc cacacaggtt    600
gcccgttacg agaataaggc cgaggaagaa cacgacgcgg ataagccgag tttcaaagag    660
atcatcagtg ttttcaagct caagcagttg tgggaattgg ttttcttcat tattttcagc    720
gggtcctttt acacggtctt tgaccagcag atgtttcccc agttctttac ccaattttc    780
aagacggcgg cccagggaaa cacggcctac ggaatcctca attcgattga agtcttcctc    840
gaagcaatta tgatggcgat tgttccctgg attatgaaga gatcgggggt ccgcaagacc    900
ctcttgattg gggtcaccat tatgttcttg cggatcggcc tctgcggcct ggtcgtcagc    960
ccggtcggga tctcgattgt gaagctcttt cacgccccgg aaacggccat ctttgccctg   1020
gcgatgttcc gctatttgac cctccacttt gacacccggc tatcggcgac gatgtacatg   1080
gtggttgggc agattgccgg tcaaatcggc cagatcatcc tgtcgacgcc cctgggaatg   1140
ctccacgacc ggatcggcta ccgggcgacc ttcctggtta tttcgctgat tgtgatttgc   1200
gctgcggtat acgcattcgt catttttgcgc aaggataacc aggaggttga cggtcaacca   1260
ctagaaaaca actaa                                                   1275
```

<210> SEQ ID NO 86
<211> LENGTH: 424
<212> TYPE: PRT
<213> ORGANISM: Lactobacillus antri

<400> SEQUENCE: 86

```
Met Lys Asn Ser Lys Leu Ser Ala Phe Lys Asn Ser Phe Tyr Leu Glu
1               5                   10                  15

Ser Ser Leu Ser Leu Leu Phe Phe Ala Ala Trp Gly Ile Trp Trp
            20                  25                  30

Ser Phe Phe Gln Ile Trp Leu Thr Asn Asp Leu Gly Phe Ser Gly Ala
            35                  40                  45

Lys Val Gly Met Ile Tyr Thr Phe Asp Ser Ala Ile Thr Leu Val Leu
        50                  55                  60

Met Phe Ile Tyr Gly Ser Val Gln Asp Lys Leu Gly Ile Lys Arg Arg
65                  70                  75                  80

Leu Leu Ile Gly Val Thr Ile Leu Glu Met Leu Leu Gly Pro Phe Phe
                85                  90                  95

Thr Trp Ile Tyr Ala Pro Leu Leu His Ser Asn Phe Ile Leu Gly Ala
            100                 105                 110

Phe Leu Gly Ser Leu Tyr Leu Ser Phe Ala Phe Leu Ala Ala Ser Pro
            115                 120                 125

Thr Phe Glu Ala Leu Ala Glu Arg Met Ser Arg Arg Tyr Ser Phe Glu
            130                 135                 140

Tyr Gly Arg Ala Arg Ala Trp Gly Ser Phe Gly Tyr Ala Val Ser Ala
145                 150                 155                 160

Leu Cys Ala Gly Tyr Leu Phe Thr Ile Ser Pro Tyr Ile Val Phe Trp
                165                 170                 175

Leu Ser Ser Gly Ile Ser Leu Leu Thr Phe Leu Leu Cys Phe Gly
            180                 185                 190

Arg Thr Lys Ser Pro Thr Gln Val Ala Arg Tyr Glu Asn Lys Ala Glu
            195                 200                 205

Glu Glu His Asp Ala Asp Lys Pro Ser Phe Lys Glu Ile Ile Ser Val
    210                 215                 220

Phe Lys Leu Lys Gln Leu Trp Glu Leu Val Phe Phe Ile Ile Phe Ser
225                 230                 235                 240

Gly Ser Phe Tyr Thr Val Phe Asp Gln Gln Met Phe Pro Gln Phe Phe
                245                 250                 255

Thr Gln Phe Phe Lys Thr Ala Ala Gln Gly Asn Thr Ala Tyr Gly Ile
            260                 265                 270

Leu Asn Ser Ile Glu Val Phe Leu Glu Ala Ile Met Met Ala Ile Val
            275                 280                 285

Pro Trp Ile Met Lys Lys Ile Gly Val Arg Lys Thr Leu Leu Ile Gly
        290                 295                 300

Val Thr Ile Met Phe Leu Arg Ile Gly Leu Cys Gly Leu Val Val Ser
305                 310                 315                 320

Pro Val Gly Ile Ser Ile Val Lys Leu Phe His Ala Pro Glu Thr Ala
            325                 330                 335

Ile Phe Ala Leu Ala Met Phe Arg Tyr Leu Thr Leu His Phe Asp Thr
            340                 345                 350

Arg Leu Ser Ala Thr Met Tyr Met Val Gly Gln Ile Ala Gly Gln
            355                 360                 365

Ile Gly Gln Ile Ile Leu Ser Thr Pro Leu Gly Met Leu His Asp Arg
    370                 375                 380

Ile Gly Tyr Arg Ala Thr Phe Leu Val Ile Ser Leu Ile Val Ile Cys
385                 390                 395                 400

Ala Ala Val Tyr Ala Phe Val Ile Leu Arg Lys Asp Asn Gln Glu Val
            405                 410                 415
```

Asp Gly Gln Pro Leu Glu Asn Asn
            420

<210> SEQ ID NO 87
<211> LENGTH: 1323
<212> TYPE: DNA
<213> ORGANISM: Lactobacillus ruminis

<400> SEQUENCE: 87

| | |
|---|---|
| atgatgccga tttctgacaa ttggaaagga attttattta tgaacgatat gaataaaagc | 60 |
| ggacggatgt cacaactgaa gaatccgttc tttacaagca atgcgacaaa tattctcatg | 120 |
| ttctttgctg gctggggcat ctggtggtca ttcttccaga tctggctgac aaccaagcag | 180 |
| gggttcaccg agcccaggt tggcgagata tactccttca actcggcgtt ctcactgatt | 240 |
| gccaaccttg tttacagcaa cattcaggac aggctcggcc tcaaacgcaa ccttttgatc | 300 |
| ttctgcgcct gcctgcaggt gttcctcggg cccttcttca cgttcctctt cgtgccgatg | 360 |
| cttcatgcca accttgaact cggcgctctg atcggttcat gctacctgac gcttgcctat | 420 |
| cttttccgcat ccccgatgtt cgaggcactg acggaacgtg caagccgccg cttcaactat | 480 |
| cagtatgggt cagcgcgtgc ctggggctcg ttcggatatg ccgtatccgc cttgcttgca | 540 |
| ggattcgtct tcacaatcaa tccgtcgctg ctgttctgga tcggctctgc catcgctgtt | 600 |
| gtccttcttc tcctgctttt gttctggaac cctgtccgca caaggagac ggttgccaga | 660 |
| tttgaaaatg aaatggtcag ggaacgtgag aactccaagc ctgggtcaag ggacttcctc | 720 |
| aatgtcttca aggttcgcag cctttgggaa atcgccattt tccttgtctt cagcggtaca | 780 |
| ttctacacga ttttcgatca gcagatgttt cctcagttct tcactcagtt cttcaagacc | 840 |
| caggcaatgg gcgatcacat gtatgggatc ctgaactcgg ttgaggtgtt cctcgaagca | 900 |
| ctcatgatgg gcctggttcc gcttctcatg aagaagatcg gcgtccgccg cacgattctt | 960 |
| gtcggcgtga cgttcatgtt catcagaatc ggtggctgcg gtctgattac gaaccctctt | 1020 |
| ggcgttttcaa tgatcaagct tctccatgcg cctgaaacgg ccattttctg cgtcgtaatg | 1080 |
| ttccgttact acactctgca ctacgatccg cgagtatcag ccacgatcaa tatcgtaacg | 1140 |
| ggcattgcgg gttcgttcgg ccagatactt ctctcaacgc cgcttggact tctgcgtgac | 1200 |
| cacatcggct atcagccgac cttcctggta atcgccggca tcgtattctg cgccggcatc | 1260 |
| tacggcttat tcatcattcg aagggatgat caggaagtaa acggagagag gctgtctgaa | 1320 |
| taa | 1323 |

<210> SEQ ID NO 88
<211> LENGTH: 440
<212> TYPE: PRT
<213> ORGANISM: Lactobacillus ruminis

<400> SEQUENCE: 88

Met Met Pro Ile Ser Asp Asn Trp Lys Gly Ile Leu Phe Met Asn Asp
1               5                  10                  15

Met Asn Lys Ser Gly Arg Met Ser Gln Leu Lys Asn Pro Phe Phe Thr
            20                  25                  30

Ser Asn Ala Thr Asn Ile Leu Met Phe Phe Ala Gly Trp Gly Ile Trp
        35                  40                  45

Trp Ser Phe Phe Gln Ile Trp Leu Thr Thr Lys Gln Gly Phe Thr Gly
    50                  55                  60

Ala Gln Val Gly Glu Ile Tyr Ser Phe Asn Ser Ala Phe Ser Leu Ile
65                  70                  75                  80

```
Ala Asn Leu Val Tyr Ser Asn Ile Gln Asp Arg Leu Gly Leu Lys Arg
                85                  90                  95

Asn Leu Leu Ile Phe Cys Ala Cys Leu Gln Val Phe Leu Gly Pro Phe
            100                 105                 110

Phe Thr Phe Leu Phe Val Pro Met Leu His Ala Asn Leu Glu Leu Gly
        115                 120                 125

Ala Leu Ile Gly Ser Cys Tyr Leu Thr Leu Ala Tyr Leu Ser Ala Ser
130                 135                 140

Pro Met Phe Glu Ala Leu Thr Glu Arg Ala Ser Arg Arg Phe Asn Tyr
145                 150                 155                 160

Gln Tyr Gly Ser Ala Arg Ala Trp Gly Ser Phe Gly Tyr Ala Val Ser
                165                 170                 175

Ala Leu Leu Ala Gly Phe Val Phe Thr Ile Asn Pro Ser Leu Leu Phe
            180                 185                 190

Trp Ile Gly Ser Ala Ile Ala Val Val Leu Leu Leu Leu Leu Leu Phe
        195                 200                 205

Trp Asn Pro Val Arg Asn Lys Glu Thr Val Ala Arg Phe Glu Asn Glu
210                 215                 220

Met Val Arg Glu Arg Glu Asn Ser Lys Pro Gly Ser Arg Asp Phe Leu
225                 230                 235                 240

Asn Val Phe Lys Val Arg Ser Leu Trp Glu Ile Ala Ile Phe Leu Val
                245                 250                 255

Phe Ser Gly Thr Phe Tyr Thr Ile Phe Asp Gln Gln Met Phe Pro Gln
            260                 265                 270

Phe Phe Thr Gln Phe Phe Lys Thr Gln Ala Met Gly Asp His Met Tyr
        275                 280                 285

Gly Ile Leu Asn Ser Val Glu Val Phe Leu Glu Ala Leu Met Met Gly
290                 295                 300

Leu Val Pro Leu Leu Met Lys Lys Ile Gly Val Arg Arg Thr Ile Leu
305                 310                 315                 320

Val Gly Val Thr Phe Met Phe Ile Arg Ile Gly Gly Cys Gly Leu Ile
                325                 330                 335

Thr Asn Pro Leu Gly Val Ser Met Ile Lys Leu Leu His Ala Pro Glu
            340                 345                 350

Thr Ala Ile Phe Cys Val Val Met Phe Arg Tyr Tyr Thr Leu His Tyr
        355                 360                 365

Asp Pro Arg Val Ser Ala Thr Ile Asn Ile Val Thr Gly Ile Ala Gly
370                 375                 380

Ser Phe Gly Gln Ile Leu Leu Ser Thr Pro Leu Gly Leu Leu Arg Asp
385                 390                 395                 400

His Ile Gly Tyr Gln Pro Thr Phe Leu Val Ile Ala Gly Ile Val Phe
                405                 410                 415

Cys Ala Gly Ile Tyr Gly Leu Phe Ile Ile Arg Arg Asp Asp Gln Glu
            420                 425                 430

Val Asn Gly Glu Arg Leu Ser Glu
        435                 440

<210> SEQ ID NO 89
<211> LENGTH: 1242
<212> TYPE: DNA
<213> ORGANISM: Yersinia frederiksenii

<400> SEQUENCE: 89
atgaaacatt ctgtccgtaa tcaatatctg atcttaagtg gcttattgtt tacgttttc     60
```

```
tttacttggt catcggcatt ctctttattc tccatatggc tcaatcaata tgtaggatta    120
aaaggtaccg aaacaggggc gacttttttcc gccattgcct taacggcact ttgcgctcaa   180
ccgctttatg gcgtgataca agataagttg gggctaaaaa aacatctttt atgggccatt    240
ggtattttgc tgctgatcag tggcccttttt ttatttatg tttatgcccc tttattgcgt    300
gtcaacatgc tggttggtgc cgttaccggt ggcttatata tggggatgac gttctttgcc    360
ggtattggtg cgcttgagtc ttataccgaa cgagtgagcc gtattagtgg gtttgagttt    420
ggtaaagccc gtatgtgggg atcgctgggg tgggcgggtg caacctttttt tgctggcatg   480 ttgtttaata ttaatcccaa cattaatttc tggatggcat cggcatcggc cgcgatattt    540
ttactgttgt tgtggcactt acatgaagtt aaaacagcgg ctatggggca gttggaatac    600
ggtaagaata gtgccctgac actgagtgat acattgtcac tgtttcgtat gccgcgtttc    660
tgggcgctgg tggtatttgt caccggtgtg agcgtttata acgtctatga ccagcaattt    720
ccggtctatt tctcctctct atttactgac cgacgccacg gcaatgaaat gtacggcttt    780
cttaattcac tacaggtatt cctagaggct ggtggtatgt tcctcgcgcc ttttctggtt    840
aaccgtattg gcgcgaaaaa gggcttactg ctgagcggat taatcatggc aatgcgcata    900
ttgggttcag ggttggcaca agatgcagtc accatctcat tgatgaagtt attacatgca    960
gtggagttgc ctattttgct cattgcgatg tttaagtata tcgccgccaa tttcgacccg   1020
cgtttgtcag ccacgcttta tctggtggga tttcagttta ttacccaagt ctatgccagc   1080
gtattttcgc cgttggcagg taaaggctat gacctgatcg ggttcgctga tacctatctg   1140
atcatgggag gcattgtcct cggattaaca gcaatttctt gttttatgct gcgcggcgag   1200
tcgcgtacgg atgatccttc cctacaatta accactaagt ga                     1242

<210> SEQ ID NO 90
<211> LENGTH: 413
<212> TYPE: PRT
<213> ORGANISM: Yersinia frederiksenii

<400> SEQUENCE: 90

Met Lys His Ser Val Arg Asn Gln Tyr Leu Ile Leu Ser Gly Leu Leu
1               5                   10                  15

Phe Thr Phe Phe Phe Thr Trp Ser Ser Ala Phe Ser Leu Phe Ser Ile
            20                  25                  30

Trp Leu Asn Gln Tyr Val Gly Leu Lys Gly Thr Glu Thr Gly Ala Thr
        35                  40                  45

Phe Ser Ala Ile Ala Leu Thr Ala Leu Cys Ala Gln Pro Leu Tyr Gly
    50                  55                  60

Val Ile Gln Asp Lys Leu Gly Leu Lys Lys His Leu Leu Trp Ala Ile
65                  70                  75                  80

Gly Ile Leu Leu Leu Ile Ser Gly Pro Phe Phe Ile Tyr Val Tyr Ala
                85                  90                  95

Pro Leu Leu Arg Val Asn Met Leu Val Gly Ala Val Thr Gly Gly Leu
            100                 105                 110

Tyr Met Gly Met Thr Phe Phe Ala Gly Ile Gly Ala Leu Glu Ser Tyr
        115                 120                 125

Thr Glu Arg Val Ser Arg Ile Ser Gly Phe Glu Phe Gly Lys Ala Arg
    130                 135                 140

Met Trp Gly Ser Leu Gly Trp Ala Gly Ala Thr Phe Phe Ala Gly Met
145                 150                 155                 160
```

Leu Phe Asn Ile Asn Pro Asn Ile Asn Phe Trp Met Ala Ser Ala Ser
            165                 170                 175

Ala Ala Ile Phe Leu Leu Leu Leu Trp His Leu His Glu Val Lys Thr
        180                 185                 190

Ala Ala Met Gly Gln Leu Glu Tyr Gly Lys Asn Ser Ala Leu Thr Leu
    195                 200                 205

Ser Asp Thr Leu Ser Leu Phe Arg Met Pro Arg Phe Trp Ala Leu Val
210                 215                 220

Val Phe Val Thr Gly Val Ser Val Tyr Asn Val Tyr Asp Gln Gln Phe
225                 230                 235                 240

Pro Val Tyr Phe Ser Ser Leu Phe Thr Asp Arg Arg His Gly Asn Glu
                245                 250                 255

Met Tyr Gly Phe Leu Asn Ser Leu Gln Val Phe Leu Glu Ala Gly Gly
            260                 265                 270

Met Phe Leu Ala Pro Phe Leu Val Asn Arg Ile Gly Ala Lys Lys Gly
        275                 280                 285

Leu Leu Leu Ser Gly Leu Ile Met Ala Met Arg Ile Leu Gly Ser Gly
    290                 295                 300

Leu Ala Gln Asp Ala Val Thr Ile Ser Leu Met Lys Leu Leu His Ala
305                 310                 315                 320

Val Glu Leu Pro Ile Leu Leu Ile Ala Met Phe Lys Tyr Ile Ala Ala
                325                 330                 335

Asn Phe Asp Pro Arg Leu Ser Ala Thr Leu Tyr Leu Val Gly Phe Gln
            340                 345                 350

Phe Ile Thr Gln Val Tyr Ala Ser Val Phe Ser Pro Leu Ala Gly Lys
        355                 360                 365

Gly Tyr Asp Leu Ile Gly Phe Ala Asp Thr Tyr Leu Ile Met Gly Gly
    370                 375                 380

Ile Val Leu Gly Leu Thr Ala Ile Ser Cys Phe Met Leu Arg Gly Glu
385                 390                 395                 400

Ser Arg Thr Asp Asp Pro Ser Leu Gln Leu Thr Thr Lys
                405                 410

<210> SEQ ID NO 91
<211> LENGTH: 1260
<212> TYPE: DNA
<213> ORGANISM: Serratia proteamaculans

<400> SEQUENCE: 91
atgaaccgcg aaacaaaaaa atattatgtg cttctcagcg gcctgttgtt tttcttcttc      60
tttacctggt catccagctt ttcactgatc tccatctggc tgaaccagaa atcggcctg     120 aaagggactg aaaccgggct gatcttcgcg gcaatgtcga tcatggcgtt gtgcgcccaa     180
ccgctgtacg gctttattca ggacaaactt gggctgcgta agcacctgct gctgtttgtc     240
ggcgtgctgc tgttgctcac cggcccgttc tttatctatg tctacgcccc gctgctgcag     300
agcaaccttg tggtcggcgc actggtgggc ggcgtgtttg tcagcctggc gttcaatgcc     360
ggtattggcg cgctggaatc ctataccgaa cgagtcagcc gcatcgtcgg tttcgaattc     420
ggccgggcgc gtatgtgggg gtcattgggc tgggccagcg ccaccttctt tgccggcttt     480
aactacaata tcgaccccaa tatcaacttc tggatcgctt cggcctcggc ggcagtgttt     540
ctgctgttgc tgtggcaagt gcgtgagctg aaacccaacg ccatggccgg tctggaatac     600
ggcaagccga aaaacctgaa gctgcaggac gcattggccc tgctgcgcct gccggggttc     660
tgggcgctgg tggtgtttgt gctgggcacc agcatctacg gcgtgtttga ccagcagttc     720

-continued

```
ccggtgtatt tcgcctcgca gttccccacc cacgaagaag gcaaccgcat gtacggtttc    780
cttaattcgc tgcaggtgtt tctggaggcc ggtggcatgt tcctggcccc gctgctggtt    840
aaccgcattg gcataaagca aagcctgttg ctggccagca gcgtgatggc gctgcgcatg    900
gtcggttccg gctttgccag cggcgccctg atgatttccg ccatgaaact gctgcacgcc    960
gtagaattgc caatcctgct ggtggcgatg ttcaagtaca tcaccacccg tttcgacagc   1020
cgcctgtcct ccacgctgta cctggtgggc ttccagttta tcagccaaat tgtcgccggt   1080
tttctggcac cgctggccgg ttatggttac gaccgcatcg gctttgccga cacctatttg   1140
ctgatgggtt gcgcggtggc cgggaccacg ctgatttcct gcttcctgct gcgcggcgag   1200
accgtcgcca gtgcgcctca atttcaatcc acgttaaaat caagtgagcc aacccaatga   1260
```

<210> SEQ ID NO 92
<211> LENGTH: 419
<212> TYPE: PRT
<213> ORGANISM: Serratia proteamaculans

<400> SEQUENCE: 92

```
Met Asn Arg Glu Thr Lys Lys Tyr Tyr Val Leu Leu Ser Gly Leu Leu
1               5                   10                  15

Phe Phe Phe Phe Phe Thr Trp Ser Ser Ser Phe Ser Leu Ile Ser Ile
                20                  25                  30

Trp Leu Asn Gln Lys Ile Gly Leu Lys Gly Thr Glu Thr Gly Leu Ile
            35                  40                  45

Phe Ala Ala Met Ser Ile Met Ala Leu Cys Ala Gln Pro Leu Tyr Gly
        50                  55                  60

Phe Ile Gln Asp Lys Leu Gly Leu Arg Lys His Leu Leu Leu Phe Val
65                  70                  75                  80

Gly Val Leu Leu Leu Leu Thr Gly Pro Phe Phe Ile Tyr Val Tyr Ala
                85                  90                  95

Pro Leu Leu Gln Ser Asn Leu Val Val Gly Ala Leu Val Gly Gly Val
                100                 105                 110

Phe Val Ser Leu Ala Phe Asn Ala Gly Ile Gly Ala Leu Glu Ser Tyr
            115                 120                 125

Thr Glu Arg Val Ser Arg Ile Val Gly Phe Glu Phe Gly Arg Ala Arg
        130                 135                 140

Met Trp Gly Ser Leu Gly Trp Ala Ser Ala Thr Phe Phe Ala Gly Phe
145                 150                 155                 160

Asn Tyr Asn Ile Asp Pro Asn Ile Asn Phe Trp Ile Ala Ser Ala Ser
                165                 170                 175

Ala Ala Val Phe Leu Leu Leu Trp Gln Val Arg Glu Leu Lys Pro
            180                 185                 190

Asn Ala Met Ala Gly Leu Glu Tyr Gly Lys Pro Glu Asn Leu Lys Leu
        195                 200                 205

Gln Asp Ala Leu Ala Leu Leu Arg Leu Pro Gly Phe Trp Ala Leu Val
    210                 215                 220

Val Phe Val Leu Gly Thr Ser Ile Tyr Gly Val Phe Asp Gln Gln Phe
225                 230                 235                 240

Pro Val Tyr Phe Ala Ser Gln Phe Pro Thr His Glu Glu Gly Asn Arg
                245                 250                 255

Met Tyr Gly Phe Leu Asn Ser Leu Gln Val Phe Leu Glu Ala Gly Gly
            260                 265                 270

Met Phe Leu Ala Pro Leu Leu Val Asn Arg Ile Gly Ile Lys Gln Ser
```

```
              275                 280                 285
Leu Leu Leu Ala Ser Ser Val Met Ala Leu Arg Met Val Gly Ser Gly
    290                 295                 300

Phe Ala Ser Gly Ala Leu Met Ile Ser Ala Met Lys Leu Leu His Ala
305                 310                 315                 320

Val Glu Leu Pro Ile Leu Leu Val Ala Met Phe Lys Tyr Ile Thr Thr
                325                 330                 335

Arg Phe Asp Ser Arg Leu Ser Ser Thr Leu Tyr Leu Val Gly Phe Gln
            340                 345                 350

Phe Ile Ser Gln Ile Val Ala Gly Phe Leu Ala Pro Leu Ala Gly Tyr
        355                 360                 365

Gly Tyr Asp Arg Ile Gly Phe Ala Asp Thr Tyr Leu Leu Met Gly Cys
    370                 375                 380

Ala Val Ala Gly Thr Thr Leu Ile Ser Cys Phe Leu Leu Arg Gly Glu
385                 390                 395                 400

Thr Val Ala Ser Ala Pro Gln Phe Gln Ser Thr Leu Lys Ser Ser Glu
                405                 410                 415

Pro Thr Gln

<210> SEQ ID NO 93
<211> LENGTH: 1239
<212> TYPE: DNA
<213> ORGANISM: Escherichia coli

<400> SEQUENCE: 93
atgaaaaaac ggcctactcg aagttacatg ctgctcagcg ctctgctgtt ctttttcttt      60
gtgacctggt cctcatcaag ttcactgctc tcaatctggc ttcaccagga agtggggcta     120
aaagcatcgg aaaccggcat tattttttca gtattatccg tctccgcgct cttcgcgcag     180
gtctgttatg gctttattca ggaccgactt ggtctgcgca acatttgtt atggtttatc      240 accgcgttgt tgatcctctc cggcccggct tatctgcttt ttagttattt gctgagcgtt     300
aatattctgc tgggcagcgt attcggggc ttatttatcg ggctgacgtt taatggggt      360 atcggcgttc tggagtccta taccgagcgc gtcgcgcgtc aaagtacctt tgagtttggg     420
cgggcacgca tgtggggtc tctgggctgg gcagttgcca cgttttttgc cgggttactg     480
tttaatatca accctgacct taacttcctg gtggcttcat gctcagggtt aatcttcttc     540
tgcctcctgg cccgattaaa ggtggccgcg ccggcaagca tggagaaact cgaaattggc     600
gctaaaaaag tttctctgga agacgccctg cgtctgctta ctctgccgcg cttctgggca     660
ctgatattct tcgtggtcgg aacctgcatt tacggcgtat acgatcagca attcccggtc     720
tatttctcat acagttccc gacattacgc gaagggaacg agatgtttgg ctatttaaac     780
tctttccagg tctttctcga ggccgcaggt atgttttgtg cgccgtggct ggttaatcgc     840
attggtgcta aaaatggtct gatattcgca ggaatggtga tggcgctgcg catgattact     900
tcagggctgt ggaaggcccc cctgcttatc tccattacca aactgcttca cgcggtcgaa     960
ctgccaatat tgttagtcgc catatttaaa tacaacagtc tgaatttcga caaacgtctc    1020
tcctccacca tttatctggt gggatttgcc tgcaccagct ccgtcattgg taccgtattg    1080
tccccgctgg caggctttag ctatgagaga tttggcttcg cccaatccta tctgatcatg    1140
ggcatcatgg tgttcagcac cacgtttatt tccattttcc ttttgcgctc aactaaatcc    1200
tcatctgagc catcttttct gcagcaaaaa gctgtgtaa                           1239
```

```
<210> SEQ ID NO 94
<211> LENGTH: 412
<212> TYPE: PRT
<213> ORGANISM: Escherichia coli

<400> SEQUENCE: 94

Met Lys Lys Arg Pro Thr Arg Ser Tyr Met Leu Leu Ser Ala Leu Leu
1               5                   10                  15

Phe Phe Phe Phe Val Thr Trp Ser Ser Ser Ser Leu Leu Ser Ile
            20                  25                  30

Trp Leu His Gln Glu Val Gly Leu Lys Ala Ser Glu Thr Gly Ile Ile
            35                  40                  45

Phe Ser Val Leu Ser Val Ser Ala Leu Phe Ala Gln Val Cys Tyr Gly
        50                  55                  60

Phe Ile Gln Asp Arg Leu Gly Leu Arg Lys His Leu Leu Trp Phe Ile
65                  70                  75                  80

Thr Ala Leu Leu Ile Leu Ser Gly Pro Ala Tyr Leu Leu Phe Ser Tyr
                85                  90                  95

Leu Leu Ser Val Asn Ile Leu Gly Ser Val Phe Gly Gly Leu Phe
            100                 105                 110

Ile Gly Leu Thr Phe Asn Gly Gly Ile Gly Val Leu Glu Ser Tyr Thr
        115                 120                 125

Glu Arg Val Ala Arg Gln Ser Thr Phe Glu Phe Gly Arg Ala Arg Met
    130                 135                 140

Trp Gly Ser Leu Gly Trp Ala Val Ala Thr Phe Phe Ala Gly Leu Leu
145                 150                 155                 160

Phe Asn Ile Asn Pro Asp Leu Asn Phe Leu Val Ala Ser Cys Ser Gly
                165                 170                 175

Leu Ile Phe Phe Cys Leu Leu Ala Arg Leu Lys Val Ala Ala Pro Ala
            180                 185                 190

Ser Met Glu Lys Leu Glu Ile Gly Ala Lys Lys Val Ser Leu Glu Asp
        195                 200                 205

Ala Leu Arg Leu Leu Thr Leu Pro Arg Phe Trp Ala Leu Ile Phe Phe
    210                 215                 220

Val Val Gly Thr Cys Ile Tyr Gly Val Tyr Asp Gln Gln Phe Pro Val
225                 230                 235                 240

Tyr Phe Ser Ser Gln Phe Pro Thr Leu Arg Glu Gly Asn Glu Met Phe
                245                 250                 255

Gly Tyr Leu Asn Ser Phe Gln Val Phe Leu Glu Ala Ala Gly Met Phe
            260                 265                 270

Cys Ala Pro Trp Leu Val Asn Arg Ile Gly Ala Lys Asn Gly Leu Ile
        275                 280                 285

Phe Ala Gly Met Val Met Ala Leu Arg Met Ile Thr Ser Gly Leu Val
    290                 295                 300

Glu Gly Pro Leu Leu Ile Ser Ile Thr Lys Leu Leu His Ala Val Glu
305                 310                 315                 320

Leu Pro Ile Leu Leu Val Ala Ile Phe Lys Tyr Asn Ser Leu Asn Phe
                325                 330                 335

Asp Lys Arg Leu Ser Ser Thr Ile Tyr Leu Val Gly Phe Ala Cys Thr
            340                 345                 350

Ser Ser Val Ile Gly Thr Val Leu Ser Pro Leu Ala Gly Phe Ser Tyr
        355                 360                 365

Glu Arg Phe Gly Phe Ala Gln Ser Tyr Leu Ile Met Gly Ile Met Val
    370                 375                 380
```

Phe Ser Thr Thr Phe Ile Ser Ile Phe Leu Leu Arg Ser Thr Lys Ser
385                 390                 395                 400

Ser Ser Glu Pro Ser Phe Leu Gln Gln Lys Ala Val
                405                 410

<210> SEQ ID NO 95
<211> LENGTH: 1290
<212> TYPE: DNA
<213> ORGANISM: Weissella paramesenteroides

<400> SEQUENCE: 95

| | | | | | |
|---|---|---|---|---|---|
| atgggggac | gtcgtatgtc | taaatatatg | aaggcttta | aaaatgagtc | ttatcttcaa | 60 |
| agttcagtga | caatgttatt | gtacttcgca | tcttggggta | tttggtggtc | tttctttcaa | 120 |
| ttatggttaa | ctgccaaaag | cggtttgaat | ttggatggta | gtgccgttgg | aacaattat | 180 |
| tctgctaatt | cattagtgac | cttagtatta | atgtttttt | atggcacttt | acaagataaa | 240 |
| ttgggaatta | aaaggcattt | actaatattc | agcggtgttt | gtgcggcatt | agtaggtcca | 300 |
| ttctttattt | atgcttatga | accaatgtta | catactaact | tcaccatggg | cttggtggtt | 360 |
| ggttcaattt | ttcttcggc | aggattttta | gcaacgacag | gtatttatga | ggcactagtt | 420 |
| gagcgcttca | gtcgcgtttt | caaatttgaa | tatggtcagg | cacgcgcatg | gggatcattt | 480 |
| ggctatgcag | tggttgcact | attggctggc | catttattg | tcattaaccc | tgatttaaat | 540 |
| ttctgggttg | gatcaatatt | tggtgtgcta | ttattgctaa | atgtttgttt | ttgggtgcca | 600 |
| aaagctgaac | gtcttgaacg | agtacgtagt | gctcaagaaa | ctgaaaaaac | agtaccaagc | 660 |
| gtaagagaaa | tgttgtcttt | gttgaaaatg | cgtgatcttt | gggtagttat | tgtcttgatt | 720 |
| ttctttacat | ggacttcta | tactgtattt | gatcaacaaa | tgtttccgag | cttctatgca | 780 |
| ggattattt | catctgttgc | acaaggtcaa | cagatgtacg | gtaatttgaa | ttcgatccag | 840 |
| gtctttgttg | aagcaattat | gatgggtatt | gtaccagtca | ttatgaataa | aattggtgtt | 900 |
| cgtaacacat | tattgttagg | aattgcaatt | atggcaattc | gaatcggatt | atgtggcttt | 960 |
| attgataacc | cagttgctat | ttcgtttgtg | aagatgttgc | actcgtttga | aacaccatta | 1020 |
| tttattctgt | cgatttttag | atattttaca | cttcatttg | atacaaaatt | atcggcaaca | 1080 |
| ttgtatatga | taggcttcca | agttgccgca | cagttaggtc | aggttttcct | ttcaacaccg | 1140 |
| ttgggtatgt | tacgagataa | ctcaggttat | gcagtgacat | tccatattat | tacaattatc | 1200 |
| gttatcgctg | cgggaatcta | tgcattcttt | gttattaaaa | aagataatca | agatgttaat | 1260 |
| ggcgagccat | tagttagtaa | agctgcttaa | | | | 1290 |

<210> SEQ ID NO 96
<211> LENGTH: 429
<212> TYPE: PRT
<213> ORGANISM: Weissella paramesenteroides

<400> SEQUENCE: 96

Met Gly Gly Arg Arg Met Ser Lys Tyr Met Lys Ala Phe Lys Asn Glu
1               5                   10                  15

Ser Tyr Leu Gln Ser Ser Val Thr Met Leu Leu Tyr Phe Ala Ser Trp
                20                  25                  30

Gly Ile Trp Trp Ser Phe Phe Gln Leu Trp Leu Thr Ala Lys Ser Gly
            35                  40                  45

Leu Asn Leu Asp Gly Ser Ala Val Gly Thr Ile Tyr Ser Ala Asn Ser
        50                  55                  60

Leu Val Thr Leu Val Leu Met Phe Phe Tyr Gly Thr Leu Gln Asp Lys

```
            65                  70                  75                  80
Leu Gly Ile Lys Arg His Leu Leu Ile Phe Ser Gly Val Cys Ala Ala
                    85                  90                  95
Leu Val Gly Pro Phe Phe Ile Tyr Ala Tyr Glu Pro Met Leu His Thr
                100                 105                 110
Asn Phe Thr Met Gly Leu Val Gly Ser Ile Phe Leu Ser Ala Gly
                115                 120                 125
Phe Leu Ala Thr Thr Gly Ile Tyr Glu Ala Leu Val Glu Arg Phe Ser
130                 135                 140
Arg Val Phe Lys Phe Glu Tyr Gly Gln Ala Arg Ala Trp Gly Ser Phe
145                 150                 155                 160
Gly Tyr Ala Val Val Ala Leu Leu Ala Gly His Leu Phe Val Ile Asn
                165                 170                 175
Pro Asp Leu Asn Phe Trp Val Gly Ser Ile Phe Gly Val Leu Leu Leu
                180                 185                 190
Leu Asn Val Cys Phe Trp Val Pro Lys Ala Glu Arg Leu Glu Arg Val
            195                 200                 205
Arg Ser Ala Gln Glu Thr Glu Lys Thr Val Pro Ser Val Arg Glu Met
210                 215                 220
Leu Ser Leu Leu Lys Met Arg Asp Leu Trp Val Ile Val Leu Ile
225                 230                 235                 240
Phe Phe Thr Trp Thr Phe Tyr Thr Val Phe Asp Gln Gln Met Phe Pro
                245                 250                 255
Ser Phe Tyr Ala Gly Leu Phe Ser Ser Val Ala Gln Gly Gln Gln Met
                260                 265                 270
Tyr Gly Asn Leu Asn Ser Ile Gln Val Phe Val Glu Ala Ile Met Met
            275                 280                 285
Gly Ile Val Pro Val Ile Met Asn Lys Ile Gly Val Arg Asn Thr Leu
                290                 295                 300
Leu Leu Gly Ile Ala Ile Met Ala Ile Arg Ile Gly Leu Cys Gly Phe
305                 310                 315                 320
Ile Asp Asn Pro Val Ala Ile Ser Phe Val Lys Met Leu His Ser Phe
                325                 330                 335
Glu Thr Pro Leu Phe Ile Leu Ser Ile Phe Arg Tyr Phe Thr Leu His
                340                 345                 350
Phe Asp Thr Lys Leu Ser Ala Thr Leu Tyr Met Ile Gly Phe Gln Val
            355                 360                 365
Ala Ala Gln Leu Gly Gln Val Phe Leu Ser Thr Pro Leu Gly Met Leu
            370                 375                 380
Arg Asp Asn Ser Gly Tyr Ala Val Thr Phe His Ile Ile Thr Ile Ile
385                 390                 395                 400
Val Ile Ala Ala Gly Ile Tyr Ala Phe Phe Val Ile Lys Lys Asp Asn
                405                 410                 415
Gln Asp Val Asn Gly Glu Pro Leu Val Ser Lys Ala Ala
            420                 425

<210> SEQ ID NO 97
<211> LENGTH: 1185
<212> TYPE: DNA
<213> ORGANISM: Bifidobacterium pseudocatenulatum

<400> SEQUENCE: 97
atgacctccg ccgagcaggg ccagatctac tccatcaact ccctggcaac cctggtcatc      60
atgttcgcct acggcgccat ccaggaccaa ctgggcatca agcgtaagct cgtgatcttc     120
```

```
gtctccgcca tcgcagcgct cgtcggcccg ttcgtgcagt tcgtgtatgc cccgatgctg    180
acagccggcg gcaccacccg tttcatcggc gtgctcatcg gctccatcgt gctgtccgca    240
ggtttcatgg ccggctgctc cctgttcgag gcactcaccg aacgctactc ccgcaagttc    300
ggcttcgaat acggccagtc ccgagcttgg ggctcattcg gctacgccat cgtggcgctg    360
tgtgcaggct tcctgttcaa tatcaacccg ctgctgaact tctgggtcgg ctccatctgc    420
ggcctcggca tgctgtgcat ctacgctttc tgggttccgg ccgagcagaa ggaagagctc    480
aagaaggaag ctgatccgaa cgcggctccg accaacccgt ccttcaagga aatgatttcc    540
gttctgaaga tgccgaccct gtgggtgctc atcgtttca tgctgttcac caacaccttc    600
tacaccgtgt cgatcagca gatgttcccg aactactacg cttccctctt ctccaccact    660
gaaatcggca acgccaccta cggcaccctg aactccttcc aggtgttcct cgagtccgcc    720
atgatgggtg tcgttccgat catcatgaag aagatcggcg tgcgcaactc cctgctgctc    780
ggtgcaaccg tgatgttcct gcgcatcggc ctgtgcggcg tgttccacga tccggtcagc    840
gtctccatcg tcaagctgtt ccactccatc gaggttccgc tgttctgcct gccggcattc    900
cgctacttca ccctgcactt cgacaccaag ctgtcggcaa ccctgtacat ggtgggcttc    960
cagatcgctt cccagatcgg ccaggtgatc ttctccaccc cgatgggcgc cctgcatgac   1020
gccatgggcg atcgcccgac cttcttcacc atctccggca tcgtgctggc agccctgatc   1080
tacggcttct tcgtgatcaa gaaggacgac caggaagtcg gcggtgatcc gttctacacc   1140
gacaagcagc tcaaggccca ggccgctgca gaagcgaatg cctga                   1185
```

<210> SEQ ID NO 98
<211> LENGTH: 394
<212> TYPE: PRT
<213> ORGANISM: Bifidobacterium pseudocatenulatum

<400> SEQUENCE: 98

```
Met Thr Ser Ala Glu Gln Gly Gln Ile Tyr Ser Ile Asn Ser Leu Ala
1               5                   10                  15

Thr Leu Val Ile Met Phe Ala Tyr Gly Ala Ile Gln Asp Gln Leu Gly
            20                  25                  30

Ile Lys Arg Lys Leu Val Ile Phe Val Ser Ala Ile Ala Ala Leu Val
        35                  40                  45

Gly Pro Phe Val Gln Phe Val Tyr Ala Pro Met Leu Thr Ala Gly Gly
    50                  55                  60

Thr Thr Arg Phe Ile Gly Val Leu Ile Gly Ser Ile Val Leu Ser Ala
65                  70                  75                  80

Gly Phe Met Ala Gly Cys Ser Leu Phe Glu Ala Leu Thr Glu Arg Tyr
                85                  90                  95

Ser Arg Lys Phe Gly Phe Glu Tyr Gly Gln Ser Arg Ala Trp Gly Ser
            100                 105                 110

Phe Gly Tyr Ala Ile Val Ala Leu Cys Ala Gly Phe Leu Phe Asn Ile
        115                 120                 125

Asn Pro Leu Leu Asn Phe Trp Val Gly Ser Ile Cys Gly Leu Gly Met
    130                 135                 140

Leu Cys Ile Tyr Ala Phe Trp Val Pro Ala Glu Gln Lys Glu Glu Leu
145                 150                 155                 160

Lys Lys Glu Ala Asp Pro Asn Ala Ala Pro Thr Asn Pro Ser Phe Lys
                165                 170                 175

Glu Met Ile Ser Val Leu Lys Met Pro Thr Leu Trp Val Leu Ile Val
```

```
                180             185             190
Phe Met Leu Phe Thr Asn Thr Phe Tyr Thr Val Phe Asp Gln Gln Met
            195                 200                 205
Phe Pro Asn Tyr Tyr Ala Ser Leu Phe Ser Thr Thr Glu Ile Gly Asn
            210                 215                 220
Ala Thr Tyr Gly Thr Leu Asn Ser Phe Gln Val Phe Leu Glu Ser Ala
225                 230                 235                 240
Met Met Gly Val Val Pro Ile Ile Met Lys Lys Ile Gly Val Arg Asn
                245                 250                 255
Ser Leu Leu Leu Gly Ala Thr Val Met Phe Leu Arg Ile Gly Leu Cys
            260                 265                 270
Gly Val Phe His Asp Pro Val Ser Val Ser Ile Val Lys Leu Phe His
            275                 280                 285
Ser Ile Glu Val Pro Leu Phe Cys Leu Pro Ala Phe Arg Tyr Phe Thr
            290                 295                 300
Leu His Phe Asp Thr Lys Leu Ser Ala Thr Leu Tyr Met Val Gly Phe
305                 310                 315                 320
Gln Ile Ala Ser Gln Ile Gly Gln Val Ile Phe Ser Thr Pro Met Gly
                325                 330                 335
Ala Leu His Asp Ala Met Gly Asp Arg Pro Thr Phe Phe Thr Ile Ser
            340                 345                 350
Gly Ile Val Leu Ala Ala Leu Ile Tyr Gly Phe Phe Val Ile Lys Lys
            355                 360                 365
Asp Asp Gln Glu Val Gly Gly Asp Pro Phe Tyr Thr Asp Lys Gln Leu
            370                 375                 380
Lys Ala Gln Ala Ala Ala Glu Ala Asn Ala
385                 390

<210> SEQ ID NO 99
<211> LENGTH: 1086
<212> TYPE: DNA
<213> ORGANISM: Bifidobacterium catenulatum

<400> SEQUENCE: 99
gtgctgcgcg gcagtggcac caacaaaaag aaacagagaa acaacatgac aagcaacact      60
cgatccgcat ggaagaatcc ttcctatctg cagagttcct tcggcatctt catgttcttc     120
tgctcgtggg gcatctggtg gtccttcttc tcccgctggc tcaccgaccc gacccacggc     180
ctgggcatga cctccgcaga gcagggccag atctactcca ttaactcctt ggcaaccctg     240
gtcatcatgt tcgcctatgg tgccatccag gatcagctgg gcatcaagcg caagctcgtg     300
atcttcgttt ccgccatcgc agcgctcgtc ggcccgttcg tacagttcgt gtacgccccg     360
atgctgactg ccgcggcac cacccgtttc atcggcgtgc tcatcggctc catcgtgctc     420
tcctcaggct tcatggccgg ctgctccctg ttcgaagcgc tcaccgaacg ctactcccgt     480
aagttcggct tcgaatacgg ccagtcccgc gcttggggct ccttcggcta cgccatcgtg     540
gcactgtgcg caggtttcct gttcaacatc aacccgctgc tgaacttctg ggtcggctcc     600
atctgcggcc ttggcatgct gtgcgtctac gctttctggg ttccggccaa gcaaaaggaa     660
gagctcaaga aagaagccga tccgaacgcg gctccaacca atccatcctt caaagagatg     720
atctccgttc tgaagatgcc gactctgtgg gtgctcatcg tcttcatgct gttcaccaac     780
accttctata ccgtgttcga ccagcagatg ttccctaact actacgcttc cctcttcccg     840
accaccgaaa tcggcaacgc cacctacggc acctgaact cctccaggt gttcctcgag     900
```

-continued

```
tccgccatga tgggcgtcgt tccgattatc atgaagaaga tcggcgttcg taactccctg    960
ctgctcggcg caaccgtgat gttcctgcgt atcggcctgt gcggcgtgtt ccacgatcca    1020
gtcagtgtct ccatcgtcaa gctgttccac tccatcgagg ttccgctgtt ctgcctaccg    1080
gcataa                                                               1086
```

<210> SEQ ID NO 100
<211> LENGTH: 361
<212> TYPE: PRT
<213> ORGANISM: Bifidobacterium catenulatum

<400> SEQUENCE: 100

```
Met Leu Arg Gly Ser Gly Thr Asn Lys Lys Gln Arg Asn Asn Met
1               5                   10                  15

Thr Ser Asn Thr Arg Ser Ala Trp Lys Asn Pro Ser Tyr Leu Gln Ser
            20                  25                  30

Ser Phe Gly Ile Phe Met Phe Phe Cys Ser Trp Gly Ile Trp Trp Ser
        35                  40                  45

Phe Phe Ser Arg Trp Leu Thr Asp Pro Thr His Gly Leu Gly Met Thr
    50                  55                  60

Ser Ala Glu Gln Gly Gln Ile Tyr Ser Ile Asn Ser Leu Ala Thr Leu
65                  70                  75                  80

Val Ile Met Phe Ala Tyr Gly Ala Ile Gln Asp Gln Leu Gly Ile Lys
                85                  90                  95

Arg Lys Leu Val Ile Phe Val Ser Ala Ile Ala Ala Leu Val Gly Pro
            100                 105                 110

Phe Val Gln Phe Val Tyr Ala Pro Met Leu Thr Ala Gly Gly Thr Thr
        115                 120                 125

Arg Phe Ile Gly Val Leu Ile Gly Ser Ile Val Leu Ser Ser Gly Phe
    130                 135                 140

Met Ala Gly Cys Ser Leu Phe Glu Ala Leu Thr Glu Arg Tyr Ser Arg
145                 150                 155                 160

Lys Phe Gly Phe Glu Tyr Gly Gln Ser Arg Ala Trp Gly Ser Phe Gly
                165                 170                 175

Tyr Ala Ile Val Ala Leu Cys Ala Gly Phe Leu Phe Asn Ile Asn Pro
            180                 185                 190

Leu Leu Asn Phe Trp Val Gly Ser Ile Cys Gly Leu Gly Met Leu Cys
        195                 200                 205

Val Tyr Ala Phe Trp Val Pro Ala Lys Gln Lys Glu Glu Leu Lys Lys
    210                 215                 220

Glu Ala Asp Pro Asn Ala Pro Thr Asn Pro Ser Phe Lys Glu Met
225                 230                 235                 240

Ile Ser Val Leu Lys Met Pro Thr Leu Trp Val Leu Ile Val Phe Met
                245                 250                 255

Leu Phe Thr Asn Thr Phe Tyr Thr Val Phe Asp Gln Gln Met Phe Pro
            260                 265                 270

Asn Tyr Tyr Ala Ser Leu Phe Pro Thr Thr Glu Ile Gly Asn Ala Thr
        275                 280                 285

Tyr Gly Thr Leu Asn Ser Phe Gln Val Phe Leu Glu Ser Ala Met Met
    290                 295                 300

Gly Val Val Pro Ile Ile Met Lys Lys Ile Gly Val Arg Asn Ser Leu
305                 310                 315                 320

Leu Leu Gly Ala Thr Val Met Phe Leu Arg Ile Gly Leu Cys Gly Val
                325                 330                 335
```

Phe His Asp Pro Val Ser Val Ser Ile Val Lys Leu Phe His Ser Ile
            340                 345                 350

Glu Val Pro Leu Phe Cys Leu Pro Ala
        355                 360

<210> SEQ ID NO 101
<211> LENGTH: 1176
<212> TYPE: DNA
<213> ORGANISM: Clostridium thermocellum

<400> SEQUENCE: 101

```
atgattttgg ataatcttaa acgttcagaa agatacccgt tctctttttat tctgttttat    60
tccttgtttt atatgggcct tgcggtattt ggcgtgttta tgcctgtgta tttggaaggg   120
ctgggctatg acaatacgga tataggaaca tttctttcaa tcagttcgtt tgtcggcctg   180
tttgcacagc ccatttgggg tgtcataagt gaccgggcaa aatccaaaaa caatgtgctg   240
aaaatgttgg tgcttttcag cagcattgcc attttttatgt ttcgtctctc gggcaactat   300
tactatatat ttgcggtaat ggttgttttat gccttttttcc aaacgcccat tactccgata   360
ggtgatgcga ttacattgga gtatattact gacacaaaat ggaagtatgg cccgataagg   420
cttgccggtg cattgggata tgcggtgatg gcatttatcg gaggggcatt gacaagaaaa   480
aatatcaacg ctatttttctt tatatgcttt gtcataggta ttatgtcttt gattacagta   540
tttagaatgc aacggtaaa aggacatcaa tcggacggaa acaagcttttc cattttagaa   600
gtttcaaaaa acagcgaact tgtgctgctt atgggattta cacttgttat tcatactacc   660
atgggttttt ataatacttt ctttccgatt tactataaaa acatggggtgc tgacaacacc   720
attctgggat tggcggtgtt tatcggctcg gcgagtgaaa taatcttcct tgtttttcggc   780
gacaggataa taaaacgttt gggaatcaag tttacgctgt tcggtgcagc ggttgttgca   840
gttgtacggt gggcaagttt gggattgatt aacaatatttt ttgcagtgct tgcactccaa   900
attctccatg gttttatatt cattgttttg gcctactcca tggcaacata tatcaataat   960
gagatgccac ctgaattgaa ggcctcagga cagacggtaa actccgtcat aggtttgggt  1020
atttccagga taattggaag tacaggcggc ggtgtgataa gtgatttaat cggaatcagg  1080
caggtattct ttttaaattc ggttattgtt cttgcttcaa ttgtcatttt tggcgcaata  1140
tttttggtaa gaagacaaaa aattacagga caatag                            1176
```

<210> SEQ ID NO 102
<211> LENGTH: 391
<212> TYPE: PRT
<213> ORGANISM: Clostridium thermocellum

<400> SEQUENCE: 102

Met Ile Leu Asp Asn Leu Lys Arg Ser Glu Arg Tyr Pro Phe Ser Phe
1               5                   10                  15

Ile Leu Phe Tyr Ser Leu Phe Tyr Met Gly Leu Ala Val Phe Gly Val
            20                  25                  30

Phe Met Pro Val Tyr Leu Glu Gly Leu Gly Tyr Asp Asn Thr Asp Ile
        35                  40                  45

Gly Thr Phe Leu Ser Ile Ser Ser Phe Val Gly Leu Phe Ala Gln Pro
    50                  55                  60

Ile Trp Gly Val Ile Ser Asp Arg Ala Lys Ser Lys Asn Asn Val Leu
65                  70                  75                  80

Lys Met Leu Val Leu Phe Ser Ser Ile Ala Ile Phe Met Phe Arg Leu
                85                  90                  95

Ser Gly Asn Tyr Tyr Tyr Ile Phe Ala Val Met Val Tyr Ala Phe
            100                 105                 110

Phe Gln Thr Pro Ile Thr Pro Ile Gly Asp Ala Ile Thr Leu Glu Tyr
            115                 120                 125

Ile Thr Asp Thr Lys Trp Lys Tyr Gly Pro Ile Arg Leu Ala Gly Ala
        130                 135                 140

Leu Gly Tyr Ala Val Met Ala Phe Ile Gly Gly Ala Leu Thr Arg Lys
145                 150                 155                 160

Asn Ile Asn Ala Ile Phe Phe Ile Cys Phe Val Ile Gly Ile Met Ser
                165                 170                 175

Leu Ile Thr Val Phe Arg Met Pro Thr Val Lys Gly His Gln Ser Asp
            180                 185                 190

Gly Asn Lys Leu Ser Ile Leu Glu Val Phe Lys Asn Ser Glu Leu Val
        195                 200                 205

Leu Leu Met Gly Phe Thr Leu Val Ile His Thr Thr Met Gly Phe Tyr
210                 215                 220

Asn Thr Phe Phe Pro Ile Tyr Tyr Lys Asn Met Gly Ala Asp Asn Thr
225                 230                 235                 240

Ile Leu Gly Leu Ala Val Phe Ile Gly Ser Ala Ser Glu Ile Ile Phe
                245                 250                 255

Leu Val Phe Gly Asp Arg Ile Ile Lys Arg Leu Gly Ile Lys Phe Thr
            260                 265                 270

Leu Phe Gly Ala Ala Val Val Ala Val Val Arg Trp Ala Ser Leu Gly
        275                 280                 285

Leu Ile Asn Asn Ile Phe Ala Val Leu Ala Leu Gln Ile Leu His Gly
        290                 295                 300

Phe Ile Phe Ile Val Leu Ala Tyr Ser Met Ala Thr Tyr Ile Asn Asn
305                 310                 315                 320

Glu Met Pro Pro Glu Leu Lys Ala Ser Gly Gln Thr Val Asn Ser Val
                325                 330                 335

Ile Gly Leu Gly Ile Ser Arg Ile Ile Gly Ser Thr Gly Gly Gly Val
            340                 345                 350

Ile Ser Asp Leu Ile Gly Ile Arg Gln Val Phe Phe Leu Asn Ser Val
        355                 360                 365

Ile Val Leu Ala Ser Ile Val Ile Phe Gly Ala Ile Phe Leu Val Arg
370                 375                 380

Arg Gln Lys Ile Thr Gly Gln
385                 390

<210> SEQ ID NO 103
<211> LENGTH: 1311
<212> TYPE: DNA
<213> ORGANISM: Granulibacter bethesdensis

<400> SEQUENCE: 103
ttggttttgg atatggacgc aatgagcggg acgatagcgg ttagtccagt cttgtcagat     60
ggtcagcccc cctctgacag tcgacaaaag cagggagaat ctgctcttct cgacaagttg    120
aatttttttc ttgctgatgt gcgggatggt ctggggcctt accttgccgt gtacctgttg    180
tcggcttcgg gcagggacgg gcgctgggac gagtccagtg tcgggctggt gctgaccatc    240
agtggtgttg tcgggctggt tgcgcaaacc cctgccggag cactggttga tcgcagtcga    300
aacaaacccc gcctgctggc tgtcgcgatc ttgctggtaa cgctcagcac tttgctgctg    360 cccttttatgt ccggtttgcc gctggtgacg ctgacccaat ctatggccgc cgtggcgggg    420

```
gcgattttcg cccctgttat tgcggcgatg acgctgggtc tggtgggaac ggatgggttt    480
gccaggcgga tcgggcgtaa cgagtctttc aatcatctcg ggaatgcagt ctcggcggca    540
attgccgggc ttctggcgtg cattacggc ccggtcgtgg tgttctggct gatgggccta    600
ctggccattg ccggactggt aacggtgctg aggattgata accggcatat agacaatgat    660
ctggccaacg ggggggaagc caatggaatg gatgggccg ctctgaagga tcaggcatcg    720
ccaggcctat ggcggattct ggcggatcat cctggcctga tgacctttgc cgtgctggtg    780
ttttttgttcc atctggccaa tgcggccatg cttacctcgg tcagtcagct tctgatgcgg    840
gaggtcggaa aggatatggc gacctctctg gcggcagcct gtattgttgc cgcccagatg    900
gtgatggtgc cggtggcgat gctggtgggg cggtttgtcg atcgtatcgg cacgcgcccg    960
atctttctgt tggcattcgg tattctggcg ctgcgtggga tgctgtatcc gctttcaggt   1020
aatccatggt ggctattggg ggtgcaattg ctggatgggg tgggcgccgg gatattcggg   1080
gccttgttcc cggtggtggt agccgatctg acgaagggaa ccgggcggtt caatatcagc   1140
cagggcgccg tggcgacggc acagggcatt ggtgctgccc tgagtgccgg tgtggcgggg   1200
ctgattatcg tcaaagccgg ttattccgtg gcgttttttct cgctggctgg tgtggctgga   1260
ctgggctttg tcctgtacgc cctgctgatg cctgaaaccc ggcacctgtg a            1311
```

<210> SEQ ID NO 104
<211> LENGTH: 436
<212> TYPE: PRT
<213> ORGANISM: Granulibacter bethesdensis

<400> SEQUENCE: 104

```
Met Val Leu Asp Met Asp Ala Met Ser Gly Thr Ile Ala Val Ser Pro
1               5                   10                  15

Val Leu Ser Asp Gly Gln Pro Pro Ser Asp Ser Arg Gln Lys Gln Gly
            20                  25                  30

Glu Ser Ala Leu Leu Asp Lys Leu Asn Phe Phe Leu Ala Asp Val Arg
        35                  40                  45

Asp Gly Leu Gly Pro Tyr Leu Ala Val Tyr Leu Leu Ser Ala Ser Gly
    50                  55                  60

Arg Asp Gly Arg Trp Asp Glu Ser Ser Val Gly Leu Val Leu Thr Ile
65                  70                  75                  80

Ser Gly Val Val Gly Leu Val Ala Gln Thr Pro Ala Gly Ala Leu Val
                85                  90                  95

Asp Arg Ser Arg Asn Lys Pro Arg Leu Leu Ala Val Ala Ile Leu Leu
            100                 105                 110

Val Thr Leu Ser Thr Leu Leu Leu Pro Phe Met Ser Gly Leu Pro Leu
        115                 120                 125

Val Thr Leu Thr Gln Ser Met Ala Ala Val Ala Gly Ala Ile Phe Ala
    130                 135                 140

Pro Val Ile Ala Ala Met Thr Leu Gly Leu Val Gly Thr Asp Gly Phe
145                 150                 155                 160

Ala Arg Arg Ile Gly Arg Asn Glu Ser Phe Asn His Leu Gly Asn Ala
                165                 170                 175

Val Ser Ala Ala Ile Ala Gly Leu Leu Ala Trp His Tyr Gly Pro Val
            180                 185                 190

Val Val Phe Trp Leu Met Gly Leu Leu Ala Ile Ala Gly Leu Val Thr
        195                 200                 205

Val Leu Arg Ile Asp Asn Arg His Ile Asp Asn Asp Leu Ala Asn Gly
```

```
Gly Glu Ala Asn Gly Met Asp Gly Ala Ala Leu Lys Asp Gln Ala Ser
225                 230                 235                 240

Pro Gly Leu Trp Arg Ile Leu Ala Asp His Pro Gly Leu Met Thr Phe
            245                 250                 255

Ala Val Leu Val Phe Leu Phe His Leu Ala Asn Ala Ala Met Leu Thr
                260                 265                 270

Ser Val Ser Gln Leu Leu Met Arg Glu Val Gly Lys Asp Met Ala Thr
            275                 280                 285

Ser Leu Ala Ala Ala Cys Ile Val Ala Gln Met Val Met Val Pro
290                 295                 300

Val Ala Met Leu Val Gly Arg Phe Val Asp Arg Ile Gly Thr Arg Pro
305                 310                 315                 320

Ile Phe Leu Leu Ala Phe Gly Ile Leu Ala Leu Arg Gly Met Leu Tyr
                325                 330                 335

Pro Leu Ser Gly Asn Pro Trp Trp Leu Leu Gly Val Gln Leu Leu Asp
            340                 345                 350

Gly Val Gly Ala Gly Ile Phe Gly Ala Leu Phe Pro Val Val Val Ala
                355                 360                 365

Asp Leu Thr Lys Gly Thr Gly Arg Phe Asn Ile Ser Gln Gly Ala Val
        370                 375                 380

Ala Thr Ala Gln Gly Ile Gly Ala Ala Leu Ser Ala Gly Val Ala Gly
385                 390                 395                 400

Leu Ile Ile Val Lys Ala Gly Tyr Ser Val Ala Phe Phe Ser Leu Ala
                405                 410                 415

Gly Val Ala Gly Leu Gly Phe Val Leu Tyr Ala Leu Leu Met Pro Glu
                420                 425                 430

Thr Arg His Leu
        435

<210> SEQ ID NO 105
<211> LENGTH: 1263
<212> TYPE: DNA
<213> ORGANISM: Cronobacter turicensis

<400> SEQUENCE: 105
atgtctgaag tcttacaatc cacacgctca gcgtatataa agctcagctt gtttgtcttt    60
ttatttactt tcacctggtc tgccggtttc ggtatgtatg ctatctggct tggtgataaa   120
gcgggactga gtgcaattga tatcggtacg gtttttgccg tcaacggtgt gtttgccgtc   180
ctggttaaac ctgtatatgg ctttatcatg gacaaaaccg gcatgaaaaa gcatttgctc   240
tatttcgtct gccttatttc cgcactgatg gccccttttt atctgtggtg ctacttgccc   300
ttactacaaa gtcactttct ggcaggcatg atcattggcg cgttattttt cagcttcggc   360
tggtacgcgg gtgtagccgc tgaagagtct tatgtggatc gttttagccg cctgtataat   420
atggagttcg gtcgtatcag aatgtgggcc gcactgggat gggcggttgc tgcatcgttt   480
tctggctacg tttataacat ttccccaata attaacttta ccatcggcag cgtatctgca   540
gtgtgtatgt tgctggtgct aatttcactt aaagttgatc atttcgggca ggaagaaaat   600
agcgttctgt ctaaagataa aattgttatc gcggatgtgt tcatctgtt cagaaatcca   660 aaattctgga tgttcgctct gtatattgca ggcgtggcct ggatgatgtt tattgccgaa   720
cagcagttct cccgttattt cgtcactttc tttaacacca aagaacaggg taatgccatg   780
tttggttata tgagcacgac ccagtcgtgt accgaattct ttggcatgat gctggttcct   840
```

```
gcgctggtca accggattgg cgccaaacag ggatgctgc tcacaggcct gatcgtcagt    900
ttgcgcctta tcatctcggg tctgacaacc gaccctctca tcatctgtct tgtaaaaccg    960
ctttacggga ttgaaatcgc gctgattctg gtctccgtct tcaagtacat tgctgagcac   1020
ttcgacaaaa ggattaacgc gaccatgtat ctgcttggct atcaggccat ggtttatgtg   1080
ggctccatcg tggttgcccc tcccgctggc tacgcctatg acaccatagg ttttgaacat   1140
acgtatctga ttatgggcac catttcacta ctgtttacga ttgtgtcggc tttcacactt   1200
tctgattgtc aaaagcataa aaaagtcacc tccgcctccc atacagatca agcattaaat   1260
taa                                                                 1263
```

```

<210> SEQ ID NO 106
<211> LENGTH: 420
<212> TYPE: PRT
<213> ORGANISM: Cronobacter turicensis

<400> SEQUENCE: 106

Met Ser Glu Val Leu Gln Ser Thr Arg Ser Ala Tyr Ile Lys Leu Ser
1               5                   10                  15

Leu Phe Val Phe Leu Phe Thr Phe Thr Trp Ser Ala Gly Phe Gly Met
            20                  25                  30

Tyr Ala Ile Trp Leu Gly Asp Lys Ala Gly Leu Ser Ala Ile Asp Ile
        35                  40                  45

Gly Thr Val Phe Ala Val Asn Gly Val Phe Ala Val Leu Val Lys Pro
    50                  55                  60

Val Tyr Gly Phe Ile Met Asp Lys Thr Gly Met Lys Lys His Leu Leu
65                  70                  75                  80

Tyr Phe Val Cys Leu Ile Ser Ala Leu Met Ala Pro Phe Tyr Leu Trp
                85                  90                  95

Cys Tyr Leu Pro Leu Leu Gln Ser His Phe Leu Ala Gly Met Ile Ile
            100                 105                 110

Gly Ala Leu Phe Phe Ser Phe Gly Trp Tyr Ala Gly Val Ala Ala Glu
        115                 120                 125

Glu Ser Tyr Val Asp Arg Phe Ser Arg Leu Tyr Asn Met Glu Phe Gly
    130                 135                 140

Arg Ile Arg Met Trp Ala Ala Leu Gly Trp Ala Val Ala Ala Ser Phe
145                 150                 155                 160

Ser Gly Tyr Val Tyr Asn Ile Ser Pro Ile Ile Asn Phe Thr Ile Gly
                165                 170                 175

Ser Val Ser Ala Val Cys Met Leu Leu Val Leu Ile Ser Leu Lys Val
            180                 185                 190

Asp His Phe Gly Gln Glu Glu Asn Ser Val Leu Ser Lys Asp Lys Ile
        195                 200                 205

Val Ile Ala Asp Val Phe His Leu Phe Arg Asn Pro Lys Phe Trp Met
    210                 215                 220

Phe Ala Leu Tyr Ile Ala Gly Val Ala Trp Met Met Phe Ile Ala Glu
225                 230                 235                 240

Gln Gln Phe Ser Arg Tyr Phe Val Thr Phe Phe Asn Thr Lys Glu Gln
                245                 250                 255

Gly Asn Ala Met Phe Gly Tyr Met Ser Thr Thr Gln Ser Cys Thr Glu
            260                 265                 270

Phe Phe Gly Met Met Leu Val Pro Ala Leu Val Asn Arg Ile Gly Ala
        275                 280                 285
```

```
Lys Gln Gly Met Leu Leu Thr Gly Leu Ile Val Ser Leu Arg Leu Ile
        290                 295                 300

Ile Ser Gly Leu Thr Thr Asp Pro Leu Ile Ile Cys Leu Val Lys Pro
305                 310                 315                 320

Leu Tyr Gly Ile Glu Ile Ala Leu Ile Leu Val Ser Val Phe Lys Tyr
                325                 330                 335

Ile Ala Glu His Phe Asp Lys Arg Ile Asn Ala Thr Met Tyr Leu Leu
                340                 345                 350

Gly Tyr Gln Ala Met Val Tyr Val Gly Ser Ile Val Val Ala Pro Pro
            355                 360                 365

Ala Gly Tyr Ala Tyr Asp Thr Ile Gly Phe Glu His Thr Tyr Leu Ile
370                 375                 380

Met Gly Thr Ile Ser Leu Leu Phe Thr Ile Val Ser Ala Phe Thr Leu
385                 390                 395                 400

Ser Asp Cys Gln Lys His Lys Lys Val Thr Ser Ala Ser His Thr Asp
                405                 410                 415

Gln Ala Leu Asn
            420

<210> SEQ ID NO 107
<211> LENGTH: 1269
<212> TYPE: DNA
<213> ORGANISM: Enterobacter sp

<400> SEQUENCE: 107
atggaaaata catcaacgaa taacagaacc gaatattaca aaatcagtat ttttatcttt      60
ctctatttct ttacgtggtc ggcaagtatt ggtttgctgg cgatctggct cggacaaaag     120
gccaatctca gcgggtcggt tatcgggacg gtatttgcgg ttaacggtat tttctccgtg     180
attttaaaac cgatctacgg ctatattctc gataagatcg ggatgagcaa ataccctgctc    240 tattttgtgg tggcgatgtc ggccctgatg gcaccgttct ttatttatgt ctatcagccg     300
ctgttaatgt ccaacacgat gctgggtatt attatcggcg cgctctattt aagctttgcc     360
tggtatgcgg gcgtggcagc gtgtgaatcc tattccgatc gtttcagtcg tctaaacggc     420
atggagtttg gtcagattcg catgtggggt tcacttggct gggcggtggc gtcgtcgttc     480
tcgggcctgc tgtttaacct ctcgcctgcg tataatttta ttctgggtag cgtggcgtca     540
gtcatcatgc tcattgttct gctgaacctg aaagtgaaca ctaactccgt tcatgccagt     600
gacgtactga ccaaagagaa aatcgcccct tcggatgttt acgcgctgct gcgcagccgc     660
aagttttggg ccttctgcct gtatgtcgcg ggcgtggcgt ggatgatgtt tatcgccgag     720
cagcagttct cgcgctactt cgtcaccttc tttgacgata ccatcaggg caacgcggta      780 ttcggctacc tcggcacggt tcagtcgggt atggaatttg tcatgtatat ggtgattccg     840
ctgttcgtga actttatcgg tgccaagcgc ggattactca tcgtcgggtt gttcgtcggg     900
gcgcgtctga ttatttccgg cctgtgcgat tcccacttat aatttccgt tctcaagcct      960 ttatacggtc tggaaatctg tttgctgctg gtgtcggtat ttaaatatat cgccgagcat    1020
ttcgataaac gtgtaaatgc caccatgtat ttattgggct atcaggcgat gctgtatgtc    1080
ggaaatgtgg ttatctcgtc accggcggga tatatgtatg accgcatcgg atttgaacag    1140
acctatatca ttatgggcgc aacggcgctg acctttacgc tgctctctgc ctttacgtta    1200
tccgcctgcc aaagcaaatg gcgtggcaca tctgcaatct ctgtagcaga acagaatcca    1260
tctcgataa                                                            1269
```

<210> SEQ ID NO 108
<211> LENGTH: 422
<212> TYPE: PRT
<213> ORGANISM: Enterobacter sp

<400> SEQUENCE: 108

```
Met Glu Asn Thr Ser Thr Asn Asn Arg Thr Glu Tyr Tyr Lys Ile Ser
1               5                   10                  15

Ile Phe Ile Phe Leu Tyr Phe Phe Thr Trp Ser Ala Ser Ile Gly Leu
            20                  25                  30

Leu Ala Ile Trp Leu Gly Gln Lys Ala Asn Leu Ser Gly Ser Val Ile
        35                  40                  45

Gly Thr Val Phe Ala Val Asn Gly Ile Phe Ser Val Ile Leu Lys Pro
    50                  55                  60

Ile Tyr Gly Tyr Ile Leu Asp Lys Ile Gly Met Ser Lys Tyr Leu Leu
65                  70                  75                  80

Tyr Phe Val Val Ala Met Ser Ala Leu Met Ala Pro Phe Phe Ile Tyr
                85                  90                  95

Val Tyr Gln Pro Leu Leu Met Ser Asn Thr Met Leu Gly Ile Ile Ile
            100                 105                 110

Gly Ala Leu Tyr Leu Ser Phe Ala Trp Tyr Ala Gly Val Ala Ala Cys
        115                 120                 125

Glu Ser Tyr Ser Asp Arg Phe Ser Arg Leu Asn Gly Met Glu Phe Gly
    130                 135                 140

Gln Ile Arg Met Trp Gly Ser Leu Gly Trp Ala Val Ala Ser Ser Phe
145                 150                 155                 160

Ser Gly Leu Leu Phe Asn Leu Ser Pro Ala Tyr Asn Phe Ile Leu Gly
                165                 170                 175

Ser Val Ala Ser Val Ile Met Leu Ile Val Leu Leu Asn Leu Lys Val
            180                 185                 190

Asn Thr Asn Ser Val His Ala Ser Asp Val Leu Thr Lys Glu Lys Ile
        195                 200                 205

Ala Pro Ser Asp Val Tyr Ala Leu Leu Arg Ser Arg Lys Phe Trp Ala
    210                 215                 220

Phe Cys Leu Tyr Val Ala Gly Val Ala Trp Met Met Phe Ile Ala Glu
225                 230                 235                 240

Gln Gln Phe Ser Arg Tyr Phe Val Thr Phe Phe Asp Asp Ile His Gln
                245                 250                 255

Gly Asn Ala Val Phe Gly Tyr Leu Gly Thr Val Gln Ser Gly Met Glu
            260                 265                 270

Phe Val Met Tyr Met Val Ile Pro Leu Phe Val Asn Phe Ile Gly Ala
        275                 280                 285

Lys Arg Gly Leu Leu Ile Val Gly Leu Phe Val Gly Ala Arg Leu Ile
    290                 295                 300

Ile Ser Gly Leu Cys Asp Ser His Leu Leu Ile Ser Val Leu Lys Pro
305                 310                 315                 320

Leu Tyr Gly Leu Glu Ile Cys Leu Leu Val Ser Val Phe Lys Tyr
                325                 330                 335

Ile Ala Glu His Phe Asp Lys Arg Val Asn Ala Thr Met Tyr Leu Leu
            340                 345                 350

Gly Tyr Gln Ala Met Leu Tyr Val Gly Asn Val Val Ile Ser Ser Pro
        355                 360                 365

Ala Gly Tyr Met Tyr Asp Arg Ile Gly Phe Glu Gln Thr Tyr Ile Ile
    370                 375                 380
```

```
Met Gly Ala Thr Ala Leu Thr Phe Thr Leu Leu Ser Ala Phe Thr Leu
385                 390                 395                 400

Ser Ala Cys Gln Ser Lys Trp Arg Gly Thr Ser Ala Ile Ser Val Ala
                405                 410                 415

Glu Gln Asn Pro Ser Arg
            420
```

```
<210> SEQ ID NO 109
<211> LENGTH: 1260
<212> TYPE: DNA
<213> ORGANISM: Citrobacter koseri

<400> SEQUENCE: 109
atgaataaaa atgatagtgc tgaaaagaac aggcgtaaaa tttatattac gctcagtctc      60
tttatcctgg tctacttctt ctcatggaaa gcgacacttg atacttattc ttttttggcta   120
tcagaaaaga taggccttga tggtgttgcg attggtattg ttttgccgc aaacggcttt    180
tgtgcggtac taatcaaacc tgtatatggg tttcttatcg atcggctagg gttaaggaaa    240
gatctgttat tctttatctc gcttatctcg ataaccgttt tccccttttt cttttatata    300
tacaaaccac tattgcagtc tgcgttgtat gctggtattg cgttgggcgg tatatttta    360
agtatgggat actacgcagg gtgtgcagcc gcagaatcat accttgatcg ctttggccgt    420
ttgtttgatc ttgagtttgg tcaaatccgc atgtggggcg cgattggttc tgtattctct    480
gctgcaagta caggctatat ttttaatatt aacccaatga tcaatttcgg gttaagttcc    540
gcaggtgcgc tgataattct tattattgtt tttacgatga gatcgaagt caatgaagag    600
gtaaaaaatc gcatcattgc taaagataaa gcgacaatat acgatattat agcattattt    660
agcacacgca atttctggac gtttgtttta tatgtttgtg gtgttgtgtg gattattttt    720
gtcgcagaac aacaatatcc acgtttcttt atcacattt atgccagtaa agaaatcggg    780
catcaaatgt ttggttatct tggtgctgcc agtctgggag tagagtttct gttcatgatg    840
attgcacctg gcattgtcaa ccgtctgggg ccaaaaaccg gcttgctgat acaggctttt    900
gttgtggccg ctagatttat tggttctggt ttggttacaa gtgcaataac aattggaatt    960
atcaaattgt cgtgggggat agaaatgtca ttcctgttgg tttcaatttt caaatatctg   1020
gaaattaact ttgataaaaa agtaaatggt tcaatgtatt tattaggcta tcaaagcgtt   1080
aactatatcg gaacagttat cttgtcgccg ttgagtggtt acttgtatga gcgattaggt   1140
ttttcacata catattttat gatgggatgt acagtattgt tttcactat tatatccgca   1200
tttcttcttc aaaataacaa acgaacagaa ccagtcattg cggagaatgc gcatgcttga   1260
```

```
<210> SEQ ID NO 110
<211> LENGTH: 577
<212> TYPE: PRT
<213> ORGANISM: Citrobacter koseri

<400> SEQUENCE: 110

Met Arg Met Leu Glu Arg Asn Met Leu Arg Glu Asn Ile Ile Asp Lys
1               5                   10                  15

Leu Tyr Asp Val Leu Asp Ser Val Val Asn Arg Thr Ile Asn Lys Glu
            20                  25                  30

Gln Ser Phe Gly Val Val Leu Thr Leu Asp Asp Pro Tyr Ala Ser
        35                  40                  45

Gly Lys Phe Ala Leu Ala Leu Ser Phe Leu Ile Glu Arg Phe Pro Ala
    50                  55                  60
```

```
Arg Ala Asp Gln Trp Ser Gly Val Trp His Glu Leu Val Lys Ala Pro
 65                  70                  75                  80

Ser Glu Asn Trp Gly Lys Tyr Tyr Phe Leu Gln Ala Leu Trp Lys Leu
                 85                  90                  95

His Cys Leu Gly Leu Leu Asn Thr Ile Phe Ser Asp Gln Gln Leu Gln
            100                 105                 110

Arg Leu Thr Glu Lys Leu Arg Trp Gln Glu Leu Val Asp Glu Glu Ser
        115                 120                 125

Trp Lys Leu Asn Pro Pro Phe Pro Thr Asn Tyr Tyr Gly Val Ala Phe
130                 135                 140

Ser Ile Ala Arg Leu Arg Phe Leu Leu Gly Trp Glu Thr Gln Phe Ala
145                 150                 155                 160

Ser Gln Lys Ile Leu Gln Gln Leu Val Glu His Tyr Arg Thr Tyr Ser
                165                 170                 175

Gln His Gly Cys Val Asp Glu Thr Glu Gly Lys Gly Arg Phe Asp Arg
            180                 185                 190

Tyr Ser Ile Leu Leu Ile Ala Glu Ile Cys Gln Arg His Ile Asp Thr
        195                 200                 205

Gly Leu Glu Ile Cys Asp Trp Leu Lys Asp Ala Leu Arg Gln Val Ser
210                 215                 220

Thr Leu Ile Leu Ala Met Leu Asn Asp Glu Gly Val Gly Phe Leu Trp
225                 230                 235                 240

Gly Arg Ser Ile Gly Ala Tyr Gly Asp Ser Ala Phe Asn Glu Ile Leu
                245                 250                 255

Thr Ile Ser Met Arg Leu Gly Leu Leu Asp Arg Gln Glu Cys Ala Ala
            260                 265                 270

Ala Ser Arg Phe Thr Leu Ala Cys Ser Glu Arg Phe Leu Asn Phe Trp
        275                 280                 285

Tyr Asp Ser Asn Glu Gln Ser Val Asn Leu Trp Phe Tyr Gly Arg Gln
290                 295                 300

Thr Asp Ala Tyr Arg Ala Glu His Arg Leu Val Gly Glu Asn Ile Ser
305                 310                 315                 320

Leu Ser Cys Gln His Leu Cys Val Gln Arg Ala Trp Ala Asp Val Ser
                325                 330                 335

Phe Asp Ala Thr Pro Phe Val Leu Pro Glu Gln Thr Leu Lys Phe Thr
            340                 345                 350

Pro Phe Cys Asn Asp Lys Tyr Thr Arg Gly Leu Phe His Trp Tyr Asp
        355                 360                 365

Gly Lys Arg Leu Phe Val Leu Pro Leu Ile Asn Gly Asp Lys His Tyr
370                 375                 380

Phe Ala Thr Ser Pro Tyr Phe Pro Val Pro Phe Ser Ala Gly Leu Ile
385                 390                 395                 400

Thr Gly Val Ala Gln Gly His Ala Pro Leu Trp Val Pro Gly Leu Val
                405                 410                 415

Asp Ser Arg Gly Cys Ile Leu Arg Pro Leu Val Trp Phe Gly Asp Cys
            420                 425                 430

Gly Tyr Gln Lys Thr Lys Asn Gly Trp Glu Ile Glu Ile Asn Tyr Ser
        435                 440                 445

Ala Leu Asn Val Val Met Glu Asn Gly Val Leu Leu Ser Glu Pro Lys
450                 455                 460

Lys Asp Tyr Ser Cys Gln Cys Arg Thr Arg Tyr Phe Ile Glu Pro Ser
465                 470                 475                 480
```

```
Thr Leu Thr Arg Val Asp Thr Phe Ser Phe Leu Lys His Ser Glu Met
                485                 490                 495

Tyr Leu Glu Leu Gln Cys Ala Val Phe Pro Glu Lys Met Arg Met Ile
            500                 505                 510

His Ser Ala Asp Ser Leu His Ile Asp Tyr Glu Ser Asn Gly Ile Gln
        515                 520                 525

Ser Leu Glu Leu Asn Gly Phe Glu Asp Tyr Cys Val Glu Arg Thr Ala
    530                 535                 540

Leu Cys Ser Pro Tyr Gly Ala Leu Gly Gln Gln Ile Thr Gly Arg Arg
545                 550                 555                 560

Asp Val Ser Gly Ala Lys Asp Val Thr Val Ser Trp Gln Ile Cys Tyr
                565                 570                 575

Cys

<210> SEQ ID NO 111
<211> LENGTH: 1242
<212> TYPE: DNA
<213> ORGANISM: Bacillus megaterium

<400> SEQUENCE: 111
atgaaaagtt caaaaagttt atattggaag ctgagtgcat attttttctt cttcttttt       60 acgtggtcgt ccagctactc tttattttct atctggttag ggcaagagat taagttgaac    120
ggatcagcaa caggcttaat cttttctgtg aacgctatct ttgctttgtg tatgcagcct    180
ttgtacggat atatatctga caggataggt ttaaagaaac acgttttatt ttttattagc    240
tgtcttttag tgtttgtagg accatttttat attttgttt atggaccttt gcttcaatac    300
aatgtggtga tagggctat tattggaggc ttatatttag gagtagcgtt tttggcgggc    360
atcggagcga ttgaaacata catagagaaa gtcagccgaa aatataaatt tgagtatgga    420
aaatctagaa tgtggggggtc attaggctgg gctgcagcta cgttttttgc aggacaatta    480
tttaatatta tccctcacat taattttttgg gtggcatctg tttcagcggt tatcctagtc    540
gctattattt tttctgtaaa agtagaaatg agcagttatg aaatggaaaa agctgaatcc    600
gtcacgctaa gagatgtagg tagttttattt ttattgaagg aattttggtt ttttatgatt    660
tatgttgttg gtgttacatg cgtatatggg gtatacgatc agcaatttcc tatctattat    720
gcatctttgt ttcctactga atcgataggt aaccaagtat ttggctactt aaattcgttt    780
caagtatttt tagaagctgg aatgatgttc gcagcaccgt ttattgtaaa taagatcggt    840
gcaaaaaata gtttaatttt agcaggattt ctaatgggat ttcgtattat tgggtcaggg    900
cttgttgttg gtccaatcgg aatatcttca atgaaactca ttcatgcatt agaacttcct    960
attatgctca ttgccatctt taaatatttg gcagctaact ttgacacgcg cctatcttcc   1020
atcctttatt tggttggatt ccaatttgct tcgcaaatag gtgcttcagt tctttcaccc   1080
atagtgggag gattatatga tagcgtaggt ttttcccgta cctatttaat tatgggaggt   1140
atggttttgg tatttaacgt tatttcgatg tttacactac taaactctaa aaaacataga   1200
tttataagaa aagatgtaca agaaaacacg cagattatat ag                       1242

<210> SEQ ID NO 112
<211> LENGTH: 413
<212> TYPE: PRT
<213> ORGANISM: Bacillus megaterium

<400> SEQUENCE: 112

Met Lys Ser Ser Lys Ser Leu Tyr Trp Lys Leu Ser Ala Tyr Phe Phe
```

```
              1               5                  10                    15
Phe Phe Phe Phe Thr Trp Ser Ser Tyr Ser Leu Phe Ser Ile Trp
                20                      25                30

Leu Gly Gln Glu Ile Lys Leu Asn Gly Ser Ala Thr Gly Leu Ile Phe
                35                      40                45

Ser Val Asn Ala Ile Phe Ala Leu Cys Met Gln Pro Leu Tyr Gly Tyr
    50                      55                60

Ile Ser Asp Arg Ile Gly Leu Lys Lys His Val Leu Phe Phe Ile Ser
65                      70                      75                80

Cys Leu Leu Val Phe Val Gly Pro Phe Tyr Ile Phe Val Tyr Gly Pro
                85                      90                95

Leu Leu Gln Tyr Asn Val Val Ile Gly Ala Ile Ile Gly Gly Leu Tyr
                100                     105               110

Leu Gly Val Ala Phe Leu Ala Gly Ile Gly Ala Ile Glu Thr Tyr Ile
                115                     120               125

Glu Lys Val Ser Arg Lys Tyr Lys Phe Glu Tyr Gly Lys Ser Arg Met
                130                     135               140

Trp Gly Ser Leu Gly Trp Ala Ala Thr Phe Phe Ala Gly Gln Leu
145                     150               155               160

Phe Asn Ile Asn Pro His Ile Asn Phe Trp Val Ala Ser Val Ser Ala
                165                     170               175

Val Ile Leu Val Ala Ile Ile Phe Ser Val Lys Val Glu Met Ser Ser
                180                     185               190

Tyr Glu Met Glu Lys Ala Glu Ser Val Thr Leu Arg Asp Val Gly Ser
                195                     200               205

Leu Phe Leu Leu Lys Glu Phe Trp Phe Phe Met Ile Tyr Val Val Gly
    210                     215               220

Val Thr Cys Val Tyr Gly Val Tyr Asp Gln Gln Phe Pro Ile Tyr Tyr
225                     230               235               240

Ala Ser Leu Phe Pro Thr Glu Ser Ile Gly Asn Gln Val Phe Gly Tyr
                245                     250               255

Leu Asn Ser Phe Gln Val Phe Leu Glu Ala Gly Met Met Phe Ala Ala
                260                     265               270

Pro Phe Ile Val Asn Lys Ile Gly Ala Lys Asn Ser Leu Ile Leu Ala
                275                     280               285

Gly Phe Leu Met Gly Phe Arg Ile Ile Gly Ser Gly Leu Val Val Gly
                290                     295               300

Pro Ile Gly Ile Ser Ser Met Lys Leu Ile His Ala Leu Glu Leu Pro
305                     310               315               320

Ile Met Leu Ile Ala Ile Phe Lys Tyr Leu Ala Ala Asn Phe Asp Thr
                325                     330               335

Arg Leu Ser Ser Ile Leu Tyr Leu Val Gly Phe Gln Phe Ala Ser Gln
                340                     345               350

Ile Gly Ala Ser Val Leu Ser Pro Ile Val Gly Gly Leu Tyr Asp Ser
                355                     360               365

Val Gly Phe Ser Arg Thr Tyr Leu Ile Met Gly Gly Met Val Leu Val
                370                     375               380

Phe Asn Val Ile Ser Met Phe Thr Leu Leu Asn Ser Lys Lys His Arg
385                     390               395               400

Phe Ile Arg Lys Asp Val Gln Glu Asn Thr Gln Ile Ile
                405                     410

<210> SEQ ID NO 113
```

<211> LENGTH: 1263
<212> TYPE: DNA
<213> ORGANISM: Providencia rustigianii

<400> SEQUENCE: 113

```
atgggaaaga taataggagc aactcggcac gcttatttta tccttagcgg cttgctattc      60
acctttttt  ggacatggtc atctgcgttt tcgctggtct ctctttggct cagtcagaag     120
gtgggcttaa aggggacgga tacgggaatt atcttctcgg tgatcagttt aaccgcattc     180
tgtgcccagc cactttatgg atttatccaa gataagcttg gattacgcaa aaacttactt    240
tggtacattg gtgtgatgct ggtgatcagt ggtccatggt ttattttgt ttgtactcca     300
ttgttacgtt ggaatatttt cctcggatca atcagtttag gcgtgtatgt cggggcaacg    360
tttttcgctg gatagggc  tttagaatct tacactgagc gtgtaagtcg aattgcggga     420
ttcgaatatg gtcgagcgcg catgtgggga tcattgggat gggctggagc gacattcttc    480
gccggtatct tattcaatat taatccaaat tataatttcg cgatgggatc ggtatccgca    540
ttaattttca tcattttatt atggagatta agtgatgttc gtcctcaagc gatgaatgag    600
ctggaatttg gtaaaagtaa tgcactaaaa ctgtcagatg ccttgggggtt actcaaaatg   660
cgttcatttt ggtctctggt cgttttgtg tgtggcgtca gcgttataa  cgtatatgac    720
caacaattcc caatctattt tgcctcacta tttagtgaac aaagtcatgg taatgaaatg    780
tttggttacc tgaattcact gcaagttttt ctagaagcag gcggcatgtt tttagcccca   840
ttcttagtca accgaattgg cgccaagaat ggattactcc tcagtggatt tgtaatggcg    900
ctacgtatct taggttcggg tttggcagat gacaccatta cgatttctt  catgaaatta    960
cttcatgccg ttgaacttcc tatcctactg atatctttat ttaaatatat cactacagtt   1020
ttcgataagc gttatctgc  cacgatttat ctcgtgggct tccagtttat tgcctcactg   1080
tgcgccacgg tgctatcccc attagctggg atcagttatg accggattgg ctttgcggat   1140
acctatatga ttttggcggg tattgtcttt acgttaacca ttatttcttg tgtgctgctg   1200
aaatctgaaa acagctcaaa agttcacaat gtcagtattc agaaaaaaac ggtagaacta   1260
tga                                                                 1263
```

<210> SEQ ID NO 114
<211> LENGTH: 420
<212> TYPE: PRT
<213> ORGANISM: Providencia rustigianii

<400> SEQUENCE: 114

```
Met Gly Lys Ile Ile Gly Ala Thr Arg His Ala Tyr Phe Ile Leu Ser
1               5                   10                  15

Gly Leu Leu Phe Thr Phe Phe Trp Thr Trp Ser Ser Ala Phe Ser Leu
            20                  25                  30

Val Ser Leu Trp Leu Ser Gln Lys Val Gly Leu Lys Gly Thr Asp Thr
        35                  40                  45

Gly Ile Ile Phe Ser Val Ile Ser Leu Thr Ala Phe Cys Ala Gln Pro
    50                  55                  60

Leu Tyr Gly Phe Ile Gln Asp Lys Leu Gly Leu Arg Lys Asn Leu Leu
65                  70                  75                  80

Trp Tyr Ile Gly Val Met Leu Val Ile Ser Gly Pro Trp Phe Ile Phe
                85                  90                  95

Val Cys Thr Pro Leu Leu Arg Trp Asn Ile Phe Leu Gly Ser Ile Ser
            100                 105                 110
```

```
Leu Gly Val Tyr Val Gly Ala Thr Phe Phe Ala Gly Ile Gly Ala Leu
            115                 120                 125

Glu Ser Tyr Thr Glu Arg Val Ser Arg Ile Ala Gly Phe Glu Tyr Gly
        130                 135                 140

Arg Ala Arg Met Trp Gly Ser Leu Gly Trp Ala Gly Ala Thr Phe Phe
145                 150                 155                 160

Ala Gly Ile Leu Phe Asn Ile Asn Pro Asn Tyr Asn Phe Ala Met Gly
                165                 170                 175

Ser Val Ser Ala Leu Ile Phe Ile Leu Leu Trp Arg Leu Ser Asp
            180                 185                 190

Val Arg Pro Gln Ala Met Asn Glu Leu Glu Phe Gly Lys Ser Asn Ala
        195                 200                 205

Leu Lys Leu Ser Asp Ala Leu Gly Leu Leu Lys Met Arg Ser Phe Trp
210                 215                 220

Ser Leu Val Val Phe Val Cys Gly Val Ser Val Tyr Asn Val Tyr Asp
225                 230                 235                 240

Gln Gln Phe Pro Ile Tyr Phe Ala Ser Leu Phe Ser Glu Gln Ser His
                245                 250                 255

Gly Asn Glu Met Phe Gly Tyr Leu Asn Ser Leu Gln Val Phe Leu Glu
            260                 265                 270

Ala Gly Gly Met Phe Leu Ala Pro Phe Leu Val Asn Arg Ile Gly Ala
        275                 280                 285

Lys Asn Gly Leu Leu Leu Ser Gly Phe Val Met Ala Leu Arg Ile Leu
290                 295                 300

Gly Ser Gly Leu Ala Asp Asp Thr Ile Thr Ile Ser Phe Met Lys Leu
305                 310                 315                 320

Leu His Ala Val Glu Leu Pro Ile Leu Leu Ile Ser Leu Phe Lys Tyr
                325                 330                 335

Ile Thr Thr Val Phe Asp Lys Arg Leu Ser Ala Thr Ile Tyr Leu Val
            340                 345                 350

Gly Phe Gln Phe Ile Ala Ser Leu Cys Ala Thr Val Leu Ser Pro Leu
        355                 360                 365

Ala Gly Ile Ser Tyr Asp Arg Ile Gly Phe Ala Asp Thr Tyr Met Ile
370                 375                 380

Leu Ala Gly Ile Val Phe Thr Leu Thr Ile Ser Cys Val Leu Leu
                390                 395                 400

Lys Ser Glu Asn Ser Ser Lys Val His Asn Val Ser Ile Gln Lys Lys
            405                 410                 415

Thr Val Glu Leu
        420

<210> SEQ ID NO 115
<211> LENGTH: 1266
<212> TYPE: DNA
<213> ORGANISM: Providencia alcalifaciens

<400> SEQUENCE: 115
atgggcaaaa aaacacgcgc taacatacat gcctatctca cattaagcgg cttattattt      60
acattctttt ggacatggtc atccgtgttt tccttagtct ctctgtggct cagccaaaaa     120
attggcttaa agggtactga taccggcatt attttttcag tcattagtct aacggctttt     180
tgtgcacagc tctgtatgg atttattcag gacagactcg gtttacgcaa aaatttatta     240
tggtttctgg gtgggttgtt attaatcagt ggacccttggt ttattttttgt ctgtactccg     300 ttattaaaat ggaacatttt tgcgggtgcc gcagcgttag ggattatgt cggagcgacg     360
```

-continued

```
ttctttgctg gtatcggtgc acttgaatcc tacactgaac gggttagccg catcgcgagc    420
tttgaatatg ggcgtgcccg tatgtgggga tcgctgggtt gggcgggcgc cactttcttt    480
gctgggctgt tatttaatat cgatcccaac ttaaatttcg ccatgggtc tgtcagcgca     540 ctgctgttta tcattctgtt atggcgttta cgtaacgttc gtcctcatac tatgaacgaa    600
cttgaattcg gtaaaactca atcgctaact gtctctgatg cgctgggact tttacgtatg    660
cgctcatttt ggtctttagt aatatttgtc tgtggtgtga gtgtttataa cgtctacgac    720
caacaatttc cagtctattt tgcctccctg tttgcgaatc aaaatgaagg caatgagatg    780
ttcggctact taaattcgct tcaggtctttt tagaggcag gcgggatgtt tttagcgcct     840
ttccttgtaa atcgtatcgg tgctaaacgg ggtctattgt taagtggttt gatcatggcg    900 ctacgtatt tgggttcagg acttgccgat gacgccatca ctatctcatt catgaagcta     960
ctgcatgccg ttgaacttcc tattctctta atttcattat ttaaatacat acgtctgta    1020 tttgataaac gctatccgc aaccatctat ttagtcggct tccagtttac ggcgtcactg    1080
tgtgcttcat tcttatcccc gttagcaggg tacggctatg acacattagg cttcgccgat   1140
acttatatga tcctcgccgc catcgtcatt tccatgacga taatctctag cgtacttctg   1200
caatcagaaa acacatcaac cgtcagcaac cccatgacaa cgtcgaaaaa aacggtggaa   1260
ttatga                                                               1266
```

<210> SEQ ID NO 116
<211> LENGTH: 421
<212> TYPE: PRT
<213> ORGANISM: Providencia alcalifaciens

<400> SEQUENCE: 116

```
Met Gly Lys Lys Thr Arg Ala Asn Ile His Ala Tyr Leu Thr Leu Ser
1               5                   10                  15

Gly Leu Leu Phe Thr Phe Phe Trp Thr Trp Ser Ser Val Phe Ser Leu
            20                  25                  30

Val Ser Leu Trp Leu Ser Gln Lys Ile Gly Leu Lys Gly Thr Asp Thr
        35                  40                  45

Gly Ile Ile Phe Ser Val Ile Ser Leu Thr Ala Phe Cys Ala Gln Pro
    50                  55                  60

Leu Tyr Gly Phe Ile Gln Asp Arg Leu Gly Leu Arg Lys Asn Leu Leu
65                  70                  75                  80

Trp Phe Leu Gly Gly Leu Leu Leu Ile Ser Gly Pro Trp Phe Ile Phe
                85                  90                  95

Val Cys Thr Pro Leu Leu Lys Trp Asn Ile Phe Ala Gly Ala Ala Ala
            100                 105                 110

Leu Gly Ile Tyr Val Gly Ala Thr Phe Phe Ala Gly Ile Gly Ala Leu
        115                 120                 125

Glu Ser Tyr Thr Glu Arg Val Ser Arg Ile Ala Ser Phe Glu Tyr Gly
    130                 135                 140

Arg Ala Arg Met Trp Gly Ser Leu Gly Trp Ala Gly Ala Thr Phe Phe
145                 150                 155                 160

Ala Gly Leu Leu Phe Asn Ile Asp Pro Asn Leu Asn Phe Ala Met Gly
                165                 170                 175

Ser Val Ser Ala Leu Leu Phe Ile Ile Leu Leu Trp Arg Leu Arg Asn
            180                 185                 190

Val Arg Pro His Thr Met Asn Glu Leu Glu Phe Gly Lys Thr Gln Ser
        195                 200                 205
```

```
Leu Thr Val Ser Asp Ala Leu Gly Leu Leu Arg Met Arg Ser Phe Trp
    210                 215                 220

Ser Leu Val Ile Phe Val Cys Gly Val Ser Val Tyr Asn Val Tyr Asp
225                 230                 235                 240

Gln Gln Phe Pro Val Tyr Phe Ala Ser Leu Phe Ala Asn Gln Asn Glu
                245                 250                 255

Gly Asn Glu Met Phe Gly Tyr Leu Asn Ser Leu Gln Val Phe Leu Glu
            260                 265                 270

Ala Gly Gly Met Phe Leu Ala Pro Phe Leu Val Asn Arg Ile Gly Ala
        275                 280                 285

Lys Arg Gly Leu Leu Leu Ser Gly Leu Ile Met Ala Leu Arg Ile Leu
    290                 295                 300

Gly Ser Gly Leu Ala Asp Asp Ala Ile Thr Ile Ser Phe Met Lys Leu
305                 310                 315                 320

Leu His Ala Val Glu Leu Pro Ile Leu Leu Ile Ser Leu Phe Lys Tyr
                325                 330                 335

Ile Thr Ser Val Phe Asp Lys Arg Leu Ser Ala Thr Ile Tyr Leu Val
            340                 345                 350

Gly Phe Gln Phe Thr Ala Ser Leu Cys Ala Ser Phe Leu Ser Pro Leu
        355                 360                 365

Ala Gly Tyr Gly Tyr Asp Thr Leu Gly Phe Ala Asp Thr Tyr Met Ile
    370                 375                 380

Leu Ala Ala Ile Val Ile Ser Met Thr Ile Ile Ser Ser Val Leu Leu
385                 390                 395                 400

Gln Ser Glu Asn Thr Ser Thr Val Ser Asn Pro Met Thr Thr Ser Lys
                405                 410                 415

Lys Thr Val Glu Leu
            420

<210> SEQ ID NO 117
<211> LENGTH: 1371
<212> TYPE: DNA
<213> ORGANISM: Serratia odorifera

<400> SEQUENCE: 117
atgttaacgt taacttttgt gattaacatc gcaatccctg atgttggtgg ctttatttgg    60 ccaaggtta acgttaacaa taaggctgac atcatccatc agggcatctc acatgaaccg    120
cgaaacaaaa aatattatgt gcttctaagc ggcctgttgt tttttcttctt ttttacctgg   180 tcggccagct tttcactgat ctccatctgg ctaaaccaga aaatcggcct gaaaggcacc    240
gaaaccggcc tgatcttctc ggccatgtcg atcatggcgc tgtgcgtgca gccgctgtac   300
gggtttgttc aggacaaact cgggttgcgt aagcatctgc tgctgttcgt cggcgtgctg   360
ttgttgctca ccgggccgtt ctttatctat gtttacgccc gctgctgca aaccaatctg    420 gtggccggcg cactggttgg cggcctgttc gtcagcctgg cgttcaacgc cggcatcggc   480
gcgctggaat cctataccga acgcgtcagc cgcatcgtcg gcttcgagtt cggccgggcg   540
cgcatgtggg gctcgctggg ctgggccagc gccaccttct tgccggcctt tatctataac    600
atcaacccga acatcaactt ttggattgcc tcggcctcgg cggcggtatt cctgctgttg   660
ctgtggcagg tgcgagagct gaaacccaac gccatggccg ggttggaata cggcaaaccg   720
gaaaacctga gttgcagga cgccctggcg ttgctgcgcc tgccggggtt ctgggcgctg   780
gtggtgttcg tgctcggcac cagcatctac ggcgtcttcg accagcagtt cccggtgtac   840
```

```
ttcgcttcgc agttcgcgac ccatgaggaa ggcaaccgca tgtacggctt ccttaactcg    900
ctgcaagtgt ttctggaggc cggtggcatg ttcctggcgc cgctgctggt caaccgtatc    960
ggtatcaagc aaagcctgct gctggccagc agcgtgatgg cgtttcgcat gttcggctct   1020
ggtttcgcca atggcgcgct gatgatttcc gccatgaaac tgctgcatgc cgtggaactg   1080
ccgattctgc tggtagccat gttcaaatac atcaccaccc gcttcgacag ccgcctgtcc   1140
tccacgctgt atctggtggg cttccagttt atcagccaga tcgtcgccgg cattctggcg   1200
ccgctggccg gtctcggcta cgaccgcatc ggctttgccg acacctattt gctgatgggc   1260
tgcgccgtcg ccggtactac gctggtttcc tgcttcctgc tgcgcggcga gactcccgcc   1320
cgcgcacctc aatttcaatc cacgataaaa tcaagtgagc caatccaatg a            1371
```

<210> SEQ ID NO 118
<211> LENGTH: 456
<212> TYPE: PRT
<213> ORGANISM: Serratia odorifera

<400> SEQUENCE: 118

```
Met Leu Thr Leu Thr Phe Val Ile Asn Ile Ala Ile Pro Asp Val Gly
1               5                   10                  15

Gly Phe Ile Trp Pro Lys Val Asn Val Asn Asn Lys Ala Asp Ile Ile
            20                  25                  30

His Gln Gly Ile Ser His Glu Pro Arg Asn Lys Lys Tyr Tyr Val Leu
        35                  40                  45

Leu Ser Gly Leu Leu Phe Phe Phe Phe Thr Trp Ser Ala Ser Phe
    50                  55                  60

Ser Leu Ile Ser Ile Trp Leu Asn Gln Lys Ile Gly Leu Lys Gly Thr
65                  70                  75                  80

Glu Thr Gly Leu Ile Phe Ser Ala Met Ser Ile Met Ala Leu Cys Val
                85                  90                  95

Gln Pro Leu Tyr Gly Phe Val Gln Asp Lys Leu Gly Leu Arg Lys His
            100                 105                 110

Leu Leu Leu Phe Val Gly Val Leu Leu Leu Thr Gly Pro Phe Phe
        115                 120                 125

Ile Tyr Val Tyr Ala Pro Leu Leu Gln Thr Asn Leu Val Ala Gly Ala
    130                 135                 140

Leu Val Gly Gly Leu Phe Val Ser Leu Ala Phe Asn Ala Gly Ile Gly
145                 150                 155                 160

Ala Leu Glu Ser Tyr Thr Glu Arg Val Ser Arg Ile Val Gly Phe Glu
                165                 170                 175

Phe Gly Arg Ala Arg Met Trp Gly Ser Leu Gly Trp Ala Ser Ala Thr
            180                 185                 190

Phe Phe Ala Gly Phe Ile Tyr Asn Ile Asn Pro Asn Ile Asn Phe Trp
        195                 200                 205

Ile Ala Ser Ala Ser Ala Ala Val Phe Leu Leu Leu Trp Gln Val
    210                 215                 220

Arg Glu Leu Lys Pro Asn Ala Met Ala Gly Leu Glu Tyr Gly Lys Pro
225                 230                 235                 240

Glu Asn Leu Lys Leu Gln Asp Ala Leu Ala Leu Leu Arg Leu Pro Gly
                245                 250                 255

Phe Trp Ala Leu Val Val Phe Val Leu Gly Thr Ser Ile Tyr Gly Val
            260                 265                 270

Phe Asp Gln Gln Phe Pro Val Tyr Phe Ala Ser Gln Phe Ala Thr His
        275                 280                 285
```

```
Glu Glu Gly Asn Arg Met Tyr Gly Phe Leu Asn Ser Leu Gln Val Phe
    290                 295                 300

Leu Glu Ala Gly Gly Met Phe Leu Ala Pro Leu Val Asn Arg Ile
305                 310                 315                 320

Gly Ile Lys Gln Ser Leu Leu Leu Ala Ser Val Met Ala Phe Arg
                325                 330                 335

Met Phe Gly Ser Gly Phe Ala Asn Gly Ala Leu Met Ile Ser Ala Met
                340                 345                 350

Lys Leu Leu His Ala Val Glu Leu Pro Ile Leu Leu Val Ala Met Phe
                355                 360                 365

Lys Tyr Ile Thr Thr Arg Phe Asp Ser Arg Leu Ser Ser Thr Leu Tyr
    370                 375                 380

Leu Val Gly Phe Gln Phe Ile Ser Gln Ile Val Ala Gly Ile Leu Ala
385                 390                 395                 400

Pro Leu Ala Gly Leu Gly Tyr Asp Arg Ile Gly Phe Ala Asp Thr Tyr
                405                 410                 415

Leu Leu Met Gly Cys Ala Val Ala Gly Thr Thr Leu Val Ser Cys Phe
                420                 425                 430

Leu Leu Arg Gly Glu Thr Pro Ala Arg Ala Pro Gln Phe Gln Ser Thr
                435                 440                 445

Ile Lys Ser Ser Glu Pro Ile Gln
    450                 455

<210> SEQ ID NO 119
<211> LENGTH: 1314
<212> TYPE: DNA
<213> ORGANISM: Streptomyces albus

<400> SEQUENCE: 119
atgaccgtcc agagccctgc ggctccgagc ccgccgcgg ccgtcccggt gcgcggccgg      60
cgtcgcctga acttcggcct gatcagcgcg gccctgttca tgttcttcgt gacctggtcg    120
ctctcctggt cactcttctc catctggctg acccaggaca tcggcctgag cccgggccgc    180
agttcgctgg tgatcggcgc caactcgctc ggctgcctgg tcacgatgcc ggtctacggc    240
ttcctccagg accggctggg cctgcgcaag aacctgctgt actggatcgg cgccctgatg    300
ctgctggtcg gccggtgta catctacgtc tacggcccgc tgctcaagtc gcacttcgcc    360
ctcggcctgg tggtcggctc ggcctacctc gcgatggcct tcgcggtcgc ggtggccacc    420
ctggagagct acgcggagcg gctgagccgg ttccacggat cgagttcgg ccgggcccgg    480 atgttcggct cgctcggctg ggcggcggcg accttcctgg ccggccgcct cttcaacatc    540
gacccggacc tgaccttctg gccgcctcc ggcacggcgg tggtcttcgt cggactgctg    600
gtggcgatcc gggtgaccga cggacggcgg gccgccgccg tcgaccacgc cgccgcctcg    660
gtctccctag ccgacgtggc cgcgctcctg cgctacccgg ccttctgggg gctgctgctc    720
ttcgtggtcg cggtgacggc gacgtacaac acctacgacg cgatgttccc ctcgtacttc    780
tcctcgctct tcgcgacgga cgccgacggc aaccggatgt acagcgatct caactccgtc    840
caggtcttcc tggaggcggg cgggatggcg ctggcgccgt tcctggtcaa ccggctcggc    900
ccgaagaagt ccctgctggt ctccggctgc gtcatggcga cccggatctt cctctccggc    960
atcgtcacgg accggtcgc gatctcggcg gtgaagctcc tgcacgccgt cgaactgccc   1020
atcatgctga tcgcgatctt caagtacgtg aaccgccact cgagccgcg tctctcctcc   1080 accatctacc tgatcggctt ccagatggcg acgcaggtcg gcgccgccgt catctccccc   1140
```

-continued

```
ttggcgggcc tgggttacga ccgcctcggc tacgccccga cgtacctggt gatgtcggcg      1200
ctggtggcca ccttcaccct ggtctcggtc ttcaccctgc gcgccgacgc caagggcacg      1260
cacgggctgc ccgcggtggg agccgccgag ggccgctccc cggcagcggg ctga            1314
```

<210> SEQ ID NO 120
<211> LENGTH: 437
<212> TYPE: PRT
<213> ORGANISM: Streptomyces albus

<400> SEQUENCE: 120

```
Met Thr Val Gln Ser Pro Ala Ala Pro Ser Pro Ala Ala Val Pro
1               5                   10                  15

Val Arg Gly Arg Arg Leu Asn Phe Gly Leu Ile Ser Ala Ala Leu
                20                  25                  30

Phe Met Phe Phe Val Thr Trp Ser Leu Ser Trp Ser Leu Phe Ser Ile
            35                  40                  45

Trp Leu Thr Gln Asp Ile Gly Leu Ser Pro Gly Arg Ser Ser Leu Val
    50                  55                  60

Ile Gly Ala Asn Ser Leu Gly Cys Leu Val Thr Met Pro Val Tyr Gly
65                  70                  75                  80

Phe Leu Gln Asp Arg Leu Gly Leu Arg Lys Asn Leu Leu Tyr Trp Ile
                85                  90                  95

Gly Ala Leu Met Leu Leu Val Gly Pro Val Tyr Ile Tyr Val Tyr Gly
            100                 105                 110

Pro Leu Leu Lys Ser His Phe Ala Leu Gly Leu Val Val Gly Ser Ala
        115                 120                 125

Tyr Leu Ala Met Ala Phe Ala Val Ala Val Ala Thr Leu Glu Ser Tyr
    130                 135                 140

Ala Glu Arg Leu Ser Arg Phe His Gly Phe Glu Phe Gly Arg Ala Arg
145                 150                 155                 160

Met Phe Gly Ser Leu Gly Trp Ala Ala Ala Thr Phe Leu Ala Gly Arg
                165                 170                 175

Leu Phe Asn Ile Asp Pro Asp Leu Thr Phe Trp Ala Ala Ser Gly Thr
            180                 185                 190

Ala Val Val Phe Val Gly Leu Leu Val Ala Ile Arg Val Thr Asp Gly
        195                 200                 205

Arg Arg Ala Ala Ala Val Asp His Ala Ala Ala Ser Val Ser Leu Ala
    210                 215                 220

Asp Val Ala Ala Leu Leu Arg Tyr Pro Ala Phe Trp Gly Leu Leu
225                 230                 235                 240

Phe Val Val Ala Val Thr Ala Thr Tyr Asn Thr Tyr Asp Ala Met Phe
                245                 250                 255

Pro Ser Tyr Phe Ser Ser Leu Phe Ala Thr Asp Ala Asp Gly Asn Arg
            260                 265                 270

Met Tyr Ser Asp Leu Asn Ser Val Gln Val Phe Leu Glu Ala Gly Gly
        275                 280                 285

Met Ala Leu Ala Pro Phe Leu Val Asn Arg Leu Gly Pro Lys Lys Ser
    290                 295                 300

Leu Leu Val Ser Gly Cys Val Met Ala Thr Arg Ile Phe Leu Ser Gly
305                 310                 315                 320

Ile Val Thr Asp Pro Val Ala Ile Ser Ala Val Lys Leu Leu His Ala
                325                 330                 335

Val Glu Leu Pro Ile Met Leu Ile Ala Ile Phe Lys Tyr Val Asn Arg
```

```
           340             345             350
His Phe Glu Pro Arg Leu Ser Ser Thr Ile Tyr Leu Ile Gly Phe Gln
        355                 360                 365

Met Ala Thr Gln Val Gly Ala Ala Val Ile Ser Pro Leu Ala Gly Leu
    370                 375                 380

Gly Tyr Asp Arg Leu Gly Tyr Ala Pro Thr Tyr Leu Val Met Ser Ala
385                 390                 395                 400

Leu Val Ala Thr Phe Thr Leu Val Ser Val Phe Thr Leu Arg Ala Asp
                405                 410                 415

Ala Lys Gly Thr His Gly Leu Pro Ala Val Gly Ala Ala Glu Gly Arg
            420                 425                 430

Ser Pro Ala Ala Gly
        435

<210> SEQ ID NO 121
<211> LENGTH: 1284
<212> TYPE: DNA
<213> ORGANISM: Azobactervinelandii

<400> SEQUENCE: 121
atgcatctcc cgttaaaacg cgaatactgg ctgatcagtg gcctgctgtt tttcttcttc       60
ttcgcctggt cgtcgagcta ttcgctgttc tcgatctggc tgcaccgggt catcggtctg      120
agcggtacgg aaaccggctt catcttcgcc gccaacgcca tcgccgcgct gttcatccag      180
cccttctacg gcgccctgca ggaccgcctg ggcctgtccc gcaggctgct ggtctggatc      240
ggcgtgctgc tcgcctgcgc gcgcccttc gcgatccacg tctacgccgg cctgctggcc       300
cacgacgtgg tgctcggcgc cctggtcggc gccgccttcc tggccttcgc catgctcgcc      360 ggcgtggggcg tcatcgagtc ctataccgag cggctgtcgc gccacgccgg cttcgagttc      420
ggcaccacgc ggatgtgggg ctcgctgggc tgggcggccg cgacgggcgt ggccggcgtg      480
gtgttcgaca tcgaccccga catcgccttc tacatgagca cgccgccgg cctgcgcttc       540 ctgctgatcc tctcccggct ggacatggac gccttcagga accacgagac gcgggccggc      600
gagtccgccc cggtacgcac cgccgacatc ctgcaactgc tgcgcctgcc gcgcttctgg      660
gcgttcagcc tgttcctgac cggggtcgcc ggggtctaca tgatctacga gcagcagttc      720
ccggtgtact tcgcctcctt cttccctacc ccggaagaag gcaccgcgc ctacggctac       780 ctgaactcct cgcaggtact ggtcgaggcc ctgctcatgc tggtcgcgcc ctgggtggtc      840
gcccgcaccg cgccaaaata cggcctgctg ctggccggca ccatcatgtt cgtgcgcatc      900
ctcggctcgg gctggccag cgatgcctgg accatcgccg cctgcaagat gctgcatgcc      960
atcgaggtgc cgatcctgtt ggtcgcggtg ttcaagtaca tctgcgtcaa cttcgatgcg     1020
cggctgtcgg ccacgctcta cctggtcagt ttccagttcg cccagcaact gaccgccatg     1080
ctgttgtcgc cggccgtggg ctatggctac gacaggctcg gcttcgccag cgtctacctg     1140
ctgctggcca gtctggtcgg cgcctgcctg ctgctgtcct ggtcgctgct gcgcgccgac     1200
ccgtccagca agaccacccg ggcggcggac ggcgccccgg aactgccggc catcgcccag     1260
gcggccaacc attacgaacc ctga                                            1284

<210> SEQ ID NO 122
<211> LENGTH: 427
<212> TYPE: PRT
<213> ORGANISM: Azobacter vinelandii

<400> SEQUENCE: 122
```

```
Met His Leu Pro Leu Lys Arg Glu Tyr Trp Leu Ile Ser Gly Leu Leu
1               5                   10                  15

Phe Phe Phe Phe Phe Ala Trp Ser Ser Ser Tyr Ser Leu Phe Ser Ile
            20                  25                  30

Trp Leu His Arg Val Ile Gly Leu Ser Gly Thr Glu Thr Gly Phe Ile
        35                  40                  45

Phe Ala Ala Asn Ala Ile Ala Ala Leu Phe Ile Gln Pro Phe Tyr Gly
    50                  55                  60

Ala Leu Gln Asp Arg Leu Gly Leu Ser Arg Arg Leu Leu Val Trp Ile
65                  70                  75                  80

Gly Val Leu Leu Ala Cys Ala Ala Pro Phe Ala Ile His Val Tyr Ala
                85                  90                  95

Gly Leu Leu Ala His Asp Val Leu Gly Ala Leu Val Gly Ala Ala
                100                 105                 110

Phe Leu Ala Phe Ala Met Leu Ala Gly Val Gly Val Ile Glu Ser Tyr
            115                 120                 125

Thr Glu Arg Leu Ser Arg His Ala Gly Phe Glu Phe Gly Thr Thr Arg
        130                 135                 140

Met Trp Gly Ser Leu Gly Trp Ala Ala Ala Thr Gly Val Ala Gly Val
145                 150                 155                 160

Val Phe Asp Ile Asp Pro Asp Ile Ala Phe Tyr Met Ser Ser Ala Ala
                165                 170                 175

Gly Leu Ala Phe Leu Leu Ile Leu Ser Arg Leu Asp Met Asp Ala Phe
            180                 185                 190

Arg Asn His Glu Thr Arg Ala Gly Glu Ser Ala Pro Val Arg Thr Ala
                195                 200                 205

Asp Ile Leu Gln Leu Leu Arg Leu Pro Arg Phe Trp Ala Phe Ser Leu
    210                 215                 220

Phe Leu Thr Gly Val Ala Gly Val Tyr Met Ile Tyr Glu Gln Gln Phe
225                 230                 235                 240

Pro Val Tyr Phe Ala Ser Phe Phe Pro Thr Pro Glu Glu Gly Thr Arg
            245                 250                 255

Ala Tyr Gly Tyr Leu Asn Ser Ser Gln Val Leu Val Glu Ala Leu Leu
        260                 265                 270

Met Leu Val Ala Pro Trp Val Val Ala Arg Thr Gly Ala Lys Tyr Gly
275                 280                 285

Leu Leu Leu Ala Gly Thr Ile Met Phe Val Arg Ile Leu Gly Ser Gly
    290                 295                 300

Leu Ala Ser Asp Ala Trp Thr Ile Ala Ala Cys Lys Met Leu His Ala
305                 310                 315                 320

Ile Glu Val Pro Ile Leu Leu Val Ala Val Phe Lys Tyr Ile Cys Val
                325                 330                 335

Asn Phe Asp Ala Arg Leu Ser Ala Thr Leu Tyr Leu Val Ser Phe Gln
            340                 345                 350

Phe Ala Gln Gln Leu Thr Ala Met Leu Leu Ser Pro Ala Val Gly Tyr
        355                 360                 365

Gly Tyr Asp Arg Leu Gly Phe Ala Ser Val Tyr Leu Leu Ala Ser
        370                 375                 380

Leu Val Gly Ala Cys Leu Leu Leu Ser Trp Ser Leu Leu Arg Ala Asp
385                 390                 395                 400

Pro Ser Ser Lys Thr Thr Arg Ala Ala Asp Gly Ala Pro Glu Leu Pro
            405                 410                 415
```

Ala Ile Ala Gln Ala Ala Asn His Tyr Glu Pro
            420                 425

<210> SEQ ID NO 123
<211> LENGTH: 1278
<212> TYPE: DNA
<213> ORGANISM: Oenococcus oeni

<400> SEQUENCE: 123

| ttgatcatga ttaaccaatc tgaaattaaa actgctaata agaaaaaaga tttctgggga | 60 |
| tttccattct ctcactttac ctatttttt atttggcaaa tcattaacgg ttatttaact | 120 |
| ctatggatgg aacagatagg acacctaaat ggtgcagaag ctggagttgt attttctatg | 180 |
| atggctggat tttctctcat ttttcaacca tcatttggaa ttatttccga taaattaatt | 240 |
| tttaagaaaa atttgattct gacaatttca atcgctggaa tcttgattgg accatatttt | 300 |
| cagtggcttt tcctaccgtt aatgaaaata aactcaacat tcgttgctat tattactggt | 360 |
| atttttttaa gttcattttt gaatggtggc gttagcgtaa tagaacaata tgttcaaaga | 420 |
| gcaagtctcg ctaaccatt tgaatacgga cattcaagaa tgggtggatc tttggcagga | 480 |
| atgtgtgcct cttttcttgg tgggcaacta ttttttgtgga gtcctaattc tattttttgg | 540 |
| gcctgcacta tttcagcaat gatccttaca ggcttgttat tattaatga caagatccat | 600 |
| atggaaaatg caaatcttgc cggtggaact tccagtcgtt taaacctaaa acagatctct | 660 |
| tcaatattta aaataaagaa tttttggttc ctctcactat tttatattgg cacggcctct | 720 |
| atttacgata tctttgatca gcaatttatt atatttttta aatcttttttt tgataccgca | 780 |
| tcacaaggaa cagctgccta tagttatatg acaactgcgc agattggtat cgaatttata | 840 |
| cttatgtttc caatgccttg gataattaat cgaattggag cgcgtaatgg cctaatagca | 900 |
| tatggaacaa ttttagctat tagaattatt ggtagtgcat tatctccaaa tctttttttgg | 960 |
| gttattttgc tacgcttgct ggctggatta gaaatgcctc ttatcctagt ttcaatcatg | 1020 |
| aaatatatat cgggtgcctt tgaccttcgc ctttatgcca ctatatatgc gctgtcatca | 1080 |
| aactttgcaa acaaataac tgaattcttt ttagcaactg ctgcaggaaa aatgtatgat | 1140 |
| tcaatcggct ttcaccatac ttatttaatt cttggagtca tcgtcgcaat ctttacgatt | 1200 |
| tttacggcac ttttttcttaa aaaagaaaac cctgttcaag caggagaaag agacagagct | 1260 |
| ggaaaccca aagcttaa | 1278 |

<210> SEQ ID NO 124
<211> LENGTH: 425
<212> TYPE: PRT
<213> ORGANISM: Oenococcus oeni

<400> SEQUENCE: 124

Met Ile Met Ile Asn Gln Ser Glu Ile Lys Thr Ala Asn Lys Lys
1               5                   10                  15

Asp Phe Trp Gly Phe Pro Phe Ser His Phe Thr Tyr Phe Phe Ile Trp
            20                  25                  30

Gln Ile Ile Asn Gly Tyr Leu Thr Leu Trp Met Glu Gln Ile Gly His
        35                  40                  45

Leu Asn Gly Ala Glu Ala Gly Val Val Phe Ser Met Met Ala Gly Phe
    50                  55                  60

Ser Leu Ile Phe Gln Pro Ser Phe Gly Ile Ile Ser Asp Lys Leu Ile
65                  70                  75                  80

Phe Lys Lys Asn Leu Ile Leu Thr Ile Ser Ile Ala Gly Ile Leu Ile

```
                85                  90                  95
Gly Pro Tyr Phe Gln Trp Leu Phe Leu Pro Leu Met Lys Ile Asn Ser
            100                 105                 110

Thr Phe Val Ala Ile Ile Thr Gly Ile Phe Leu Ser Phe Ile Leu Asn
            115                 120                 125

Gly Gly Val Ser Val Ile Glu Gln Tyr Val Gln Arg Ala Ser Leu Ala
130                 135                 140

Asn His Phe Glu Tyr Gly His Ser Arg Met Gly Gly Ser Leu Ala Gly
145                 150                 155                 160

Met Cys Ala Ser Phe Leu Gly Gly Gln Leu Phe Leu Trp Ser Pro Asn
                165                 170                 175

Ser Ile Phe Trp Ala Cys Thr Ile Ser Ala Met Ile Leu Thr Gly Leu
            180                 185                 190

Leu Leu Phe Asn Asp Lys Ile His Met Glu Asn Ala Asn Leu Ala Gly
            195                 200                 205

Gly Thr Ser Ser Arg Leu Asn Leu Lys Gln Ile Ser Ser Ile Phe Lys
210                 215                 220

Ile Lys Asn Phe Trp Phe Leu Ser Leu Phe Tyr Ile Gly Thr Ala Ser
225                 230                 235                 240

Ile Tyr Asp Ile Phe Asp Gln Gln Phe Ile Ile Phe Phe Lys Ser Phe
                245                 250                 255

Phe Asp Thr Ala Ser Gln Gly Thr Ala Ala Tyr Ser Tyr Met Thr Thr
            260                 265                 270

Ala Gln Ile Gly Ile Glu Phe Ile Leu Met Phe Pro Met Pro Trp Ile
            275                 280                 285

Ile Asn Arg Ile Gly Ala Arg Asn Gly Leu Ile Ala Tyr Gly Thr Ile
290                 295                 300

Leu Ala Ile Arg Ile Ile Gly Ser Ala Leu Ser Pro Asn Leu Phe Trp
305                 310                 315                 320

Val Ile Leu Leu Arg Leu Leu Ala Gly Leu Glu Met Pro Leu Ile Leu
                325                 330                 335

Val Ser Ile Met Lys Tyr Ile Ser Gly Ala Phe Asp Leu Arg Leu Tyr
            340                 345                 350

Ala Thr Ile Tyr Ala Leu Ser Ser Asn Phe Ala Lys Gln Ile Thr Glu
            355                 360                 365

Phe Phe Leu Ala Thr Ala Ala Gly Lys Met Tyr Asp Ser Ile Gly Phe
370                 375                 380

His His Thr Tyr Leu Ile Leu Gly Val Ile Val Ala Ile Phe Thr Ile
385                 390                 395                 400

Phe Thr Ala Leu Phe Leu Lys Lys Glu Asn Pro Val Gln Ala Gly Glu
                405                 410                 415

Arg Asp Arg Ala Gly Asn Pro Lys Ala
            420                 425

<210> SEQ ID NO 125
<211> LENGTH: 1290
<212> TYPE: DNA
<213> ORGANISM: Lactobacillus brevis

<400> SEQUENCE: 125
atggatagtg caaaaactga atcgaaacat ttctggggat ttcccctatc tcactttagc     60
tacttcttca tttgggccgt tgttaacggt tatttaaccc tctggatgga acaagttgcc    120
cacttaaacg ggaccgaatc tggtgccgtc ttctcaatga tggcgggtat ttccttgatc    180
```

```
ttccaaccta tctttggggt tgtttctgat aaattactct tcaagaaaaa cttaatctta    240
acgattgcga tcgtcgggat cttcatcggt ccttacttcc aatgggtctt catgcccatc    300
ttacacatta gcgccttctt agtagccatc gttactggga cttttctgag tttcatccta    360
aacggtgggg tgtccgtcat tgaacaatac gtacagcggg ctagtttggc taacggcttc    420
gaatatgccc actcccgggt cggtggttcc gtcgccggtg tcgttgcttc attagttgcc    480
gggcgaatct tcctctggaa gcctaactcc atcttctggg catgtaccat tgccgctatt    540
atcttaactt tcttattact cttctctgac aaggttaact tagataacgc tgccgctgct    600
ggtgacacgt ccgattcact tgatatgaag acggttctgt ctgtcttcaa acttaagaac    660
ctctgggttt tagctatttt ctacatgggc gcttctgcct tattcgatgt atttgatcaa    720
cagtttatca tcttctttaa gactttcttt gataccgctg ctcagggac cctggtttac     780
tcttacatga gttctgctca aacagctatc gaattttgtt taatgttccc aatgccatgg    840
attatcaaca aaattggttc tcgtaatggt ttgttaattt acggtttcat tacctgcatc    900
cggatcttag gttctgcttt atctcctaac tggatctggg ttgttggttt ccgtttgtta    960
gctggtttgg aaatgccatt gctattaact tccatcatga aatacattgc tggtgccttt   1020
gatattcggt tatacgccac ggtttacgca ttggcgtcaa actttgctaa acaggtatcc   1080
gtcttcatct ctccacagt tgctggtcgg atgtatgacg ttatcgggta tcaacacacg    1140
tacatcatca tggggatcgt ggtcttcttc attccttgt ttgccgtctt cttcctgaag    1200
aaagaagatc cgattcaagc cggtgaagtc gaggatccta atgttaaagc taagtggaa    1260
gcggcttctt caactgatag tcgtgaatga                                    1290
```

<210> SEQ ID NO 126
<211> LENGTH: 429
<212> TYPE: PRT
<213> ORGANISM: Lactobacillus brevis

<400> SEQUENCE: 126

```
Met Asp Ser Ala Lys Thr Glu Ser Lys His Phe Trp Gly Phe Pro Leu
1               5                   10                  15

Ser His Phe Ser Tyr Phe Phe Ile Trp Ala Val Val Asn Gly Tyr Leu
            20                  25                  30

Thr Leu Trp Met Glu Gln Val Ala His Leu Asn Gly Thr Glu Ser Gly
        35                  40                  45

Ala Val Phe Ser Met Met Ala Gly Ile Ser Leu Ile Phe Gln Pro Ile
    50                  55                  60

Phe Gly Val Val Ser Asp Lys Leu Leu Phe Lys Lys Asn Leu Ile Leu
65                  70                  75                  80

Thr Ile Ala Ile Val Gly Ile Phe Ile Gly Pro Tyr Phe Gln Trp Val
                85                  90                  95

Phe Met Pro Ile Leu His Ile Ser Ala Phe Leu Val Ala Ile Val Thr
            100                 105                 110

Gly Thr Phe Leu Ser Phe Ile Leu Asn Gly Gly Val Ser Val Ile Glu
        115                 120                 125

Gln Tyr Val Gln Arg Ala Ser Leu Ala Asn Gly Phe Glu Tyr Ala His
    130                 135                 140

Ser Arg Val Gly Gly Ser Val Ala Gly Val Val Ala Ser Leu Val Ala
145                 150                 155                 160

Gly Arg Ile Phe Leu Trp Lys Pro Asn Ser Ile Phe Trp Ala Cys Thr
                165                 170                 175
```

```
Ile Ala Ala Ile Ile Leu Thr Phe Leu Leu Phe Ser Asp Lys Val
            180                 185                 190

Asn Leu Asp Asn Ala Ala Ala Gly Asp Thr Ser Asp Ser Leu Asp
        195                 200                 205

Met Lys Thr Val Leu Ser Val Phe Lys Leu Lys Asn Leu Trp Val Leu
    210                 215                 220

Ala Ile Phe Tyr Met Gly Ala Ser Ala Leu Phe Asp Val Phe Asp Gln
225                 230                 235                 240

Gln Phe Ile Ile Phe Lys Thr Phe Phe Asp Thr Ala Ala Gln Gly
                245                 250                 255

Thr Leu Val Tyr Ser Tyr Met Ser Ser Ala Gln Thr Ala Ile Glu Phe
            260                 265                 270

Cys Leu Met Phe Pro Met Pro Trp Ile Ile Asn Lys Ile Gly Ser Arg
            275                 280                 285

Asn Gly Leu Leu Ile Tyr Gly Phe Ile Thr Cys Ile Arg Ile Leu Gly
        290                 295                 300

Ser Ala Leu Ser Pro Asn Trp Ile Trp Val Val Gly Phe Arg Leu Leu
305                 310                 315                 320

Ala Gly Leu Glu Met Pro Leu Leu Thr Ser Ile Met Lys Tyr Ile
                325                 330                 335

Ala Gly Ala Phe Asp Ile Arg Leu Tyr Ala Thr Val Tyr Ala Leu Ala
            340                 345                 350

Ser Asn Phe Ala Lys Gln Val Ser Val Phe Ile Phe Ser Thr Val Ala
            355                 360                 365

Gly Arg Met Tyr Asp Val Ile Gly Tyr Gln His Thr Tyr Ile Ile Met
    370                 375                 380

Gly Ile Val Val Phe Phe Ile Thr Leu Phe Ala Val Phe Phe Leu Lys
385                 390                 395                 400

Lys Glu Asp Pro Ile Gln Ala Gly Glu Val Glu Asp Pro Asn Val Lys
                405                 410                 415

Ala Lys Val Glu Ala Ala Ser Ser Thr Asp Ser Arg Glu
            420                 425
```

<210> SEQ ID NO 127
<211> LENGTH: 1245
<212> TYPE: DNA
<213> ORGANISM: Weissella paramesenteroides

<400> SEQUENCE: 127

```
atggatcaaa cacaaaatac acaaaaaaag cacttttgga gttttttttgg aactgatgtc   60
agttatttct ttatttggca aattgtacaa ggtttcttgg tactttggtt aaaacaagaa  120
gccgatttga gtggtggcca agccggattt gttttttcat ttttggcatt tgcctcatta  180
ttttatcaac cagtatttgg tataaatttcg gataaattgg tctttaaaaa gacgttgcta  240
ttatcaataa caattgctgc tatcctcatt ggcccatttt ccaatggttt attcatacca  300
ttacttcatt ttagttcatt attagggggcg attattggtg gcttcgcatt agcttatgta  360
cttaatggtg gtgtggcagt tattgaatct tatgtggaac gcgcaagctt agccaatggc  420
tttgaatatg gtcatgcccg tatgggagga tcaattggtg gtgcactggc atcgttcgtg  480
gcaggattgg tgtttgttaa aaatccattt ttggttttct ggatttgctc acttgctggt  540
attattttga cttgcttggt aatctttggt gatcggatta attttgctaa tgcagatgcg  600
gcagaaggag caagttcagc accattaaat gccaaaacta ttttatctat ttttaaaatt  660
aaaaatttct ggatattaag tatttttcttt atgggaacat cagcaattta tgatgtgttt  720
```

```
gatcaacagt tcccggtatt ttatcaaaca ttcttcacga gtgctgcagc tggtaccgta       780
gcctacagcc gcctactaac gacacaaatt gcgttagaag ccctattaat gattccaatg       840
ccttggataa ttaataaaat tggtgctaag aatggattga ttgcttatgg tgtgcttact       900
tttctacgta ttacgttaag cgcaattgct cctaatttct ggttcttaac atttgttcgt       960
ctacttgcat catttgaaat gccactcttc ttagtctcaa caatgaagta tattgccgga      1020
gcatttgatt taagattata cgcaaccatt tatgctttgg cgttcaattt tgctaaacag      1080
atatcgttat ttattttctc tacagttgcc ggtgatcttt atgatagcgt gggattccat      1140
acgacatatt tcatccttagc tgcattagtc gctttggtaa caatcgttgc tgtatttatg      1200
ttgaagaaag aaaatccagc tcaggcgggt gaagtcgcgg agtga                      1245
```

<210> SEQ ID NO 128
<211> LENGTH: 414
<212> TYPE: PRT
<213> ORGANISM: Weissella paramesenteroides

<400> SEQUENCE: 128

```
Met Asp Gln Thr Gln Asn Thr Gln Lys Lys His Phe Trp Ser Phe Phe
1               5                   10                  15

Gly Thr Asp Val Ser Tyr Phe Phe Ile Trp Gln Ile Val Gln Gly Phe
            20                  25                  30

Leu Val Leu Trp Leu Lys Gln Glu Ala Asp Leu Ser Gly Gly Gln Ala
        35                  40                  45

Gly Phe Val Phe Ser Phe Leu Ala Phe Ala Ser Leu Phe Tyr Gln Pro
    50                  55                  60

Val Phe Gly Ile Ile Ser Asp Lys Leu Val Phe Lys Lys Thr Leu Leu
65                  70                  75                  80

Leu Ser Ile Thr Ile Ala Ala Ile Leu Ile Gly Pro Phe Phe Gln Trp
                85                  90                  95

Leu Phe Ile Pro Leu Leu His Phe Ser Ser Leu Leu Gly Ala Ile Ile
            100                 105                 110

Gly Gly Phe Ala Leu Ala Tyr Val Leu Asn Gly Gly Val Ala Val Ile
        115                 120                 125

Glu Ser Tyr Val Glu Arg Ala Ser Leu Ala Asn Gly Phe Glu Tyr Gly
    130                 135                 140

His Ala Arg Met Gly Gly Ser Ile Gly Gly Ala Leu Ala Ser Phe Val
145                 150                 155                 160

Ala Gly Leu Val Phe Val Lys Asn Pro Phe Leu Val Phe Trp Ile Cys
                165                 170                 175

Ser Leu Ala Gly Ile Ile Leu Thr Cys Leu Val Ile Phe Gly Asp Arg
            180                 185                 190

Ile Asn Phe Ala Asn Ala Asp Ala Ala Glu Gly Ala Ser Ser Ala Pro
        195                 200                 205

Leu Asn Ala Lys Thr Ile Leu Ser Ile Phe Lys Ile Lys Asn Phe Trp
    210                 215                 220

Ile Leu Ser Ile Phe Phe Met Gly Thr Ser Ala Ile Tyr Asp Val Phe
225                 230                 235                 240

Asp Gln Gln Phe Pro Val Phe Tyr Gln Thr Phe Phe Thr Ser Ala Ala
                245                 250                 255

Ala Gly Thr Val Ala Tyr Ser Arg Leu Leu Thr Thr Gln Ile Ala Leu
            260                 265                 270

Glu Ala Leu Leu Met Ile Pro Met Pro Trp Ile Ile Asn Lys Ile Gly
```

```
            275                 280                 285
Ala Lys Asn Gly Leu Ile Ala Tyr Gly Val Leu Thr Phe Leu Arg Ile
            290                 295                 300

Thr Leu Ser Ala Ile Ala Pro Asn Phe Trp Phe Leu Thr Phe Val Arg
305                 310                 315                 320

Leu Leu Ala Ser Phe Glu Met Pro Leu Phe Leu Val Ser Thr Met Lys
                325                 330                 335

Tyr Ile Ala Gly Ala Phe Asp Leu Arg Leu Tyr Ala Thr Ile Tyr Ala
            340                 345                 350

Leu Ala Phe Asn Phe Ala Lys Gln Ile Ser Leu Phe Ile Phe Ser Thr
            355                 360                 365

Val Ala Gly Asp Leu Tyr Asp Ser Val Gly Phe His Thr Thr Tyr Phe
        370                 375                 380

Ile Leu Ala Ala Leu Val Ala Leu Val Thr Ile Val Ala Val Phe Met
385                 390                 395                 400

Leu Lys Lys Glu Asn Pro Ala Gln Ala Gly Glu Val Ala Glu
                405                 410
```

<210> SEQ ID NO 129
<211> LENGTH: 1278
<212> TYPE: DNA
<213> ORGANISM: Mannheiimia succinicproducens

<400> SEQUENCE: 129

```
gtgcttatga caagccaaaa taagataaat gcggttcctt caaatcaaaa ttttatttg      60
aacaaccgta actattggat ctttagcggt tacttttcg tctatttctt tattatggcc    120
acatgttatc ccttcttagg catttggttg ggagatatta acgtctgtc gggagaagat    180
cgaggcacag tatttgctat gatgtctttc tttgcccttt gctttcagcc tgttttggc    240
tatgtgtcag ataaattggg attgaaaaaa catctcctct gggtattagg tataagcctt    300
ttaatctatg caccttttt tatctatatt tttgcaccgt tgcttaaagt gaatgtttgg    360
ttaggttcct tggttggcgg cgcctatatc ggctttgttt tccaggcggg agcaccggct    420
tcggaagctt atattgagcg ggtcagccgt cgtagtaaat ttgaatacgg gcgggtcaga    480
atgttcggaa tgttcggctg ggctattgc gcctccatag ccggagtcct ttacgctacc    540
aatcctaatc tggtctttg gcttggttct atagcctctc taatccttt acttttgata    600
gccctagcta agccggaaca accagcact gtgcaaatcg cggagaaatt aggggctaat    660
aaaaatccgg ttaacctcag acaggcattc gctctcctca aactaccgaa attctgggcg    720
cttctggctt atgtaatggg aattgcctgt gtttacgaca tcttcgacca acaattcggt    780
aattttttta atacctttt tgaatcgcac gaacaaggaa tcaaaatgtt tggttatgta    840
accactgccg gtgaattgtt aaacgccctg attatgttct tgttccccct tatcattaac    900
cgtatcggtg ctaaaaatgc tctgcttatt gcgggaacca ttatgagcgt gcggatcatc    960
ggctcttcct atgcaatcga ggcctggcat gtggtagttt taaaaactct gcatatgttt   1020
gaagttcctt tttacctagt aggactattt aaatacattg ctaatgtgtt tgaagtacat   1080
ttttctgcga ccattatct ggtagcctgc cactttgcca aacagatcgg caatatgctg   1140
gtatcccctt tggtaggcgc ttggtacgat acctatggtt ccaagatac ttacctaatt   1200
ctaggctgca ttgccgccgg attcaccctg ctttcggttt ttacacttac cggcaaatcc   1260
ttatcgtctc aatcataa                                                  1278
```

-continued

```
<210> SEQ ID NO 130
<211> LENGTH: 425
<212> TYPE: PRT
<213> ORGANISM: Mannheimia succiniciproducens

<400> SEQUENCE: 130

Met Leu Met Thr Ser Gln Asn Lys Ile Asn Ala Val Pro Ser Asn Gln
1               5                   10                  15

Asn Phe Tyr Leu Asn Asn Arg Asn Tyr Trp Ile Phe Ser Gly Tyr Phe
            20                  25                  30

Phe Val Tyr Phe Phe Ile Met Ala Thr Cys Tyr Pro Phe Leu Gly Ile
        35                  40                  45

Trp Leu Gly Asp Ile Asn Gly Leu Ser Gly Glu Asp Arg Gly Thr Val
    50                  55                  60

Phe Ala Met Met Ser Phe Phe Ala Leu Cys Phe Gln Pro Val Phe Gly
65                  70                  75                  80

Tyr Val Ser Asp Lys Leu Gly Leu Lys Lys His Leu Leu Trp Val Leu
                85                  90                  95

Gly Ile Ser Leu Leu Ile Tyr Ala Pro Phe Phe Ile Tyr Ile Phe Ala
            100                 105                 110

Pro Leu Leu Lys Val Asn Val Trp Leu Gly Ser Leu Val Gly Gly Ala
        115                 120                 125

Tyr Ile Gly Phe Val Phe Gln Ala Gly Ala Pro Ala Ser Glu Ala Tyr
    130                 135                 140

Ile Glu Arg Val Ser Arg Arg Ser Lys Phe Glu Tyr Gly Arg Val Arg
145                 150                 155                 160

Met Phe Gly Met Phe Gly Trp Ala Ile Cys Ala Ser Ile Ala Gly Val
                165                 170                 175

Leu Tyr Ala Thr Asn Pro Asn Leu Val Phe Trp Leu Gly Ser Ile Ala
            180                 185                 190

Ser Leu Ile Leu Leu Leu Ile Ala Leu Ala Lys Pro Glu Gln Thr
        195                 200                 205

Ser Thr Val Gln Ile Ala Glu Lys Leu Gly Ala Asn Lys Asn Pro Val
    210                 215                 220

Asn Leu Arg Gln Ala Phe Ala Leu Leu Lys Leu Pro Lys Phe Trp Ala
225                 230                 235                 240

Leu Leu Ala Tyr Val Met Gly Ile Ala Cys Val Tyr Asp Ile Phe Asp
                245                 250                 255

Gln Gln Phe Gly Asn Phe Phe Asn Thr Phe Glu Ser His Glu Gln
            260                 265                 270

Gly Ile Lys Met Phe Gly Tyr Val Thr Thr Ala Gly Glu Leu Leu Asn
        275                 280                 285

Ala Leu Ile Met Phe Phe Val Pro Leu Ile Ile Asn Arg Ile Gly Ala
    290                 295                 300

Lys Asn Ala Leu Leu Ile Ala Gly Thr Ile Met Ser Val Arg Ile Ile
305                 310                 315                 320

Gly Ser Ser Tyr Ala Ile Glu Ala Trp His Val Val Leu Lys Thr
                325                 330                 335

Leu His Met Phe Glu Val Pro Phe Tyr Leu Val Gly Leu Phe Lys Tyr
            340                 345                 350

Ile Ala Asn Val Phe Glu Val His Phe Ser Ala Thr Ile Tyr Leu Val
        355                 360                 365

Ala Cys His Phe Ala Lys Gln Ile Gly Asn Met Leu Val Ser Pro Leu
    370                 375                 380
```

Val Gly Ala Trp Tyr Asp Thr Tyr Gly Phe Gln Asp Thr Tyr Leu Ile
385                 390                 395                 400

Leu Gly Cys Ile Ala Ala Gly Phe Thr Leu Leu Ser Val Phe Thr Leu
            405                 410                 415

Thr Gly Lys Ser Leu Ser Ser Gln Ser
            420                 425

<210> SEQ ID NO 131
<211> LENGTH: 1257
<212> TYPE: DNA
<213> ORGANISM: Aggregaitbacter aphrophilus

<400> SEQUENCE: 131

```
atgagtaatc aaacttcatc taaatcgcaa tacttaacca atagtaatta ttggattttt      60
agtgcgtatt ttttgctttt tttcttcatt atggcgacct gtcatccttt tttagggatt     120
tggctcggtg atattcacgg attaaaaggg gagaaaattg gctacgtctt tcgttcatt      180
tctctttttg ctttactctt tcagccatt tttaggatttt tatctgataa attaggtatt     240
cgaaaacatc tgctttggct acttgcgata ttgcttcttt tctatgcacc attctttatt     300
tatgttttg ctccgttatt gaaaactaat ttatggttgg gggttattgc cggtggtgca     360
tatatgggat ttgtgttcca agcaggcgca cctgcgtcag aagcctacat tgagcgtatt     420
agccgtttag atggatttga atatggcaga acacggctat tcgggatgtt aggttgggca     480
atctgtgcct ctattgcagg caatttatat agttctcaac gaatgcggt tttctggctt      540
ggctccgcca ccgccgttgt gttattggtt ctgatttcc ttgcgaaaac agatagcagt     600
aatacggctc aagtcgtgga taaattaggt gtaaataaaa gtccaattac actaaaacaa     660
gccttaaagc tcttttctct acctcgtttc tgggcactat taacctatgt tgttggagtg     720
gcttgtgttt atgacatttt tgaccagcaa ttcggtaatt tcttcaatac gtttttttgaa     780
tctaaagaac aaggaatgaa attctttggt tatgtaacaa cgggaggaga gctattaaat     840
gcaacaatta tgtttttcgt gcctttattg attaatcgta ttggggcgaa gaatgcgtta     900
ttgattgcag atcaattat gagtattcgc attatgggct catcttttgc aacagaagca     960
tggcacgtga ttgtattaaa aacattacat atgtttgaag tgccattcta tttggttgga    1020
gtatttaagt atattgctga tgtttttgaa gtccgttttt ctgcaaccat ttacttagtc    1080
tcttgccact tttcaaagca gattggtaat atgatttat cgcctgccgt agggacttta    1140
tatgacatgt atggttttca atctacctat tttatcttag gttgtattgc tcttacattt    1200
acatcagttt ctgtatttac tttagtaaat accaagaaat tagtgaacaa cgcttaa      1257
```

<210> SEQ ID NO 132
<211> LENGTH: 417
<212> TYPE: PRT
<213> ORGANISM: Aggregaitbacter aphrophilus

<400> SEQUENCE: 132

Met Ser Asn Gln Thr Ser Ser Lys Ser Gln Tyr Leu Thr Asn Ser Asn
1               5                   10                  15

Tyr Trp Ile Phe Ser Ala Tyr Phe Phe Ala Phe Phe Ile Met Ala
            20                  25                  30

Thr Cys His Pro Phe Leu Gly Ile Trp Leu Gly Asp Ile His Gly Leu
            35                  40                  45

Lys Gly Glu Lys Ile Gly Tyr Val Phe Ser Phe Ile Ser Leu Phe Ala
        50                  55                  60

Leu Leu Phe Gln Pro Ile Gly Phe Leu Ser Asp Lys Leu Gly Ile
 65                  70                  75                  80

Arg Lys His Leu Leu Trp Leu Leu Ala Ile Leu Leu Leu Phe Tyr Ala
             85                  90                  95

Pro Phe Phe Ile Tyr Val Phe Ala Pro Leu Leu Lys Thr Asn Leu Trp
            100                 105                 110

Leu Gly Val Ile Ala Gly Gly Ala Tyr Met Gly Phe Val Phe Gln Ala
            115                 120                 125

Gly Ala Pro Ala Ser Glu Ala Tyr Ile Glu Arg Ile Ser Arg Leu Asp
130                 135                 140

Gly Phe Glu Tyr Gly Arg Thr Arg Leu Phe Gly Met Leu Gly Trp Ala
145                 150                 155                 160

Ile Cys Ala Ser Ile Ala Gly Asn Leu Tyr Ser Ser Gln Pro Asn Ala
                165                 170                 175

Val Phe Trp Leu Gly Ser Ala Thr Ala Val Val Leu Val Leu Ile
                180                 185                 190

Phe Leu Ala Lys Thr Asp Ser Ser Asn Thr Ala Gln Val Val Asp Lys
                195                 200                 205

Leu Gly Val Asn Lys Ser Pro Ile Thr Leu Lys Gln Ala Leu Lys Leu
    210                 215                 220

Phe Ser Leu Pro Arg Phe Trp Ala Leu Leu Thr Tyr Val Val Gly Val
225                 230                 235                 240

Ala Cys Val Tyr Asp Ile Phe Asp Gln Gln Phe Gly Asn Phe Phe Asn
                245                 250                 255

Thr Phe Phe Glu Ser Lys Glu Gln Gly Met Lys Phe Phe Gly Tyr Val
                260                 265                 270

Thr Thr Gly Gly Glu Leu Leu Asn Ala Thr Ile Met Phe Phe Val Pro
        275                 280                 285

Leu Leu Ile Asn Arg Ile Gly Ala Lys Asn Ala Leu Leu Ile Ala Gly
        290                 295                 300

Ser Ile Met Ser Ile Arg Ile Met Gly Ser Ser Phe Ala Thr Glu Ala
305                 310                 315                 320

Trp His Val Ile Val Leu Lys Thr Leu His Met Phe Glu Val Pro Phe
                325                 330                 335

Tyr Leu Val Gly Val Phe Lys Tyr Ile Ala Asp Val Phe Glu Val Arg
                340                 345                 350

Phe Ser Ala Thr Ile Tyr Leu Val Ser Cys His Phe Ser Lys Gln Ile
            355                 360                 365

Gly Asn Met Ile Leu Ser Pro Ala Val Gly Thr Leu Tyr Asp Met Tyr
370                 375                 380

Gly Phe Gln Ser Thr Tyr Phe Ile Gly Cys Ile Ala Leu Thr Phe Thr
385                 390                 395                 400

Ser Val Ser Val Phe Thr Leu Val Asn Thr Lys Lys Leu Val Asn Asn
                405                 410                 415

Ala

<210> SEQ ID NO 133
<211> LENGTH: 9317
<212> TYPE: DNA
<213> ORGANISM: Artificial Sequence
<220> FEATURE:
<223> OTHER INFORMATION: Plasmid

<400> SEQUENCE: 133
tcgaggaatt cgcaggaccg tgatacacgg gacaggtcac tgaatgacga caatgtcctg      60

-continued

| | |
|---|---|
| gaaatcagcg aaccgcgcat ctgaagtaca tttgagcgac tgtaccagaa catgaatgag | 120 |
| gcgtttggat taggcgatta ttagcagggc taagcatttt actattatta ttttccggtt | 180 |
| gagggatata gagctatcga caacaaccgg aaaaagttta cgtctatatt gctgaaggta | 240 |
| caggcgtttc cataactatt tgctcgcgtt ttttactcaa gaagaaaatg ccaaatagca | 300 |
| acatcaggca gacaataccc gaaattgcga agaaaactgt ctggtagcct gcgtggtcaa | 360 |
| agagtatccc agtcggcgtt gaaagcagca caatcccaag cgaactggca atttgaaaac | 420 |
| caatcagaaa gatcgtcgac gacaggcgct tatcaaagtt tgccacgctg tatttgaaga | 480 |
| cggatatgac acaaagtgga acctcaatgg catgtaacaa cttcactaat gaaataatcc | 540 |
| aggggttaac gaacagcgcg caggaaagga tacgcaacgc cataatcaca actccgataa | 600 |
| gtaatgcatt ttttggccct acccgattca caaagaaagg aataatcgcc atgcacagcg | 660 |
| cttcgagtac cacctggaat gagttgagat aaccatacag gcgcgttcct acatcgtgtg | 720 |
| attcgaataa acctgaataa aagacaggaa aaagttgttg atcaaaaatg ttatagaaag | 780 |
| accacgtccc cacaataaat atgacgaaaa cccagaagtt tcgatccttg aaaactgcga | 840 |
| taaaatcctc ttttttttacc cctcccgcat ctgccgctac gcactggtga tccttatctt | 900 |
| taaaacgcat gttgatcatc ataaatacag cgccaaatag cgagaccaac cagaagttga | 960 |
| tatgggact gatactaaaa aatatgccgg caaagaacgc gccaatagca tagccaaaag | 1020 |
| atccccaggc gcgcgctgtt ccatattcga aatgaaaatt tcgcgccatt ttttcggtga | 1080 |
| agctatcaag caaaccgcat cccgccagat accccaagcc aaaaaatagc gcccccagaa | 1140 |
| ttagacctac agaaaaattg ctttgcagta acggttcata acgtaaatc ataaacggtc | 1200 |
| cggtcaagac caggatgaaa ctcatacacc agatgagcgg tttcttcaga ccgagtttat | 1260 |
| cctgaacgat gccgtagaac atcataaata gaatgctggt aaactggttg accgaataaa | 1320 |
| gtgtacctaa ttccgtccct gtcaacccta gatgtccttt cagccaaata gcgtataacg | 1380 |
| accaccacag cgaccaggaa ataaaaaaga gaaatgagta actggatgca aaacgatagt | 1440 |
| acgcatttct gaatgaaata ttcagtgcca taattacctg cctgtcgtta aaaaattcac | 1500 |
| gtcctattta gagataagag cgacttcgcc gtttacttct cactattcca gttcttgtcg | 1560 |
| acatggcagc gctgtcattg ccccttttcgc cgttactgca agcgctccgc aacgttgagc | 1620 |
| gagatcgata attcgtcgca tttctctctc atctgtagat aatcccgtag aggacagacc | 1680 |
| tgtgagtaac ccggcaacga acgcatctcc cgccccgtg ctatcgacac aattcacaga | 1740 |
| cattccagca aaatggtgaa cttgtcctcg ataacagacc accacccctt ctgcacccttt | 1800 |
| agtcaccaac agcatggcga tctcatactc ttttgccagg gcgcatatat cctgatcgtt | 1860 |
| ctgtgttttt ccactgataa gtcgccattc ttcttccgag agcttgacga catccgccag | 1920 |
| ttgtagcgcc tgccgcaaac acaagcggag caaatgctcg tcttgccata gatcttcacg | 1980 |
| aatattagga tcgaagctga caaaacctcc ggcatgccgg atcgccgtca tcgcagtaaa | 2040 |
| tgcgctggta cgcgaaggct cggcagacaa cgcaattgaa cagagatgta accattcgcc | 2100 |
| atgtcgccag cagggcaagt ctgtcgtctc taaaaaaaga tcggcactgg ggcggaccat | 2160 |
| aaacgtaaat gaacgttccc cttgatcgtt cagatcgaca agcaccgtgg atgtccggtg | 2220 |
| ccattcatct tgcttcagat acgtgatatc gactccctca gttagcagcg ttctttgcat | 2280 |
| taacgcacca aaaggatcat cccccacccg acctataaac ccacttgttc cgcctaatct | 2340 |
| ggcgattccc accgcaacgt tagctggcgc gccgccagga caaggcagta ggcgccggtc | 2400 |

```
tgattctggc aagagatcta cgaccgcatc ccctaaaacc catactttgg ctgacatttt      2460
tttcccttaa attcatctga gttacgcata gtgataaacc tcttttcgc aaaatcgtca       2520 tggatttact aaaacatgca tattcgatca caaaacgtca tagttaacgt taacatttgt     2580
gatattcatc gcatttatga agtaaggga ctttatttt ataaaagtta acgttaacaa       2640
ttcaccaaat ttgcttaacc aggatgatta aaatgacgca atctcgattg catgcggcgc    2700
aaaacgccct agcaaaactt catgagcacc ggggtaacac tttctatccc cattttcacc    2760
tcgcgcctcc tgccgggtgg atgaacgatc caaacggcct gatctggttt aacgatcgtt    2820
atcacgcgtt ttatcaacat catccgatga gcgaacactg ggggccaatg cactggggac    2880
atgccaccag cgacgatatg atccactggc agcatgagcc tattgcgcta gcgccaggag   2940
acgataatga caaagacggg tgttttcag gtagtgctgt cgatgacaat ggtgtcctct    3000
cacttatcta caccggacac gtctggctcg atggtgcagg taatgacgat gcaattcgcg   3060
aagtacaatg tctggctacc agtcgggatg gtattcattt cgagaaacag ggtgtgatcc  3120
tcactccacc agaaggaatc atgcacttcc gcgatcctaa agtgtggcgt gaagccgaca   3180
catggtggat ggtagtcggg gcgaaagatc caggcaacac ggggcagatc ctgctttatc   3240
gcggcagttc gttgcgtgaa tggaccttcg atcgcgtact ggcccacgct gatgcgggtg   3300
aaagctatat gtgggaatgt ccggactttt tcagccttgg cgatcagcat tatctgatgt   3360
tttccccgca gggaatgaat gccgagggat acagttaccg aaatcgcttt caaagtggcg   3420
taatacccgg aatgtggtcg ccaggacgac ttttttgcaca atccgggcat tttactgaac  3480
ttgataacgg gcatgacttt tatgcaccac aaagcttttt agcgaaggat ggtcggcgta   3540
ttgttatcgg ctggatggat atgtgggaat cgccaatgcc ctcaaaacgt gaaggatggg   3600
caggctgcat gacgctggcg cgcgagctat cagagagcaa tggcaaactt ctacaacgcc   3660
cggtacacga agctgagtcg ttacgccagc agcatcaatc tgtctctccc cgcacaatca   3720
gcaataaata tgttttgcag gaaaacgcgc aagcagttga gattcagttg cagtgggcgc   3780
tgaagaacag tgatgccgaa cattacggat tacagctcgg cactggaatg cggctgtata   3840
ttgataacca atctgagcga cttgttttgt ggcggtatta cccacacgag aatttagacg   3900
gctaccgtag tattcccctc ccgcagcgtg acacgctcgc cctaaggata tttatcgata   3960
catcatccgt ggaagtattt attaacgacg gggaagcggt gatgagtagt cgaatctatc   4020
cgcagccaga agaacgggaa ctgtcgcttt atgcctccca cggagtggct gtgctgcaac  4080
atggagcact ctggctactg ggttaacata atatcaggtg gaacaacgga tcaacagcgg   4140
gcaagggatc cacgaagctt cccatggtga cgtcaccggt aaaccagcaa tagacataag   4200
cggctattta acgaccctgc cctgaaccga cgaccgggtc gaatttgctt tcgaatttct    4260
gccattcatc cgcttattat acttattcag gcgtagcacc aggcgtttaa gggcaccaat    4320
aactgcctta aaaaattac gccccgccct gccactcatc gcagtactgt tgtaattcat   4380
taagcattct gccgacatgg aagccatcac agacggcatg atgaacctga atcgccagcg   4440
gcatcagcac cttgtcgcct tgcgtataat atttgcccat ggtgaaaacg ggggcgaaga   4500
agttgtccat attggccacg tttaaatcaa aactggtgaa actcacccag ggattggctg    4560
agacgaaaaa catattctca ataaaccctt tagggaaata ggccaggttt tcaccgtaac    4620
acgccacatc ttgcgaatat atgtgtagaa actgccggaa atcgtcgtgg tattcactcc   4680
agagcgatga aaacgtttca gtttgctcat ggaaaacggt gtaacaaggg tgaacactat   4740
cccatatcac cagctcaccg tctttcattg ccatacggaa ttccggatga gcattcatca   4800
```

```
ggcgggcaag aatgtgaata aaggccggat aaaacttgtg cttattttc tttacggtct    4860 ttaaaaaggc cgtaatatcc agctgaacgg tctggttata ggtacattga gcaactgact    4920
gaaatgcctc aaaatgttct ttacgatgcc attgggatat atcaacggtg gtatatccag    4980
tgattttttt ctccatttta gcttccttag ctcctgaaaa tctcgataac tcaaaaaata    5040
cgcccggtag tgatcttatt tcattatggt gaaagttgga acctcttacg tgccgatcaa    5100
cgtctcattt tcgccaaaag ttgggccagg gcttcccggt atcaacaggg acaccaggat    5160
ttatttattc tgcgaagtga tcttccgtca caggtattta ttcggcgcaa agggcctcgt    5220
gatacgccta ttttatagg ttaatgtcat gataataatg gtttcttaga cgtcaggtgg    5280
cacttttcgg ggaaatgtgc gcgcccgcgt tcctgctggc gctgggcctg tttctggcgc    5340
tggacttccc gctgttccgt cagcagcttt tcgcccacgg ccttgatgat cgcggcggcc    5400
ttggcctgca tatcccgatt caacggcccc agggcgtcca gaacgggctt caggcgctcc    5460
cgaaggtctc gggccgtctc ttgggcttga tcggccttct tgcgcatctc acgcgctcct    5520
gcggcggcct gtagggcagg ctcatacccc tgccgaaccg cttttgtcag ccggtcggcc    5580
acggcttccg cgtctcaac gcgctttgag attcccagct tttcggccaa tccctgcggt    5640
gcataggcgc gtggctcgac cgcttgcggg ctgatggtga cgtggcccac tggtggccgc    5700
tccagggcct cgtagaacgc ctgaatgcgc gtgtgacgtg ccttgctgcc ctcgatgccc    5760
cgttgcagcc ctagatcggc cacagcggcc gcaaacgtgg tctggtcgcg ggtcatctgc    5820
gctttgttgc cgatgaactc cttggccgac agcctgccgt cctgcgtcag cggcaccacg    5880
aacgcggtca tgtgcgggct ggtttcgtca cggtggatgc tggccgtcac gatgcgatcc    5940
gccccgtact tgtccgccag ccacttgtgc gccttctcga agaacgccgc ctgctgttct    6000
tggctggccg acttccacca ttccgggctg gccgtcatga cgtactcgac cgccaacaca    6060
gcgtccttgc gccgcttctc tggcagcaac tcgcgcagtc ggcccatcgc ttcatcggtg    6120
ctgctggccg cccagtgctc gttctctggc gtcctgctgg cgtcagcgtt gggcgtctcg    6180
cgctcgcggt aggcgtgctt gagactggcc gccacgttgc ccattttcgc cagcttcttg    6240
catcgcatga tcgcgtatgc cgccatgcct gcccctccct tttggtgtcc aaccggctcg    6300 acggggcag cgcaaggcgg tgcctccggc gggccactca atgcttgagt atactcacta    6360
gactttgctt cgcaaagtcg tgaccgccta cggcggctgc ggcgccctac gggcttgctc    6420
tccgggcttc gccctgcgcg gtcgctgcgc tcccttgcca gcccgtggat atgtggacga    6480
tggccgcgag cggccaccgg ctggctcgct tcgctcggcc cgtggacaac cctgctggac    6540
aagctgatgg acaggctgcg cctgcccacg agcttgacca cagggattgc ccaccggcta    6600
cccagccttc gaccacatac ccaccggctc caactgcgcg gcctgcggcc ttgccccatc    6660
aattttttta attttctctg gggaaaagcc tccggcctgc ggcctgcgcg cttcgcttgc    6720
cggttggaca ccaagtggaa ggcgggtcaa ggctcgcgca gcgaccgcgc agcggcttgg    6780
ccttgacgcg cctggaacga cccaagccta tgcgagtggg ggcagtcgaa ggcgaagccc    6840
gcccgcctgc cccccgagac ctgcagggg gggggggcgc tgaggtctgc ctcgtgaaga    6900
aggtgttgct gactcatacc aggcctgaat cgccccatca tccagccaga agtgaggga    6960 gccacggttg atgagagctt tgttgtaggt ggaccagttg gtgattttga acttttgctt    7020
tgccacggaa cggtctgcgt tgtcgggaag atgcgtgatc tgatccttca actcagcaaa    7080
agttcgattt attcaacaaa gccgccgtcc cgtcaagtca gcgtaatgct ctgccagtgt    7140
```

```
tacaaccaat taaccaattc tgattagaaa aactcatcga gcatcaaatg aaactgcaat    7200
ttattcatat caggattatc aataccatat ttttgaaaaa gccgtttctg taatgaagga    7260
gaaaactcac cgaggcagtt ccataggatg gcaagatcct ggtatcggtc tgcgattccg    7320
actcgtccaa catcaataca acctattaat ttcccctcgt caaaaataag gttatcaagt    7380
gagaaatcac catgagtgac gactgaatcc ggtgagaatg gcaaaagctt atgcatttct    7440
ttccagactt gttcaacagg ccagccatta cgctcgtcat caaaatcact cgcatcaacc    7500
aaaccgttat tcattcgtga ttgcgcctga gcgagacgaa atacgcgatc gctgttaaaa    7560
ggacaattac aaacaggaat cgaatgcaac cggcgcagga acactgccag cgcatcaaca    7620
atattttcac ctgaatcagg atattcttct aatacctgga atgctgtttt cccggggatc    7680
gcagtggtga gtaaccatgc atcatcagga gtacggataa aatgcttgat ggtcggaaga    7740
ggcataaatt ccgtcagcca gtttagtctg accatctcat ctgtaacatc attggcaacg    7800
ctacctttgc catgtttcag aaacaactct ggcgcatcgg gcttcccata caatcgatag    7860
attgtcgcac ctgattgccc gacattatcg cgagcccatt tatacccata taaatcagca    7920
tccatgttgg aatttaatcg cggcctcgag caagacgttt ccgttgaat atggctcata    7980 acacccttg tattactgtt tatgtaagca gacagttttta ttgttcatga tgatatattt    8040
ttatcttgtg caatgtaaca tcagagattt tgagacacaa cgtggctttc cccccccccc    8100
ctgcaggtcc cgagcctcac ggcggcgagt gcggggttc caaggggca cgccaccttt    8160 gggcaaggcc gaaggccgcg cagtcgatca acaagccccg gaggggccac ttttttgccgg    8220 aggggagcgc gcgccgaagg cgtggggggaa ccccgcaggg gtgcccttct ttgggcacca    8280
aagaactaga tagggcgaa aatgcgaaag acttaaaaat caacaactta aaaaaggggg    8340
gtacgcaaca gctcattgcg gcaccccccg caatagctca ttgcgtaggt taagaaaat    8400 ctgtaattga ctgccacttt tacgcaacgc ataattgttg tcgcgctgcc gaaaagttgc    8460
agctgattgc gcatggtgcc gcaaccgtgc ggcaccctac cgcatggaga taagcatggc    8520
cacgcagtcc agagaaatcg gcattcaagc caagaacaag cccggtcact gggtgcaaac    8580
ggaacgcaaa gcgcatgagg cgtgggccgg gcttattgcg aggaaaccca cggcggcaat    8640
gctgctgcat cacctcgtgg cgcagatggg ccaccagaac gccgtggtgg tcagccagaa    8700
gacactttcc aagctcatcg gacgttcttt gcggacggtc caatacgcag tcaaggactt    8760
ggtggccgag cgctggatct ccgtcgtgaa gctcaacggc cccggcaccg tgtcggccta    8820
cgtggtcaat gaccgcgtgg cgtggggcca gccccgcgac cagttgcgcc tgtcggtgtt    8880
cagtgccgcc gtggtggttg atcacgacga ccaggacgaa tcgctgttgg ggcatggcga    8940
cctgcgccgc atcccgaccc tgtatccggg cgagcagcaa ctaccgaccg gcccggcga    9000 ggagccgccc agccagcccg gcattccggg catggaacca gacctgccag ccttgaccga    9060
aacggaggaa tgggaacggc gcgggcagca gcgcctgccg atgcccgatg agccgtgttt    9120
tctggacgat ggcgagccgt tggagccgcc gacacgggtc acgctgccgc gccggtagca    9180
cttgggttgc gcagcaaccc gtaagtgcgc tgttccagac tatcggctgt agccgcctcg    9240
ccgccctata ccttgtctgc ctccccgcgt tgcgtcgcgg tgcatggagc cgggccacct    9300
cgacctgaat ggaagcc                                                  9317
```

<210> SEQ ID NO 134
<211> LENGTH: 60
<212> TYPE: DNA
<213> ORGANISM: Artificial Sequence

```
<220> FEATURE:
<223> OTHER INFORMATION: Primer

<400> SEQUENCE: 134
accattgtgg cgatgggttg cttctacagc ctgaacgaga ggatcccttg cccgctgttg    60

<210> SEQ ID NO 135
<211> LENGTH: 60
<212> TYPE: DNA
<213> ORGANISM: Artificial Sequence
<220> FEATURE:
<223> OTHER INFORMATION: Primer

<400> SEQUENCE: 135
ttacgggctt ctatctcttc cacaatgcgg acatacatct gaattcgcag gaccgtgata    60

<210> SEQ ID NO 136
<211> LENGTH: 60
<212> TYPE: DNA
<213> ORGANISM: Artificial Sequence
<220> FEATURE:
<223> OTHER INFORMATION: Primer

<400> SEQUENCE: 136
attaggtaca ctttattcgg tcaaccagtt taccagcatt cgtcttgagc gattgtgtag    60

<210> SEQ ID NO 137
<211> LENGTH: 60
<212> TYPE: DNA
<213> ORGANISM: Artificial Sequence
<220> FEATURE:
<223> OTHER INFORMATION: Primer

<400> SEQUENCE: 137
tcggcgttga aagcagcaca atcccaagcg aactggcaat tgaatatcct ccttagttcc    60

<210> SEQ ID NO 138
<211> LENGTH: 21
<212> TYPE: DNA
<213> ORGANISM: Artificial Sequence
<220> FEATURE:
<223> OTHER INFORMATION: Primer

<400> SEQUENCE: 138
atggcactga atattccatt c                                              21

<210> SEQ ID NO 139
<211> LENGTH: 20
<212> TYPE: DNA
<213> ORGANISM: Artificial Sequence
<220> FEATURE:
<223> OTHER INFORMATION: Primer

<400> SEQUENCE: 139
ctatattgct gaaggtacag                                                20

<210> SEQ ID NO 140
<211> LENGTH: 447
<212> TYPE: DNA
<213> ORGANISM: Artificial Sequence
<220> FEATURE:
<223> OTHER INFORMATION: Promoter/MCS/terminator insert

<400> SEQUENCE: 140
aggaattccc taggcgatct gtgctgtttg ccacggtatg cagcaccagc gcgagattat    60
```

```
gggctcgcac gctcgactgt cggacggggg cactggaacg agaagtcagg cgagccgtca    120
cgcccttgac gatgccacat cctgagcaaa taattcaacc actaaacaaa tcaaccgcgt    180
ttcccggagg taaccaagct tgcccggatc cgcatgcgcg gccgcgtcga ctctagttta    240 aaccccccggg tgatcgatag ctcttaatta agttgtttgc caatgtaatg ccgctgcacc    300
caggcatcaa ataaaacgaa aggctcagtc gaaagactgg gcctttcgtt ttatctgttg    360
tttgtcggtg aacgctctct actagagtca cactggctca ccttcgggtg ggcctttctg    420
cgtttataca gctgtcggta ccgccag                                        447
```

<210> SEQ ID NO 141
<211> LENGTH: 1260
<212> TYPE: DNA
<213> ORGANISM: Artificial Sequence
<220> FEATURE:
<223> OTHER INFORMATION: codon optimized CDS from Citrobacter sp

<400> SEQUENCE: 141

```
atgaaaatca atatgccgtt ctccaatgac aaataccgtt atagttcggg ctacctgctg     60
ttcttcttcg ctgcgtggtc cctgtggtgg agtttctacg caatctggct gaaaaacaaa    120
ctgggcctgt ccggcaccga actgggcatg ctgtatgctg ttaatcagtt tttctccatg    180
ctgttcatgc tggtctacgg ctttctgcaa gataaactgg gcacccgtaa acatctgatt    240
tggctgatgg gcattgtgat cacgctgtca ggtccgttcc tgatctatgt ttacgaaccg    300
ctgctgacct cgaactttaa actgggcatg gcactgggtg ctattttctt tggtctgggt    360
tatctggcag gttgcggcct ggtggaatct tttgtggaaa agtttctcg taaattcaac    420 ttcgaatttg gcaccgcacg tctgtggggc tctctgggtt acgcggccgg tacgttcgtt    480
ggcggtattt tctttagcat caacccgcac attaattttt ggtgtgtctc tgtgatgggc    540
gtcctgttcc tgctgatcaa cgtgctgttt aaaaccaata gtccggcacc gagctctgtg    600
aaaacccgtt ccccggaacc ggatgctctg acgcgcaaag acttcctgac catctttaaa    660
gatacgcagt tctggttttt cgttattttt gtggttggca cgtggagttt ctattccatc    720
tacgaccagc aaatgttccc ggtgtttat gcgagcctgt tgatgaccc ggaactggcc    780 ccgcgtgttt atggttacct gaactctgtt caagtcttca tggaagcggt tggcatggcc    840
ctggtcccgt ttctgattaa tcgtatcgg ccgaaaagcg cactgctgct gggcggcacc    900
atcatggcat gccgcattct gggttcagct ctgtttacgg atatctacat catctcgctg    960
atcaaaatgc tgcatgcgct ggaagtcccg ctgttcgtca tttcagtgtt caaattttcg   1020
gtggccaact ttgacaaacg cctgagttcc accatttacc tgatcggctt taatatcgcg   1080
tcatcgattg gtattatcgt gctgagtctg ccggttggca aactgttcga taagttggt   1140 tatcaggaaa ttttctgat catggccagc atcgtcatta tcaccctgat tttcggctac   1200
tttagcctgt ctaaaaaaca tcaccagcaa aaatgggta acgaactggt gacggaataa   1260
```

<210> SEQ ID NO 142
<211> LENGTH: 1314
<212> TYPE: DNA
<213> ORGANISM: Artificial Seqeunce
<220> FEATURE:
<223> OTHER INFORMATION: codon optimized CDS from Enterococcus faecium

<400> SEQUENCE: 142

```
atgaaaggtg ataccaacat tagcctggaa gacaaaaata tgagcaaagt caacgtgttc     60
aaaaaccaat cctatctgca atcgtccgcc accctgctgc tgtttttcgc atcatggggc    120
```

```
gtttggtggt cgttttttcca actgtggctg accagcgaat ctaatggcct gggtctgagt      180
ggctccgctg tcggtacggt gttttcagcg aactcgctgg tcaccctgat cctgatgttc      240
atttatggta cgctgcagga taaactgtac atcaaacgta atctgctgat ttttgcttct      300
gttctggcga cccctggtcgg cccgttttc atctggattt atggtccgct gctggacaac      360
aattttaacc tgggcattat catgggtgct ctgttcctga gcgccggcta cctggcatct      420
gtgggtgttt ttgaagcggt tagcgaacgt ttctctcgcc tgtttggctt cgaatatggt      480
caggcacgtg cttggggcag ctttggttac gcgctggttg ccctgctggc aggctttctg      540
ttcgtcaaaa atccgcatct gaacttctgg gccggcagct ttttcggttc cctgctgctg      600
ctgaatctgc tgttttggaa cccgaaagtg aacgcgaag ctaaccagaa tttcaaccag       660
gaacaagcgg aatcaaattc gatcccgagc ctgaaagaaa tgtttgatct gatgaaactg      720
ccgcaactgt ggaccattat cattttttatt gtcttcacct ggacgtttta cggtgttc       780 gaccagcaaa tgtttccggg cttctacacc ggtctgttta gcacgtctgc aaatggcgaa      840
aaaatctatg gcaccctgaa cgccattcag gttttctgcg aagcactgat gatgggcatc      900
gtgccgatca ttatgcgtaa actgggcgtt cgcaatacgc tgctgctggg gtgaccatc       960 atgtgcgttc gtattggcct gtgtggtttt gccagcaccc cgctgagtgt ctcctgtatt     1020
aaaatgctgc atgcactgga agtgccgctg tttacgctgc cgatgtttcg ctatttcacc     1080
ctgcacttcg atacgaaact gagtgccacc ctgtacatga tcggctttca gattgcggcc     1140
cagatcggtc aagttattct gtccaccccg ctgggcatcc tgcgcgataa cgtcggttat     1200
caaccgacgt ttaaaatcat tagtctgatt gtgctgctgg ctggtatcta cgcgttttc      1260 attctgaaac aggatgaccg tgatgtgcaa ggcgacccgt ttattcgcgg ttaa            1314
```

<210> SEQ ID NO 143
<211> LENGTH: 1299
<212> TYPE: DNA
<213> ORGANISM: Artificial Sequence
<220> FEATURE:
<223> OTHER INFORMATION: codon optimized CDS from Corynebacterium glucuronolyticum

<400> SEQUENCE: 143

```
atgtcaaaat tcatgcaaca actgaaaaat acggcttacc aacaatcatc ggcacaactg       60
ctgctgttct ttatgtcgtg gggcatttgg tggagctttt tccaactgtg gctgagctct      120
gaaacccgtg gcctgggttt taatggttcc gaaattggca cgatctatag cgtgaactct      180
gcagtgaccc tggttctgat gctggtttac ggcacggctc aggataaact gcgcacccgt      240
cgcaatctgg ttattggtat cgcggtcctg atgagcctga cgggcccgtt tttcatgtgg      300
gtgtattggc cgctgctgca aagtgaatcc ctgtacgtcc tgggtgtggg tctgggtgcg      360 attttttatcg gcaccgcatt cgtgggcagt tgcccgctgt tgaagcgct ggccgaacgt      420 atgtcccgca acataacttt gaatatggt caggcacgtg cttggggtag tttcggctac      480
gcaattgtgg ctctgctggc gggctttaac ttcaccatta atccggcaat caacttttgg      540
atggcgagcg ccttcggtgt tctgctgctg ctgattctgg tgttttggaa agaaccggtt      600
gcaccgcgca atgaaatcgc tgaagaagaa gtggaaaaca ccacgccgtc agtgaaagaa      660
atggtttcgg tcctgaaagt gccggccctg tgggtggtta cgtgctggt gttttttcacc     720 tggacgtttt atacggtttt cgatcagcaa atgtttccgc agttctacac cagcctgttt     780
tcagactcgg cgaccggtga acgtacgtat ggcgtcctga acagcgtcca gtgtttgtt      840
```

```
gaagccctga tgatgggcat tgttccgatc tacatgcgta aagtcggtgt gaaaaacacc    900
ctgatgacgg gctttgccgt gatggcactg cgcattctgg gttgcgctgt gttcgcggat    960
ccggttacca tcagctttgt caaaatgttc catgcgctgg aagtgccgct gtgtattctg   1020
ccgatctttc gctatttcac cctgcacttt ccgacgaaaa tttcagcgac cctgtacatg   1080
gttggtttcc agatcgcctc gcaagtcggc aatgtcgtga tgagtccgat tctgggttcc   1140
ctgcgtgatc gcctgggctt tcagccgacc ttctatgtga ttagcggtat cgttctggtc   1200
tctgccatct ttgcatggct ggctctgaaa ggtgacaaag aacaggttga aggcgatccg   1260
ttctatcgtg actctgaact gaaagaaatt caccaataa                          1299

<210> SEQ ID NO 144
<211> LENGTH: 1326
<212> TYPE: DNA
<213> ORGANISM: Artificial Sequence
<220> FEATURE:
<223> OTHER INFORMATION: codon optimized CDS from Bifidobacterium
      animalis

<400> SEQUENCE: 144
atggcgacca cgaccaaagt ctggcgtaat ccgagttatc tgcaatcctc cacgggcatt     60
tttctgttct ctgttcctg gggcatctgg tggagctttt ccagcgttg gctgaactcc    120 atgggcctga tggtgctga agttggcacc atttatagta tcaactccct ggcgacgctg    180
attctgatgt ttggctacgg tctgatccag gataatctgg gcctgaaacg tcgcctggtg    240
ctggttatta gcgcaatcgc agccctggtg gtccgtttg tgcaattcgt ttatgcaccg    300
ctgatgcgca ccaacatgat ggcggcggcg ctggttggca gcgtggttct gtctgcaggc    360
tttatggctg gttgcagcct gattgaagcc gtcacggaac gttattctcg tgctttaac    420 ttcgaatacg gtcagagtcg cgcgtggggc tccttcggtt acgctatcgt cgcgctggtt    480
gcgggctttg ttttcaacat caacccgatg atcaacttct ggctgggttc tgccttcggc    540
gtgggtatgc tgattgttta tctgacctgg tatccggcgg aacaacgtga agcactgaaa    600
gaagccgcag atccgaacgc tgcgccgacc aatccgacga ttaaagacat gctgggcgtg    660
ctgaaaatgc cgaccctgtg ggttctgatc gtctttatgc tgctgaccaa cacgttttat    720
accgttttcg atcagcaaat gttccgacg tattacgcga gtctgttccc gaacgaagcg    780
accggcaatg ccgtttacgg tacgctgaac agcgtccagg tgttttgtga atctgctatg    840
atgggtgtcg tgccgattat catgcgtaaa gttggcgtcc gcaatgcact gctgctgggt    900
agcaccgtga tgtttctgcg tattggcctg tgcggtatct tccatgatcc ggtcagcatt    960
tctatcgtga aaatgtttca cgctattgaa gtcccgctgt tctgtctgcc ggcgtttcgc   1020
tatttcaccc tgcattttaa tccgaaactg agtgccacgc tgtacatggt gggctttcag   1080
attgcatcac agatcggtca agttgtcttc tcgaccccgc tgggcatgct gcacgatcgt   1140
atgggtgacc gcaccacgtt tctgaccatt ccgcgatcg ttctggccgc aacggtctat   1200 ggcttttcg tgattaaacg tgatgacgaa caagtggatg gtgacccgtt catccgcgat   1260
agcaaaaaac tgccgtcgct ggcaaccgac gaagctattc tgtcagcgga ttcggaagac   1320
atgtaa                                                              1326

<210> SEQ ID NO 145
<211> LENGTH: 1398
<212> TYPE: DNA
<213> ORGANISM: Artificial Sequence
```

<220> FEATURE:
<223> OTHER INFORMATION: codon optimized CDS from Bifidobacterium gallicum

<400> SEQUENCE: 145

```
atggtcaata aaccgaaaac cgctaaaatc tggagcaatc cgtcatacct gcaatcttcc      60
tttggcatct tcctgttctt ctgttcctgg ggcatctggt ggagcttttt ccagcgctgg     120
ctgaacacca ttggcctgaa tggtgcggaa gtcggcaccg tgtatagtat caactccctg     180
gccacgctga ttctgatgtt tggctacggt attatccaag ataatctggg catcaaacgt     240
cgcctggtgg ttgtcattgc aaccatcgcg ccctgattg gtccgtttgt tcagttcgtc      300
tatgctccgc tgatgcaaac gaacatcatg gcggcggcac tgattggcag tgtggttctg     360
tccgcaggct ttatgtcagg ttgctcgctg atcgaagctc tgaccgaacg ctatagccgt     420
aaatttggct cgaatacgg tcagagccgc gcgtgggct ttttggtta cgccattgtc        480
gcactgattg ctggcatcgt gttcaacatc aacccgatga tcaacttctg gctgggttcc     540
gcgttcggcg tcggtatgct gattgtgtat ctgacctggt atccggcgga acagcgtcaa     600
gccctgaaag aagccgcaga tccgaacgcc gaaaaagca tccgtctttt aaagacatg       660
gttaacgtcc tgaaaatgcc gacgctgtgg ttctgatta tcttcatgct gctgaccaat      720
acgttttata ccgtgttcga tcagcaaatg tttccgacgt attacgcctc actgttcccg     780
tcgatcgaaa ccggcaacac ggtgtacggt gttctgaata gtattcaggt gttttgcgaa     840
tccgcaatga tgggtgtcgt gccgattatc atgcgcaaaa tcggcgttcg taacgcactg     900
ctgctgggtg ctaccgtgat gtttctgcgc atcggcctgt gcggtatttt ccatgatccg     960
gttgcaatta gtatcgtcaa aatgtttcac gctattgaag tgccgctgtt ctgtctgccg    1020
gcgtttcgtt atttcaccct gcattttaat ccgaaactgt ctgcgacgct gtacatggtt    1080
ggctttcaga ttgcctcaca gatcggtcaa gtgattttct cgaccccgct gggcatgctg    1140
cacgatcgct tggtgaccg taccacgttc ctgagcattt ctggcatcgt gctgctggca    1200
acgatctatg cttttttcgt tattaaacgt gatgacgaac atgtcgatgg cgaccgttt    1260
ctgcgtgatc gcgaccgtaa agaaatggaa ctgattgaag aaaacctgca gccggatgcc    1320
gaactggaaa ccagcccggt gggtgttgct gcacaagtgc gtgacaatcg tgcggttcaa    1380
ccggaatatg cctcttaa                                                  1398
```

<210> SEQ ID NO 146
<211> LENGTH: 1338
<212> TYPE: DNA
<213> ORGANISM: Artificial Sequence
<220> FEATURE:
<223> OTHER INFORMATION: codon optimized CDS from Bifidobacterium longum

<400> SEQUENCE: 146

```
atggcgtcag cgaccaaatc ggcgtggaaa aacccgtcct atctgcaatc ctcattcggc      60
atcttcatgt tcttctgttc gtggggcatt tggtggtcat ttttccagcg ttggctgatc     120
tcgggcgtgg gtctgacgaa cgccgaagtt ggcaccattt atagcatcaa ttctctggca     180
accctggtga ttatgtttgt gtacggcgtt attcaggatc aactgggtat caaacgtaaa     240
ctggttattg tggttagcgt catcgcggcc tgcgtgggtc cgtttgtcca gttcgtgtat     300
gcaccgatga ttctggcggg cggcaccacg cgttggatcg tgctctgat tggttcaatc     360
gtgctgtcgg cgggctttat gagtggttgc tccctgttcg aagctgttac cgaacgttat     420
tctcgcaaaa tttggcttcga atacggtcag agccgcgcct ggggctcttt tggttatgca     480
```

```
attgtggctc tgtgtgcggg ctttctgttc aacattaatc cgctgatcaa cttttgggtt      540
ggttcagcat tcggtccggg catgctgctg gtttacgctt tttgggtccc ggcggaacaa      600
aaagaagaac tgaaaaaaga aacggatccg aacgcagctc cgaccaatcc gtcgctgaaa      660
gaaatggttg cggtcctgaa aatgccgacg ctgtgggttc tgattgtctt tatgctgctg      720
accaacacgt tttataccgt gttcgaccag caaatgtttc cgacgtatta cgctaacctg      780
tttccgaccg aagaaatcgg caacgcgacc tacggcacgc tgaatggttt tcaggttttc      840
ctggaaagcg ccatgatggg tgtcgtgccg attatcatga agaaaattgg cgttcgtaat      900
gccctgctgc tgggtgcaac ggtcatgttt ctgcgcatcg gcctgtgcgg tgtgttccat      960
gatccggtta ccattagtat cgtcaaactg tttcactcca ttgaagtgcc gctgttctgt     1020
ctgccggcgt tcgttatttt cacccctgcat tttgacacga aactgagcgc caccctgtac    1080
atggttggct tccagattgc aagccaagtg gtcaagtta tcttttctac gccgctgggc      1140
gccttccacg ataaaatggc acaaatcctg ccgaacaatg acatgggtag tcgtgtcacc     1200
ttttgggtga tttccgctat cgtgctgtgt gcgctgattt atggcttttt cgtcatcaaa     1260
catgatgacc aggaagtggg cggtgatccg ttctacaccg caaacaact gcgccaaatg      1320 gaagcggcca aagcgtaa                                                    1338

<210> SEQ ID NO 147
<211> LENGTH: 1422
<212> TYPE: DNA
<213> ORGANISM: Artificial Sequence
<220> FEATURE:
<223> OTHER INFORMATION: codon optimized CDS from Bifidobacterium
      adolescentis

<400> SEQUENCE: 147
atgaaatcgg aacaggctca ggctaaaacg acctcagaag caatcgcggc tgcccgtcaa       60
cgccaacgtg aagaaaaaaa acgcatcaaa atggcgtcaa aaacccgttc ggtgtggaaa      120
aacccgagtt atctgcagag ctcttttggc attttcatgt ttttctgctc ctggggtatc      180
tggtggagct ttttctctcg ctggctgacc gatccgacgc atggcctggg tatgagttcc      240
gccgaacagg gccaaattta tagtatcaat tccctggcaa cgctggtcat tatgtttgtg      300
tacggcacca ttcaggacca actgggtatc aaacgtaaac tggttatttt catcagcgca      360
gttgcggcct gtgtcggtcc gtttgtccag ttcgtgtatc aaccgatgct gaccgcgggc      420
ggcaccacgc gttttattgg tgtcctgctg ggtagcatcg tgctgtctgc cggctttatg      480
gcaggttgca gcctgttcga agctattacc gaacgttatt ctcgcaaatt tggcttcgaa      540
tacggtcaga gtcgtgcctg gggctccttt ggttatgcag tggttgctct gtgtgcgggc      600
tttctgttca acattaatcc gctgctgaac ttttgggtgg ctcaatctg cggtctgtcg      660 atgctgtgtg tgtacgcctt ctgggttccg gcagaacaga agaagaact gaaaaaagaa       720 gctgatccga acgcgacccc gacgaatccg agctttaaag aaatggtttc tgtcctgaaa      780
atgccgacgc tgtgggttct gattgtcttt atgctgttca ccaacacgtt ttataccgtg      840
ttcgatcagc aaatgtttcc gaattattac gctagtctgt tcccgaccac ggaaatcggc      900
aacgcgacct acggtacgct gaatagtttt caggttttcc tggaatccgc catgatgggc      960
gtcgtgccga ttatcatgaa gaaaattggc gtgcgtaatt ctctgctgct gggtgctacc     1020
gttatgtttg cgcgcatcgg cctgtgcggt gtcttccatg atccggtgtc agtttcgatt     1080
gttaaactgt ttcacagcat cgaagtcccg ctgttctgtc tgccggcgtt tcgttatttc     1140
```

```
accctgcatt ttgacacgaa actgtcagcc accctgtaca tggtgggctt tcagattgca    1200
tcacaagtgg gtcaagttat cttctcgacc ccgatgggtg cactgcacga tgcaatgggt    1260
gaccgcccga ccttttttcac gattagcgcc atcgtctttg cagctctggt gtatggcttt    1320
ttcgttatca aaaagatga ccaggaagtg ggcggtgatc cgttttacac cgacaaacaa    1380
ctgaaagcaa tgaaagcggc cgatgctgaa gttaaagcgt aa                       1422
```

<210> SEQ ID NO 148
<211> LENGTH: 1503
<212> TYPE: DNA
<213> ORGANISM: Artificial Sequence
<220> FEATURE:
<223> OTHER INFORMATION: codon optimized CDS from Bifidobacterium longum

<400> SEQUENCE: 148

```
atgcgtgtcg aacaagtccg ccatgctgat ctgcgccagt ccattgacgt gaaccgcctg     60
acctcacata caactacta cattaccacc agcacgaaag ctcgtccgcc ggaacagaaa    120
cgctatatta cgaacaatca gccgagctct aaccaacgta tgatcatggc aagtgctacc    180
aaatccgcat ggaaaaatcc gtcatacctg cagagttcct ttggcatttt catgtttttc    240
tgcagttggg gtatctggtg gtcctttttc aacgctggc tgatttcggg cgtgggtctg    300
acgaacgctg aagttggcac catttattca atcaattcgc tggcgaccct ggtgatcatg    360
tttgtgtacg gcgttattca ggatcaactg gtatcaaac gtaaactggt tattgttgtt    420
agtgtcatcg cggcctgtgt gggtccgttt gtccagttcg tgtatgctcc gatgattctg    480
gcgggcggca ccacgcgttg gatcggtgcc ctgattggtt caatcgtgct gtcggcaggc    540
tttatgagcg gttgctctct gttcgaagcc gttaccgaac gttatagccg caaatttggc    600
ttcgaatacg gtcagagccg tgcatggggc tcttttggtt atgcgattgt ggccctgtgt    660
gcaggctttc tgttcaacat taatccgctg atcaactttt gggttggtag cgccttcggt    720
ccgggcatgc tgctggttta tgccttttgg gtcccggcag aacagaaaga agaactgaaa    780
aaagaaacgg atccgaacgc agctccgacc aatccgtctc tgaaagaaat ggttgcggtc    840
ctgaaaatgc cgacgctgtg ggttctgatt gtctttatgc tgctgaccaa cacgttttat    900
accgtgttcg accagcaaat gtttccgacg tattacgcca acctgtttcc gaccgaagaa    960
atcggcaacg caacctacgg cacgctgaat ggttttcagg ttttcctgga atccgccatg   1020
atgggtgtcg tgccgattat catgaagaaa attggcgttc gtaatgctct gctgctgggt   1080
gcgacggtca tgtttctgcg catcggcctg tgcggtgtgt ccatgatcc ggttaccatt   1140 tcaatcgtca aactgtttca ctcgattgaa gtgccgctgt tctgtctgcc ggcgtttcgc   1200
tatttcaccc tgcattttga cacgaaactg tctgctaccc tgtacatggt tggcttccag   1260
attgcgagcc aagtgggtca agttatcttt tctaccccgc tgggcgcttt ccacgataaa   1320
atggcgcaaa ttctgccgaa caatgacatg ggtagtcgtg tcacctttg ggtgatttcc   1380 gccatcgtgc tgtgcgcact gatttatggc ttttcgtca tcaaacatga tgaccaggaa   1440
gtgggcggtg atccgttta caccgacaaa caactgcgcc aaatggaagc ggccaaagcg   1500
taa                                                                1503
```

<210> SEQ ID NO 149
<211> LENGTH: 1266
<212> TYPE: DNA
<213> ORGANISM: Artificial Sequence
<220> FEATURE:

<223> OTHER INFORMATION: codon optimized CDS from Mitsuokella multacida

<400> SEQUENCE: 149

```
atgggtaatc tgctgaaagc gttctcgaat ccgttttatc gcacctcctc cctggaaatc      60
ctgctgttct tgctggttg gggtatttgg tggagctttt tccagatttg gctgaccacg      120
aaacagggct ttacgggtgc acaagtgggc accatctaca gctttggttc tgcagtcgct     180
ctggtgctga tgttcgttta tggcagcctg caggataaac tgggtatgaa gaaaaccatg     240
ctgaaatttt tcgcggtttg ccaaattctg gtcggcccgt ttttcacctg gtttatgtg      300
ccgatgctgg cggccaactt ttacgtgggc gcggtggttg gtgccgtgta tctggcggtt    360
gcctttctgg cagcttgccc ggtcttcgaa gccgtgaccg aacgtctgag tcgtcgctat    420
tcctttgaat acggtcaggc acgcgcttgg ggctccttcg gttacgctgt tgcggccctg    480
tgtgcgggct ttctgttcac gatgaacccg aatctgatct tttggaccgg ttcagcggtt    540
gcggcggtgc aactgatcgt tctggtctcg atgacgccgg aaaatgatgc aagcctgacc    600
gctcaatatg aagtgaaagc cgaatcaatt aaagaatcga aaccccgag ctttggcgaa     660
attgtgggtg ttttcaaact gatcgaagtg tggaaaatga ttgtctttgt gatcatgtcg    720
tggacctttt acacggtttt cgaccagcaa atgtttccgg aattttttcac ccgtttctt    780
gcgacgccgg aagccggcca gcaagcatat ggtgtgctga actccattga agttttctg    840
gaatttctga tgatgggcct ggtgccgatt ctgatgcgtc gcatcggcgt tcgtaaagcc    900
attctgctgg gttgcgcaat tatgatcgtc cgcatcggcg ttgtggcct ggtgacgaat    960
ccgctggggt tgccgtcat taaactgctg catgctccgg aaaccgcgct gtttatcctg   1020
gctgtgtttc gttacttcac cctgcacttc gatacgcgca tttctgcaac cctgtatatg   1080
gttggctttc agatcgcggc ccaggtcggt caaattatct tcagtacgcc gctgggcgcg   1140
ctgcatgact ctattggtta ccagagtacc tttctggtga tttccggcat cgtgtgtgtt    1200
gcctcactgt atgcattcgt catcctgaaa aagatgacc agcaagttga tggtcagccg   1260
ctgtaa                                                                1266
```

<210> SEQ ID NO 150
<211> LENGTH: 1275
<212> TYPE: DNA
<213> ORGANISM: Artificial Sequence
<220> FEATURE:
<223> OTHER INFORMATION: codon optimized CDS from Lactobacillus antri

<400> SEQUENCE: 150

```
atgaaaaact ctaaactgag cgcattcaaa aactcgttct atctggaaag tagcctgtcc     60
ctgctgctgt tcttcgccgc ctgggggtatt tggtggagct ttttccagat ctggctgacc    120
aacgatctgg gctttagtgg tgcaaaagtc ggcatgattt atacgttcga ctccgcgatc    180
accctggttc tgatgtttat ttacggctca gtccaggata aactgggtat taaacgtcgc    240
ctgctgattg gcgttacgat cctggaaatg ctgctgggtc gttttttcac ctggatctat    300
gcgccgctgc tgcatagtaa tttcattctg ggcgcatttc tgggttcact gtacctgtcg    360
tttgctttcc tggcggccag cccgaccttt gaagcactgg ctgaacgtat gagccgtcgc    420
tattctttcg aatacggtcg tgcgcgtgcg tggggctcat tggttatgc agtgtcggca    480
ctgtgcgcag ctacctgtt tacgattcg ccgtacatcg tgttttggct gagctctggc    540
attagcctgc tgaccttcct gctgctgtgt tttggtcgta ccaaaagccc gacgcaggtg   600
gctcgctatg aaaacaaagc ggaagaagaa cacgatgccg acaaaccgag cttcaaagaa   660
```

```
atcatctctg tcttcaaact gaaacaactg tgggaactgg tgttttcat tatctttagt      720 ggctccttct atacggtttt tgatcagcaa atgtttccgc agttttcac ccaattttc      780 aaaacggcag ctcagggcaa caccgcctac ggcattctga acagcatcga agttttctg      840 gaagctatta tgatggcgat cgtcccgtgg attatgaaga aaattggcgt gcgtaaaacg      900
ctgctgattg gtgttaccat catgtttctg cgcatcggcc tgtgcggtct ggtggttagc      960
ccggtgggca tttccatcgt taaactgttc catgccccgg aaaccgcaat tttcgcactg     1020
gctatgtttc gttatctgac cctgcacttt gatacgcgcc tgtctgcgac catgtacatg     1080
gtcgtgggtc agattgccgg ccagatcggt caaattatcc tgagtacgcc gctgggcatg     1140
ctgcatgacc gtatcggtta tcgcgccacc ttcctggtca tttccctgat tgtgatctgt     1200
gcggccgttt acgcatttgt cattctgcgc aaagataatc aggaagtgga cggtcaaccg     1260
ctggaaaaca attaa                                                     1275
```

<210> SEQ ID NO 151
<211> LENGTH: 1323
<212> TYPE: DNA
<213> ORGANISM: Artificial Sequence
<220> FEATURE:
<223> OTHER INFORMATION: codon optimized CDS from Lactobacillus ruminis

<400> SEQUENCE: 151

```
atgatgccga ttagcgacaa ctggaaaggt atcctgttta tgaatgacat gaacaaaagc       60
ggtcgtatga gccaactgaa aaacccgttt tcacctcaa acgctacgaa tattctgatg      120 ttttcgcgg gctggggtat ttggtggtcg tttttccaga tctggctgac cacgaaacag      180
ggctttaccg tgcccaagt gggtgaaatt tatagtttta actccgcttt ctcactgatt      240
gcgaacctgg tttacagcaa tatccaggat cgtctgggtc tgaaacgcaa tctgctgatc      300
ttttgcgcgt gtctgcaagt cttcctgggc ccgttttca cctttctgtt cgttccgatg      360
ctgcatgcta acctggaact gggtgcgctg attggtagct gctatctgac cctggcttac      420
ctgagcgcgt ctccgatgtt cgaagccctg acggaacgtg catctcgtcg ctttaactat      480
cagtacggtt ctgcgcgtgc gtggggcagt ttcggttatg cggtttccgc cctgctggca      540
ggttttgtct tcaccatcaa tccgtcactg ctgttttgga ttggctcggc aatcgctgtg      600
gttctgctgc tgctgctgct gttctggaac ccggtgcgta taaagaaac cgttgcccgc      660 tttgaaaacg aaatggtgcg tgaacgcgaa aattcgaaac cgggtagccg tgattttctg      720
aatgtcttca aagtgcgcag tctgtgggaa attgcaatct ttctggtttt ctccggcacc      780
ttctacacga tcttcgatca gcaaatgttc ccgcagtttt tcacccaatt tttcaaaacg      840
caggctatgg gtgaccatat gtacggcatc ctgaatagcg ttgaagtctt tctggaagcg      900
ctgatgatgg gtctggtgcc gctgctgatg aagaaattg tgttcgtcg caccatcctg      960 gtgggcgtta cgtttatgtt cattcgtatc ggcggttgcg gtctgattac caacccgctg     1020
ggcgtgagta tgatcaaact gctgcatgcc ccggaaaccg caatcttttg cgtcgtgatg     1080
ttccgttatt acacgctgca ctatgatccg cgcgtctctg ccaccattaa tatcgtgacg     1140
ggcattgcag gtagctttgg ccagatcctg ctgtctaccc cgctgggtct gctgcgtgac     1200
cacattggct atcaaccgac gtttctggtt attgccggta tcgtcttctg tgcaggtatc     1260
tacggcctgt ttattatccg tcgcgatgac caggaagtga atggcgaacg cctgtccgaa     1320
taa                                                                  1323
```

<210> SEQ ID NO 152
<211> LENGTH: 1248
<212> TYPE: DNA
<213> ORGANISM: Artificial Sequence
<220> FEATURE:
<223> OTHER INFORMATION: codon optimized CDS from Yersinia frederiksenii

<400> SEQUENCE: 152

```
aagcttatga acatagcgt ccgtaaccaa tacctgattc tgagcggtct gctgttcacc        60
ttcttcttta cctggtcgtc ggcatttagc ctgttcagta tttggctgaa ccagtatgtt       120
ggcctgaaag gcaccgaaac gggtgcgacc ttttccgcaa ttgctctgac ggcactgtgc       180
gcacagccgc tgtacggtgt catccaagat aaactgggcc tgaaaaaaca tctgctgtgg       240
gcgattggta tcctgctgct gattagcggc ccgttttttca tctatgtcta cgcgccgctg       300
ctgcgtgtga atatgctggt tggtgccgtc accggcggtc tgtatatggg catgacgttt       360
ttcgcgggca ttggtgccct ggaatcatac accgaacgtg tgtcacgcat ctcgggtttt       420
gaatttggca agcccgcat gtgggctcg ctgggttggg caggtgcaac gttttcgca        480
ggcatgctgt caacatcaa cccgaacatc aacttctgga tggcaagtgc ttccgcggcc       540
atctttctgc tgctgctgtg gcatctgcac gaagtgaaaa ccgcagctat gggtcaactg       600
gaatatggca aaaacagcgc actgaccctg agtgatacgc tgtccctgtt ccgtatgccg       660
cgcttttggg ccctggtggt ttttgttacc ggtgtctctg tgtataatgt ttacgatcag       720
caatttccgg tctatttcag ctctctgttt acggaccgtc gccatggtaa cgaaatgtac       780
ggcttcctga atagtctgca ggtctttctg gaagcaggcg gtatgttcct ggctccgttt       840
ctggtgaacc gtattggtgc gaaaaaggc ctgctgctgt ctggcctgat tatggctatg       900
cgcatcctgg gcagcggtct ggcacaagat gctgtgacca tctctctgat gaaactgctg       960
cacgcagttg aactgccgat tctgctgatc gctatgttca aatatattgc ggccaatttt      1020
gacccgcgtc tgagcgcgac cctgtatctg gtgggttttc agttcattac gcaagtgtac      1080
gcgagcgttt tctctccgct ggccggcaaa ggttatgatc tgatcggctt gcggacacc      1140
tacctgatta tgggcggtat cgttctgggt ctgacggcca tttcctgttt tatgctgcgt      1200
ggcgaatcac gcaccgatga cccgtcgctg caactgacca cgaaataa                  1248
```

<210> SEQ ID NO 153
<211> LENGTH: 1260
<212> TYPE: DNA
<213> ORGANISM: Artificial Sequence
<220> FEATURE:
<223> OTHER INFORMATION: codon optimized CDS from Serratia
       proteamaculans

<400> SEQUENCE: 153

```
atgaatcgtg aaaccaaaaa atactatgtc ctgctgtcgg gtctgctgtt cttcttcttc        60
tttacctggt cttcgtcgtt ctcgctgatt caatctggc tgaaccagaa aattggcctg       120
aaaggcaccg aaacgggcct gatctttgcg gccatgtcga ttatggcgct gtgcgcccag       180
ccgctgtatg gctttatcca agataaactg gtctgcgta acatctgct gctgttcgtt       240
ggcgtcctgc tgctgctgac cggtccgttt tcatttatg tgtacgcacc gctgctgcag       300
tcaaacctgg tggttggcgc tctggttggc ggtgtgtttg tttcgctggc attcaatgct       360
ggcatcggtg cgctggaaag ctataccgaa cgtgtctctc gcattgtggg ctttgaattt       420
ggtcgtgcac gcatgtgggg ctcactgggt tgggcatcgg caacgttttt cgcgggtttc       480
```

```
aactacaata ttgacccgaa catcaatttt tggattgcaa gcgctagcgc ggcggtgttt    540
ctgctgctgc tgtggcaggt ccgtgaactg aaaccgaacg cgatggccgg cctggaatat    600
ggtaaaccgg aaaatctgaa actgcaagat gcactggctc tgctgcgcct gccgggtttt    660
tgggcgctgg tcgtgttcgt gctgggcacc agcatctatg gtgtgtttga ccagcaattc    720
ccggtttact ttgcctctca gttcccgacg catgaagaag caaccgcat gtacggcttt    780
ctgaacagcc tgcaagtctt cctggaagca ggcggtatgt ttctggctcc gctgctggtt    840
aatcgtattg gcatcaaaca gtctctgctg ctggcgagct ctgttatggc cctgcgcatg    900
gtcggcagtg gttttgcgtc cggtgccctg atgattagtg cgatgaaact gctgcacgcc    960
gtcgaactgc cgatcctgct ggttgcgatg ttcaaatata ttaccacgcg ttttgatagt   1020
cgcctgagtt ccaccctgta cctggtgggc tttcagttca tttcccaaat cgttgccggt   1080
tttctggcac cgctggctgg ctatggttac gatcgtatcg gctttgcaga cacctatctg   1140
ctgatgggtt gcgcagtggc aggcaccacg ctgattagct gttttctgct gcgcggtgaa   1200
acggttgcaa gtgctccgca gttccaatcc accctgaaat catcggaacc gacgcagtaa   1260
```

<210> SEQ ID NO 154
<211> LENGTH: 1239
<212> TYPE: DNA
<213> ORGANISM: Artificial Sequence
<220> FEATURE:
<223> OTHER INFORMATION: codon optimized CDS from Escherichia coli

<400> SEQUENCE: 154

```
atgaaaaaac gcccgacccg ctcatacatg ctgctgtccg cactgctgtt cttcttcttc     60
gtgacctgga gttcgtcctc ttctctgctg agcatttggc tgcatcagga agtgggcctg    120
aaagcgtctg aaaccggtat tatctttagt gtcctgtccg tgtcagcact gtttgctcag    180
gtttgctatg gcttcatcca agatcgtctg gtctgcgca acacctgct gtggtttatt    240
accgcactgc tgatcctgtc gggcccggct tatctgctgt ctcttacct gctgagtgtg    300
aacattctgc tgggtagcgt ttttggcggt ctgttcattg gcctgacgtt taatggcggt    360
atcggtgtgc tggaatcgta taccgaacgt gttgcgcgcc agagcacgtt tgaatttggt    420
cgtgcacgta tgtggggctc tctgggttgg gcagtcgcaa ccttttttcgc gggtctgctg    480
tttaacatta atccggacct gaacttcctg gttgcctcgt gcagcggcct gatctttttc    540
tgtctgctgg cacgtctgaa agtggcagca ccggcctcca tggaaaaact ggaaattggt    600
gcgaaaaaag tttcactgga agatgctctg cgtctgctga ccctgccgcg ctttttgggcg    660
ctgattttct ttgtggttgg cacgtgcatc tatggtgtct acgaccagca atttccggtg    720
tatttcagct ctcagtttcc gaccctgcgc gaaggcaacg aaatgtttgg ttacctgaat    780
agctttcaag ttttcctgga agcggcgggt atgttctgtg cgccgtggct ggtcaaccgt    840
attggcgcca aaaatggtct gatctttgcg gcatggtca tggccctgcg catgattacc    900
tctggcctgg tggaaggtcc gctgctgatt agtatcacga aactgctgca tgcagttgaa    960
ctgccgattc tgctggtcgc tatcttcaaa tacaactctc tgaacttcga taaacgtctg   1020
agttccacca tttacctggt gggctttgca tgtacctcat cggttatcgg tacggtcctg   1080
tcgccgctgg caggcttcag ctatgaacgt tttggtttcg ctcagagtta cctgattatg   1140
ggcatcatgg tgttctccac cacgtttatt tcaatcttcc tgctgcgctc cacgaaaagc   1200
tctagtgaac cgtcatttct gcagcaaaaa gccgtttaa                           1239
```

<210> SEQ ID NO 155
<211> LENGTH: 1263
<212> TYPE: DNA
<213> ORGANISM: Artificial Sequence
<220> FEATURE:
<223> OTHER INFORMATION: codon optimized CDS from Cronobacter turicensis

<400> SEQUENCE: 155

```
atgagcgaag tcctgcaatc aacccgttcc gcctacatca aactgagcct gttcgtcttt     60
ctgttcacct ttacctggag tgctggcttt ggcatgtatg cgatttggct gggcgataaa    120
gccggtctga gtgcaattga catcggcacg gtctttgctg tgaacggtgt tttcgcggtc    180
ctggtgaaac cggtttatgg cttcatcatg gataaaaccg gtatgaaaaa acatctgctg    240
tactttgtgt gcctgattag cgcactgatg gctccgttct atctgtggtg ttacctgccg    300
ctgctgcagt cacactttct ggccggcatg attatcggtg cactgttttt ctcgttcggc    360
tggtatgcgg gtgttgcggc cgaagaaagc tatgtcgatc gtttttctcg cctgtacaat    420
atggaatttg gccgtatccg catgtgggca gctctgggtt gggcagtggc agccagcttt    480
tctggctatg tttacaacat tagcccgatt atcaatttca ccatcggtag tgtctccgca    540
gtgtgcatgc tgctggtcct gatttctctg aaagtggacc attttggcca ggaagaaaac    600
agcgtgctgt ctaaagataa aattgttatc gcggacgtct ttcacctgtt ccgtaatccg    660
aaattttgga tgttcgcact gtatatcgcg ggtgttgcct ggatgatgtt tattgctgaa    720
cagcaattta gccgctattt cgtgaccttt ttcaacacga aagaacaggg caatgccatg    780
ttcggttaca tgagtaccac gcaatcctgc acggaatttt tcggcatgat gctggtgccg    840
gccctggtta accgtatcgg cgcaaaacag ggtatgctgc tgaccggtct gattgttagt    900
ctgcgcctga ttatctccgg cctgaccacg gatccgctga ttatctgtct ggtgaaaccg    960
ctgtatggta ttgaaatcgc actgattctg gtttctgtct ttaaatacat cgctgaacat   1020
ttcgacaaac gtattaatgc gaccatgtat ctgctgggct accaagccat ggtgtatgtt   1080
ggtagtatcg tggttgcacc gccggctggc tatgcgtacg ataccattgg ttttgaacac   1140
acgtacctga ttatgggcac catctccctg ctgtttacga ttgtctcagc cttcaccctg   1200
tcggattgtc agaaacataa aaaagtgacc tcagcttcgc acacggacca agcgctgaac   1260
taa                                                                 1263
```

<210> SEQ ID NO 156
<211> LENGTH: 1269
<212> TYPE: DNA
<213> ORGANISM: Artificial Sequence
<220> FEATURE:
<223> OTHER INFORMATION: codon optimized CDS from Enterobacter sp

<400> SEQUENCE: 156

```
atggaaaata cctcaacgaa caatcgcacc gaatactata aaatcagcat cttcatcttc     60
ctgtacttct tcacctggtc agcgtcaatt ggcctgctgg ctatctggct gggtcagaaa    120
gcgaacctgt caggctcggt gatcggcacc gtgtttgcag ttaatggcat cttcagcgtt    180
attctgaaac cgatctatgg ctacattctg gacaaaatcg gcatgtcgaa atatctgctg    240
tactttgtgg ttgcaatgag cgctctgatg gcgccgtttt tcatttatgt ttaccagccg    300
ctgctgatgt ctaacaccat gctgggcatt atcattggtg ccctgtatct gagtttcgca    360
tggtacgccg gtgtggcagc atgcgaaagc tattctgatc gtttttcccg cctgaatggc    420
atggaatttg gtcagatccg tatgtggggc tcactgggtt gggcagttgc tagctctttt    480
```

```
tctggcctgc tgttcaacct gagtccggcc tataatttta ttctgggtag tgtcgcatcc    540
gtgatcatgc tgattgttct gctgaacctg aaagttaaca ccaatagcgt ccatgcgtct    600
gatgtgctga cgaaagaaaa aatcgccccg tccgacgtct atgcactgct gcgttcacgc    660
aaatttgggg ccttctgtct gtacgttgct ggcgtcgcgt ggatgatgtt tatcgcagaa    720
cagcaatttt cgcgctattt cgtgaccttt ttcgatgaca ttcaccaggg caacgccgtt    780
tttggctatc tgggtacggt ccaaagcggt atggaatttg tgatgtacat ggttattccg    840
ctgtttgtta atttcatcgg cgcaaaacgt ggtctgctga ttgtcggcct gtttgtgggt    900
gctcgcctga tcatttcagg cctgtgcgat tcgcatctgc tgattagcgt gctgaaaccg    960
ctgtatggtc tggaaatctg tctgctgctg gttagtgtct taaatacat tgctgaacac    1020
ttcgacaaac gtgtcaacgc gaccatgtat ctgctgggct accaggccat gctgtatgtg    1080
ggtaatgtcg tgatcagttc cccggcgggt tatatgtacg atcgcattgg ttttgaacaa    1140
acctacatca ttatgggcgc gacggccctg acctttacgc tgctgtctgc tttcaccctg    1200
agtgcgtgcc agtccaaatg gcgtggtacg agcgccattt cggtggcaga acaaaatccg    1260
agccgctaa                                                            1269
```

<210> SEQ ID NO 157
<211> LENGTH: 1260
<212> TYPE: DNA
<213> ORGANISM: Artificial Sequence
<220> FEATURE:
<223> OTHER INFORMATION: codon optimized CDS from Citrobacter koseri

<400> SEQUENCE: 157

```
atgaacaaaa atgactcggc ggaaaaaaat cgtcgcaaaa tctacatcac gctgtcgctg    60
tttattctgg tttacttctt ctcctggaaa gcgaccctgg atacgtactc ctttggctg    120
tcagaaaaaa ttggcctgga cggtgtcgcg attggcatcg tgtttgcggc caacggtttc    180
tgcgccgttc tgattaaacc ggtctatggc tttctgatcg atcgtctggg tctgcgcaaa    240
gacctgctgt ttttcattag tctgatttcc atcaccgtgt tcccgttttt cttttatatc    300
tacaaaccgc tgctgcagtc tgctctgtac gcgggcattg ccctgggcgg tatcttctg    360
tcgatgggct attacgcagg ttgtgcggcg gcggaaagct atctggatcg tttcggccgc    420
ctgtttgacc tggaatttgg tcaaattcgt atgtggggcg cgatcggttc agtcttttcg    480
gccgcaagca ccggttacat cttcaacatc aacccgatga tcaacttcgg cctgagctct    540
gctggtgcgc tgatcatcct gatcatcgtt tcaccatga aaatcgaagt gaacgaagaa    600
gttaaaaacc gtatcatcgc aaaagataaa gctacgatct acgacatcat cgccctgttt    660
agcacccgca atttctggac gtttgttctg tacgtctgcg gcgtggttg gattatcttc    720
gtggcagaac agcaatatcc gcgcttcttt atcaccttct acgcttctaa agaaatcggt    780
catcagatgt tcggctatct gggtgctgcg agtctgggcg tcgaatttct gttatgatg    840
attgcgccgg gtatcgtgaa tcgtctgggc ccgaaaaccg gtctgctgat tacgggcttt    900
gtcgtggccg cacgcttcat cggctcgggt ctggttacca gcgcaattac gatcggcatt    960
atcaaactga gctggggtat tgaaatgtct tttctgctgg ttagcatctt caaatacctg    1020
gaaatcaact tcgataaaaa agtcaacggc tccatgtatc tgctgggtta ccagtcagtg    1080
aactacattg gcaccgttat cctgtctccg ctgagtggct atctgtacga acgtctgggt    1140
ttttcccata cgtatttcat gatggggttgt accgtgctgt tctttacgat tatcagtgcg    1200
tttctgctgc aaaacaataa acgcaccgaa ccggttattg ccgaaaatgc ccacgcataa    1260
```

<210> SEQ ID NO 158
<211> LENGTH: 1242
<212> TYPE: DNA
<213> ORGANISM: Artificial Sequence
<220> FEATURE:
<223> OTHER INFORMATION: codon optimized CDS from Bacillus megaterium

<400> SEQUENCE: 158

| | |
|---|---|
| atgaaatcct caaaatcgct gtattggaaa ctgtcggctt acttcttctt cttcttcttt | 60 |
| acctggtcat cctcttattc gctgttcagc atttggctgg ccaggaaat caaactgaac | 120 |
| ggctcagcca ccgtctgat ttttagcgtg aatgctatct cgcgctgtg catgcaaccg | 180 |
| ctgtatggct acatttcaga tcgtatcggt ctgaaaaaac atgttctgtt tttcatttcg | 240 |
| tgtctgctgg tgtttgttgg cccgttttat atcttcgtgt acggtccgct gctgcagtat | 300 |
| aacgtggtta ttggcgctat tatcggcggt ctgtacctgg tgttgccctt ctggcaggc | 360 |
| attggtgcaa tcgaaacgta catcgaaaaa gtcagtcgta atacaaatt cgaatacggc | 420 |
| aaaagccgta tgtggggctc tctgggttgg gcggccgcaa cctttttcgc gggtcaactg | 480 |
| tttaacatta tccgcacat caatttctgg gtggctagcg tttctgcggt cattctggtg | 540 |
| gcgattatct ttagcgtcaa agtggaaatg agctcttatg aaatggaaaa agccgaaagt | 600 |
| gttacgctgc gtgatgtcgg ctccctgttt ctgctgaaag aattttggtt tttcatgatc | 660 |
| tacgtcgtgg gcgttacgtg cgtctatggt gtgtacgacc agcaatttcc gatttattac | 720 |
| gcaagtctgt tcccgaccga atccatcggc aaccaggtct ttggctatct gaacagcttt | 780 |
| caagtgttcc tggaagcggg catgatgttt gctgcgccgt tcattgtgaa caaaatcggt | 840 |
| gctaaaaata gcctgattct ggcgggcttt ctgatgggtt tccgcattat cggctctggt | 900 |
| ctggttgtcg gcccgattgg tatcagttcc atgaaactga ttcatgccct ggaactgccg | 960 |
| atcatgctga ttgcaatctt taaatatctg gccgcaaact tcgataccccg tctgtcatcg | 1020 |
| attctgtacc tggttggctt tcagttcgcc tctcaaattg gtgcaagtgt gctgtccccg | 1080 |
| atcgttggcg gtctgtatga ctcagttggt ttttcgcgca cctacctgat tatgggcggt | 1140 |
| atggttctgg tctttaacgt gatcagcatg ttcacgctgc tgaacagcaa aaacaccgt | 1200 |
| tttattcgca aagacgtgca ggaaaatacc caaattatct aa | 1242 |

<210> SEQ ID NO 159
<211> LENGTH: 1263
<212> TYPE: DNA
<213> ORGANISM: Artificial Sequence
<220> FEATURE:
<223> OTHER INFORMATION: codon optimized CDS from Providencia
      rustigianii

<400> SEQUENCE: 159

| | |
|---|---|
| atgggcaaaa tcattggtgc gacccgtcac gcctacttta tcctgagcgg cctgctgttt | 60 |
| accttcttct ggacctggag ttcggcattt agcctggttc tctgtggct gtctcagaaa | 120 |
| gtcggcctga aaggcaccga tacgggtatt atcttcagtg ttatctccct gaccgcattt | 180 |
| tgcgctcagc cgctgtatgg tttcattcaa gacaaactgg gcctgcgtaa aaacctgctg | 240 |
| tggtacattg gtgtgatgct ggttatcagt ggcccgtggt ttattttcgt tgtaccccg | 300 |
| ctgctgcgct ggaatatttt tctgggcagt atccctgg gtgtctatgt gggcgcgacc | 360 |
| tttttcgccg gcatcggtgc actggaatcc tatacggaac gtgtgtcacg cattgctggt | 420 |
| tttgaatacg gtcgtgcacg tatgtggggc tcgctgggtt gggcaggtgc aacctttttc | 480 |

```
gcaggtattc tgttcaacat caacccgaac tacaatttcg ccatgggctc agtgtcggca    540 ctgatctta ttatcctgct gtggcgtctg agcgatgttc gcccgcaggc aatgaacgaa    600
ctggaatttg gtaaatcgaa tgctctgaaa ctgagcgacg cgctgggcct gctgaaaatg    660
cgttcattct ggagcctggt ggtgtttgtg tgcggtgtta cgtctataa cgtttacgat     720 cagcaatttc cgatttattt cgccagcctg ttttctgaac agagtcatgg taacgaaatg    780
tttggctatc tgaacagcct gcaagttttc ctggaagccg gcggtatgtt cctggcaccg    840
tttctggtca accgtatcgg tgctaaaaat ggcctgctgc tgtcaggctt tgtcatggct    900
ctgcgcattc tgggctcggg tctggcggat gacaccatta cgatcagctt tatgaaactg    960
ctgcacgcgg tggaactgcc gattctgctg atctctctgt tcaaatacat caccacggtt   1020 tcgataaac gtctgtctgc caccatctac ctggtcggtt ttcagttcat tgctagtctg    1080
tgcgcaacgg tgctgtctcc gctggcaggt attagttatg atcgcatcgg ctttgccgac   1140
acctacatga ttctgcagg catcgtcttc accctgacga ttatcctg tgtgctgctg      1200 aaatcagaaa acagctctaa agtccataat gtgagcattc agaagaaaac cgtggaactg   1260
taa                                                                 1263
```

<210> SEQ ID NO 160
<211> LENGTH: 1266
<212> TYPE: DNA
<213> ORGANISM: Artificial Sequence
<220> FEATURE:
<223> OTHER INFORMATION: codon optimized CDS from Providencia
      alcalifaciens

<400> SEQUENCE: 160

```
atgggcaaaa aaacccgtgc taacattcat gcttatctga ccctgagcgg cctgctgttc     60
accttcttct ggacgtggtc gagcgtgttt tcactggtgt cgctgtggct gtctcagaaa    120
attggcctga aggcaccga tacgggtatt atcttcagcg ttatctctct gaccgctttt    180
tgcgcgcagc cgctgtatgg tttcattcaa gaccgtctgg gcctgcgcaa aaacctgctg    240
tggtttctgg gcggtctgct gctgattagc ggtccgtggt ttatcttcgt gtgtaccccg    300
ctgctgaaat ggaatattt tgcgggcgcg ccgcactgg gtatctacgt tggcgctacc    360 ttttcgcgg gcattggtgc cctggaatcc tatacggaac gtgtcagtcg catcgcatcc    420
tttgaatacg gtcgtgctcg tatgtggggc tcactgggtt gggcaggtgc aaccttttc    480 gccggtctgc tgtttaacat tgatccgaac ctgaatttcg caatgggcag tgtctccgct    540
ctgctgttta ttatcctgct gtggcgtctg cgcaacgtgc gtccgcatac catgaatgaa    600
ctggaatttg gtaaaaccca gtcactgacg gtgtcggatg cactgggtct gctgcgtatg    660 cgcagttct ggtccctggt catctttgtg tgcggtgtgt ctgtttataa cgtttacgac     720
cagcaatttc cggtctattt cgcaagtctg tttgctaacc agaatgaggg taacgaaatg    780
tttggctatc tgaacagcct gcaagtgttc ctggaagcgg cggtatgtt cctggccccg     840 tttctggtta atcgtattgg tgcaaaacgc ggcctgctgc tgagcggcct gattatggct    900
ctgcgtatcc tgggctccgg tctggccgat gacgcaatta ccatctcatt tatgaaactg    960
ctgcacgccg ttgaactgcc gattctgctg atcagcctgt tcaaatacat cacgtctgtt   1020 tcgataaac gcctgagtgc aaccatctac ctggtcggtt ttcagttcac ggcgagcctg    1080
tgtgcctcat ttctgtcgcc gctggcgggc tatggttacg ataccctggg cttcgccgac   1140
acgtatatga ttctggctgc gattgtgatc tcgatgacca ttatcagctc tgttctgctg   1200
```

```
caaagcgaaa acaccagcac ggtctctaat ccgatgacca cgagcaagaa aaccgtggaa    1260
ctgtaa                                                              1266

<210> SEQ ID NO 161
<211> LENGTH: 1290
<212> TYPE: DNA
<213> ORGANISM: Artificial Sequence
<220> FEATURE:
<223> OTHER INFORMATION: codon optmized CDS from Weissella
      paramesenteroides

<400> SEQUENCE: 161
atgggtggtc gccgtatgtc aaaatatatg aaagccttca aaaacgaaag ctacctgcaa     60
tcctcggtca cgatgctgct gtacttcgct agctggggca tttggtggag cttttttccaa   120 ctgtggctga ccgcgaaatc aggtctgaac ctggatggct cggccgtggg tacgatctat   180
agtgcaaatt ccctggttac cctggtcctg atgttttttct acggcacgct gcaagacaaa   240
ctgggtatta acgtcatct gctgatcttt agcggtgttt gcgcagccct ggtcggtccg    300
tttttcattt atgcgtacga accgatgctg cacaccaact ttacgatggg cctggtggtt   360
ggttcaattt ttctgtcggc tggcttcctg gcgaccacgg gtatctatga agccctggtc   420
gaacgtttta ccgcgtgtt taaattcgaa tatggccagg cgcgtgcctg gggctctttt   480
ggttacgcag tcgtggctct gctggcgggt cacctgtttg tgattaaccc ggatctgaat   540 ttttggttg cagtatctt cggtgtcctg ctgctgctga atgtctgttt ttgggtgccg    600
aaagccgaac gcctggaacg tgttcgcagc gcacaggaaa ccgaaaaaac ggtgccgagt   660
gttcgtgaaa tgctgtccct gctgaaaatg cgcgatctgt gggttgtcat tgtgctgatc   720
tttttcacct ggacgttta taccgttttc gaccagcaaa tgtttccgag tttctacgct   780
ggcctgttta gctctgtggc gcagggccag caaatgtatg gtaacctgaa cagcattcaa   840
gtgttcgttg aagccattat gatgggtatc gtcccggtga ttatgaacaa atcggcgtt   900 cgtaatacc tgctgctggg tattgccatc atggcaattc gcatcggcct gtgcggtttt   960
attgataacc cggtggcaat cagcttcgtt aaaatgctgc attctttga aacgccgctg   1020 ttcattctgt caatctttcg ttatttcacc ctgcactttg acacgaaact gtcggcgacc   1080
ctgtacatga ttggctttca ggtcgcagct caactgggtc aagtgttcct gagtaccccg   1140
ctgggcatgc tgcgcgataa ttccggttat gccgttacgt ttcacattat caccattatc   1200
gtcattgcgg cgggtatcta cgcattttc gtgatcaaaa aagataacca ggacgtgaat   1260
ggtgaaccgc tggtttctaa agcagcttaa                                    1290

<210> SEQ ID NO 162
<211> LENGTH: 1185
<212> TYPE: DNA
<213> ORGANISM: Artificial Sequence
<220> FEATURE:
<223> OTHER INFORMATION: codon optimized CDS from Bifidobacterium
      pseudocatenulatu

<400> SEQUENCE: 162
atgacctcgg cggaacaagg ccaaatctac tcaatcaact cgctggctac cctggttatt    60
atgttcgctt atggtgctat ccaagaccaa ctgggcatca acgtaaaact ggttatcttt   120
gtcagcgcga ttcggccct ggttggtccg tttgtgcaat tcgtttatgc accgatgctg   180
accgcgggcg gcaccacgcg tttcattggt gttctgattg gttcaatcgt cctgtcggca   240
```

| | |
|---|---|
| ggctttatgg ctggttgcag tctgttcgaa gcactgaccg aacgttattc ccgcaaattt | 300 |
| ggcttcgaat acggtcagag ccgtgctgg ggctcttttg gttatgctat cgtggcgctg | 360 |
| tgtgccggct ttctgttcaa cattaatccg ctgctgaact tttgggtggg tagcatctgc | 420 |
| ggcctgggta tgctgtgtat ttacgcgttc tgggttccgg ccgaacaaaa agaagaactg | 480 |
| aaaaaagaag cggatccgaa cgcagctccg acgaatccga gttttaaaga aatgatctcc | 540 |
| gtcctgaaaa tgccgaccct gtgggtcctg attgtgttta tgctgttcac caacacgttt | 600 |
| tataccgtgt cgatcagca aatgtttccg aattattacg cgagtctgtt ctccaccacg | 660 |
| gaaattggca cgccaccta cggtacgctg aacagctttc aggttttcct ggaatcggcc | 720 |
| atgatgggcg tggttccgat tatcatgaag aaaattggcg ttcgtaatag cctgctgctg | 780 |
| ggtgcaaccg tcatgtttct gcgcattggc ctgtgcggtg tgttccatga tccggtcagc | 840 |
| gtgtctatcg tgaaactgtt tcactcaatt gaagttccgc tgttctgtct gccggcgttt | 900 |
| cgttatttca ccctgcattt tgacacgaaa ctgtcggcaa ccctgtacat ggttggcttt | 960 |
| cagattgcta gccagatcgg tcaagtcatt ttctctacgc cgatgggtgc actgcacgat | 1020 |
| gcaatgggtg accgcccgac cttttttcacg atttctggca tcgtgctggc ggccctgatc | 1080 |
| tatggctttt tcgtcatcaa aaaagatgac caggaagtgg gcggtgatcc gttttacacc | 1140 |
| gacaaacaac tgaaagccca agcggcggcg aagccaacg cataa | 1185 |

<210> SEQ ID NO 163
<211> LENGTH: 1086
<212> TYPE: DNA
<213> ORGANISM: Artificial Sequence
<220> FEATURE:
<223> OTHER INFORMATION: codon oprimzed CDS from Bifidobacterium catenulatum

<400> SEQUENCE: 163

| | |
|---|---|
| atgctgcgtg gctctggcac caataaaaaa aaacaacgta ataacatgac ctcaaacacc | 60 |
| cgctccgcct ggaaaaatcc gtcctacctg cagagctctt ttggcatttt catgtttttc | 120 |
| tgctcatggg gtatctggtg gtcatttttc tcgcgttggc tgaccgatcc gacgcatggc | 180 |
| ctgggtatga cctcggccga acagggccaa atttatagca tcaactctct ggcaacgctg | 240 |
| gtgatcatgt ttgcgtacgg cgccattcag gaccaactgg gtatcaaacg taaactggtc | 300 |
| attttcgtga gtgccatcgc ggccctggtt ggtccgtttg ttcagttcgt ctatgcaccg | 360 |
| atgctgaccg cgggcggcac cacgcgtttt attggtgtgc tgattggttc tatcgttctg | 420 |
| agttccggct ttatgccgg ttgcagtctg ttcgaagcac tgaccgaacg ttattcccgc | 480 |
| aaatttggct cgaatacgg tcagagtcgc gcctggggct cctttggtta tgcaattgtt | 540 |
| gctctgtgtg cgggctttct gttcaacatc aatccgctgc tgaattttg ggtcggtagc | 600 |
| atttgcggcc tgggtatgct gtgtgtctac gctttctggg tgccggcgaa acaaaaagaa | 660 |
| gaactgaaaa agaagcgga tccgaacgca gctccgacca tccgtcatt taagaaatg | 720 |
| atctcggtgc tgaaaatgcc gacgctgtgg gtgctgattg ttttatgct gttcaccaac | 780 |
| acgttttata ccgtttttcga ccagcaaatg tttccgaatt attacgcttc cctgttcccg | 840 |
| accacggaaa ttggcaacgc gacctacggt acgctgaata gctttcaggt gttcctggaa | 900 |
| tctgctatga tgggcgtggt tccgattatc atgaagaaaa ttggcgtccg taacagcctg | 960 |
| ctgctgggtg caaccgtgat gtttctgcgc attggcctgt gtggtgtttt ccacgatccg | 1020 |
| gtctctgtga gcatcgtgaa actgttccat agcattgaag tcccgctgtt ctgtctgccg | 1080 | gcgtaa                                                                  1086

<210> SEQ ID NO 164
<211> LENGTH: 1176
<212> TYPE: DNA
<213> ORGANISM: Artificial Sequence
<220> FEATURE:
<223> OTHER INFORMATION: codon optimized CDS from Clostridium
      thermocellum

<400> SEQUENCE: 164
atgattctgg acaacctgaa acgctccgaa cgctatccgt tctctttat cctgttttac        60
tccctgtttt acatgggtct ggctgtgttt ggtgttttca tgccggtcta cctggaaggt       120
ctgggctatg ataacaccga catcggcacg tttctgagca ttagctcttt tgtcggtctg       180
ttcgcacagc cgatctgggg cgtgattagc gatcgtgcca atctaaaaaa caatgtgctg       240
aaaatgctgg ttctgtttag ttccattgcg atctttatgt tccgcctgag cggtaattat       300
tactatattt tcgcggtgat ggtggtttac gccttttttcc aaaccccgat tacgccgatc       360
ggtgatgcca tcaccctgga atacattacc gacacgaaat ggaaatatgg tccgatccgt       420
ctggcaggtg ctctgggtta tgcggtgatg gcctttattg cggtgcact gacccgcaaa        480
aacatcaacg ctatcttttt catttgcttt gttatcggca tcatgagcct gattaccgtc       540
ttccgtatgc cgacggtgaa aggtcatcag tcagacggca acaaactgtc gatcctggaa       600
gttttcaaaa attctgaact ggtcctgctg atgggtttta ccctggtgat ccacaccacg       660
atgggcttct acaacacgtt tttcccgatc tactacaaaa acatgggtgc ggataatacg       720
atcctgggtc tggcagtgtt tattggctca gcttcggaaa ttatctttct ggttttcggc       780
gaccgtatta tcaaacgcct gggtattaaa tttaccctgt tcggtgcggc cgtcgtggca       840
gttgtccgtt gggcttcact gggtctgatc aacaatattt ttgcagtgct ggctctgcag       900
atcctgcatg gctttatttt catcgttctg gcgtactcga tggccaccta tattaacaat       960
gaaatgccgc cggaactgaa agcgagcggt cagacgtca actctgtgat cggtctgggc      1020
attagtcgta ttatcggttc caccggcggt ggcgttatca gtgatctgat ggcatccgc      1080
caagtcttt tcctgaatag tgtgattgtt ctggcgtcca ttgtgatctt tggtgccatc      1140
ttcctggttc gtcgccagaa aattaccggc caataa                              1176

<210> SEQ ID NO 165
<211> LENGTH: 1311
<212> TYPE: DNA
<213> ORGANISM: Artificial Sequence
<220> FEATURE:
<223> OTHER INFORMATION: codon optimized CDS from Granulibacter
      bethesdensis

<400> SEQUENCE: 165
atggttctgg atatggatgc gatgagcggt acgattgccg tgagcccggt cctgtcggat        60
ggtcagccgc cgtcggattc ccgtcagaaa cagggcgaat ccgcgctgct ggataaactg       120
aacttttttcc tggcagatgt gcgtgacggt ctgggtccgt atctggcagt ttacctgctg       180
agtgcttccg tcgtgatgg ccgctgggac gaaagctctg tgggcctggt tctgaccatt       240
agtggtgtgg ttggcctggt cgcgcagacg ccggccggtg cactggttga tcgttcccgc       300
aacaaaccgc gtctgctggc tgttgcgatc ctgctggtca ccctgagtac gctgctgctg       360
ccgtttatgt ccggtctgcc gctggtgacc ctgacgcaaa gcatggcggc cgttgccggt       420
gcaatttctcg ccccggtcat cgcagctatg accctgggtc tggtgggcac ggatggtttt       480

```
gcacgtcgca ttggccgcaa cgaatcattc aatcatctgg gtaacgcagt ttcggcggcc      540
atcgcaggtc tgctggcatg gcactatggt ccggtcgtgg tgttttggct gatgggcctg      600
ctggctattg cgggtctggt caccgtgctg cgtattgata atcgccatat cgataatgac      660
ctggcaaacg gcggtgaagc taacggcatg gatggtgcag ctctgaaaga ccaggcatca      720
ccgggcctgt ggcgcatcct ggcagaccat ccgggtctga tgacgtttgc cgttctggtc      780
tttctgttcc acctggcaaa tgcggccatg ctgacctcag tgtcgcaact gctgatgcgt      840
gaagttggta agatatggc gacgtcgctg gcggcggcat gcattgtggc agcacaaatg      900
gtgatggttc cggtcgccat gctggtcggc cgttttgtgg accgcattgg cacccgtccg      960
atctttctgc tggcattcgg cattctggca ctgcgtggta tgctgtaccc gctgagcggc     1020
aatccgtggt ggctgctggg tgtgcaactg ctggatggcg ttggtgcagg catctttggc     1080
gctctgttcc cggtcgtggt tgcggacctg accaagggta cgggccgttt taacattagc     1140
cagggtgccg tggcaaccgc tcaaggtatc ggtgctgcac tgtctgcggg cgtcgcaggt     1200
ctgattatcg tgaaagcggg ctatagcgtt gccttttct ctctggcagg tgtcgctggt     1260
ctgggcttcg tgctgtacgc gctgctgatg ccggaaaccc gtcacctgta a             1311
```

<210> SEQ ID NO 166
<211> LENGTH: 1371
<212> TYPE: DNA
<213> ORGANISM: Artificial Sequence
<220> FEATURE:
<223> OTHER INFORMATION: codon optimized CDS from Serratia odorifera

<400> SEQUENCE: 166

```
atgctgaccc tgaccttcgt tatcaatatc gctatcccgg acgtgggcgg ttttatctgg       60
ccgaaagtga atgtgaacaa caaagctgat attatccatc agggcatttc tcacgaaccg      120
cgtaacaaaa aatattacgt tctgctgagt ggtctgctgt tttctttttt ctttacctgg      180
agcgcgtctt ttagtctgat ttctatctgg ctgaatcaga aaatcggcct gaaaggcacc      240
gaaacgggcc tgattttag cgcgatgagc atcatggccc tgtgcgtcca gccgctgtat      300
ggcttcgtgc aagacaaact gggtctgcgc aaacatctgc tgctgtttgt cggtgtgctg      360
ctgctgctga ccggtccgtt ctttatttat gtgtacgcac cgctgctgca gacgaacctg      420
gtggcaggcg ctctggttgg cggtctgttc gtcagcctgg cgtttaatgc cggcattggt      480
gccctggaat cctataccga acgtgtttca cgcatcgtcg gcttcgaatt tggtcgtgca      540
cgcatgtggg gctctctggg ttgggcgagt gccacgttct ttgcgggttt catctacaac      600
atcaacccga acatcaattt ctggatcgca tccgcttcag cggccgtctt tctgctgctg      660
ctgtggcaag tgcgtgaact gaaaccgaac gcgatggccg gctggaata tggtaaaccg      720 gaaaatctga actgcaagat gcactggct ctgctgcgtc tgccgggttt ctgggcgctg      780
gttgtgtttg ttctgggcac ctccatttat ggtgttttcg accagcaatt ccggtctac      840 ttcgcatcac agtttgctac gcatgaagaa ggcaaccgta tgtacggttt cctgaatagc      900
ctgcaagttt ttctggaagc gggcggtatg ttcctggcac cgctgctggt gaaccgtatt      960
ggcatcaaac agtccctgct gctggcaagc tctgtgatgg ctttccgcat gtttggctcg     1020
ggttttgcaa atggtgctct gatgattagc gcaatgaaac tgctgcacgc tgtggaactg     1080
ccgattctgc tggttgccat gtttaaatat atcaccacgc gtttcgattc gcgcctgagt     1140 tccacccctgt acctggttgg cttccagttt attagccaaa tcgtcgcagg tattctggca     1200
```

| | |
|---|---|
| ccgctggcag gtctgggtta tgatcgcatc ggctttgcag acacctacct gctgatgggt | 1260 |
| tgcgcagtgg caggcaccac gctggtttct tgtttcctgc tgcgtggtga acccccggca | 1320 |
| cgcgctccgc agtttcaaag tacgattaaa tcatcggaac cgatccagta a | 1371 |

<210> SEQ ID NO 167
<211> LENGTH: 1314
<212> TYPE: DNA
<213> ORGANISM: Artificial Sequence
<220> FEATURE:
<223> OTHER INFORMATION: codon optimized CDS from Streptomyces albus

<400> SEQUENCE: 167

| | |
|---|---|
| atgacggtcc agtccccggc tgctccgagt ccggctgctg ctgtcccggt gcgtggtcgt | 60 |
| cgccgcctga attttggtct gattagtgcg gccctgttca tgttttcgt tacctggagc | 120 |
| ctgtcttgga gtctgttttc gatttggctg acgcaggata tcggcctgtc tccgggccgt | 180 |
| agctctctgg tgattggcgc gaactctctg ggttgcctgg tcaccatgcc ggtgtacggc | 240 |
| tttctgcaag accgtctggg tctgcgcaaa atctgctgt attggattgg cgccctgatg | 300 |
| ctgctggttg gcccggttta tatctacgtt tatggcccgc tgctgaaatc tcatttcgca | 360 |
| ctgggcctgt tggttggtag tgcttacctg gccatggcat ttgctgtggc ggttgccacc | 420 |
| ctggaatcct atgcggaacg tctgtcacgc ttccacggct tgaatttgg tcgtgcccgc | 480 |
| atgtttggct ctctggttg gcggcggca acgttcctgg caggtcgtct gtttaacatt | 540 |
| gatccggacc tgaccttctg ggcagcaagt ggcacggcgg tcgtgttgt tggtctgctg | 600 |
| gtcgccatcc gtgtgaccga tggtcgtcgc gctgcggccg ttgaccatgc ggcggcgagc | 660 |
| gtgagcctgg cagatgtcgc cgcactgctg cgctatccgg cgttctgggg tctgctgctg | 720 |
| tttgttgtcg cagtgaccgc tacgtacaac acctatgatg cgatgtttcc gagctacttc | 780 |
| agttccctgt ttgcgacgga tgccgacggc aaccgcatgt attcggacct gaatagcgtc | 840 |
| caggtgttcc tggaagcagg cggtatggca ctggctccgt ttctggttaa tcgtctgggc | 900 |
| ccgaaaaaat ctctgctggt tagcggttgt gtcatggcca cccgcatttt tctgtccggt | 960 |
| atcgtgacgg atccggttgc aattagcgcg gtgaaactgc tgcatgcagt ggaactgccg | 1020 |
| atcatgctga ttgctatctt caaatacgtg aatcgtcact tgaaccgcg cctgtcatcg | 1080 |
| accatttatc tgatcggctt tcagatggcg acgcaagtcg gtgctgcggt gatcagcccg | 1140 |
| ctggcaggtc tgggttatga tcgtctgggc tacgcaccga cctatctggt gatgtcggcg | 1200 |
| ctggttgcca ccttcacgct ggttagcgtc tttaccctgc gtgcagacgc aaaaggcacg | 1260 |
| cacggtctgc cggccgtggg cgccgcagaa ggtcgctccc cggctgcggg ttaa | 1314 |

<210> SEQ ID NO 168
<211> LENGTH: 1284
<212> TYPE: DNA
<213> ORGANISM: Artificial Sequence
<220> FEATURE:
<223> OTHER INFORMATION: codon optimized CDS from Azotobacter vinelandii

<400> SEQUENCE: 168

| | |
|---|---|
| atgcacctgc cgctgaaacg cgaatactgg ctgatctcgg tctgctgtt cttcttcttc | 60 |
| tttgctggt cgtcatccta ctcactgttc tcaatttggc tgcatcgtgt tatcggcctg | 120 |
| tcgggcaccg aaacgggctt tattttcgcg ccaacgcca ttgcagctct gttcatccag | 180 |
| ccgttttatg gcgcactgca agaccgtctg ggtctgagcc gtcgcctgct ggtctggatt | 240 |
| ggtgtgctgc tggcatgcgc agcaccgttt gcaatccatg tgtacgccgg tctgctggca | 300 |

```
cacgatgtgg ttctgggcgc actggttggt gcagcttttc tggctttcgc gatgctggcg      360
ggcgtgggtg ttattgaatc atataccgaa cgtctgtcgc gccatgccgg ctttgaattt      420
ggcaccacgc gtatgtgggg ctccctgggt tgggcggccg caaccggtgt ggcaggtgtc      480
gtgttcgata ttgacccgga tatcgccttt tacatgagct ctgctgcggg cctggcattc      540
ctgctgatcc tgagccgtct ggacatggat gcctttcgta accacgaaac ccgcgctggt      600
gaatctgcgc cggttcgcac ggcggatatt ctgcaactgc tgcgtctgcc gcgcttttgg      660
gccttcagtc tgtttctgac cggcgtggca ggtgtttata tgatctacga acagcaattc      720
ccggtgtatt ttgcgagctt tttcccgacc ccggaagaag cacgcgcgc ctatggttac       780 ctgaatagtt cccaagtcct ggtggaagct ctgctgatgc tggtcgcgcc gtgggttgtc      840
gcacgtaccg gtgcaaaata cggtctgctg ctggcgggca cgattatgtt tgtgcgcatc      900
ctgggcagtg gtctggcttc cgacgcgtgg accattgccg catgcaaaat gctgcatgct      960
attgaagtgc cgatcctgct ggttgcggtc ttcaaataca tctgtgttaa cttcgatgct     1020
cgtctgagcg cgaccctgta cctggtctct tttcagttcg cccagcaact gacggcaatg     1080
ctgctgagcc cggctgttgg ctatggttac gatcgcctgg gctttgcgag tgtttatctg     1140
ctgctggctt ccctggtcgg tgcgtgtctg ctgctgagct ggtctctgct gcgtgccgac     1200
ccgtcatcga aaccacgcg cgctgcggat ggtgcaccgg aactgccggc cattgcacag     1260
gccgcaaatc actatgaacc gtaa                                            1284

<210> SEQ ID NO 169
<211> LENGTH: 1278
<212> TYPE: DNA
<213> ORGANISM: Artificial Sequence
<220> FEATURE:
<223> OTHER INFORMATION: codon optimized CDS from Oenococcus oeni

<400> SEQUENCE: 169
atgattatga tcaaccaatc cgaaattaaa accgccaaca aaaaaaaaga cttctggggc       60
ttcccgttct cgcacttcac ctacttcttt atctggcaga ttatcaacgg ttatctgacc      120
ctgtggatgg aacaaattgg ccatctgaat ggtgcggaag ccggcgtggt tttcagtatg      180
atggccggtt tttcccctgat tttccagccg tcatttggca tcatctcgga taaactgatc      240
ttcaagaaaa acctgatcct gaccattagt atcgcaggta ttctgatcgg cccgtatttc      300
caatggctgt tctgccgct gatgaaaatc aacagcacct tgtcgcgat tatcacgggc        360 atctttctga gtttcattct gaatggcggt gtctccgtga ttgaacagta tgttcaacgt      420
gcaagcctgg ctaaccattt tgaatacggt cacagccgca tgggcggttc tctggcaggc      480
atgtgcgcta gcttcctggg cggtcaactg tttctgtgga gcccgaacag catcttctgg      540
gcatgtacca tttctgctat gatcctgacg ggtctgctgc tgtttaacga taaaattcac      600
atggaaaacg caaatctggc gggcggcacc agctctcgtc tgaacctgaa acagatcagt      660
tccatcttca aaatcaaaaa cttctggttc ctgtcactgt tttatattgg cacggcgtcg      720
atctacgata tcttcgacca gcaattcatc atcttttca aatcattttt cgacaccgca      780
tcgcagggta cggcggccta ttcctacatg accacggcac aaattggcat cgaatttatt      840
ctgatgtttc cgatgccgtg gattatcaac cgtatcggtg cacgcaatgg cctgattgct      900
tatggcacca tcctggcgat tcgtattatc ggcagtgctc tgtccccgaa cctgttttgg      960
gtgattctgc tgcgcctgct ggccggtctg gaaatgccgc tgattctggt tagcatcatg     1020
```

-continued

```
aaatacattt ctggcgccttt cgatctgcgc ctgtatgcga ccatctacgc cctgtcatcg     1080
aactttgcta acagattac cgaattttttc ctggcgaccg cggcgggcaa aatgtatgac     1140
tctatcggct tccatcacac gtacctgatt ctgggtgtta tcgtcgccat ttttaccatc     1200
ttcacggcac tgtttctgaa aaaagaaaac ccggtgcagg caggtgaacg tgatcgcgcg     1260
ggcaatccga aagcctaa                                                   1278
```

<210> SEQ ID NO 170
<211> LENGTH: 1290
<212> TYPE: DNA
<213> ORGANISM: Artificial Sequence
<220> FEATURE:
<223> OTHER INFORMATION: codon optimized CDS from Lactobacillus brevis

<400> SEQUENCE: 170

```
atggactccg caaaaaccga atcgaaacac ttctggggct tcccgctgtc gcacttctcc       60
tacttcttta tctgggccgt cgtgaatggc tatctgaccc tgtggatgga acaggttgcc      120
catctgaacg gcacggaaag tggtgccgtc ttttccatga tggcaggcat ttcactgatc      180
tttcaaccga ttttcggtgt ggtttcggat aaactgctgt ttaagaaaaa cctgatcctg      240
accattgcga tcgtgggcat tttcatcggt ccgtactttc agtgggtttt catgccgatt      300
ctgcatatca gtgcgtttct ggtggccatt gttaccggca cgtttctgag tttcattctg      360
aacggcggtg tctccgtgat cgaacagtat gtgcaacgtg cgagcctggc caatggtttt      420
gaatacgcac actcacgcgt tggcggttcg gtcgcaggtg tcgtggctag cctggttgcg      480
ggtcgtattt ttctgtggaa accgaactct attttctggg cgtgcaccat cgcggccatt      540
atcctgacgt ttctgctgct gttctccgac aaagtgaacc tggataatgc ggcggcggcg      600
ggtgatacct cagactcgct ggatatgaaa acggtcctga gtgtgtttaa actgaaaaat      660
ctgtgggtcc tggccatttt ctatatgggc gcatccgctc tgtttgacgt tttcgatcag      720
caattcatca tctttttcaa aacctttttc gacacggcag ctcagggcac cctggtgtat      780
agctacatga gctctgcaca aacggctatt gaattttgcc tgatgttccc gatgccgtgg      840
attatcaaca aaatcggctc tcgtaatggt ctgctgattt atggctttat cacctgtatt      900
cgcatcctgg gtagcgctct gtctccgaac tggatttggg ttgtcggctt ccgtctgctg      960
gcaggtctgg aaatgccgct gctgctgacc tcaattatga aatatatcgc gggtgccttt     1020
gacatccgcc tgtatgctac ggtgtacgca ctggcttcga atttcgcgaa acaagttagc     1080
gtctttattt tctctaccgt cgcgggccgt atgtacgatg tgatcggtta tcaacacacc     1140
tacattatca tgggcattgt ggtgttttc atcacgctgt ttgccgtgtt tttcctgaaa     1200
aaagaagacc cgattcaggc cggtgaagtt gaagatccga acgtgaaagc aaaagttgaa     1260
gcggccagtt ccaccgattc tcgcgaataa                                     1290
```

<210> SEQ ID NO 171
<211> LENGTH: 1245
<212> TYPE: DNA
<213> ORGANISM: Artificial Sequence
<220> FEATURE:
<223> OTHER INFORMATION: codon optimized CDS from Weissella
      paramesenteroides

<400> SEQUENCE: 171

```
atggatcaga cgcagaatac gcagaaaaaa cactttttggt cgttcttcgg cacggatgtc       60
agctacttct tcatttggca gattgtgcag ggctttctgg tcctgtggct gaaacaggaa      120
```

```
gctgatctga gcggcggtca agcgggtttt gttttcagct ttctggcctt cgcatctctg    180
ttttaccagc cggtgttcgg cattatcagc gacaaactgg ttttaagaa aaccctgctg     240
ctgtctatta cgatcgcggc cattctgatc ggtccgtttt tccaatggct gttcattccg    300
ctgctgcatt ttagctctct gctgggcgca attatcggcg tttcgctct ggcgtatgtc     360
ctgaacggcg gtgtggcggt tattgaaagt tacgtggaac gtgcctccct ggcaaatggc    420
tttgaatatg gtcacgctcg catgggcggt tcaatcggcg gtgcactggc atcgttcgtt    480
gcaggtctgg tctttgtgaa aaacccgttc ctggtctttt ggatttgcag tctggcgggc    540
attatcctga cctgtctggt gatcttcggt gatcgtatta actttgctaa tgcagacgcg    600
gcggaaggtg ctagttccgc accgctgaac gccaaaacca tcctgtctat cttcaaaatc    660
aaaaacttct ggatcctgag cattttcttt atgggtacgt ctgcaattta tgatgtcttt    720
gaccagcaat tcccggtgtt ttaccagacc ttttcacga gtgcggccgc aggcaccgtg    780
gcatactccc gtctgctgac cacgcaaatc gccctggaag cactgctgat gattccgatg    840
ccgtggatta tcaacaaaat cggcgctaaa atggtctga ttgcgtatgg tgttctgacc    900
ttcctgcgta tcacgctgag cgccattgca ccgaacttct ggtttctgac ctttgtgcgc    960
ctgctggcgt cattcgaaat gccgctgttt ctggtttcga ccatgaaata tatcgctggc    1020
gcgtttgatc tgcgtctgta tgccacgatt tacgccctgg cattcaattt tgcaaaacag    1080
atctcactgt tcatttttag caccgttgcc ggcgatctgt atgactccgt cggtttccat    1140
accacgtact ttatcctggc tgcgctggtt gcgctggtta cgattgttgc agtctttatg    1200
ctgaaaaaag aaaatccggc tcaggcgggt gaagtggcgg aataa                     1245
```

<210> SEQ ID NO 172
<211> LENGTH: 1278
<212> TYPE: DNA
<213> ORGANISM: Artificial Sequence
<220> FEATURE:
<223> OTHER INFORMATION: codon optimized CDS from Mannheimia
      succiniciproducens

<400> SEQUENCE: 172

```
atgctgatga cctcgcaaaa taaaatcaac gccgtgccgt cgaaccaaaa cttctacctg    60
aataaccgca actactggat cttctcaggt tatttctttg tttacttttt catcatggcg    120
acctgctatc cgtttctggg catttggctg ggtgatatca acggcctgtc aggtgaagac    180
cgtggcacgg tgttcgcaat gatgtcgttt ttcgctctgt gttttcagcc ggttttcggc    240
tacgtcagcg ataaactggg tctgaaaaaa catctgctgt gggttctggg tatttctctg    300
ctgatctatg caccgttttt catttacatc tttgctccgc tgctgaaagt gaatgtttgg    360
ctgggcagtc tggtgggcgg tgcatatatt ggctttgttt tccaggcagg tgctccggcg    420
tccgaagcct atatcgaacg tgtttcacgt cgctcgaaat ttgaatacgg tcgtgtccgc    480
atgtttggca tgtcggttg ggccatttgc gcaagcatcg ctggtgtcct gtatgcaacc    540
aacccgaatc tggtgttttg gctgggcagc attgcttctc tgatcctgct gctgctgatt    600
gccctggcaa aaccggaaca gacctctacg gtgcaaatcg cggaaaaact gggcgccaac    660
aaaaatccgg ttaacctgcg ccaggctttt gcgctgctga actgccgaa attctgggcg    720
ctgctggcct atgttatggg tattgcgtgt gtctacgata tctttgacca gcaattcggc    780
aacttttttca atacctttt cgaaagccac gaacaaggca ttaaaatgtt tggttatgtc    840
accacggcgg gtgaactgct gaatgccctg attatgtttt cgtgccgct gattatcaac    900
```

```
cgtatcggcg caaaaaatgc tctgctgatt gccggcacca tcatgagcgt gcgcattatc    960
ggcagctctt acgcgattga agcctggcat gtggttgtcc tgaaaacgct gcacatgttt   1020
gaagtcccgt tctatctggt gggtctgttt aaatacatcg cgaacgtctt tgaagtgcat   1080
ttctcagcca ccatttatct ggttgcatgc cacttcgcta acagatcgg caatatgctg    1140 gtgtcgccgc tggttggcgc gtggtatgat acctacggtt ttcaagacac gtacctgatt   1200
ctgggctgta tcgcggccgg ttttacgctg ctgagtgtgt tcaccctgac gggcaaaagt   1260
ctgagttccc agtcctaa                                                 1278
```

<210> SEQ ID NO 173
<211> LENGTH: 1257
<212> TYPE: DNA
<213> ORGANISM: Artificial Sequence
<220> FEATURE:
<223> OTHER INFORMATION: codon optimized CDS from Aggregatibacter
      aphrophilus

<400> SEQUENCE: 173

```
atgagcaatc aaacctcctc taaatcgcaa tacctgacca cagcaactga ctggatcttc     60
tcggcatact tcttcgcctt tttctttatt atggcaaccct gccatccgtt tctgggcatt   120
tggctgggtg atatccacgg cctgaaaggt gaaaaaatcg gttacgtgtt tagtttcatc   180
tccctgtttg cgctgctgtt ccagccgatt ctgggctttc tgagcgacaa actgggtatc   240
cgtaaacatc tgctgtggct gctggcaatt ctgctgctgt tttatgctcc gttttcatc    300 tacgttttcg ctccgctgct gaaaaccaac ctgtggctgg gtgtgattgc cggcggtgca   360
tatatgggct ttgttttcca ggcgggtgcc ccggcaagtg aagcctatat tgaacgtatc   420
tcccgcctgg atggctttga atacggtcgt accgcctgt tcggcatgct gggttgggct    480
atttgcgcga gtatcgccgg taacctgtac agctctcaac gaatgccgt cttttggctg    540 ggctctgcta cggcggtggt tctgctggtg ctgatttttcc tggcgaaaac cgatagttcc    600
aacacggccc aggtcgtgga caaactgggt gtgaataaat caccgatcac cctgaaacaa   660
gcgctgaaac tgttttcgct gccgcgtttc tgggcactgc tgacgtatgt tgtcggtgtg    720
gcttgtgttt acgatatttt tgaccagcaa ttcggcaact ttttcaacac cttttttcgaa   780 agcaaagaac agggcatgaa attttttcggt tatgttacca cgggcggtga actgctgaat    840
gccacgatca tgttttttcgt cccgctgctg attaaccgta tcggcgcaaa aaatgctctg   900
ctgattgcag gttcaatcat gtcgattcgc atcatgggct catcgtttgc gaccgaagcc   960
tggcatgtga ttgttctgaa aacgctgcac atgtttgaag ttccgttcta tctggtcggc   1020
gtgtttaaat acattgcgga tgtctttgaa gtgcgcttct ccgccaccat ctatctggtg   1080
agctgccact tttctaaaca gattggtaac atgatcctga gccggcagt tggcaccctg    1140 tatgacatgt acggtttttca atctacgtac ttcattctgg gctgtatcgc tctgaccttt   1200
acgagcgttt ctgtcttcac cctggttaat acgaaaaaac tggtcaacaa tgcgtaa      1257
```

<210> SEQ ID NO 174
<211> LENGTH: 100
<212> TYPE: DNA
<213> ORGANISM: Artificial Sequence
<220> FEATURE:
<223> OTHER INFORMATION: Primer

<400> SEQUENCE: 174

```
cgtctaccct tgttataccct cacaccgcaa ggagacgatc atgaccaata atccccttc     60
```

```
agcacagatt aagcccggcg gtgtaggctg gagctgcttc                           100

<210> SEQ ID NO 175
<211> LENGTH: 100
<212> TYPE: DNA
<213> ORGANISM: Artificial Sequence
<220> FEATURE:
<223> OTHER INFORMATION: Primer

<400> SEQUENCE: 175
gcatcaggca atgaataccc aatgcgacca gcttcttata tcagaacagc cccaacggtt     60
tatccgagta gctcaccagc catatgaata tcctccttag                          100

<210> SEQ ID NO 176
<211> LENGTH: 22
<212> TYPE: DNA
<213> ORGANISM: Artificial Sequence
<220> FEATURE:
<223> OTHER INFORMATION: Primer

<400> SEQUENCE: 176
atgaccaata atcccccttc ag                                              22

<210> SEQ ID NO 177
<211> LENGTH: 21
<212> TYPE: DNA
<213> ORGANISM: Artificial Sequence
<220> FEATURE:
<223> OTHER INFORMATION: Primer

<400> SEQUENCE: 177
gcttcttata tcagaacagc c                                               21
```